US008501739B2

(12) United States Patent
Hohlweg et al.

(10) Patent No.: US 8,501,739 B2
(45) Date of Patent: Aug. 6, 2013

(54) MEDICAMENTS

(75) Inventors: Rolf Hohlweg, Humlebaek (DK); Knud Erik Andersen, Brondby (DK); Jan Lindy Sorensen, Farum (DK); Jane Marie Lundbeck, Glostrup (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 859 days.

(21) Appl. No.: 11/917,823

(22) PCT Filed: Jun. 30, 2006

(86) PCT No.: PCT/EP2006/063753
§ 371 (c)(1),
(2), (4) Date: Jun. 8, 2009

(87) PCT Pub. No.: WO2007/003604
PCT Pub. Date: Jan. 11, 2007

(65) Prior Publication Data
US 2009/0312309 A1    Dec. 17, 2009

(30) Foreign Application Priority Data

| Jul. 4, 2005 | (EP) | 05106037 |
| Jul. 4, 2005 | (EP) | 05106038 |
| Oct. 18, 2005 | (EP) | 05109674 |
| May 29, 2006 | (EP) | 06114615 |

(51) Int. Cl.
*A61K 31/50* (2006.01)
*C07D 401/00* (2006.01)

(52) U.S. Cl.
USPC .................. 514/252.02; 544/238

(58) Field of Classification Search
USPC .................. 544/238; 514/252.02
See application file for complete search history.

(56) References Cited

U.S. PATENT DOCUMENTS

| 2,724,713 A | 11/1955 | Goldman et al. |
| 2,993,899 A | 7/1961 | Dawson |
| 3,164,598 A | 1/1965 | Freed |
| 3,309,370 A | 3/1967 | Schut |
| 3,753,988 A | 8/1973 | Rodway et al. |
| 3,886,161 A | 5/1975 | Hardtmann |
| 4,026,891 A | 5/1977 | Austel et al. |
| 4,163,849 A | 8/1979 | Lumma, Jr. et al. |
| 4,223,036 A | 9/1980 | Heeres et al. |
| 4,251,658 A | 2/1981 | Szilagyi et al. |
| 4,265,894 A | 5/1981 | Gootjes |
| 4,339,579 A | 7/1982 | Freed |
| 4,616,014 A | 10/1986 | Teraji et al. |
| 4,673,675 A | 6/1987 | Robba et al. |
| 4,758,566 A | 7/1988 | Uno et al. |
| 4,824,846 A | 4/1989 | Kampe et al. |
| 4,935,426 A | 6/1990 | Zipplies et al. |
| 5,001,125 A | 3/1991 | Stokbroekx et al. |
| 5,643,495 A | 7/1997 | Bartmann et al. |
| 5,670,505 A | 9/1997 | Matsuo et al. |
| 5,929,089 A | 7/1999 | Jegham et al. |
| 6,130,217 A | 10/2000 | Arnold et al. |
| 6,316,475 B1 | 11/2001 | Bennani et al. |
| 6,482,479 B1 | 11/2002 | Dubal et al. |
| 6,864,261 B2 | 3/2005 | Gharagozloo et al. |
| 6,906,060 B2 | 6/2005 | Peschke et al. |
| 7,115,634 B2 | 10/2006 | Thurieau et al. |
| 7,229,997 B2 | 6/2007 | Nilsson et al. |
| 7,294,626 B2 | 11/2007 | Hohlweg |
| 7,494,994 B2 | 2/2009 | Desos et al. |
| 7,494,995 B2 | 2/2009 | Desos et al. |
| 7,547,693 B2 | 6/2009 | Ohtake et al. |
| 7,687,503 B2 | 3/2010 | Abouabdellah et al. |
| 7,790,929 B2 | 9/2010 | Reiffenrath et al. |
| 7,820,647 B2 | 10/2010 | Schwogler et al. |
| 2003/0073672 A1 | 4/2003 | Breitenbucher et al. |
| 2003/0236259 A1 | 12/2003 | Hohlweg et al. |
| 2004/0023946 A1 | 2/2004 | Peschke et al. |
| 2005/0028438 A1 | 2/2005 | Campana |
| 2007/0032477 A1 | 2/2007 | Waer et al. |
| 2009/0176793 A1 | 7/2009 | Hohlweg |
| 2009/0312309 A1 | 12/2009 | Hohlweg et al. |
| 2010/0267721 A1 | 10/2010 | Hohlweg et al. |
| 2010/0298316 A1 | 11/2010 | Dorwald et al. |
| 2011/0071159 A1 | 3/2011 | Lundbeck et al. |

FOREIGN PATENT DOCUMENTS

| AU | 639529 | 5/1991 |
| DE | 2609746 A1 | 10/1976 |
| DE | 2804096 A1 | 8/1978 |

(Continued)

OTHER PUBLICATIONS

Abdel-Magid et al., "Reductive Amination of Aldehydes and Ketones with Sodium Triacetoxyborohydride. Studies on Direct and Indirect Reductive Amination Procedures," J. Org. Chem., 61:3849-3862 (1996).

Ballaben et al., "Reactivity of cyclopentanone enamines towards non-symmetric electrophilic diazenes," Gazetta Chimica Italiana, 123(7):387-391(1993).

Byrn et al., "Hydrates and Solvates," Solid-State Chemistry of Drugs, 2nd Ed., Chapter 11, pp. 233-247 (1999).

(Continued)

*Primary Examiner* — Paul V. Ward
(74) *Attorney, Agent, or Firm* — Samuel B. Rollins

(57) ABSTRACT

Novel compounds which interact with the histamine H3 receptor are defined. These compounds are particularly useful in the treatment of a variety of diseases or conditions in which histamine H3 interactions are beneficial. Thus, the compounds may find use, e.g., in the treatment of diseases of the central nervous system, the peripheral nervous system, the cardiovascular system, the pulmonary system, the gastrointestinal system and the endocrinological system. The novel compounds have a core consisting of a 6 membered aromatic ring containing at least one nitrogen atom and two carbon atoms in the ring and, at the remaining positions in the ring, there is either a carbon or a nitrogen atom.

13 Claims, No Drawings

(56) References Cited

FOREIGN PATENT DOCUMENTS

| | | |
|---|---|---|
| DE | 2824764 | 12/1979 |
| DE | 3803860 A1 | 8/1989 |
| DE | 4423044 A1 | 1/1996 |
| DE | 4425642 A1 | 1/1996 |
| EP | 0034752 B1 | 6/1983 |
| EP | 0177392 A1 | 4/1986 |
| EP | 0184012 A1 | 6/1986 |
| EP | 0236140 A2 | 9/1987 |
| EP | 0327912 B1 | 4/1992 |
| EP | 0200024 B1 | 7/1992 |
| EP | 0385237 B1 | 6/1994 |
| EP | 0320032 B1 | 1/1995 |
| EP | 0459819 B1 | 8/1996 |
| EP | 0927992 A1 | 7/1999 |
| EP | 0978512 A1 | 2/2000 |
| EP | 1020445 B1 | 8/2008 |
| GB | 753166 | 7/1956 |
| GB | 1345880 | 2/1974 |
| JP | 2003-277755 A | 10/2003 |
| WO | WO 94/14780 A1 | 7/1994 |
| WO | WO 94/22846 A1 | 10/1994 |
| WO | WO 94/26720 A1 | 11/1994 |
| WO | WO 97/02245 A1 | 1/1997 |
| WO | WO 98/27081 A1 | 6/1998 |
| WO | WO 99/21845 A2 | 5/1999 |
| WO | WO 00/66578 | 11/2000 |
| WO | WO 00/69987 A1 | 11/2000 |
| WO | WO 01/32646 A2 | 5/2001 |
| WO | WO 01/32659 A1 | 5/2001 |
| WO | WO 01/42241 A1 | 6/2001 |
| WO | WO 01/44201 A1 | 6/2001 |
| WO | WO 01/64645 A2 | 9/2001 |
| WO | WO 01/66534 A2 | 9/2001 |
| WO | WO 01/74773 A2 | 10/2001 |
| WO | WO 01/74810 A2 | 10/2001 |
| WO | WO 01/74813 A2 | 10/2001 |
| WO | WO 01/74814 A1 | 10/2001 |
| WO | WO 01/74815 A2 | 10/2001 |
| WO | WO 02/12190 A2 | 2/2002 |
| WO | WO 02/060392 A2 | 8/2002 |
| WO | WO 03/066604 A2 | 8/2003 |
| WO | WO 03/104235 A1 | 12/2003 |
| WO | WO 2004/054973 A2 | 7/2004 |
| WO | WO 2005/009976 A1 | 2/2005 |
| WO | WO 2005/009976 A1 | 3/2005 |
| WO | WO 2005/028438 A1 | 3/2005 |
| WO | WO 2005/046603 A2 | 5/2005 |
| WO | WO 2005/085212 A1 | 9/2005 |
| WO | WO 2005/100344 A1 | 10/2005 |
| WO | WO 2005/112938 A2 | 12/2005 |
| WO | WO 2005/117883 A1 | 12/2005 |
| WO | WO 2006/004589 A2 | 1/2006 |
| WO | WO 2006/050389 A2 | 5/2006 |
| WO | WO 2006/058649 A1 | 6/2006 |
| WO | WO 2006/090273 A2 | 8/2006 |
| WO | WO 2006/113704 A2 | 10/2006 |
| WO | WO 2006/124874 A2 | 11/2006 |
| WO | WO 2007/003604 A2 | 1/2007 |
| WO | WO 2007/011820 A2 | 1/2007 |
| WO | WO 2007/016496 A2 | 2/2007 |

OTHER PUBLICATIONS

Celanire et al., "Keynote review: Histamine H3 receptor antagonists reach out for the clinic," Drug Discovery Today, 10(23/24):1613-1627 (2005).

Eguchi et al., "Studies on Antiatherosclerotic Agents. Synthesis and Inhibitory Activities on Platelet Aggregation of 4-Aryl Derivatives of 7-Ethoxycarbonyl-6,8-dimethyl-1(2H)-phthalazinone," Chemical & Pharmaceutical Bulletin, 39(8):2009-2015 (1991).

Falorni et al., "Chiral Ligands Containing Heteroatoms. 7. An Investigation on the Stereochemistry of the Ketone Reductions by Chiral Diamines/Tin Hydride Systems.," Tetrahedron: Asymmetry, 2(4):287-298 (1991).

Ganellin et al., "Synthesis of Potent Non-imidazole Histamine H3-Receptor Antagonists," Arch. Pharm. Pharm. Med. Chem., 331:395-404 (1998).

Giannangeli et al., "Effect of Modifications of the Alkylpiperazine Moiety of Trazodone on 5HT2A and alpha1 Receptor Binding Affinity," J. Med. Chem., 42(3):336-345 (1999).

Grant et al., eds., Grant & Hackh's Chemical Dictionary, 5th Ed., McGraw Hill, New York, pp. 147 and 289 (1987).

Guery et al., "Synthesis of 4-Aryl-1-(4-methylpiperazin-1-yl)phthalazines by Suzuki-type Cross-coupling Reaction," Synthesis, No. 5, pp. 699-701 (2001).

Guillory, "Generation of Polymorphs, Hydrates, Solvates, and Amorphous Solids." In: Polymorphism in Pharmaceutical Solids, Harry G. Brittain, ed., Chapter 5, pp. 183-226 (1999).

Haider et al., "Product Class 10: Phthalazines." In: Science of Synthesis: Houben-Weyl Methods of Molecular Transformations, Y. Yamamoto, ed., Georg Thieme Verlag, Stuttgart, pp. 315-372 (2004).

Hancock, "The challenge of drug discovery of a GPCR target: Analysis of preclinical pharmacology of histamine H3 antagonists/inverse agonists," Biochemical Pharmacology, 71:1103-1113 (2006).

Hori et al., "Novel 4-substituted 2-piperazinylquinazolines as potent anticonvulsive and antihypoxic agents," Chemical & Pharmaceutical Bulletin, 38(5):1286-1291 (1990).

Hori et al., "Potential nootropic agents, 4-alkoxy-2-(1-piperazinyl)quinazoline derivatives," Chemical & Pharmaceutical Bulletin, 39(2):367-371 (1991).

Hu et al., "Development of a novel therapeutic suppressor of brain proinflammatory cytokine up-regulation that attenuates synaptic dysfunction and behavioral deficits," Bioorganic & Medicinal Chemistry Letters, 17:414-418 (2007).

International Search Report and Written Opinion for PCT Application No. PCT/DK2004/000483, mailed Sep. 28, 2004.

International Search Report and Written Opinion for PCT Application No. PCT/EP2007/052571, mailed Jun. 27, 2007.

International Search Report and Written Opinion for PCT Application No. PCT/EP2007/054849, mailed Sep. 3, 2007.

International Search Report and Written Opinion for PCT application No. PCT/EP2007/054940, mailed Oct. 25, 2007.

International Search Report and Written Opinion for related PCT application, PCT/EP2006/063753, mailed Apr. 27, 2007.

International Search Report for PCT Application No. PCT/DK2003/000071, mailed Jul. 29, 2003.

International Search Report for PCT Application No. PCT/US2008/064106, mailed Aug. 15, 2008.

Leurs et al., "The Histamine H3 Receptor: from Gene Cloning to H3 Receptor Drugs," Nature Reviews/Drug Discovery, 4:107-120 (2005).

Leurs et al., "The medicinal chemistry and therapeutic potentials of ligands of the histamine H3 receptor." In: Progress in Drug Research, Ernst Jucker, ed., 45:107-165 (1995).

Leurs et al., "Therapeutic potential of histamine H3 receptor agonists and antagonists," Trends in Pharmacological Sciences, 19(5):177-183 (1998).

Mackins et al., "Therapeutic potential of H3-receptor agonists in myocardial infarction," Expert Opinion on Investigational Drugs, 9(11):2537-2542 (2000).

Malmlof et al., "Targeting of the Central Histaminergic System for Treatment of Obesity and Associated Metabolic Disorders," Drug Development Research, 67:651-665 (2006).

Mazarguil et al., "Enamines of N-methyl- and N-phenylpiperazine. I. Synthesis and physicochemical study," Bulletin de la Societe Chimique de France, 1:319-324 (1969).

Mazarguil et al., "Enamines of N-methyl and N-phenylpiperazines. Synthesis of unsymmetrical N,N'-disubstituted and N-monosubstituted piperazines," Sciences Chimique, 267(12):724-727 (1968).

McIntyre et al., "Pyridazine Based Inhibitors of p38 MAPK," Bioorganic & Medicinal Chemistry Letters, 12:689-692 (2002).

McLeod et al., "Sch 50971, an Orally Active Histamine H3 Receptor Agonist, Inhibits Central Neurogenic Vascular Inflammation and Produces Sedation in the Guinea Pig," J. Pharmacol. Exp. Ther., 287(1):43-50 (1998).

Mir et al., "Nucleophilic Substitution Reactions of Heterocyclic Amines and Acyclic Diamines with Chlorofluoroolefins and Hexafluoropropylene Oxide," J. Org. Chem., 59(1):173-177 (1994).

Mokrosz et al., "Structure-Activity Relationship Studies of Central Nervous System Agents. 5. Effect of the Hydrocarbon Chain on the Affinity of 4-Substituted 1-(3-Chlorophenyl)piperazines for 5-HT1A Receptor Site," J. Med. Chem., 35:2369-2374 (1992).

Morisset et al., "High constitutive activity of native H3 receptors regulates histamine neurons in brain," Nature, 408:860-864 (2000).

Prasad et al., "Potential Antihypertensive Agents. II. Unsymmetrically 1,4-Disubstituted Piperazines," J. Med. Chem., 11:1144-1150 (1968).

Refaat et al., "Synthesis and Antidepressant Activity of Novel Pyridazine Derivatives," Bulletin of the Faculty of Pharmacy, Cairo University, 42(2):415-423 (2004).

Rodriguez-Spong et al., "General principles of pharmaceutical solid polymorphism: a supramolecular perspective," Advanced Drug Delivery Reviews, 56:241-274 (2004).

Rohet et al., "Synthesis and Analgesic Effects of 3-Substituted 4,6-Diarylpyridazine Derivatives of the Arylpiperazine Class," Bioorganic & Medicinal Chemistry, 5(4):655-659 (1997).

Stark et al., "Developments of histamine H3-receptor antagonists," Drugs of the Future, 21(5):507-520 (1996).

Tamayo et al., "Design and synthesis of potent pyridazine inhibitors of p38 MAP kinase," Bioorganic & Medicinal Chemistry Letters, 15:2409-2413 (2005).

Tozer et al., "Histamine H3 receptor antagonists," Expert Opinion on Therapeutic Patents, 10(7):1045-1055 (2000).

Vippagunta et al., "Crystalline solids," Advanced Drug Discovery Reviews 48:3-26 (2001).

Walczynski et al., "Non-Imidazole Histamine H3 Ligands, Part 2: New 2-Substituted Benzothiazoles as Histamine H3 Antagonists," Arch. Pharm. Pharm. Med. Chem., 332:389-398 (1999).

Walczynski et al., "Non-imidazole histamine H3 ligands. Part I. Synthesis of 2-(1-piperazinyl)- and 2-(hexahydro-1H-1,4-diazepin-1-yl)benzothiazole derivatives as H3-antagonists with H1 blocking activities," II Farmaco, 54:684-694 (1999).

Walczynski et al., "Non-imidazole histamine H3 ligands. Part III. New 4-n-propylpiperazines as non-imidazole histamine H3-antagonists," European Journal of Medicinal Chemistry, 40:15-23 (2005).

Written Opinion for PCT Application No. PCT/US2008/064106, mailed Aug. 15, 2008.

Wu et al., "Synthesis and platelet aggregation activity of 6-[4-substituted-piperazinyl)phenyl]-4,5-dihydro-3(2H)-pyridazinones," Zhongguo Yaowu Huaxue Zazhi Bianjibu, 9(3):172-175, 185 (1999).

Xu et al., "Studies on synthesis and anticonvulsant activity of 3-substituted piperazino-6-(substituted-phenyl) pyridazines," Journal of Beijing Medical University, 23(6):477-480 (1991).

Xu et al., "Synthesis and anticonvulsant activity of 6-aryl-3-(4-methylpiperazine)-pyridazine compounds," Chinese Journal of Medicinal Chemistry 1(1):42-48 (1990).

Zaragoza et al., "2-(4-Alkylpiperazin-1-yl)quinolines as a New Class of Imidazole-Free Histamine H3 Receptor Antagonists," Journal of Medicinal Chemistry, 48(1):306-311 (2005).

Linney, I. D. et al., "Design, Synthesis, and Structure—Activity Relationships of Novel Non-Imidazole Histamine $H_3$ Receptor Antagonists", Journal of Medicinal Chemistry, 2000, vol. 43, pp. 2362-2370.

Contreras, J-M et al., "Aminopyridazines as Acetylcholinesterase Inhibitors", Journal of Medicinal Chemistry, 1999, vol. 42, No. 4, pp. 730-741.

Parrot, I. et al., "Synthesis of Substituted 3-Amino-6-arylpyridazines via Suzuki Reaction", Synthesis, 1999, vol. 7, pp. 1163-1168.

Klauschenz, E. et al., "Synthesis and Cardiotonic Activity of 6-Substituted 5-Cyano-(3,4'-bipyridine)-1'-Oxides and Related Compounds: Molecular Structure of 5-cyano-y-morpholino-(3,4'-bipyridine)-1'-oxide (AWD 122-239)", European Journal of Medicinal Chemistry, 1994, vol. 29, No. 3, pp. 175-184.

Contreras, J-M et al., "Design, Synthesis, and Structure—Activity Relationships of a Series of 3-[2-(1-Benzylpiperidin-4-yl)ethylamino] pyridazine Derivatives as Acetylcholinesterase Inhibitors", Journal of Medicinal Chemistry, 2001, vol. 44, No. 17, pp. 2707-2718.

Brown, D. J. et al., "Unfused Heterobicycles as Amplifiers of Phleomycin. III Thiazolylpyridines and Bipyrimidines with Strongly Basic Side Chains", Australian Jounal of Chemistry, 1981, vol. 34, No. 11, pp. 2423-2429.

XP-002355793, Heterocycles, 1994.

XP-002355794, Heterocycles, 1994.

Coppola, G. M. et al., "Pyrimidones. 2. Synthesis and Reactions of 2-Chloropyrimidines", Journal of Heterocyclic Chemistry, 1980, vol. 17, No. 7, pp. 1479-1482.

Werbel, L. M. et al., "Synthesis and Antimalarial Effects of $N,N$-Dialkyl-y-(substituted phenyl)-1,2,4,5-tetrazin-e-amines (1,2)", Journal of Heterocyclic Chemistry, 1979, vol. 16, No. 5, pp. 881-894.

XP-002355795, Heterocycles, 1991.

XP-002355796, Pharmazie, 1989.

Steck, E. A. et al., "Pyridazines VIII. Some 6-Aryl-3-(basically-substituted) Pyridazines (1)", Journal of Heterocyclic Chemistry, 1975, vol. 12, No. 5, pp. 1009-1013.

Lumma, W. C. et al., "Piperazinylpyrazines with Central Serotoninmimetic Activity", Journal of Medicinal Chemistry, 1978, vol. 21, No. 6, pp. 536-542.

Kawaguchi, K. et al., "Parallel Dose-Response Studies of the Voltage-Dependent Na+ Channel AntagonistBW619C89, and the Voltage-Dependent Ca2+ Channel Antagonist Nimodipine, in Rat Transient Focal Cerebral Ischaemia", European Journal of Pharmacology, 1999, vol. 364, Nos. 2-3, pp. 99-105.

Tafesse, L. et al., "Synthesis and Evaluation of Pyridazinylpiperazines as Vanilloid Receptor 1 Antagonists", Bioorganic & Medicinal Chemistry Letters, 2004, vol. 14, No. 22, pp. 5513-5519.

Rival, Y. et al., "5-HT3 Antagonists Derived from Aminopyridazine-type Muscarinic M1 Agonists", Journal of Medicinal Chemistry, 1998, vol. 41, pp. 311-317.

Haugwitz, R. D. et al., "Antiparasitic Agents. 5.[1] Synthesis and Anthelmintic Activities of Novel 2-Heteroaromatic-Substituted Isothiocyanatobenzoxazoles and Benzothiazoles", Journal of Medicinal Chemistry, 1982, vol. 25, No. 8, pp. 969-974.

Levay, B. et al., "Correlation of the Chemical Reactivity of Some Tetrazine Derivatives with Their Reactivity Toward Orthopositronium Atoms and Their LUMO Energies", Journal of Physical Chemistry, 2004, vol. 108, pp. 1753-1756.

Adam, I. et al., "Concise Synthesis of 1$H$-Pyrazin-2-ones and 2-Aminopyrazines", Synlett, 2004, vol. 11, pp. 2031-2033.

Office action for related Australian Application No. 2006264966, dated Oct. 13, 2011.

Office action for related Japanese Application No. 2008-519917, dated Feb. 21, 2012.

Office action for related Russian Application No. 2007147044/04, dated May 14, 2010.

Office action for related Russian Application No. 2007147044/04, dated Nov. 17, 2010.

Silverman, The Organic Chemistry of Drug Design and Drug Action, 2nd Ed., Elsevier Academic Press, Burlington, MA, pp. 29-34 (2004).

Written Opinion for PCT/DK/2003/000071, mailed Oct. 6, 2003.

International Search Report and Written Opinion for PCT Application No. PCT/EP2007/052751, mailed Jun. 27, 2007.

MEDICAMENTS

CROSS-REFERENCE TO RELATED APPLICATIONS

This application is a 35 U.S.C. §371 national stage application of International Patent Application PCT/EP2006/063753 (published as WO 2007/003604 A2), filed Jun. 30, 2006, which claimed priority of European Patent Application 05106037.4, filed Jul. 4, 2005, and European Patent Application 05106038.2, filed Jul. 4, 2005, and European Patent Application 05109674.1, filed Oct. 18, 2005, and European Patent Application 06114615.5, filed May 29, 2006.

FIELD OF THIS INVENTION

The present invention relates to novel compounds, to the use of these compounds in pharmaceutical compositions, to pharmaceutical compositions comprising the compounds, and to methods of treatment employing these compounds or compositions. The present compounds show a high and selective binding affinity for the histamine H3 receptor, indicating histamine H3 receptor antagonistic, inverse agonistic or agonistic activity. As a result, the compounds are useful for the treatment of diseases or disorders related to the histamine H3 receptor.

BACKGROUND OF THIS INVENTION

The existence of the histamine H3 receptor has been known for several years and the receptor is of current interest for the development of new medicaments. Recently, the human histamine H3 receptor has been cloned. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor shows intrinsic, constitutive activity, in vitro as well as in vivo (i.e., it is active in the absence of an agonist). Compounds acting as inverse agonists can inhibit this activity. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

In view of the art's interest in histamine H3 receptor agonists, inverse agonists and antagonists, novel compounds which interact with the histamine H3 receptor would be a highly desirable contribution to the art. Several publications disclose the preparation and use of histamine H3 agonists and antagonists. Most of these are imidazole derivatives. However, recently some imidazole-free ligands of the histamine H3 receptor have been described (see e.g. Linney et al., *J. Med. Chem.* 2000, 43, 2362-2370; U.S. Pat. No. 6,316,475, WO 01/66534 and WO 01/74810).

WO 00/66578 claims certain 3- or 4-(imidazol-2-yl)pyridines being substituted in the 4 position of the imidazole ring. It is mentioned that mammals having a disease or condition mediated by NPY can be treated with such a compound.

Our earlier application, WO 2003/066604 (our internal ref.: 6447), claims certain piperazines being substituted in the 1 and 4 positions.

Our earlier application, WO 2005/009976 A1 (our internal ref.: 6739), claims certain 3-(4-isopropylpiperazin-1-yl)-6-phenylpyrazines being substituted in the para position of the phenyl ring. In the specification, no pharmacological data are given for the compounds prepared.

WO 2005/028438 claims certain piperidines being substituted in the 1 and 4 position.

The object of this invention is to overcome or ameliorate at least some of the disadvantages of the prior art. Hence, not all the objects mentioned below may be fully overcome or ameliorated. Further objects of this invention are mentioned below.

DEFINITIONS

In the structural formulae given herein and throughout the present specification, the following terms have the indicated meaning:

The term "hydroxy" shall mean the radical —OH, the term "oxy" shall mean the radical —O—, the term "oxo" shall mean the radical =O, the term "carbonyl" shall mean the radical —C(=O)—, the term "sulfinyl" shall mean the radical —(S=O)—, the term "sulfonyl" shall mean the radical —S(=O)$_2$—, the term "carboxy" shall mean the radical —(C=O)O— and —C(=O)OH, the term "amino" shall mean the radical —NH$_2$, the term "nitro" shall mean the radical —NO$_2$ and the term "cyano" shall mean the radical —CN.

The term "$C_{2-6}$-alkenyl" as used herein represents a branched or straight hydrocarbon group having from 2 to 6 carbon atoms and at least one double bond, e.g. $C_{2-6}$-alkenyl, $C_{3-6}$-alkenyl, and the like. Representative examples are ethenyl (or vinyl), propenyl (e.g., prop-1-enyl and prop-2-enyl), butadienyl (e.g., buta-1,3-dienyl), butenyl (e.g., but-1-en-1-yl and but-2-en-1-yl), pentenyl (e.g., pent-1-en-1-yl and pent-2-en-2-yl), hexenyl (e.g., hex-1-en-2-yl and hex-2-en-1-yl), 1-ethylprop-2-enyl, 1,1-(dimethyl)prop-2-enyl, 1-ethylbut-3-enyl, 1,1-(dimethyl)but-2-enyl, and the like.

Analogously, the term "$C_{3-8}$-alkenyl" as used herein represents a branched or straight hydrocarbon group having from 3 to 8 carbon atoms and at least one double bond, e.g. $C_{3-6}$-alkenyl, and the like. Representative examples are propenyl (e.g., prop-1-enyl and prop-2-enyl), butadienyl (e.g., buta-1,3-dienyl), butenyl (e.g., but-1-en-1-yl and but-2-en-1-yl), pentenyl (e.g., pent-1-en-1-yl and pent-2-en-2-yl), hexenyl (e.g., hex-1-en-2-yl and hex-2-en-1-yl), 1-ethylprop-2-enyl, 1,1-(dimethyl)prop-2-enyl, 1-ethylbut-3-enyl, 1,1-(dimethyl)but-2-enyl, and the like.

The term "$C_{1-6}$-alkoxy" as used herein refers to the radical $C_{1-6}$-alkyl-O—. Representative examples are methoxy, ethoxy, propoxy (e.g., 1-propoxy and 2-propoxy), butoxy (e.g., 1-butoxy, 2-butoxy and 2-methyl-2-propoxy), pentoxy (1-pentoxy and 2-pentoxy), hexoxy (1-hexoxy and 3-hexoxy), and the like.

The term "$C_{1-6}$-alkoxy-$C_{1-6}$-alkyl" as used herein refers to $C_{1-6}$-alkyl substituted with $C_{1-6}$-alkoxy at any carbon atom. Representative examples are methoxymethyl, ethoxymethyl, 2-methoxyethyl, 2-ethoxyethyl, 3-methoxyprop-1-yl, and the like.

The term "$C_{1-6}$-alkoxycarbonyl" as used herein refers to the radical $C_{1-6}$-alkoxy-C(=O)—. Representative examples are methoxycarbonyl, ethoxycarbonyl, 1-propoxycarbonyl, 2-propoxycarbonyl, 1-butoxycarbonyl, 2-butoxycarbonyl, 2-methyl-2-propoxycarbonyl, 3-methylbutoxycarbonyl, 1-hexoxycarbonyl, and the like.

The term "$C_{1-6}$-alkyl" as used herein represents a saturated, branched or straight hydrocarbon group having from 1 to 6 carbon atoms, e.g. $C_{1-3}$-alkyl, $C_{1-4}$-alkyl, $C_{2-6}$-alkyl, $C_{3-6}$-alkyl, and the like. Representative examples are methyl, ethyl, propyl (e.g., prop-1-yl and prop-2-yl (or isopropyl)), butyl (e.g., 2-methylprop-2-yl (or tert-butyl), but-1-yl and but-2-yl), pentyl (e.g., pent-1-yl, pent-2-yl and pent-3-yl), 2-methylbut-1-yl, 3-methylbut-1-yl, hexyl (e.g., hex-1-yl), heptyl (e.g., hept-1-yl) and the like.

Analogously, the term "$C_{1-8}$-alkyl" as used herein represents a saturated, branched or straight hydrocarbon group having from 1 to 8 carbon atoms, e.g. $C_{1-3}$-alkyl, $C_{1-4}$-alkyl, $C_{1-6}$-alkyl, $C_{2-6}$-alkyl, $C_{3-6}$-alkyl, $C_{1-8}$-alkyl, and the like. Representative examples are methyl, ethyl, propyl (e.g., prop-1-yl and prop-2-yl (or isopropyl)), butyl (e.g., 2-methylprop-2-yl (or tert-butyl), but-1-yl and but-2-yl), pentyl (e.g., pent-1-yl, pent-2-yl and pent-3-yl), 2-methylbut-1-yl, 3-methylbut-1-yl, hexyl (e.g., hex-1-yl), heptyl (e.g., hept-1-yl), octyl (e.g., oct-1-yl), and the like.

The term "$C_{1-6}$-alkylcarbonyl" as used herein refers to the radical $C_{1-6}$-alkyl-C(=O)—. Representative examples are acetyl (e.g., methylcarbonyl), propionyl (e.g, ethylcarbonyl), butanoyl (e.g., prop-1-ylcarbonyl and prop-2-ylcarbonyl), and the like.

The term "$C_{1-6}$-alkylcarbonylamino" as used herein, refers to the radical $C_{1-6}$-alkyl-C(=O)—NH—. Representative examples are acetylamino, propionylamino, pivaloylamino, valeroylamino, and the like.

The term "$C_{1-6}$-alkylcarbonylamino-$C_{1-6}$-alkyl" as used herein, refers to $C_{1-6}$-alkyl substituted at any carbon atom with $C_{1-6}$-alkylcarbonylamino. Representative examples are acetylaminomethyl, 1-(acetylamino)ethyl, propionylaminomethyl, and the like.

The term "$C_{1-6}$-alkylcarboxy" as used herein refers to the radical $C_{1-6}$-alkyl-C(=O)O—. Representative examples are methylcarboxy, ethylcarboxy, propylcarboxy (e.g., prop-1-ylcarboxy, prop-2-ylcarboxy), and the like.

The term "$C_{1-6}$-alkylsulfanyl" as used herein refers to the radical $C_{1-6}$-alkyl-S—. Representative examples are methylthio, ethylthio, propylthio (e.g., 1-propylthio, 2-propylthio and 3-propylthio), butylthio, pentylthio, hexylthio, and the like.

The term "$C_{1-6}$-alkylsulfinyl" as used herein refers to the radical $C_{1-6}$-alkyl-S(=O)—. Representative examples are methylsulfinyl, ethylsulfinyl, propylsulfinyl, butylsulfinyl, pentylsulfinyl, hexylsulfinyl, and the like.

The term "$C_{1-6}$-alkylsulfonyl" as used herein refers to the radical $C_{1-6}$-alkyl-S(=O)$_2$—. Representative examples are methylsulfonyl, ethylsulfonyl, propylsulfonyl, butylsulfonyl, pentylsulfonyl, hexylsulfonyl, and the like.

The term "$C_{3-8}$-alkynyl" as used herein represents a branched or straight hydrocarbon group having from 3 to 8 carbon atoms and at least one triple bond. Representative examples are propynyl (e.g., prop-1-ynyl and prop-2-ynyl), butynyl (e.g., but-1-ynyl and but-2-ynyl), pentynyl (e.g., pent-1-ynyl and pent-2-ynyl), hexynyl (e.g., hex-1-ynyl and hex-2-ynyl), 1-ethylprop-2-ynyl, 1,1-(dimethyl)prop-2-ynyl, 1-ethylbut-3-ynyl, 1,1-(dimethyl)but-2-ynyl, and the like.

The term "aryl" as used herein is intended to include monocyclic, bicyclic or polycyclic carbocyclic aromatic rings. Representative examples are phenyl, naphthyl (e.g., naphth-1-yl and naphth-2-yl), anthryl (e.g., anthr-1-yl and anthr-9-yl), phenanthryl (e.g., phenanthr-1-yl and phenanthr-9-yl), and the like. Aryl is also intended to include monocyclic, bicyclic or polycyclic carbocyclic aromatic rings substituted with carbocyclic aromatic rings. Representative examples are biphenyl (e.g., biphenyl-2-yl, biphenyl-3-yl and biphenyl-4-yl), phenylnaphthyl (e.g. 1-phenylnaphth-2-yl and 2-phenylnaphth-1-yl), and the like. Aryl is also intended to include partially saturated bicyclic or polycyclic carbocyclic rings with at least one unsaturated moiety (e.g., a benzo moiety). Representative examples are, indanyl (e.g., indan-1-yl, indan-5-yl), indenyl (e.g., inden-1-yl and inden-5-yl), 1,2,3,4-tetrahydronaphthyl (e.g., 1,2,3,4-tetrahydronaphth-1-yl, 1,2,3,4-tetrahydronaphth-2-yl and 1,2,3,4-tetrahydronaphth-6-yl), 1,2-dihydronaphthyl (e.g., 1,2-dihydronaphth-1-yl, 1,2-dihydronaphth-4-yl and 1,2-dihydronaphth-6-yl), fluorenyl (e.g., fluoren-1-yl, fluoren-4-yl and fluoren-9-yl), and the like. Aryl is also intended to include partially saturated bicyclic or polycyclic carbocyclic aromatic rings containing one or two bridges. Representative examples are, benzonorbornyl (e.g., benzonorborn-3-yl and benzonorborn-6-yl), 1,4-ethano-1,2,3,4-tetrahydronapthyl (e.g., 1,4-ethano-1,2,3,4-tetrahydronapth-2-yl and 1,4-ethano-1,2,3,4-tetrahydronapth-10-yl), and the like. Aryl is also intended to include partially saturated bicyclic or polycyclic carbocyclic aromatic rings containing one or more spiro atoms. Representative examples are spiro[cyclopentane-1,1'-indane]-4-yl, spiro[cyclopentane-1,1'-indene]-4-yl, spiro[piperidine-4,1'-indane]-1-yl, spiro[piperidine-3,2'-indane]-1-yl, spiro[piperidine-4,2'-indane]-1-yl, spiro[piperidine-4,1'-indane]-3'-yl, spiro[pyrrolidine-3,2'-indane]-1-yl, spiro[pyrrolidine-3,1'-(3',4'-dihydronaphthalene)]-1-yl, spiro[piperidine-3,1'-(3',4'-dihydronaphthalene)]-1-yl, spiro[piperidine-4,1'-(3',4'-dihydronaphthalene)]-1-yl, spiro[imidazolidine-4,2'-indane]-1-yl, spiro[piperidine-4,1'-indene]-1-yl, and the like.

The term "aryl-$C_{1-6}$-alkoxycarbonyl" as used herein refers to the radical aryl-$C_{1-6}$-alkoxy-C(=O)—. Representative examples are benzyloxycarbonyl, phenylethoxycarbonyl (e.g., (2-phenylethoxy)carbonyl and (1-phenylethoxy)carbonyl), and the like.

The term "arylcarbonyl" as used herein, refers to the radical aryl-C(=O)—. Representative examples are benzoyl, naphthylcarbonyl, 4-phenylbenzoyl, anthrylcarbonyl, phenanthrylcarbonyl, and the like.

The term "arylcarbonylamino" as used herein, refers to the radical aryl-C(=O)—NH—. Representative examples are benzoylamino, naphthylcarbonylamino, 4-phenylbenzoylamino, and the like.

The term "arylcarbonylamino-$C_{1-6}$-alkyl" as used herein, refers to $C_{1-6}$-alkyl substituted at any carbon atom with arylcarbonylamino. Representative examples are benzoylaminomethyl, naphthylcarbonylaminomethyl, 2-(4-phenylbenzoylamino)ethyl, and the like.

The term "arylsulfonyl" as used herein refers to the radical aryl-S(=O)$_2$—. Representative examples are phenylsulfonyl, (4-methylphenyl)sulfonyl, (4-chlorophenyl)sulfonyl, naphthylsulfonyl, and the like.

The term "cyano-$C_{1-6}$-alkyl" as used herein refers to $C_{1-6}$-alkyl, substituted at any carbon atom(s) with cyano. Representative examples are cyanomethyl, 2-cyanoethyl, and the like.

The term "$C_{3-8}$-cycloalkenyl" as used herein represents a partially saturated monocyclic carbocyclic ring having from 3 to 8 carbon atoms and at least one double bond. Representative examples are cyclopropenyl, cyclobutenyl, cyclopentenyl, cyclohexenyl, cycloheptenyl, cyclooctenyl, cyclohex-1,3-dienyl, and the like.

Obviously, the term "$C_{3-8}$-cycloalkenyl-$C_{1-3}$-alkyl" is a combination of $C_{3-8}$-cycloalkenyl and $C_{1-3}$-alkyl. Representative examples are cyclopenten-1-ylmethyl, 3-(cyclohexen-1-yl)propyl, and the like.

The term "$C_{3-8}$-cycloalkyl" as used herein represents a saturated monocyclic carbocyclic ring having from 3 to 8 carbon atoms, e.g. $C_{3-6}$-alkyl, and the like. Representative examples are cyclopropyl, cyclobutyl, cyclopentyl, cyclohexyl, cycloheptyl, cyclooctyl, and the like. $C_{3-8}$-cycloalkyl is also intended to represent a saturated bicyclic carbocyclic ring having from 4 to 8 carbon atoms. Representative examples are decahydronaphthalenyl, bicycle-[3.3.0]octanyl, and the like. $C_{3-8}$-cycloalkyl is also intended to represent a saturated carbocyclic ring having from 3 to 8 carbon atoms and containing one or two carbon bridges. Representative examples are adamantyl, norbornanyl, nortricyclyl, bicyclo[3.2.1]octanyl, bicyclo-[2.2.2]octanyl, tricyclo[5.2.1.0/2,6]decanyl, bicyclo[2.2.1]heptyl, and the like. $C_{3-8}$-cycloalkyl is also intended to represent a saturated carbocyclic ring having from 3 to 8 carbon atoms and containing one or more spiro atoms. Representative examples are spiro[2.5]octanyl, spiro-[4.5]decanyl, and the like.

Obviously, the term "$C_{3-8}$-cycloalkyl-$C_{1-3}$-alkyl" is a combination of $C_{3-8}$-cycloalkyl and $C_{1-3}$-alkyl. Representative examples are cyclopropylmethyl, 2-cyclohexylethyl, 3-cyclopentylprop-1-yl, 1-cyclohexylethyl, adamantylmethyl, and the like.

Representative examples of "$C_{3-8}$-cycloalkylcarbonylamino-$C_{1-6}$-alkyl" as used herein is cyclopentylcarbonylamino-methyl, 3-(cyclohexylcarbonylamino)propyl, and the like.

The term "halo-$C_{1-6}$-alkyl" as used herein refers to $C_{1-6}$-alkyl, substituted one or more times at any carbon atom(s) with any halogen. Representative examples are trifluoromethyl, 2,2,2-trifluoroethyl, and the like.

The term "halo-$C_{1-6}$-alkoxy" as used herein refers to $C_{1-6}$-alkoxy, substituted one or more times at any carbon atom(s) with any halogen. Representative examples are trifluoromethoxy and 2,2,2-trifluoroethoxy, and the like.

The term "halogen" or "halo" means fluorine, chlorine, bromine or iodine. The term "heteroaryl" as used herein is intended to include monocyclic heterocyclic aromatic rings containing one or more heteroatoms selected from nitrogen, oxygen, sulfur, SO and $S(=O)_2$. Representative examples are pyrrolyl (e.g., pyrrol-1-yl, pyrrol-2-yl and pyrrol-3-yl), furanyl (e.g., furan-2-yl and furan-3-yl), thienyl (e.g., thien-2-yl and thien-3-yl), oxazolyl (e.g., oxazol-2-yl, oxazol-4-yl and oxazol-5-yl), thiazolyl (e.g., thiazol-2-yl, thiazol-4-yl and thiazol-5-yl), imidazolyl (e.g., imidazol-2-yl, imidazol-4-yl and imidazol-5-yl), pyrazolyl (e.g., pyrazol-1-yl, pyrazol-3-yl and pyrazol-5-yl), isoxazolyl (e.g., isoxazol-3-yl, isoxazol-4-yl and isoxazol-5-yl), isothiazolyl (e.g., isothiazol-3-yl, isothiazol-4-yl and isothiazol-5-yl), 1,2,3-triazolyl (e.g., 1,2,3-triazol-1-yl, 1,2,3-triazol-4-yl and 1,2,3-triazol-5-yl), 1,2,4-triazolyl (e.g., 1,2,4-triazol-1-yl, 1,2,4-triazol-3-yl and 1,2,4-triazol-5-yl), 1,2,3-oxadiazolyl (e.g., 1,2,3-oxadiazol-4-yl and 1,2,3-oxadiazol-5-yl), 1,2,4-oxadiazolyl (e.g., 1,2,4-oxadiazol-3-yl and 1,2,4-oxadiazol-5-yl), 1,2,5-oxadiazolyl (e.g., 1,2,5-oxadiazol-3-yl and 1,2,5-oxadiazol-4-yl), 1,3,4-oxadiazolyl (e.g., 1,3,4-oxadiazol-2-yl and 1,3,4-oxadiazol-5-yl), 1,2,3-thiadiazolyl (e.g., 1,2,3-thiadiazol-4-yl and 1,2,3-thiadiazol-5-yl), 1,2,4-thiadiazolyl (e.g., 1,2,4-thiadiazol-3-yl and 1,2,4-thiadiazol-5-yl), 1,2,5-thiadiazolyl (e.g., 1,2,5-thiadiazol-3-yl and 1,2,5-thiadiazol-4-yl), 1,3,4-thiadiazolyl (e.g., 1,3,4-thiadiazol-2-yl and 1,3,4-thiadiazol-5-yl), tetrazolyl (e.g., tetrazol-1-yl and tetrazol-5-yl), pyranyl (e.g., pyran-2-yl), pyridinyl (e.g., pyridine-2-yl, pyridine-3-yl and pyridine-4-yl), pyridazinyl (e.g., pyridazin-2-yl and pyridazin-3-yl), pyrimidinyl (e.g., pyrimidin-2-yl, pyrimidin-4-yl and pyrimidin-5-yl), pyrazinyl, 1,2,3-triazinyl, 1,2,4-triazinyl, 1,3,5-triazinyl, thiadiazinyl, azepinyl, azecinyl, and the like. Heteroaryl is also intended to include bicyclic heterocyclic aromatic rings containing one or more heteroatoms selected from nitrogen, oxygen, sulfur, $S(=O)$ and $S(=O)_2$. Representative examples are indolyl (e.g., indol-1-yl, indol-2-yl, indol-3-yl and indol-5-yl), isoindolyl, benzofuranyl (e.g., benzo[b]furan-2-yl, benzo[b]furan-3-yl, benzo[b]furan-5-yl, benzo[c]furan-2-yl, benzo[c]furan-3-yl and benzo[c]furan-5-yl), benzothienyl (e.g., benzo[b]thien-2-yl, benzo[b]thien-3-yl, benzo[b]thien-5-yl, benzo[c]thien-2-yl, benzo[c]-thien-3-yl and benzo[c]thien-5-yl), indazolyl (e.g., indazol-1-yl, indazol-3-yl and indazol-5-yl), indolizinyl (e.g., indolizin-1-yl and indolizin-3-yl), benzopyranyl (e.g., benzo[b]pyran-3-yl, benzo[b]pyran-6-yl, benzo[c]pyran-1-yl and benzo[c]pyran-7-yl), benzimidazolyl (e.g., benzimidazol-1-yl, benzimidazol-2-yl and benzimidazol-5-yl), benzothiazolyl (e.g., benzothiazol-2-yl and benzothiazol-5-yl), benzisothiazolyl, benzoxazolyl, benzisoxazolyl, benzoxazinyl, benzotriazolyl, naphthyridinyl (e.g., 1,8-naphthyridin-2-yl, 1,7-naphthyridin-2-yl and 1,6-naphthyridin-2-yl), phthalazinyl (e.g., phthalazin-1-yl and phthalazin-5-yl), pteridinyl, purinyl (e.g., purin-2-yl, purin-6-yl, purin-7-yl, purin-8-yl and purin-9-yl), quinazolinyl (e.g., quinazolin-2-yl, quinazolin-4-yl and quinazolin-6-yl), cinnolinyl, quinoliny (e.g., quinolin-2-yl, quinolin-3-yl, quinolin-4-yl and quinolin-6-yl), isoquinolinyl (e.g., isoquinolin-1-yl, isoquinolin-3-yl and isoquinolin-4-yl), quinoxalinyl (e.g., quinoxalin-2-yl and quinoxalin-5-yl), pyrrolopyridinyl (e.g., pyrrolo[2,3-b]pyridinyl, pyrrolo[2,3-c]pyridinyl and pyrrolo[3,2-c]pyridinyl), furopyridinyl (e.g., furo[2,3-b]pyridinyl, furo[2,3-c]pyridinyl and furo[3,2-c]pyridinyl), thienopyridinyl (e.g., thieno-[2,3-b]pyridinyl, thieno[2,3-c]pyridinyl and thieno[3,2-c]pyridinyl), imidazopyridinyl (e.g., imidazo[4,5-b]pyridinyl, imidazo[4,5-c]pyridinyl, imidazo[1,5-a]pyridinyl and imidazo[1,2-a]-pyridinyl), imidazopyrimidinyl (e.g., imidazo[1,2-a]pyrimidinyl and imidazo[3,4-a]pyrimidinyl), pyrazolopyridinyl (e.g., pyrazolo[3,4-b]pyridinyl, pyrazolo[3,4-c]pyridinyl and pyrazolo[1,5-a]-pyridinyl), pyrazolopyrimidinyl (e.g., pyrazolo[1,5-a]pyrimidinyl and pyrazolo[3,4-d]pyrimidinyl), thiazolopyridinyl (e.g., thiazolo[3,2-d]pyridinyl), thiazolopyrimidinyl (e.g., thiazolo[5,4-d]pyrimidinyl), imidazothiazolyl (e.g., imidazo[2,1-b]thiazolyl), triazolopyridinyl (e.g., triazolo-[4,5-b]pyridinyl), triazolopyrimidinyl (e.g., 8-azapurinyl), and the like. Heteroaryl is also intended to include polycyclic heterocyclic aromatic rings containing one or more heteroatoms selected from nitrogen, oxygen, sulfur, $S(=O)$ and $S(=O)_2$. Representative examples are carbazolyl (e.g., carbazol-2-yl, carbazol-3-yl, carbazol-9-yl), phenoxazinyl (e.g., phenoxazin-10-yl), phenazinyl (e.g., phenazin-5-yl), acridinyl (e.g., acridin-9-yl and acridin-10-yl), phenolthiazinyl (e.g., phenothiazin-10-yl), carbolinyl (e.g., pyrido[3,4-b]indol-1-yl, pyrido[3,4-b]indol-3-yl), phenanthrolinyl (e.g., phenanthrolin-5-yl), and the like. Heteroaryl is also intended to include partially saturated monocyclic, bicyclic or polycyclic heterocyclic rings containing one or more heteroatoms selected from nitrogen, oxygen, sulfur, $S(=O)$ and $S(=O)_2$. Representative examples are pyrrolinyl, pyrazolinyl, imidazolinyl (e.g., 4,5-dihydroimidazol-2-yl and 4,5-dihydroimidazol-1-yl), indolinyl (e.g., 2,3-dihydroindol-1-yl and 2,3-dihydroindol-5-yl), dihydrobenzofuranyl (e.g., 2,3-dihydrobenzo[b]furan-2-yl and 2,3-dihydrobenzo[b]furan-4-yl), dihydrobenzothienyl (e.g., 2,3-dihydrobenzo[b]thien-2-yl and 2,3-dihydrobenzo[b]thien-5-yl), 4,5,6,7-tetrahydrobenzo[b]furan-5-yl), dihydrobenzopyranyl (e.g., 3,4-dihydrobenzo[b]pyran-3-yl, 3,4-dihydrobenzo[b]pyran-6-yl, 3,4-dihydrobenzo[c]pyran-1-yl and dihydrobenzo[c]pyran-7-yl), oxazolinyl (e.g., 4,5-dihydrooxazol-2-yl, 4,5-dihydrooxazol-4-yl and 4,5-dihydrooxazol-5-yl), isoxazolinyl, oxazepinyl, 2,4-dioxodihydropyrimidin-3-yl, tetrahydroindazolyl (e.g., 4,5,6,7-tetrahydroindazol-1-yl, 4,5,6,7-tetrahydroindazol-3-yl, 4,5,6,7-tetrahydroindazol-4-yl and 4,5,6,7-tetrahydroindazol-6-yl), tetrahydrobenzimidazolyl (e.g., 4,5,6,7-tetrahydrobenzimidazol-1-yl and 4,5,6,7-tetrahydrobenzimidazol-5-yl), tetrahydroimidazo[4,5-c]pyridyl (e.g., 4,5,6,7-tetrahydroimidazo[4,5-c]pyrid-1-yl, 4,5,6,7-tetrahydroimidazo[4,5-c]pyrid-5-yl and 4,5,6,7-tetrahydroimidazo[4,5-c]pyrid-6-yl), tetrahydroquinolinyl (e.g., 1,2,3,4-tetrahydroquinolinyl and 5,6,7,8-tetrahydroquinolinyl), tetrahydroisoquinolinyl (e.g., 1,2,3,4-tetrahydroisoquinolinyl and 5,6,7,8-tetrahydroisoquinolinyl), tetrahydroquinoxalinyl (e.g., 1,2,3,4-tetrahydroquinoxalinyl and 5,6,7,8-tetrahydroquinoxalinyl), 2,3-dihydrobenzo[1,4]dioxin-6-yl, 2,3-dihydrobenzo[1,4]dioxin-5-yl, 2,3-dihydrobenzo[1,4]dioxin-2-yl, benzo[1,3]dioxol-4-yl, benzo-[1,3]dioxol-5-yl, benzo[1,3]dioxol-2-yl, 3,4-dihydro-2H-benzo[1,4]oxazin-7-yl, 4-methyl-3,4-dihydro-2H-benzo[1,4]oxazin-7-yl and the like. Heteroaryl is also intended to include partially saturated bicyclic or polycyclic heterocyclic rings containing one or more spiro atoms. Representative examples are spiro[isoquinoline-3,1'-cyclohexan]-1-yl, spiro[piperidine-4,1'-benzo-[c]thiophen]-1-yl, spiro[piperidine-4,1'-benzo[c]furan]-1-yl, spiro[piperidine-4,3'-benzo[b]-furan]-1-yl, spiro[piperidine-4,3'-coumarin]-1-yl, and the like.

The term "heteroarylcarbonyl" as used herein refers to the radical heteroaryl-C(=O)—. Representative examples are pyridinylcarbonyl (e.g., pyridin-2-ylcarbonyl and pyridin-4-ylcarbonyl), quinolinylcarbonyl (e.g., 2-(quinolin-2-yl)carbonyl and 1-(quinolin-2-yl)carbonyl), imidazolylcarbonyl (e.g., imidazol-2-ylcarbonyl and imidazol-5-ylcarbonyl), and the like.

The term "heteroarylcarbonylamino" as used herein, refers to the radical heteroaryl-C(=O)—NH—. Representative examples are pyridinylcarbonylamino (e.g., pyridin-2-ylcarbonylamino and pyridin-4-ylcarbonylamino), quinolinylcarbonylamino (e.g., 2-(quinolin-2-yl)carbonylamino and 1-(quinolin-2-yl)carbonylamino), and the like.

The term "heteroarylcarbonylamino-$C_{1-6}$-alkyl" as used herein, refers to $C_{1-6}$-alkyl substituted at any carbon atom with heteroarylcarbonylamino. Representative examples are pyridinylcarbonylaminomethyl (e.g., pyridin-2-ylcarbonylaminomethyl and pyridin-4-ylcarbonylaminomethyl), 2-(quinolinylcarbonylamino)ethyl (e.g., 2-(2-(quinolin-2-yl)carbonylamino)ethyl and 2-(1-(quinolin-2-yl)carbonylamino)ethyl), and the like.

The term "heterocyclyl" as used herein represents a saturated 3 to 8 membered monocyclic ring, containing one or more heteroatoms selected from nitrogen, oxygen, sulfur, S(=O) and S(=O)$_2$. Representative examples are aziridinyl (e.g., aziridin-1-yl), azetidinyl (e.g., azetidin-1-yl and azetidin-3-yl), oxetanyl, pyrrolidinyl (e.g., pyrrolidin-1-yl, pyrrolidin-2-yl and pyrrolidin-3-yl), 2-oxo-pyrrolidin-1-yl, 2,5-dioxo-pyrrolidin-1-yl, imidazolidinyl (e.g., imidazolidin-1-yl, imidazolidin-2-yl and imidazolidin-4-yl), 2,4-dioxo-imidazolidin-3-yl, 2,4-dioxo-1-methylimidazolidin-3-yl, 2,4-dioxo-1,5,5-trimethylimidazolidin-3-yl, 2,4-dioxo-5,5-dimethylimidazolidin-3-yl, oxazolidinyl (e.g., oxazolidin-2-yl, oxazolidin-3-yl and oxazolidin-4-yl), 2-oxo-oxazolidin-3-yl, thiazolidinyl (e.g., thiazolidin-2-yl, thiazolidin-3-yl and thiazolidin-4-yl), 2,4-dioxo-thiazolidin-3-yl, isothiazolidinyl, 1,1-dioxo-isothiazolidin-2-yl, 1,1-dioxo-[1,2,5]thiadiazolidin-2-yl, piperidinyl (e.g., piperidin-1-yl, piperidin-2-yl, piperidin-3-yl and piperidin-4-yl), 2-oxo-piperidin-1-yl, 2,6-dioxo-piperidin-1-yl, homopiperidinyl (e.g., homopiperidin-1-yl, homopiperidin-2-yl, homopiperidin-3-yl and homopiperidin-4-yl), piperazinyl (e.g., piperazin-1-yl and piperazin-2-yl), morpholinyl (e.g., morpholin-2-yl, morpholin-3-yl and morpholin-4-yl), 2-oxo-[1,3]oxazinan-3-yl, thiomorpholinyl (e.g., thiomorpholin-2-yl, thiomorpholin-3-yl and thiomorpholin-4-yl), 1-oxo-thiomorpholinyl, 1,1-dioxo-thiomorpholinyl, tetrahydrofuranyl (e.g., tetrahydrofuran-2-yl and tetrahydrofuran-3-yl), tetrahydrothienyl, tetrahydro-1,1-dioxothienyl, tetrahydropyranyl (e.g., 2-tetrahydropyranyl), tetrahydrothiopyranyl (e.g., 2-tetrahydrothiopyranyl), 1,4-dioxanyl, 1,3-dioxanyl, and the like. Heterocyclyl is also intended to represent a saturated 6 to 12 membered bicyclic ring containing one or more heteroatoms selected from nitrogen, oxygen, sulfur, S(=O) and S(=O)$_2$. Representative examples are octahydroindolyl (e.g., octahydroindol-1-yl, octahydroindol-2-yl, octahydroindol-3-yl and octahydroindol-5-yl), decahydroquinolinyl (e.g., decahydroquinolin-1-yl, decahydroquinolin-2-yl, decahydroquinolin-3-yl, decahydroquinolin-4-yl and decahydroquinolin-6-yl), decahydroquinoxalinyl (e.g., decahydroquinoxalin-1-yl, decahydroquinoxalin-2-yl and decahydroquinoxalin-6-yl) and the like. Heterocyclyl is also intended to represent a saturated 6 to 12 membered ring containing one or more heteroatoms selected from nitrogen, oxygen, sulfur, S(=O) and S(=O)$_2$ and having one or two bridges. Representative examples are 3-azabicyclo[3.2.2]nonyl, 2-azabicyclo[2.2.1]heptyl, 3-azabicyclo[3.1.0]hexyl, 2,5-diazabicyclo[2.2.1]heptyl, atropinyl, tropinyl, quinuclidinyl, 1,4-diazabicyclo[2.2.2]octanyl, and the like. Heterocyclyl is also intended to represent a 6 to 12 membered saturated ring containing one or more heteroatoms selected from nitrogen, oxygen, sulfur, S(=O) and S(=O)$_2$ and containing one or more spiro atoms. Representative examples are 1,4-dioxaspiro[4.5]decanyl (e.g., 1,4-dioxaspiro[4.5]decan-2-yl and 1,4-dioxaspiro[4.5]decan-7-yl), 1,4-dioxa-8-azaspiro[4.5]decanyl (e.g., 1,4-dioxa-8-azaspiro-[4.5]decan-2-yl and 1,4-dioxa-8-azaspiro[4.5]decan-8-yl), 8-azaspiro[4.5]decanyl (e.g., 8-azaspiro[4.5]decan-1-yl and 8-azaspiro[4.5]decan-8-yl), 2-azaspiro[5.5]undecanyl (e.g., 2-azaspiro[5.5]undecan-2-yl), 2,8-diazaspiro[4.5]decanyl (e.g., 2,8-diazaspiro[4.5]decan-2-yl and 2,8-diazaspiro[4.5]decan-8-yl), 2,8-diazaspiro[5.5]undecanyl (e.g., 2,8-diazaspiro[5.5]-undecan-2-yl), 1,3,8-triazaspiro[4.5]decanyl (e.g., 1,3,8-triazaspiro[4.5]decan-1-yl and 1,3,8-triazaspiro[4.5]decan-3-yl, 1,3,8-triazaspiro[4.5]decan-8-yl), and the like.

The term "heterocyclyl-$C_{1-6}$-alkoxy" as used herein refers to the radical heterocyclyl-$C_{1-6}$-alkoxy. Representative examples are piperidin-1-ylmethoxy, 2-(piperidin-1-yl)ethoxy, 3-(piperidin-1-yl)prop-3-oxy, piperazin-1-ylmethoxy, 2-(piperazin-1-yl)ethoxy, 3-(piperazin-1-yl)prop-3-oxy, morpholin-4-ylmethoxy, 2-(morpholin-4-yl)ethoxy, 3-(morpholin-4-yl)prop-3-oxy, and the like.

The term "heterocyclyl-$C_{1-6}$-alkyl" as used herein refers to the radical heterocyclyl-$C_{1-6}$-alkyl. Representative examples are piperidin-1-ylmethyl, 2-(piperidin-1-yl)ethyl, 3-hydroxy-3-(piperidin-1-yl)propyl, piperazin-1-ylmethyl, 2-(piperazin-1-yl)ethyl, 3-hydroxy-3-(piperazin-1-yl)propyl, morpholin-4-ylmethyl, 2-(morpholin-4-yl)ethyl, 3-hydroxy-3-(morpholin-4-yl)propyl, and the like.

The term "heterocyclylcarbonyl" as used herein refers to the radical heterocyclyl-C(=O)—. Representative examples are piperidinylcarbonyl (e.g., piperidin-2-ylcarbonyl, piperidin-3-ylcarbonyl and piperidin-4-ylcarbonyl), piperazinylcarbonyl (e.g., piperazin-1-ylcarbonyl and piperazin-2-ylcarbonyl), and the like.

The term "hydroxy-$C_{1-6}$-alkyl" as used herein refers to $C_{1-6}$-alkyl substituted one or more times at any carbon atom(s) with hydroxyl. Representative examples are hydroxymethyl, hydroxyethyl (e.g., 1-hydroxyethyl and 2-hydroxyethyl), and the like.

The term "N—($C_{1-6}$-alkylcarbonyl)-N—($C_{1-6}$-alkyl)amino" as used herein is an amino group with two substituents, i.e., a $C_{1-6}$-alkylcarbonyl group and an $C_{1-6}$-alkyl group. Analogously, the following terms cover groups wherein an amino group has two substituents: N—($C_{3-8}$-cycloalkylcarbonyl)-N—($C_{1-6}$-alkyl)amino and N—($C_{3-8}$-cycloalkyl-$C_{1-6}$-alkylcarbonyl)-N—($C_{1-6}$-alkyl)amino. Analogously, the following terms cover groups wherein there are two substituents on the nitrogen atom in the amino-$C_{1-6}$-alkyl moiety: N—($C_{1-6}$-alkylcarbonyl)-N—($C_1$-$C_6$-alkyl)amino-$C_{1-6}$-alkyl, N—($C_{3-8}$-cycloalkylcarbonyl)-N—($C_{1-6}$-alkyl)amino-$C_{1-6}$-alkyl and N—($C_{3-8}$-cycloalkyl-$C_{1-6}$-alkylcarbonyl)-N—($C_{1-6}$-alkyl)amino-$C_{1-6}$-alkyl. Representative examples are N-cyclohexylcarbonyl-N-methylamino, 2-(N-cyclopentylcarbonyl-N-methylamino)ethyl and the like.

The term "bridge" as used herein represents a connection in a saturated or partly saturated ring between two atoms of such ring that are not neighbors through a chain of 1 to 4 atoms selected from carbon, nitrogen, oxygen and sulfur. Representative examples of such connecting chains are —$CH_2$—, —$CH_2CH_2$—, —$CH_2NHCH_2$—, —$CH_2CH_2CH_2$—, —$CH_2OCH_2$—, and the like.

The term "spiro atom" as used herein represents a carbon atom in a saturated or partly saturated ring that connects both ends of a chain of 3 to 8 atoms selected from carbon, nitrogen, oxygen and sulfur. Representative examples are —$(CH_2)_5$—, —$(CH_2)_3$—, —$(CH_2)_4$—, —$CH_2NHCH_2CH_2$—, —$CH_2CH_2NHCH_2CH_2$—, —$CH_2NHCH_2CH_2CH_2$—, —$CH_2CH_2OCH_2$—, —$OCH_2CH_2O$— and the like.

The term "optionally substituted" as used herein means that the groups in question are either unsubstituted or substituted with one or more of the substituents specified. When the group(s) in question are substituted with more than one substituent the substituents may be the same or different.

Certain of the defined terms may occur more than once in the structural formulae, and upon such occurrence each term shall be defined independently of the other.

Certain of the defined terms may occur in combinations, and it is to be understood that the first mentioned radical is a substituent on the subsequently mentioned radical, where the point of substitution, i.e. the point of attachment to another part of the molecule, is on the last mentioned of the radicals.

The term "solvate" as used herein is a complex of defined stoichiometry formed by a solute (in casu, a compound according to the present invention) and a solvent. Solvents are those commonly used in the pharmaceutical art, by way of example, water, ethanol, acetic acid, and the like. The term "hydrate" refers to the complex where the solvent molecule is water.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "prodrug" as used herein includes biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

The term "biohydrolyzable ester" as used herein is an ester of a drug substance (in this invention, a compound of formula I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is trans-formed to (I) in plasma. Many examples of such are known in the art and include by way of example lower alkyl esters (e.g., $C_{1-4}$), lower acyloxyalkyl esters, lower alkoxyacyloxyalkyl esters, alkoxyacyloxy esters, alkyl acylamino alkyl esters, and choline esters.

The term "biohydrolyzable amide" as used herein is an amide of a drug substance (in this invention, a compound of general formula I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "metabolite" as used herein is any intermediate or product resulting from metabolism.

The term "metabolism" as used herein refer to the biotransformation of a drug substance (in this invention, a compound of general formula I) administered to a patient.

The representative examples mentioned above are specific embodiments of this invention.

In the examples below, the following terms are intended to have the following, general meanings: d is day(s), g is gram(s), h is hour(s), Hz is hertz, kD is kiloDalton(s), L is liter(s), M is molar, mbar is millibar, mg is milligram(s), min is minute(s), mL is milliliter(s), mM is millimolar, mmol is millimole(s), mol is mole(s), N is normal, ppm is parts per million, psi is pounds per square inch, APCI is atmospheric pressure chemical ionization, ESI is electrospray ionization, I.v. is intravenous, m/z is mass to charge ratio, mp/Mp is melting point, MS is mass spectrometry, HPLC is high pressure liquid chromatography, RP is reverse phase, HPLC-MS is high pressure liquid chromatography—mass spectrometry, NMR is nuclear magnetic resonance spectroscopy, p.o. is per oral, $R_f$ is relative TLC mobility, rt is room temperature, s.c. is subcutaneous, TLC is thin layer chromatography, $t_r$ is retention time, BOP is (1-benzotriazolyloxy)tris(dimethylamino)phosphoniumhexafluorophosphate, CDI is carbonyldiimidazole, DCM is dichloromethane, $CH_2Cl_2$ is methylenechloride, DIBAL-His diisobutylaluminiumhydride, DBU is 1,8-diazabicyclo[5.4.0]undec-7-ene, DEAD is diethyl azodicarboxylate, DIC is 1,3-diisopropylcarbodiimide, DIPEA is N,N-diisopropylethylamine, DMA is N,N-dimethylacetamide, DMF is N,N-dimethylformamide, DMPU is N,N'-dimethylpropyleneurea, 1,3-dimethyl-2-oxo-hexahydropyrimidine, DMSO is dimethylsulfoxide, EDAC is 1-ethyl-3-(3-dimethylaminopropyl)carbodiimide hydrochloride, $Et_2O$ is diethyl ether, EtOAc is ethyl acetate, HMPA is hexamethylphosphoric acid triamide, HOAt is 1-hydroxy-7-azabenzotriazole, HOBt is 1-hydroxybenzotriazole, LAH is lithium aluminum hydride ($LiAlH_4$), LDA is lithium diisopropylamide, MeCN is acetonitrile, MeOH is methanol, NMM is N-methylmorpholine (4-methylmorpholine), NMP is N-methylpyrrolidin-2-one, TEA is triethylamine, TFA is trifluoroacetic acid, THF is tetrahydrofuran, THP is tetrahydropyranyl, TTFH is fluoro-N,N,N,N'-tetramethylformamidinium hexafluorophosphate, $CDCl_3$ is deuterio chloroform, $CD_3OD$ is tetradeuterio methanol and DMSO-$d_6$ is hexadeuterio dimethylsulfoxide.

SUMMARY OF THIS INVENTION

The invention relates to compounds of the general formula I specified in the claims below.

The compounds of this invention differ structurally from the known compounds.

The invention also relates to the use of said compounds in therapy, and in particular to pharmaceutical compositions comprising said compounds.

In another embodiment, the invention relates to methods of treatment, the method comprising administering to a subject in need thereof an effective amount of one or more compounds according to formula I.

In a still further embodiment, the invention relates to the use of compounds according to formula I in the manufacture of medicaments.

DETAILED DESCRIPTION OF THIS INVENTION

Due to their interaction with the histamine H3 receptor, the compounds of this invention as defined in the claims below and elsewhere in this specification are useful in the treatment of a wide range of conditions and disorders in which an interaction with the histamine H3 receptor is beneficial. Thus, the compounds may find use, e.g., in the treatment of diseases of the central nervous system, the peripheral nervous system, the cardiovascular system, the pulmonary system, the gastrointestinal system and the endocrinological system.

In an embodiment, this invention relates to a compound of the general formula I:

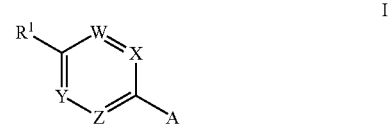

I wherein W, X, Y, Z independent of each other is a moiety of the formula $—C(R^2)=$ or $—N=$ (i.e. nitrogen), with the proviso that at least one of the symbols W, X, Y or Z must be the moiety $—N=$; $R^2$ is hydrogen, halogen, cyano, $C_{1-6}$-alkyl, $C_{1-6}$-alkoxy, halo-$C_{1-6}$-alkyl or halo-$C_{1-6}$-alkoxy; $R^1$ represents the following possibilities i) and ii): where possibility i) is a group of the general formula $—NR^3R^4$, wherein $R^3$ is hydrogen, $C_{1-6}$-alkyl, $C_{2-6}$-alkenyl or $C_{3-8}$-cycloalkyl; and $R^4$ is $C_{1-6}$-alkyl, $C_{2-6}$-alkenyl or $C_{3-8}$-cycloalkyl, each of which are substituted with a group selected from $—NR^5R^6$ and heterocyclyl; $R^5$ and $R^6$ independently represent hydrogen or $C_{1-6}$-alkyl; and where possibility ii) is a group of one of the general formulas II to VII:

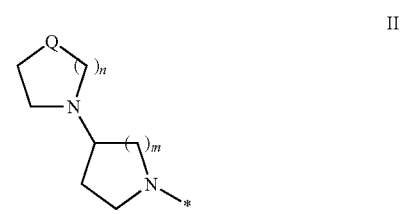

II

III

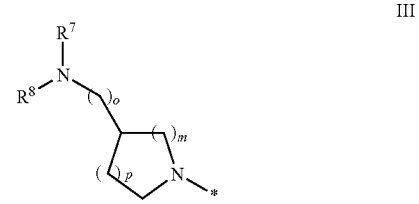

IV

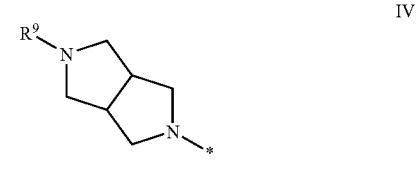

V

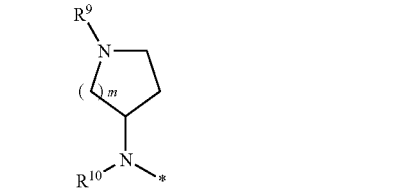

VI

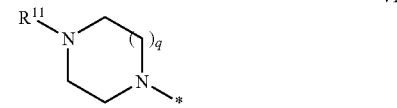

-continued

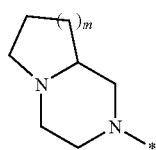
VII wherein the star indicates the position of the free bond (and not a methyl group), and wherein m is 0 (zero), 1, 2 or 3; n is 1, 2 or 3; o is 0 (zero), 1, 2, 3 or 4; p is 0 (zero), 1 or 2; q is 1 or 2; Q represents a moiety of the formula —$CH_2$—, —O—, —S— or >$NR^3$, wherein $R^3$ is as defined above; $R^7$ and $R^8$ independent of each other is hydrogen or $C_{1-6}$-alkyl, or $R^7$ and $R^8$ can together with the nitrogen to which they are attached form a heterocyclyl group; $R^9$ is $C_{1-6}$-alkyl or $C_{3-8}$-cycloalkyl, which both may be substituted with a group of the general formula —$NR^7R^8$, wherein $R^7$ and $R^8$ are as defined above; $R^{10}$ is hydrogen or $C_{1-6}$-alkyl; $R^{11}$ is hydrogen, $C_{1-8}$-alkyl, $C_{3-8}$-alkenyl, $C_{3-8}$-alkynyl, $C_{3-8}$-cycloalkyl, $C_{3-8}$-cycloalkenyl, $C_{3-8}$-cycloalkyl-$C_{1-3}$-alkyl or $C_{3-8}$-cycloalkenyl-$C_{1-3}$-alkyl, or $C_{1-6}$-alkyl or $C_{3-8}$-cycloalkyl, which both are substituted with at least one substituent selected from the group consisting of hydroxy, $C_{1-6}$-alkoxy, $C_{1-6}$-alkylcarbonyl, cyano, —$NR^5R^6$, —C(=O)$NR^5R^6$, arylcarbonyl, heteroarylcarbonyl, $C_{1-6}$-alkylsulfonyl, arylsulfonyl, heterocyclylcarbonyl, $C_{1-6}$-alkoxycarbonyl, aryl-$C_{1-6}$-alkoxycarbonyl, heteroaryl and heterocyclyl, which heterocyclyl may be substituted with $C_{1-6}$-alkyl, where applicable; $R^5$ and $R^6$ are as defined above; A is aryl or heteroaryl, each of which may optionally be substituted with one or more substituents independently selected from $R^{12}$; $R^{12}$ is halogen, hydroxy, cyano, $C_{1-6}$-alkyl, $C_{3-8}$-cycloalkyl, halo-$C_{1-6}$-alkyl, $C_{1-6}$-alkoxy, halo-$C_{1-6}$-alkoxy, $C_{1-6}$-alkylsulfonyl, $C_{1-6}$-alkylsulfinyl, —V—$(CH_2)_s$—(C=O)$_r$—$NR^{13}R^{14}$, $C_{1-6}$-alkylcarbonyl, $C_6$-alkoxycarbonyl, $C_{1-6}$-alkylcarboxy, cyano-$C_{1-6}$-alkyl, hydroxy-$C_{1-6}$-alkyl, $C_{1-6}$-alkoxy-$C_{1-6}$-alkyl, $C_{1-6}$-alkylcarbonylamino, N—($C_{1-6}$-alkylcarbonyl)-N—($C_{1-6}$-alkyl)amino, $C_{1-6}$-alkylcarbonylamino-$C_{1-6}$-alkyl or N—($C_{1-6}$-alkylcarbonyl)-N—($C_{1-6}$-alkyl)amino-$C_{1-6}$-alkyl; or heterocyclyl-$C_{1-6}$-alkyl, heterocyclyl-$C_{1-6}$-alkoxy, heterocyclylcarbonyl, $C_{3-8}$-cycloalkylcarbonylamino, N—($C_{3-8}$-cycloalkylcarbonyl)N—($C_{1-6}$-alkyl)amino, $C_{3-8}$-cycloalkylcarbonylamino-$C_{1-6}$-alkyl or N—($C_{3-8}$-cycloalkylcarbonyl)-N—($C_{1-6}$-alkyl)amino-$C_{1-6}$-alkyl, $C_{3-8}$-cycloalkyl-$C_{1-6}$-alkylcarbonylamino, N—($C_{3-8}$-cycloalkyl-$C_{1-6}$-alkylcarbonyl)-N—($C_{1-6}$-alkyl)amino, $C_{3-8}$-cycloalkyl-$C_{1-6}$-alkylcarbonylamino-$C_{1-6}$-alkyl or N—($C_{3-8}$-cycloalkyl-$C_{1-6}$-alkylcarbonyl)-N—($C_{1-6}$-alkyl)amino-$C_{1-6}$-alkyl, arylcarbonylamino, aryl-$C_{1-6}$-alkylcarbonylamino, arylcarbonylamino-$C_{1-6}$-alkyl, aryl-$C_{1-6}$-alkylcarbonylamino-$C_{1-6}$-alkyl, heteroarylcarbonylamino or heteroarylcarbonylamino-$C_{1-6}$-alkyl, wherein each of said aryl, heteroaryl, $C_{3-8}$-cycloalkyl and heterocyclyl may optionally be substituted with halogen, hydroxy, cyano, $C_{1-6}$-alkyl, $C_{3-8}$-cycloalkyl, halo-$C_{1-6}$-alkyl, $C_{1-6}$-alkoxy, halo-$C_{1-6}$-alkoxy, $C_{1-6}$-alkylsulfonyl, $C_{1-6}$-alkylsulfinyl, $C_{1-6}$-alkylcarbonyl, $C_{1-6}$-alkoxycarbonyl, $C_{1-6}$-alkylcarboxy, cyano-$C_{1-6}$-alkyl, hydroxy-$C_{1-6}$-alkyl or $C_{1-6}$-alkoxy-$C_{1-6}$-alkyl; or aryl or heteroaryl, each of which may be substituted with halogen, hydroxy, carboxy, nitro, cyano, $C_{1-6}$-alkyl, $C_{3-8}$-cycloalkyl, $C_{1-6}$-alkoxy, $C_{1-6}$-alkylsulfanyl, $C_{1-6}$-alkylsulfonyl, $C_{1-6}$-alkylcarbonyl, $C_{1-6}$-alkylcarbonylamino, $C_{1-6}$-alkylcarbonylamino-$C_{1-6}$-alkyl, $C_{1-6}$-alkoxycarbonyl, $C_{1-6}$-alkylcarboxy, halo-$C_{1-6}$-alkyl, halo-$C_{1-6}$-alkoxy, hydroxy-$C_{1-6}$-alkyl, $C_{1-6}$-alkoxy-$C_{1-6}$-alkyl, aryl, arylcarbonylamino, arylcarbonylamino-$C_{1-6}$-alkyl, heteroaryl, heteroarylcarbonylamino, heteroarylcarbonylamino-$C_{1-6}$-alkyl or —$(CH_2)_s$—(C=O)$_r$—$NR^{13}R^{14}$; r is 0 (zero) or 1; s is 0 (zero), 1, 2 or 3; V represents a bond or moiety of the formula, —O—, —S— or >$NR^3$, wherein $R^3$ is as defined above; $R^{13}$ is hydrogen, $C_{1-6}$-alkyl, $C_{3-8}$-cycloalkyl or $C_{1-6}$-alkylcarbonyl; $R^{14}$ is hydrogen, $C_{1-6}$-alkyl or $C_{3-8}$-cycloalkyl with the proviso that $R^{14}$ is hydrogen when $R^{13}$ is $C_{1-6}$-alkylcarbonyl; or $R^{13}$ and $R^{14}$ can together with the attached nitrogen form a heterocyclyl group; and pharmaceutically acceptable salts and solvates thereof; with the following provisos a) through g): a) when $R^1$ is a group of the formula VI; W is —N=; X, Y and Z is each a moiety of the general formula —C($R^2$)=; wherein $R^2$ is as defined above; then A cannot be imidazolyl; b) when $R^1$ is a group of the formula VI; q is 1; X is —C($R^2$)=; $R^{11}$ is branched $C_{4-6}$-alkyl, branched $C_{4-6}$-alkenyl, branched $C_{4-6}$-alkynyl, $C_{3-5}$-cycloalkyl, $C_{3-7}$-cycloalkenyl, $C_{3-6}$-cycloalkyl-$C_{1-3}$-alkyl or $C_{3-6}$-cycloalkenyl-$C_{1-3}$-alkyl; and W, Y, Z is each a moiety of the formula —C($R^2$)= or —N=; wherein $R^2$ is as defined above; then $R^{12}$ can not be halogen, hydroxy, trifluoromethyl, trifluoromethoxy, $C_{1-6}$-alkoxy, $C_{1-6}$-alkyl, $C_{1-6}$-alkylsulfonyl, cyano, aryl, heteroaryl, $C_{3-8}$-cycloalkyl or a group of the formula —V—$(CH_2)_s$—(C=O)$_r$—$NR^{13}R^{14}$, wherein V is a bond, wherein r and s each is 0 (zero), and $R^{13}$ and $R^{14}$ each is hydrogen or $C_{1-6}$-alkyl; c) when $R^1$ is a group of the formula VII; m is 1, 2 or 3; X is a moiety of the formula —C($R^2$)=; and W, Y, Z is each a moiety of the formula —C($R^2$)= or —N=; wherein $R^2$ is as defined above; then $R^{12}$ can not be halogen, hydroxy, trifluoromethyl, trifluoromethoxy, $C_{1-6}$-alkoxy, $C_{1-6}$-alkyl, $C_{1-6}$-alkylsulfonyl, cyano, aryl, heteroaryl, $C_{3-8}$-cycloalkyl or a group of the formula —V—$(CH_2)_s$—(C=O)$_r$—$NR^{13}R^{14}$, wherein V is a bond, r and s each is 0 (zero), and $R^{13}$ and $R^{14}$ each is hydrogen or $C_{1-6}$-alkyl; d) when $R^1$ is a group of the formula VI; q is 1; $R^{11}$ is ethyl, n-propyl or isopropyl; Y and Z is each —N=; X is a moiety of the formula —C($R^2$)=, and W is a moiety of the formula —C($R^2$)= or —N=; wherein $R^2$ is as defined above; then $R^{12}$ can not be halogen, hydroxy, trifluoromethyl, trifluoromethoxy, $C_{1-6}$-alkoxy, $C_{1-6}$-alkyl, $C_{1-6}$-alkylsulfonyl, cyano, aryl, heteroaryl, $C_{3-8}$-cycloalkyl or a group of the formula —$(CH_2)_s$—(C=O)$_r$—$NR^{13}R^{14}$, wherein r and s each is 0 (zero), and $R^{13}$ and $R^{14}$ each is hydrogen or $C_{1-6}$-alkyl; e) when $R^1$ is a group of the formula VII; m is 1, 2 or 3; Y and Z is each —N=; X is a moiety of the formula —C($R^2$)=; and W is a moiety of the formula —C($R^2$)= or —N=; wherein $R^2$ is as defined above; then $R^{12}$ can not be halogen, hydroxy, trifluoromethyl, trifluoromethoxy, $C_{1-6}$-alkoxy, $C_{1-6}$-alkyl, $C_{1-6}$-alkylsulfonyl, cyano, aryl, heteroaryl, $C_{3-8}$-cycloalkyl or a group of the formula —$(CH_2)_s$—(C=O)$_r$—$NR^{13}R^{14}$, wherein r and s each is 0 (zero), and $R^{13}$ and $R^{14}$ each is hydrogen or $C_{1-6}$-alkyl; f) when $R^1$ is formula VI, q is 1, X and W is each a moiety of the general formula —C($R^2$)=, wherein $R^2$ is as defined above, Y and Z is each —N=, $R^{11}$ is isopropyl, and A is phenyl, then $R^{12}$ can not be fluoro, bromo, iodo, hydroxy, trifluoromethoxy, $C_{2-6}$-alkoxy, $C_{1-6}$-alkyl, $C_{2-6}$-alkylsulfanyl, $C_{2-6}$-alkylsulfinyl, $C_{2-6}$-alkylsulfonyl, cyano, aryl, heteroaryl, $C_{3-8}$-cycloalkyl or a group of the formula —$(CH_2)_s$—(C=O)$_r$—$NR^{13}R^{14}$ wherein r and s each is 0 (zero), and $R^{13}$ and $R^{14}$ each is hydrogen or $C_{1-6}$-alkyl; and g) when X and Z is each —C($R^2$)=; and one or both of W and Y are —N=; then $R^1$ cannot be a group of the formula II, wherein m is 2.

In an embodiment, this invention relates to a compound of the general formula I, to the extent possible according to claim 1:

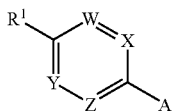

I wherein W, X, Y, Z independent of each other is a moiety of the formula —C(R$^2$)= or —N= (i.e. nitrogen), with the proviso that at least one of the symbols W, X, Y or Z must be the moiety —N=; R$^2$ is hydrogen, halogen, cyano, C$_{1-6}$-alkyl, C$_{1-6}$-alkoxy, halo-C$_{1-6}$-alkyl or halo-C$_{1-6}$-alkoxy; R$^1$ represents the following possibilities i) and ii): where possibility i) is a group of the general formula —NR$^3$R$^4$, wherein R$^3$ is hydrogen, C$_{1-6}$-alkyl, C$_{2-6}$-alkenyl or C$_{3-8}$-cycloalkyl; and R$^4$ is C$_{1-6}$-alkyl, C$_{2-6}$-alkenyl or C$_{3-8}$-cycloalkyl, each of which are substituted with a group selected from —NR$^5$R$^6$ and heterocyclyl; R$^5$ and R$^6$ independently represent hydrogen or C$_{1-6}$-alkyl; and possibility ii) is a group of one of the general formulas II to VII:

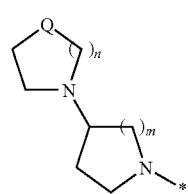

II

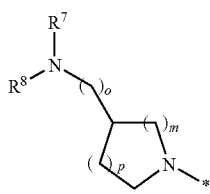

III

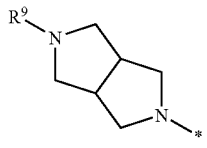

IV

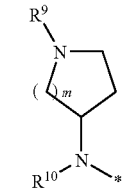

V

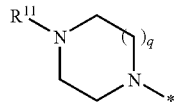

VI

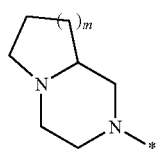

VII wherein the star indicates the position of the free bond (and not a methyl group), and wherein m is 0 (zero), 1, 2 or 3; n is 1, 2 or 3; o is 0 (zero), 1, 2, 3 or 4; p is 0 (zero), 1 or 2; q is 1 or 2; Q represents a moiety of the formula —CH$_2$—, —O—, —S— or >NR$^3$, wherein R$^3$ is as defined above; R$^7$ and R$^8$ independent of each other is hydrogen or C$_{1-6}$-alkyl, or R$^7$ and R$^8$ can together with the nitrogen to which they are attached form a heterocyclyl group; R$^9$ is C$_{1-6}$-alkyl or C$_{3-8}$-cycloalkyl, which both may be substituted with a group of the general formula —NR$^7$R$^8$, wherein R$^7$ and R$^8$ are as defined above; R$^{10}$ is hydrogen or C$_{1-6}$-alkyl; R$^{11}$ is hydrogen, C$_{1-8}$-alkyl, C$_{3-8}$-alkenyl, C$_{3-8}$-alkynyl, C$_{3-8}$-cycloalkyl, C$_{3-8}$-cycloalkenyl, C$_{3-8}$-cycloalkyl-C$_{1-3}$-alkyl or C$_{3-8}$-cycloalkenyl-C$_{1-3}$-alkyl, or C$_{1-6}$-alkyl or C$_{3-8}$-cycloalkyl, which both are substituted with at least one substituent selected from the group consisting of hydroxy, C$_{1-6}$-alkoxy, C$_{1-6}$-alkylcarbonyl, cyano, —NR$^5$R$^6$, —C(=O)NR$^5$R$^6$, arylcarbonyl, heteroarylcarbonyl, C$_{1-6}$-alkylsulfonyl, arylsulfonyl, heterocyclylcarbonyl, C$_{1-6}$-alkoxycarbonyl, aryl-C$_{1-6}$-alkoxycarbonyl, heteroaryl and heterocyclyl, which heterocyclyl may be substituted with C$_{1-6}$-alkyl, where applicable; R$^5$ and R$^6$ are as defined above; A is aryl or heteroaryl, each of which may optionally be substituted with one or more substituents independently selected from R$^{12}$; R$^{12}$ is halogen, hydroxy, cyano, C$_{1-6}$-alkyl, C$_{3-8}$-cycloalkyl, halo-C$_{1-6}$-alkyl, C$_{1-6}$-alkoxy, halo-C$_{1-6}$-alkoxy, C$_{1-6}$-alkylsulfonyl, C$_{1-6}$-alkylsulfinyl, —(CH$_2$)$_s$—(C=O)$_r$—NR$^{13}$R$^{14}$, C$_{1-6}$-alkylcarbonyl-C$_{1-6}$-alkoxycarbonyl, C$_{1-6}$-alkylcarboxy, cyano-C$_{1-6}$-alkyl, hydroxy-C$_{1-6}$-alkyl, C$_{1-6}$-alkoxy-C$_{1-6}$-alkyl, C$_{1-6}$-alkylcarbonylamino or C$_{1-6}$-alkylcarbonylamino-C$_{1-6}$-alkyl; or heterocyclyl-C$_{1-6}$-alkyl, heterocyclyl-C$_{1-6}$-alkoxy, heterocyclylcarbonyl, arylcarbonylamino, arylcarbonylamino-C$_{1-6}$-alkyl, heteroarylcarbonylamino or heteroarylcarbonylamino-C$_{1-6}$-alkyl, wherein each of said aryl, heteroaryl and heterocyclyl may optionally be substituted with halogen, hydroxy, cyano, C$_{1-6}$alkyl, C$_{3-8}$-cycloalkyl, halo-C$_{1-6}$-alkyl, C$_{1-6}$-alkoxy, halo-C$_{1-6}$-alkoxy, C$_{1-6}$-alkylsulfonyl, C$_{1-6}$-alkylsulfinyl, C$_{1-6}$-alkylcarbonyl, C$_{1-6}$-alkoxycarbonyl, C$_{1-6}$-alkylcarboxy, cyano-C$_{1-6}$-alkyl, hydroxy-C$_{1-6}$-alkyl or C$_{1-6}$-alkoxy-C$_{1-6}$-alkyl; or aryl or heteroaryl, each of which may be substituted with halogen, hydroxy, carboxy, nitro, cyano, C$_{1-6}$-alkyl, C$_{3-8}$-cycloalkyl, C$_{1-6}$-alkoxy, C$_{1-6}$-alkylsulfanyl, C$_{1-6}$-alkylsulfonyl, C$_{1-6}$-alkylcarbonyl, C$_{1-6}$-alkylcarbonylamino, C$_{1-6}$-alkylcarbonylamino-C$_{1-6}$-alkyl, C$_{1-6}$-alkoxycarbonyl, C$_{1-6}$-alkylcarboxy, halo-C$_{1-6}$-alkyl, halo-C$_{1-6}$-alkoxy, hydroxy-C$_{1-6}$-alkyl, C$_{1-6}$-alkoxy-C$_{1-6}$-alkyl, aryl, arylcarbonylamino, arylcarbonylamino-C$_{1-6}$-alkyl, heteroaryl, heteroarylcarbonylamino, heteroarylcarbonylamino-C$_{1-6}$-alkyl or —(CH$_2$)$_s$—(C=O)$_r$—NR$^{13}$R$^{14}$; r is 0 (zero) or 1; s is 0 (zero), 1, 2 or 3; R$^{13}$ is hydrogen, C$_{1-6}$-alkyl, C$_{3-8}$-cycloalkyl or C$_{1-6}$-alkylcarbonyl; R$^{14}$ is hydrogen, C$_{1-6}$-alkyl or C$_{3-8}$-cycloalkyl with the proviso that R$^{14}$ is hydrogen when R$^{13}$ is C$_{1-6}$-alkylcarbonyl; or R$^{13}$ and R$^{14}$ can together with the attached nitrogen form a heterocyclyl group; and pharmaceutically acceptable salts and solvates thereof; with the following provisos a) through g): a) when R$^1$ is a group of the formula VI; W is —N=; X, Y and Z is each a moiety of the general formula —C(R$^2$)=; wherein R$^2$ is as defined above; then A cannot be imidazolyl; b) when R$^1$ is a group of the formula VI; q is 1; X is —C(R$^2$)=; R$^{11}$ is branched C$_{4-6}$-alkyl, branched C$_{4-6}$-alkenyl, branched C$_{4-6}$-alkynyl, C$_{3-5}$-cycloalkyl, C$_{3-7}$-cycloalkenyl, C$_{3-6}$-cycloalkyl-C$_{1-3}$-alkyl or C$_{3-6}$-cycloalkenyl-C$_{1-3}$-alkyl; and W, Y, Z is each a moiety of the formula —C(R$^2$)= or —N=; wherein R$^2$ is as defined above; then R$^{12}$ can not be halogen, hydroxy, trifluoromethyl, trifluoromethoxy, C$_{1-6}$-alkoxy, C$_{1-6}$-alkyl, C$_{1-6}$-alkylsulfonyl, cyano, aryl, heteroaryl, C$_{3-8}$-cycloalkyl or a group of the formula —(CH$_2$)$_s$—(C=O)$_r$—NR$^{13}$R$^{14}$ wherein r and s each is 0 (zero), and R$^{13}$ and R$^{14}$ each is hydrogen or $C_{1-6}$-alkyl; c) when $R^1$ is a group of the formula VII; m is 1, 2 or 3; X is a moiety of the formula —$C(R^2)$=; and W, Y, Z is each a moiety of the formula —$C(R^2)$= or —N=; wherein $R^2$ is as defined above; then $R^{12}$ can not be halogen, hydroxy, trifluoromethyl, trifluoromethoxy, $C_{1-6}$-alkoxy, $C_{1-6}$-alkyl, $C_{1-6}$-alkylsulfonyl, cyano, aryl, heteroaryl, $C_{3-8}$-cycloalkyl or a group of the formula —$(CH_2)_s$—$(C=O)_r$—$NR^{13}R^{14}$ wherein r and s each is 0 (zero), and $R^{13}$ and $R^{14}$ each is hydrogen or $C_{1-6}$-alkyl; d) when $R^1$ is a group of the formula VI; q is 1; $R^{11}$ is ethyl, n-propyl or isopropyl; Y and Z is each —N=; X is a moiety of the formula —$C(R^2)$=, and W is a moiety of the formula —$C(R^2)$= or —N=; wherein $R^2$ is as defined above; then $R^{12}$ can not be halogen, hydroxy, trifluoromethyl, trifluoromethoxy, $C_{1-6}$-alkoxy, $C_{1-6}$-alkyl, $C_{1-6}$-alkylsulfonyl, cyano, aryl, heteroaryl, $C_{3-8}$-cycloalkyl or a group of the formula —$(CH_2)_s$—$(C=O)_r$—$NR^{13}R^{14}$, wherein r and s each is 0 (zero), and $R^{13}$ and $R^{14}$ each is hydrogen or $C_{1-6}$-alkyl; e) when $R^1$ is a group of the formula VII; m is 1, 2 or 3; Y and Z is each —N=; X is a moiety of the formula —$C(R^2)$=; and W is a moiety of the formula —$C(R^2)$= or —N=; wherein $R^2$ is as defined above; then $R^{12}$ can not be halogen, hydroxy, trifluoromethyl, trifluoromethoxy, $C_{1-6}$-alkoxy, $C_{1-6}$-alkyl, $C_{1-6}$-alkylsulfonyl, cyano, aryl, heteroaryl, $C_{3-8}$-cycloalkyl or a group of the formula —$(CH_2)_s$—$(C=O)_r$—$NR^{13}R^{14}$, wherein r and s each is (zero), and $R^{13}$ and $R^{14}$ each is hydrogen or $C_{1-6}$-alkyl; f) when $R^1$ is formula VI, q is 1, X and W is each a moiety of the general formula —$C(R^2)$=, wherein $R^2$ is as defined above, Y and Z is each —N=, $R^{11}$ is isopropyl, and A is phenyl, then $R^{12}$ can not be fluoro, bromo, iodo, hydroxy, trifluoromethoxy, $C_{2-6}$-alkoxy, $C_{1-6}$-alkyl, $C_{2-6}$-alkylsulfanyl, $C_{2-6}$-alkylsulfinyl, $C_{2-6}$-alkylsulfonyl, cyano, aryl, heteroaryl, $C_{3-8}$-cycloalkyl or a group of the formula —$(CH_2)_s$—$(C=O)_r$—$NR^{13}R^{14}$, wherein r and s each is 0 (zero), and $R^{13}$ and $R^{14}$ each is hydrogen or $C_{1-6}$-alkyl; and g) when X and Z is each —$C(R^2)$=; and one or both of W and Y are —N=; then $R^1$ cannot be a group of the formula II, wherein m is 2.

In an embodiment of this invention, it relates to compounds wherein W is —N=; and X, Y and Z each is a moiety of the general formula —$C(R^2)$=, wherein $R^2$ is as defined herein; such compounds having the general formul I-2:

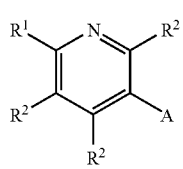

I-2 wherein A and $R^1$ are as defined herein, and the three symbols $R^2$ are the same or different and each is as defined herein.

In an embodiment of this invention, this invention relates to compounds wherein W and Y each is —N=; and X and Z each is a moiety of the general formula —$C(R^2)$=, wherein $R^2$ is as defined herein; such compounds having the general formula I-3:

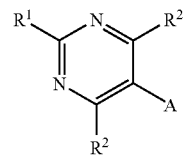

I-3 wherein A and $R^1$ are as defined herein, and the two symbols $R^2$ are the same or different and each is as defined herein.

In an embodiment of this invention, this invention relates to compounds wherein W and X each is —N=; and Y and Z each is a moiety of the general formula —$C(R^2)$=, wherein $R^2$ is as defined herein; such compounds having the general formula I-4:

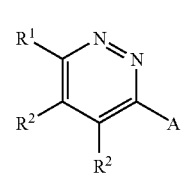

I-4 wherein A and $R^1$ are as defined herein, and the two symbols $R^2$ are the same or different and each is as defined herein.

In an embodiment of this invention, this invention relates to compounds wherein W and Z each is —N=; and X and Y each is a moiety of the general formula —$C(R^2)$=, wherein $R^2$ is as defined herein; such compounds having the general formula I-5:

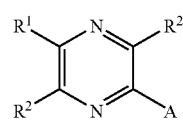

I-5 wherein A and $R^1$ are as defined herein, and the two symbols $R^2$ are the same or different and each is as defined herein.

In an embodiment of this invention, this invention relates to compounds having one of the general formulas I-6a, I-6b or I-6c:

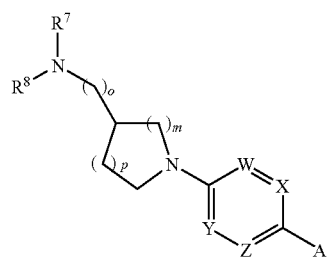

I-6a

-continued

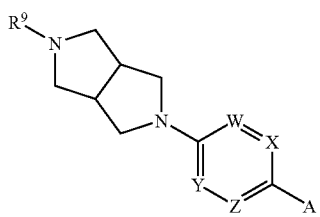
I-6b

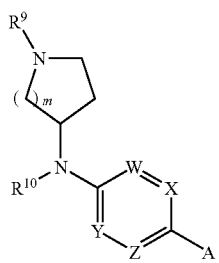
I-6c wherein A, m, o, p, $R^7$, $R^8$, $R^9$, $R^{10}$, W, X, Y, and Z each is as defined herein.

In an embodiment of this invention, this invention relates to compounds having one of the general formulas I-7a or I-7b:

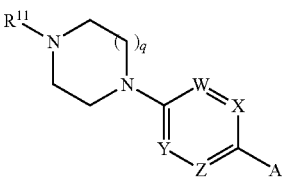
I-7a

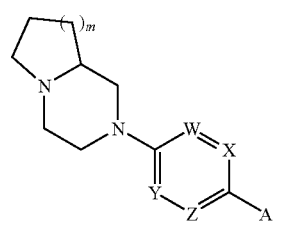
I-7b wherein W, X, Y, Z, m, q, $R^{11}$, and A each is as defined herein.

In an embodiment of this invention, this invention relates to compounds having the general formula I-8:

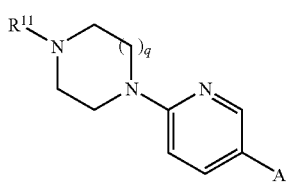
I-8 wherein q, $R^{11}$, and A each is as defined herein.

In an embodiment of this invention, this invention relates to compounds having the general formula I-9:

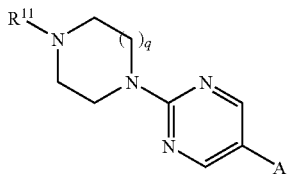
I-9 wherein q, $R^{11}$, and A each is as defined herein.

In an embodiment of this invention, this invention relates to compounds having the general formula I-10:

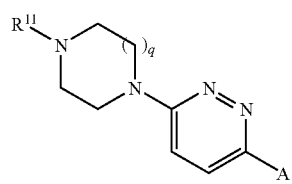
I-10 wherein q, $R^{11}$, and A each is as defined herein.

In an embodiment of this invention, this invention relates to compounds having the general formula I-11:

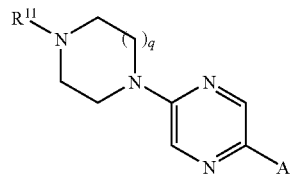
I-11 wherein q, $R^{11}$, and A each is as defined herein.

In an embodiment of this invention, this invention relates to compounds having the general formula I-12:

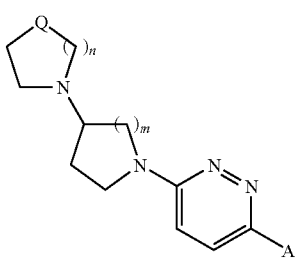
I-12 wherein Q, n, m, and A each is as defined herein.

In an embodiment of this invention, this invention relates to compounds having the general formula I-13:

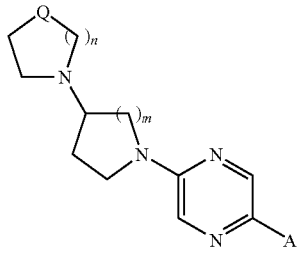

I-13 wherein Q, m, n, and A each is as defined herein.

In an embodiment of this invention, this invention relates to compounds having the general formula I-14:

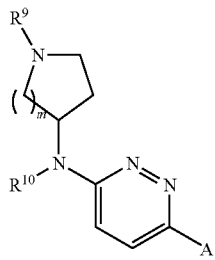

I-14 wherein m, $R^9$, $R^{10}$, and A each is as defined herein.

In an embodiment of this invention, A is aryl, 2-pyridyl, 3-pyridyl or 4-pyridyl.

In an embodiment of this invention, A is phenyl, benzofuranyl, benzodioxinyl, benzodioxolyl, benzoxazinyl, dihydrobenzodioxinyl, indolyl, pyrazinyl, pyridinyl, oxadiazolyl, quinolyl or thienyl.

In an embodiment of this invention, Q is —$CH_2$— or —O—.

In an embodiment of this invention, W is nitrogen (—N=).

In an embodiment of this invention, W is a group of the general formula —C($R^2$)=, wherein $R^2$ is hydrogen, i.e., carbon (—CH=).

In an embodiment of this invention, X is nitrogen.

In an embodiment of this invention, X is carbon (—CH=).

In an embodiment of this invention, X is nitrogen (—N=) or carbon (—CH=).

In an embodiment of this invention, Y is nitrogen.

In an embodiment of this invention, Y is carbon (—CH=).

In an embodiment of this invention, Y is nitrogen (—N=) or carbon (—CH=).

In an embodiment of this invention, Z is nitrogen.

In an embodiment of this invention, Z is carbon (—CH=).

In an embodiment of this invention, Z is nitrogen (—N=) or carbon (—CH=).

In an embodiment of this invention, W and Y are each nitrogen.

In an embodiment of this invention, W and X are each nitrogen.

In an embodiment of this invention, W and Z are each nitrogen.

In an embodiment of this invention, one or two of the symbols W, X, Y and Z is nitrogen (—N=) and the remaining are a group of the general formula —C($R^2$)=, wherein $R^2$ is as defined herein.

In an embodiment of this invention, the aromatic, divalent, 6-membered ring containing the symbols W, X, Y and Z is pyridine, pyridazine, pyrimidine or pyrazine from which hydrogen is removed from two opposite carbon atoms (para position in relation to each other).

In an embodiment of this invention, $R^1$ is a group of formula II

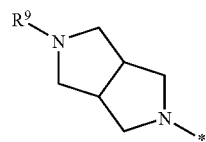

II wherein m, n and Q each is as defined in the claims below.

In an embodiment of this invention, $R^1$ is a group of formula III

III wherein m, o, p, $R^7$ and $R^8$ each is as defined in the claims below.

In an embodiment of this invention, $R^1$ is a group of formula III wherein m is 0, 1 or 2, is 0, 1 or 2, p is 1 or 2, and $R^7$ and $R^8$ are each hydrogen or $R^7$ and $R^8$ form together with the nitrogen atom to which they are attached a pyrrolidinyl or piperidinyl group.

In an embodiment of this invention, $R^1$ is a group of formula IV

IV wherein $R^9$ is as defined in the claims below.

In an embodiment of this invention, $R^1$ is a group of formula V

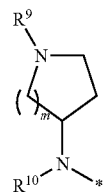

V wherein m, $R^9$ and $R^{10}$ each is as defined in the claims below.

In an embodiment of this invention, $R^1$ is a group of formula V wherein m is 2, $R^9$ is $C_{1-6}$-alkyl, and $R^{10}$ is hydrogen.

In an embodiment of this invention, $R^1$ is a group of formula VI

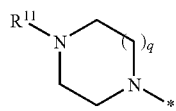

VI wherein q and $R^{11}$ each is as defined in the claims below.

In an embodiment of this invention, $R^1$ is a group of formula VI wherein $R^{11}$ is hydrogen, $C_{1-8}$-alkyl, $C_{3-8}$-alkenyl, $C_{3-8}$-cycloalkyl, heterocyclyl, $C_{1-8}$-alkyl substituted by $C_{1-6}$-alkoxy, by cyano or by $C_{1-6}$-alkylcarbonyl or by piperidinyl which optionally is substituted by $C_{1-6}$-alkyl, $R^5R^6N$— wherein $R^5$ and $R^6$ are each 1-6-alkyl, or $R^5R^6N$—$C(\!=\!O)$— wherein $R^5$ and $R^6$ are each $C_{1-6}$-alkyl.

In an embodiment of this invention, heterocyclyl is tetrahydropyranyl.

In an embodiment of this invention, $R^1$ is a group of formula VI wherein $R^{11}$ is hydrogen, methyl, isopropyl, propyl, cyclopentyl, cyclohexyl, propenyl, methoxyethyl, cyanoethyl, piperidinylpropyl, N-methylpiperidinylmethyl, methylcarbonylmethyl, N,N-dimethylaminoethyl, N,N-dimethylaminopropyl, N,N-diethylaminoethyl, N,N-dimethylaminocarbonylmethyl or tetrahydropyranyl.

In an embodiment of this invention, $R^1$ is a group of formula VII

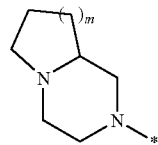

VII wherein m is as defined in the claims below.

In an embodiment of this invention, $R^1$ is a group of formula VII wherein m is 2.

In an embodiment of this invention, $R^1$ is piperazinyl, piperidinyl, pyrrolidinyl, piperidinylamino or diazepanyl.

In an embodiment of this invention, $R^2$ is hydrogen, $C_{1-6}$-alkyl or halogen.

In an embodiment of this invention, $R^2$ is hydrogen, methyl or isopropyl.

In an embodiment of this invention, $R^2$ is hydrogen or $C_{1-6}$-alkyl.

In an embodiment of this invention, $R^7$ is hydrogen or $C_{1-6}$-alkyl.

In an embodiment of this invention, $R^3$ is hydrogen or $C_{1-6}$-alkyl.

In an embodiment of this invention, $R^7$ and $R^8$ together with the nitrogen to which they are attached form a heterocyclyl group.

In an embodiment of this invention, $R^9$ is $C_{1-6}$-alkyl.

In an embodiment of this invention, $R^9$ is pentyl, more preferred pent-3-yl.

In an embodiment of this invention, $R^{10}$ is hydrogen or $C_{1-6}$-alkyl.

In an embodiment of this invention, $R^{10}$ is hydrogen.

In an embodiment of this invention, $R^{11}$ is hydrogen, $C_{1-8}$-alkyl, $C_{3-8}$-alkenyl, $C_{3-8}$-alkynyl, $C_{3-8}$-cycloalkyl, $C_{3-8}$-cycloalkenyl, $C_{3-8}$-cycloalkyl-$C_{1-3}$-alkyl or $C_{3-8}$-cycloalkenyl-$C_{1-3}$-alkyl.

In an embodiment of this invention, $R^{11}$ is $C_{1-8}$-alkyl, $C_{3-8}$-cycloalkyl or $C_{3-8}$-cycloalkyl-$C_{1-3}$-alkyl.

In an embodiment of this invention, $R^{11}$ is $C_{3-8}$-alkyl, $C_{3-8}$-cycloalkyl or $C_{3-8}$-cycloalkyl-$C_{1-3}$-alkyl.

In an embodiment of this invention, $R^{11}$ is $C_{1-6}$-alkyl or $C_{3-8}$-cycloalkyl, which both are substituted with at least one substituent selected from the group consisting of hydroxy, $C_{1-6}$-alkoxy, $C_{1-6}$-alkylcarbonyl, cyano, —$NR^5R^6$, —$C(\!=\!O)NR^5R^6$, arylcarbonyl, heteroarylcarbonyl, $C_{1-6}$-alkylsulfonyl, arylsulfonyl, heterocyclylcarbonyl, $C_{1-6}$-alkoxycarbonyl, aryl-$C_{1-6}$-alkoxycarbonyl, heteroaryl and heterocyclyl, which heterocyclyl may be substituted with $C_{1-6}$-alkyl, where applicable; and $R^5$ and $R^6$ are as defined herein.

In an embodiment of this invention, $R^{11}$ cannot be hydrogen.

In an embodiment of this invention, $R^{11}$ is hydrogen, $C_{1-8}$-alkyl, $C_{3-8}$-alkenyl or $C_{3-8}$-cycloalkyl or $C_{1-6}$-alkyl which is substituted with at least one substituent selected from the group consisting of $C_{1-6}$-alkoxy, $C_{1-6}$-alkylcarbonyl, cyano, —$NR^5R^6$, —$C(\!=\!O)NR^5R^6$ and heterocyclyl, which heterocyclyl may be substituted with $C_{1-6}$-alkyl; and $R^5$ and $R^6$ are each $C_{1-6}$-alkyl.

In an embodiment of this invention, $R^{11}$ is piperidinylpropyl, N,N-dimethylaminopropyl, N-methylpiperidinylmethyl, methyl, N,N-dimethylaminoethyl, tetrahydropyranyl, hydrogen, propyl, cyclohexyl, methylcarbonylmethyl, N,N-dimethylaminocarbonylmethyl, cyanoethyl; N,N-diethylaminoethyl, methoxyethyl, propenyl, cyclobutyl, cyclopentyl, cyclopropyl, cyclopropylmethyl, ethyl, hydrogen or isopropyl.

In an embodiment of this invention, the heterocyclyl group is piperidinyl.

In an embodiment of this invention, $R^{12}$ is halogen, cyano, $C_{1-6}$-alkyl, $C_{3-8}$-cycloalkyl, halo-$C_{1-6}$-alkyl, $C_{1-6}$-alkoxy, halo-$C_{1-6}$-alkoxy, $C_{1-6}$-alkylsulfonyl, $C_{1-6}$-alkylsulfinyl, —$(CH_2)_s$—$(C\!=\!O)_r$—$NR^{13}R^{14}$, heterocyclyl-$C_{1-6}$-alkyl, heterocyclyl-$C_{1-6}$-alkoxy, heterocyclylcarbonyl, $C_{1-6}$-alkylcarbonyl, $C_{1-6}$-alkoxycarbonyl, $C_{1-6}$-alkylcarboxy, cyano-$C_{1-6}$-alkyl, $C_{1-6}$-alkylcarbonylamino, $C_{1-6}$-alkylcarbonylamino-$C_{1-6}$-alkyl, arylcarbonylamino, arylcarbonylamino-$C_{1-6}$-alkyl, heteroarylcarbonylamino or heteroarylcarbonylamino-$C_{1-6}$-alkyl.

In an embodiment of this invention, $R^{12}$ is aryl or heteroaryl, each of which may be substituted with halogen, cyano, $C_{1-6}$-alkyl, $C_{3-8}$-cycloalkyl, $C_{1-6}$-alkoxy, $C_{1-6}$-alkylsulfanyl, $C_{1-6}$-alkylsulfonyl, $C_{1-6}$-alkylcarbonyl, $C_{1-6}$-alkylcarbonylamino, $C_{1-6}$-alkoxycarbonyl, $C_{1-6}$-alkylcarboxy, halo-$C_{1-6}$-alkyl, halo-$C_{1-6}$-alkoxy, $C_{1-6}$-alkoxy-$C_{1-6}$-alkyl, aryl, arylcarbonylamino, heteroaryl, heteroarylcarbonylamino or —$(CH_2)_s$—$(C\!=\!O)_r$—$NR^{13}R^{14}$.

In an embodiment of this invention, $R^{12}$ is halogen, hydroxy, cyano, $C_{1-6}$-alkyl, $C_{3-8}$-cycloalkyl, halo-$C_{1-6}$-alkyl, $C_{1-6}$-alkoxy, halo-$C_{1-6}$-alkoxy, $C_{1-6}$-alkylsulfonyl, $C_{1-6}$-alkylsulfinyl, —$(CH_2)_s$—$(C\!=\!O)_r$—$NR^{13}R^{14}$, $C_{1-6}$-alkylcarbonyl, $C_{1-6}$-alkoxycarbonyl, $C_{1-6}$-alkylcarboxy, cyano-$C_{1-6}$-alkyl, hydroxy-$C_{1-6}$-alkyl, $C_{1-6}$-alkoxy-$C_{1-6}$-alkyl, $C_{1-6}$-alkylcarbonylamino or $C_{1-6}$-alkylcarbonylamino-$C_{1-6}$-alkyl.

In an embodiment of this invention, $R^{12}$ is heterocyclyl-$C_{1-6}$-alkyl, heterocyclyl-$C_{1-6}$-alkoxy, heterocyclylcarbonyl, arylcarbonylamino, arylcarbonylamino-$C_{1-6}$-alkyl, heteroarylcarbonylamino or heteroarylcarbonylamino-$C_{1-6}$- alkyl, wherein each said aryl, heteroaryl and heterocyclyl may optionally be substituted with halogen, hydroxy, cyano, $C_{1-6}$-alkyl, $C_{3-8}$-cycloalkyl, halo-$C_{1-6}$-alkyl, $C_{1-6}$-alkoxy, halo-$C_{1-6}$-alkoxy, $C_{1-6}$-alkylsulfonyl, $C_{1-6}$-alkylsulfinyl, $C_{1-6}$-alkylcarbonyl, $C_{1-6}$-alkoxycarbonyl, $C_{1-6}$-alkylcarboxy, cyano-$C_{1-6}$-alkyl, hydroxy-$C_{1-6}$-alkyl or $C_{1-6}$-alkoxy-$C_{1-6}$-alkyl.

In an embodiment of this invention, $R^{12}$ is aryl or heteroaryl, each of which may be substituted with halogen, hydroxy, carboxy, nitro, cyano, $C_{1-6}$-alkyl, $C_{3-8}$-cycloalkyl, $C_{1-6}$-alkoxy, $C_{1-6}$-alkylsulfanyl, $C_{1-6}$-alkylsulfonyl, $C_{1-6}$-alkylcarbonyl, $C_{1-6}$-alkylcarbonylamino, $C_{1-6}$-alkylcarbonylamino-$C_{1-6}$-alkyl, $C_{1-6}$-alkoxycarbonyl, $C_{1-6}$-alkylcarboxy, halo-$C_{1-6}$-alkyl, halo-$C_{1-6}$-alkoxy, hydroxy-$C_{1-6}$-alkyl, $C_{1-6}$-alkoxy-$C_{1-6}$-alkyl, aryl, arylcarbonylamino, arylcarbonylamino-$C_{1-6}$-alkyl, heteroaryl, heteroarylcarbonylamino, heteroarylcarbonylamino-$C_{1-6}$-alkyl or —(CH$_2$)$_s$—(C=O)$_r$—NR$^{13}$R$^{14}$.

In an embodiment of this invention, $R^{12}$ is halogen, hydroxy, cyano, $C_{1-6}$-alkyl, $C_{3-8}$-cycloalkyl, halo-$C_{1-6}$-alkyl, $C_{1-6}$-alkoxy, halo-$C_{1-6}$-alkoxy, $C_{1-6}$-alkylsulfanyl, $C_{1-6}$-alkylsulfonyl, $C_{1-6}$-alkylsulfinyl, —V—(CH$_2$)$_s$—(C=o)$_r$—NR$^{13}$R$^{14}$, $C_{1-6}$-alkoxycarbonyl, cyano-$C_{1-6}$-alkyl, $C_{1-6}$-alkylcarbonylamino, N—($C_{1-6}$-alkylcarbonyl)-N—($C_{1-6}$-alkyl)amino, $C_{1-6}$-alkylcarbonylamino-$C_{1-6}$-alkyl, or heterocyclyl, heterocyclyl-$C_{1-6}$-alkyl, heterocyclylcarbonyl, $C_{3-8}$-cycloalkylcarbonylamino, N—($C_{3-8}$-cycloalkylcarbonyl)-N—($C_{1-6}$-alkyl)amino, $C_{3-8}$-cycloalkyl-$C_{1-6}$-alkylcarbonylamino or heterocyclylcarbonylamino wherein said heterocyclyl and $C_{3-8}$-cycloalkyl, optionally, is substituted by oxo, $C_{1-6}$-alkyl, $C_{1-6}$-alkoxy or $C_{1-6}$-alkoxy-$C_{1-6}$-alkyl; or phenyl or heteroaryl substituted by cyano, by halo-$C_{1-6}$-alkyl, by $C_{1-6}$-alkyl, by halo-$C_{1-6}$-alkyl or by —(CH$_2$)$_s$—(C=O)$_r$—NR$^{13}$R$^{14}$, wherein s, r, $R^{13}$ and $R^{14}$ are as defined above.

In an embodiment of this invention, r is 0 or 1, s is 0 or 1, $R^{13}$ is hydrogen or $C_{1-6}$-alkyl, and $R^{14}$ is hydrogen or $C_{1-6}$-alkyl, or $R^{13}$ and $R^{14}$ form together with the adjacent nitrogen atom a heterocyclyl group, for example, piperidinyl, optionally substituted by aminocarbonyl, and V is a bond.

In an embodiment of this invention, heterocyclyl is morpholinyl, piperazinyl, piperidinyl or tetrahydropyranyl.

In an embodiment of this invention, heteroaryl is oxadiazolyl.

In an embodiment of this invention, $R^{12}$ is methoxy, chloro, fluoro, trifluoromethyl, trifluoromethoxy, acetyl, acetylamino, acetylaminomethyl, cyanomethyl, ethanesulfanyl, butylsulfanyl, methanesulfonyl, ethanesulfonyl, ethanesulfinyl, methyloxadiazolyl, cyclopropylcarbonylamino, cyclopropylmethylcarbonylamino, methoxycyclohexylcarbonylamino, morpholinylmethyl, methyloxadiazolyl, chloromethylphenyl, cyanophenyl, cyclopropyl, piperidinylmethylphenyl, aminocarbonylpiperidinylmethylphenyl, N-acetyl-N-methylamino, amino, aminomethyl, cyclohexylcarbonylamino, N-cyclopropylcarbonyl-N-methylamino, cyclohexylcarbonylamino, dimethylaminomethyl, dimethylamino, dimethylaminocarbonyl, (2,2-dimethylpropyl)carbonylaminomethyl, diisopropylaminocarbonyl, 4-(1,1-dioxoisothiazolidinyl)phenyl, ethoxy, hydroxyl, (4-hydroxymethylpiperidinyl)carbonyl, (4-hydroxymethylpiperidinyl)methyl, isopropylcarbonylaminomethyl, 4-isopropylpiperazinyl, (4-methylpiperazinyl)carbonyl, (4-methylpiperazinyl)methyl, (4-methylpiperidinyl)carbonyl, (4-methoxymethylpiperidinyl)carbonyl, methyl, methylamino, morpholinyl, morpholinylcarbonyl, piperidinylmethyl, piperidinyl, piperidinylcarbonyl, piperidinylsulfonyl, tetrahydropyranylcarbonylamino, tert.butylcarbonylamino and tert.butylcarbonylaminomethyl.

In an embodiment of this invention, $R^{13}$ is hydrogen or $C_{1-6}$-alkyl.

In an embodiment of this invention, $R^{14}$ is hydrogen or $C_{1-6}$-alkyl.

In an embodiment of this invention, $R^{13}$ and $R^{14}$ together with the attached nitrogen form a heterocyclyl group.

In an embodiment of this invention, m is 0, 1 or 2.
In an embodiment of this invention, m is 0.
In an embodiment of this invention, m is 1 or 2.
In an embodiment of this invention, n is 1 or 2.
In an embodiment of this invention, o is 1.
In an embodiment of this invention, p is 1 or 2.
In an embodiment of this invention, m is 0 and p is 2.
In an embodiment of this invention, m is 0, p is 2 and o is 1.
In an embodiment of this invention, q is 1.
In an embodiment of this invention, r is 0 or 1.
In an embodiment of this invention, s is 0 or 1.

In an embodiment, this invention relates to compounds wherein A is aryl, 2-pyridyl, 3-pyridyl or 4-pyridyl; and/or Q is —CH$_2$— or —O—; and/or W is nitrogen; and/or W is a group of the general formula —C(R$^2$)=, wherein R$^2$ is hydrogen; and/or X is nitrogen; and/or X is a group of the general formula —C(R$^2$)=, wherein R$^2$ is hydrogen; and/or Y is nitrogen; and/or Y is a group of the general formula —C(R$^2$)=, wherein R$^2$ is hydrogen; and/or Z is nitrogen; and/or Z is a group of the general formula —C(R$^2$)=, wherein R$^2$ is hydrogen; and/or W and Y is nitrogen; and/or W and X is nitrogen; and/or W and Z is nitrogen; and/or $R^1$ is a group of formula II

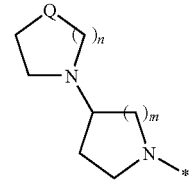

II wherein m, n and Q each is as defined in the claims below; and/or $R^1$ is a group of formula III

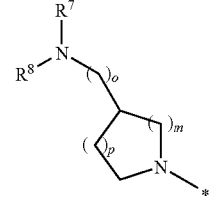

III wherein m, o, p, $R^7$ and $R^8$ each is as defined in the claims below; and/or $R^1$ is a group of formula IV

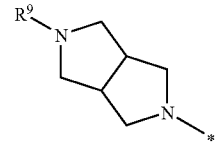

IV wherein $R^9$ is as defined in the claims below; and/or $R^1$ is a group of formula V

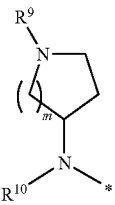

V wherein m, $R^9$ and $R^{10}$ each is as defined in the claims below; and/or $R^1$ is a group of formula VI

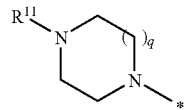

VI wherein q and $R^{11}$ each is as defined in the claims below; and/or $R^1$ is a group of formula VII

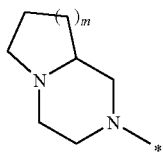

VII wherein m is as defined in the claims below; and/or $R^2$ is hydrogen, $C_{1-6}$-alkyl or halogen; and/or $R^7$ is hydrogen or $C_{1-6}$-alkyl; and/or $R^8$ is hydrogen or $C_{1-6}$-alkyl; and/or $R^7$ and $R^8$ together with the nitrogen to which they are attached form a heterocyclyl group; and/or $R^9$ is $C_{1-6}$-alkyl; and/or $R^{10}$ is hydrogen or $C_{1-6}$-alkyl; and/or $R^{11}$ is hydrogen, $C_{1-8}$-alkyl, $C_{3-8}$-alkenyl, $C_{3-8}$-alkynyl, $C_{3-8}$-cycloalkyl, $C_{3-8}$-cycloalkenyl, $C_{3-8}$-cycloalkyl-$C_{1-3}$-alkyl or $C_{3-8}$-cycloalkenyl-$C_{1-3}$-alkyl; and/or $R^{11}$ is $C_{1-8}$-alkyl, $C_{3-8}$-cycloalkyl or $C_{3-8}$-cycloalkyl-$C_{1-3}$-alkyl; and/or $R^{11}$ is $C_{3-8}$-alkyl, $C_{3-8}$-cycloalkyl or $C_{3-8}$-cycloalkyl-$C_{1-3}$-alkyl; and/or $R^{11}$ is $C_{1-6}$-alkyl or $C_{3-8}$-cycloalkyl, which both are substituted with at least one substituent selected from the group consisting of hydroxy, $C_{1-6}$-alkoxy, $C_{1-6}$-alkylcarbonyl, cyano, —$NR^5R^6$, —C(=O)$NR^5R^6$, arylcarbonyl, heteroarylcarbonyl, $C_{1-6}$-alkylsulfonyl, arylsulfonyl, heterocyclylcarbonyl, $C_{1-6}$-alkoxycarbonyl, aryl-$C_{1-6}$-alkoxycarbonyl, heteroaryl and heterocyclyl, which heterocyclyl may be substituted with $C_{1-6}$-alkyl, where applicable; and $R^5$ and $R^6$ are as defined herein; and/or $R^{11}$ cannot be hydrogen; and/or $R^{12}$ is halogen, cyano, $C_{1-6}$-alkyl, $C_{3-8}$-cycloalkyl, halo-$C_{1-6}$-alkyl, $C_{1-6}$-alkoxy, halo-$C_{1-6}$-alkoxy, $C_{1-6}$-alkylsulfonyl, $C_{1-6}$-alkylsulfinyl, —(CH$_2$)$_s$—(C=O)$_r$—NR$^{13}$R$^{14}$, heterocyclyl-$C_{1-6}$-alkyl, heterocyclyl-$C_{1-6}$-alkoxy, heterocyclylcarbonyl, $C_{1-6}$-alkylcarbonyl, $C_{1-6}$-alkoxycarbonyl, $C_{1-6}$-alkylcarboxy, cyano-$C_{1-6}$-alkyl, $C_{1-6}$-alkylcarbonylamino, $C_{1-6}$-alkylcarbonylamino-$C_{1-6}$-alkyl, arylcarbonylamino, arylcarbonylamino-$C_{1-6}$-alkyl, heteroarylcarbonylamino or heteroarylcarbonylamino-$C_{1-6}$-alkyl; and/or $R^{12}$ is aryl or heteroaryl, each of which may be substituted with halogen, cyano, $C_{1-6}$-alkyl, $C_{3-8}$-cycloalkyl, $C_{1-6}$-alkoxy, $C_{1-6}$-alkylsulfanyl, $C_{1-6}$-alkylsulfonyl, $C_{1-6}$-alkylcarbonyl, $C_{1-6}$-alkylcarbonylamino, $C_{1-6}$-alkoxycarbonyl, $C_{1-6}$-alkylcarboxy, halo-$C_{1-6}$-alkyl, halo-$C_{1-6}$-alkoxy, $C_{1-6}$-alkoxy-$C_{1-6}$-alkyl, aryl, arylcarbonylamino, heteroaryl, heteroarylcarbonylamino or —(CH$_2$)$_s$—(C=O)$_r$—NR$^{13}$R$^{14}$; and/or $R^{12}$ is halogen, hydroxy, cyano, $C_{1-6}$-alkyl, $C_{3-8}$-cycloalkyl, halo-$C_{1-6}$-alkyl, $C_{1-6}$-alkoxy, halo-$C_{1-6}$-alkoxy, $C_{1-6}$-alkylsulfonyl, $C_{1-6}$-alkylsulfinyl, —(CH$_2$)$_s$—(C=O)$_r$—NR$^{13}$R$^{14}$, $C_{1-6}$-alkylcarbonyl, $C_{1-6}$-alkoxycarbonyl, $C_{1-6}$-alkylcarboxy, cyano-$C_{1-6}$-alkyl, hydroxy-$C_{1-6}$-alkyl, $C_{1-6}$-alkoxy-$C_{1-6}$-alkyl, $C_{1-6}$-alkylcarbonylamino or $C_{1-6}$-alkylcarbonylamino-$C_{1-6}$-alkyl; and/or $R^{12}$ is heterocyclyl-$C_{1-6}$-alkyl, heterocyclyl-$C_{1-6}$-alkoxy, heterocyclylcarbonyl, arylcarbonylamino, arylcarbonylamino-$C_{1-6}$-alkyl, heteroarylcarbonylamino or heteroarylcarbonylamino-$C_{1-6}$-alkyl, wherein each said aryl, heteroaryl and heterocyclyl may optionally be substituted with halogen, hydroxy, cyano, $C_{1-6}$-alkyl, $C_{3-8}$-cycloalkyl, halo-$C_{1-6}$-alkyl, $C_{1-6}$-alkoxy, halo-$C_{1-6}$-alkoxy, $C_{1-6}$-alkylsulfonyl, $C_{1-6}$-alkylsulfinyl, $C_{1-6}$-alkylcarbonyl, $C_{1-6}$-alkoxycarbonyl, $C_{1-6}$-alkylcarboxy, cyano-$C_{1-6}$-alkyl, hydroxy-$C_{1-6}$-alkyl or $C_{1-6}$-alkoxy-$C_{1-6}$-alkyl; and/or $R^{12}$ is aryl or heteroaryl, each of which may be substituted with halogen, hydroxy, carboxy, nitro, cyano, $C_{1-6}$-alkyl, $C_{3-8}$-cycloalkyl, $C_{1-6}$-alkoxy, $C_{1-6}$-alkylsulfanyl, $C_{1-6}$-alkylsulfonyl, $C_{1-6}$-alkylcarbonyl, $C_{1-6}$-alkylcarbonylamino, $C_{1-6}$-alkylcarbonylamino-$C_{1-6}$-alkyl, $C_{1-6}$-alkoxycarbonyl, $C_{1-6}$-alkylcarboxy, halo-$C_{1-6}$-alkyl, halo-$C_{1-6}$-alkoxy, hydroxy-$C_{1-6}$-alkyl, $C_{1-6}$-alkoxy-$C_{1-6}$-alkyl, aryl, arylcarbonylamino, arylcarbonylamino-$C_{1-6}$-alkyl, heteroaryl, heteroarylcarbonylamino, heteroarylcarbonylamino-$C_{1-6}$-alkyl or —V—(CH$_2$)$_s$—(C=O)$_r$—NR$^{13}$R$^{14}$, wherein V is a bond; and/or $R^{13}$ is hydrogen or $C_{1-6}$-alkyl; and/or $R^{14}$ is hydrogen or $C_{1-6}$-alkyl; and/or $R^{13}$ and $R^{14}$ together with the attached nitrogen form a heterocyclyl group; and/or m is 0, 1 or 2; and/or m is 0; and/or m is 1 or 2; and/or n is 1 or 2; and/or o is 1; and/or p is 1 or 2; and/or m is 0 and p is 2; and/or m is 0, p is 2 and o is 1; and/or q is 1; and/or r is 0 or 1; and/or s is 0 or 1.

In an embodiment of this invention, the moiety V is a bond.

In an embodiment, this invention relates to any one of the following compounds: 1-[5-(4-chlorophenyl)pyridin-2-yl]-4-isopropylpiperazine; 1-isopropyl-4-[5-(4-methoxyphenyl)pyridin-2-yl]piperazine; 1-isopropyl-4-[5-(4-trifluoromethoxyphenyl)pyridin-2-yl]piperazine; 1-{4-[6-(4-isopropylpiperazin-1-yl)pyridin-3-yl]phenyl}ethanone; 1-[5-(2,6-difluorophenyl)pyridin-2-yl]-4-isopropylpiperazine; 1-[5-(4-fluorophenyl)pyridin-2-yl]-4-isopropylpiperazine; 1-[5-(3-fluorophenyl)pyridin-2-yl]-4-isopropylpiperazine; 1-[5-(2-fluorophenyl)pyridin-2-yl]-4-isopropylpiperazine; 1-{4-[6-(4-cyclopentylpiperazin-1-yl)pyridin-3-yl]phenyl}ethanone; 4-[6-(4-isopropylpiperazin-1-yl)pyridin-3-yl]benzonitrile; (4-(2-pyrrolidin-1-ylethyl)piperidin-1-yl)-5-(4-trifluoromethylphenyl)pyridine; 1-(3-piperidin-1-ylpropyl)-4-[5-(4-trifluoromethylphenyl)pyridin-2-yl]piperazine; 1'-[6-(4-methanesulfonylphenyl)pyridazin-3-yl]-[1,4']bipiperidinyl; dimethyl-(3-{4-[6-(4-trifluoromethylphenyl)pyridazin-3-yl]piperazin-1-yl}propyl)amine; 3-[4-(1-methylpiperidin-3-ylmethyl)piperazin-1-yl]-6-(4-trifluoromethylphenyl)pyridazine; 3-[4-(1-methylpiperidin-4-ylmethyl)piperazin-1-yl]-6-(4-trifluoromethylphenyl)pyridazine; 4-{6-[4-(1-methylpiperidin-4-ylmethyl)piperazin-1-yl]pyridazin-3-yl}benzonitrile; 4-{6-[4-(1-methylpiperidin-3-ylmethyl)piperazin-1-yl]pyridazin-3-yl}benzonitrile; (S)-3-(4-butylsulfanylphenyl)-6-(2-pyrrolidin-1-ylmethylpyrrolidin-1-yl)pyridazine; (S)-3-(4-ethanesulfonylphenyl)-6-(2-pyrrolidin-1-ylmethylpyrrolidin-1-yl)pyridazine; (S)-3-(4- ethanesulfinylphenyl)-6-(2-pyrrolidin-1-ylmethylpyrrolidin-1-yl)pyridazine; (S)-3-(4-ethylsulfanylphenyl)-6-(2-pyrrolidin-1-ylmethylpyrrolidin-1-yl)pyridazine; 5-(4-chlorophenyl)-2-(4-isopropylpiperazin-1-yl)pyrimidine; 2-(4-isopropylpiperazin-1-yl)-5-(4-trifluoromethylphenyl) pyrimidine; 4-[2-(4-isopropylpiperazin-1-yl)pyrimidin-5-yl]benzonitrile; 5-(4-fluorophenyl)-2-(4-isopropylpiperazin-1-yl)pyrimidine; 2-(4-isopropylpiperazin-1-yl)-5-(4-trifluoromethoxyphenyl)pyrimidine; 2-(4-isopropylpiperazin-1-yl)-5-(4-methoxyphenyl)pyrimidine; (S)-3-(2-pyrrolidin-1-ylmethylpyrrolidin-1-yl)-6-(4-trifluoromethylphenyl)pyridazine; N-{4-[6-(4-isopropylpiperazin-1-yl)pyridazin-3-yl]phenyl}acetamide; [1-(1-ethylpropyl) piperidin-4-yl]-[6-(3-fluoro-4-methoxyphenyl)pyridazin-3-yl]amine; [1-(1-ethylpropyl)piperidin-4-yl]-[6-(4-methanesulfonylphenyl)pyridazin-3-yl]amine; 1-isopropyl-4-[5-(4-trifluoromethylphenyl)pyridin-2-yl]piperazine; 3-(2,3-dihydrobenzo[1,4]dioxin-6-yl)-6-(4-isopropylpiperazin-1-yl)pyridazine; 4-{6-[1-(1-ethylpropyl)piperidin-4-ylamino]pyridazin-3-yl}-benzonitrile; dimethyl-(2-{4-[5-(4-trifluoromethylphenyl)pyridin-2-yl]piperazin-1-yl}ethyl) amine; 1-(tetrahydropyran-4-yl)-4-[5-(4-trifluoromethylphenyl)pyridin-2-yl]piperazine; 1-[6-(4-trifluoromethylphenyl)pyridazin-3-yl]piperidin-3-ylamine; N-{4-[6-(4-isopropylpiperazin-1-yl)pyridin-3-yl]benzyl}acetamide; 1-isopropyl-4-{5-[4-(5-methyl[1,2,4]oxadiazol-3-yl)phenyl]pyridin-2-yl}-piperazine; 1-(5-(5-(4-chloromethylphenyl)[1,2,4]oxadiazol-3-yl)pyridine-2-yl)-4-isopropylpiperazine; 4-{3-[6-(4-isopropylpiperazin-1-yl) pyridin-3-yl][1,2,4]oxadiazol-5-yl}benzonitrile; 1-[5-(5-cyclopropyl[1,2,4]oxadiazol-3-yl)pyridin-2-yl]-4-isopropylpiperazine; 1-isopropyl-4-{5-[5-(4-piperidin-1-ylmethylphenyl)[1,2,4]oxadiazol-3-yl]pyridin-2-yl}piperazine; 1-(4-{3-[6-(4-isopropylpiperazin-1-yl) pyridin-3-yl][1,2,4]oxadiazol-5-yl}benzyl)piperidine-4-carboxylic acid amide; 1-propyl-4-[5-(4-trifluoromethylphenyl)pyridin-2-yl]piperazine; 1-cyclohexyl-4-[5-(4-trifluoromethylphenyl)pyridin-2-yl] piperazine; 1-{4-[6-(4-isopropylpiperazin-1-yl)pyridazin-3-yl]-phenyl}ethanone; 1-{4-[5-(4-trifluoromethylphenyl)pyridin-2-yl]piperazin-1-yl}propan-2-one; N,N-dimethyl-2-{4-[5-(4-trifluoromethylphenyl)pyridin-2-yl]piperazin-1-yl}acetamide; 3-{4-[5-(4-trifluoromethylphenyl)pyridin-2-yl]piperazin-1-yl}propionitrile; diethyl-(2-{4-[5-(4-trifluoromethylphenyl)pyridin-2-yl]piperazin-1-yl}ethyl) amine; 1-(2-methoxyethyl)-4-[5-(4-trifluoromethylphenyl) pyridin-2-yl]piperazine; 1-allyl-4-[5-(4-trifluoromethylphenyl)pyridin-2-yl]-piperazine; 1-isopropyl-4-[6-(4-trifluoromethylphenyl)pyridazin-3-yl]-[1,4]diazepane; N-[4-(4-isopropyl-3,4,5,6-tetrahydro-2H-[1,2']bipyrazinyl-5'-yl)phenyl]acetamide; [4-(4-isopropyl-3,4,5,6-tetrahydro-2H-[1,2']bipyrazinyl-5'-yl)phenyl]acetonitrile and 5-(4-ethanesulfonylphenyl)-4-isopropyl-3,4,5,6-tetrahydro-2H-[1,2']bipyrazinyl, and salts thereof such as hydrochlorides, dihydrochlorides, trihydrochlorides, trifluoroacetates and dimethanesulfonates.

In an embodiment, this invention relates to any one of the following compounds: N-{4-[6-(4-isopropylpiperazin-1-yl) pyridin-3-yl]phenyl}acetamide; cyclopropanecarboxylic acid [4-(4-isopropyl-3,4,5,6-tetrahydro-2H-[1,2']bipyrazinyl-5'-yl)phenyl]amide; 2-cyclopropyl-N-[4-(4-isopropyl-3,4,5,6-tetrahydro-2H-[1,2']bipyrazinyl-5'-yl)phenyl]acetamide; 4-methoxycyclohexanecarboxylic acid [4-(4-isopropyl-3,4,5,6-tetrahydro-2H-[1,2']bipyrazinyl-5'-yl) phenyl]-amide; 4-{4-[6-(4-isopropylpiperazin-1-yl)pyridin-3-yl]benzyl}morpholine; 4-[2-(4-isopropylpiperazin-1-yl) pyrimidin-5-yl]benzonitrile and N-{4-[2-(4-isopropylpiperazin-1-yl)pyrimidin-5-yl]benzyl}acetamide and salts thereof such as hydrochlorides, dihydrochlorides, trihydrochlorides, trifluoroacetates and dimethanesulfonates.

In an embodiment, this invention relates to any one of the following compounds: 4-[6-(4-cyclopropylpiperazin-1-yl) piperidin-3-yl]-N,N-dimethylbenzamide and N-{4-[6-(4-cyclopropylpiperazin-1-yl)pyridazin-3-yl]-2-methoxyphenyl}acetamide, and salts thereof such as hydrochlorides, dihydrochlorides, trihydrochlorides, trifluoroacetates and dimethanesulfonates.

In an embodiment, this invention relates to any one of the following compounds: N-{3-[6-(4-isopropylpiperazin-1-yl)-4-methylpyridin-3-yl]phenyl}acetamide; N-{3-[6-(4-isopropylpiperazin-1-yl)-5-methylpyridin-3-yl]phenyl}acetamide; N-{4-[6-(4-isopropylpiperazin-1-yl)-4-methylpyridin-3-yl]phenyl}acetamide; N-{4-[6-(4-isopropylpiperazin-1-yl)-5-methylpyridin-3-yl]phenyl}acetamide; N-{4-[6-(4-isopropylpiperazin-1-yl)-4-methylpyridazin-3-yl]phenyl}-acetamide; N-{3-[6-(4-cyclopropylpiperazin-1-yl)-4-methylpyridin-3-yl]phenyl}acetamide; 3-[6-(4-cyclopropylpiperazin-1-yl)-4-methylpyridin-3-yl]-N,N-dimethylbenzamide; N-{4-[6-(4-cyclopropylpiperazin-1-yl)-4-methylpyridin-3-yl]phenyl}acetamide; 4-[6-(4-cyclopropylpiperazin-1-yl)-4-methylpyridin-3-yl]-N,N-dimethylbenzamide; 5-1,3-benzodioxol-5-yl-2-(4-cyclopropylpiperazin-1-yl)pyrimidine; N-{4-[6-(4-isopropylperhydro-1,4-diazepin-1-yl)pyridazin-3-yl]-phenyl}acetamide; 4-[6-(4-isopropylperhydro-1,4-diazepin-1-yl)pyridazin-3-yl]phenylamine; N-{4-[6-(4-cyclopropyl-[1,4]diazepan-1-yl)pyridazin-3-yl]phenyl}acetamide; 7-[6-(4-cyclopropylpiperazin-1-yl)-pyridazin-3-yl]-4-methyl-3,4-dihydro-2H-1,4-benzoxazine; 3-(4-cyclopropylpiperazin-1-yl)-6-(2,3-dihydro-1,4-benzodioxin-6-yl)pyridazine; 5-[6-(4-cyclopropylpiperazin-1-yl)pyridazin-3-yl]-1H-indole; {4-[2-(4-isopropylpiperazin-1-yl)pyrimidin-5-yl]-phenyl}acetonitrile; N-{4-[2-(4-isopropylpiperazin-1-yl)pyrimidin-5-yl]phenyl}acetamide; 1-{4-[2-(4-isopropylpiperazin-1-yl)pyrimidin-5-yl]phenyl}ethanone; 2-(4-isopropylpiperazin-1-yl)-5-pyridin-3-ylpyrimidine; 2-(4-isopropylpiperazin-1-yl)-5-pyridin-4-ylpyrimidine; {4-[2-(4-isopropylpiperazin-1-yl)pyrimidin-5-yl] phenyl}dimethylamine; 3-[2-(4-isopropylpiperazin-1-yl) pyrimidin-5-yl]-N,N-dimethylbenzamide; N,N-diisopropyl-4-(4-isopropyl-3,4,5,6-tetrahydro-2H-[1,2']bipyrazinyl-5'-yl)benzamide; [4-(4-isopropyl-3,4,5,6-tetrahydro-2H-[1,2'] bipyrazinyl-5'-yl)phenyl]-(4-methylpiperidin-1-yl) methanone; 4-(4-isopropyl-3,4,5,6-tetrahydro-2H-[1,2']-bipyrazinyl-5'-yl)-N,N-dimethylbenzamide; [3-(4-isopropyl-3,4,5,6-tetrahydro-2H-[1,2']bipyrazinyl-5'-yl) phenyl]morpholin-4-ylmethanone; N-{4-[5-(octahydropyrido[1,2-a]pyrazin-2-yl)pyrazin-2-yl] phenyl}acetamide; 4-(4-isopropyl-3,4,5,6-tetrahydro-2H-[1,2']bipyrazinyl-5'-yl)phenol; N-[4-(4-isopropyl-3,4,5,6-tetrahydro-2H-[1,2']bipyrazinyl-5'-yl)phenyl]-N-methylamine; 4-isopropyl-5'-(4-morpholin-4-ylphenyl)-3,4,5,6-tetrahydro-2H-[1,2']bipyrazinyl; 5'-1,3-benzodioxol-5-yl-4-isopropyl-3,4,5,6-tetrahydro-2H-1,2'-bipyrazinyl; 4-(4-isopropyl-3,4,5,6-tetrahydro-2H-[1,2']bipyrazinyl-5'-yl)-2-methoxyphenylamine; 2-chloro-4-(4-isopropyl-3,4,5,6-tetrahydro-2H-[1,2']bipyrazinyl-5'-yl)-6-methoxyphenol; 5'-(3,4-dimethoxyphenyl)-4-isopropyl-3,4,5,6-tetrahydro-2H-[1,2']bipyrazinyl; 4-isopropyl-5'-(3,4,5-trimethoxyphenyl)-3,4,5,6-tetrahydro-2H-[1,2']bipyrazinyl; N-[4-(4-isopropyl-3,4,5,6-tetrahydro-2H-[1,2']bipyrazinyl-5'-yl)benzyl] acetamide; 4,4'''-diisopropyl-3,4,5,6,3''',4''',5''',6'''-octahydro-2H,2'''H-[1,2';5',2'';5'',1''']-quaterpyrazine;

4-isopropyl-5'-(6-methoxypyridin-3-yl)-3,4,5,6-tetrahydro-2H-[1,2']bipyrazinyl; N,N-diisopropyl-4-[6-(4-isopropylpiperazin-1-yl)pyridin-3-yl]benzamide; {4-[6-(4-isopropylpiperazin-1-yl)pyridin-3-yl]}-(4-methylpiperidin-1-yl)methanone; 6'-(4-isopropylpiperazin-1-yl)-6-methoxy-[3,3']bipyridinyl; 4-(4-isopropyl-3,4,5,6-tetrahydro-2H-[1,2']bipyrazinyl-5'-yl)benzonitrile; 4-isopropyl-5'-(4-trifluoromethylphenyl)-3,4,5,6-tetrahydro-2H-[1,2']bipyrazinyl; 6'-(4-isopropylpiperazin-1-yl)-5-trifluoromethyl-[2,3']bipyridinyl; 4-isopropyl-5'-[4-(piperidine-1-sulfonyl)phenyl]-3,4,5,6-tetrahydro-2H-[1,2']bipyrazinyl; 4-isopropyl-5'-(4-(piperidin-1-yl)phenyl)-3,4,5,6-tetrahydro-2H-[1,2']bipyrazinyl; [4-(4-isopropyl-3,4,5,6-tetrahydro-2H-[1,2']bipyrazinyl-5'-yl)-2-methylphenyl]dimethylamine; 5'-(6-ethoxypyridin-3-yl)-4-isopropyl-3,4,5,6-tetrahydro-2H-[1,2']bipyrazinyl; 5'-benzofuran-2-yl-4-isopropyl-3,4,5,6-tetrahydro-2H-[1,2']bipyrazinyl; 5-(4-isopropyl-3,4,5,6-tetrahydro-2H-[1,2']bipyrazinyl-5'-yl)thiophene-2-carbonitrile; 4-isopropyl-5'-(2-methylpyridin-4-yl)-3,4,5,6-tetrahydro-2H-[1,2']bipyrazinyl; (R)-2-(6-1,3-benzodioxol-5-ylpyridazin-3-yl)octahydropyrido[1,2-a]pyrazine; 4-isopropyl-5'-(5-trifluoromethyl-pyridin-2-yl)-3,4,5,6-tetrahydro-2H-[1,2']bipyrazinyl; N-{4-[6-(4-cyclobutylpiperazin-1-yl)pyridin-3-yl]phenyl}acetamide; 4-[6-(4-cyclobutylpiperazin-1-yl)pyridin-3-yl]-N,N-dimethylbenzamide; N-{4-[6-(4-cyclobutylpiperazin-1-yl)pyridazin-3-yl]-2-methoxyphenyl}acetamide; {4-[6-(4-isopropylpiperazin-1-yl)pyridazin-3-yl]phenyl}piperidin-1-ylmethanone; {4-[6-(4-cyclopropylmethylpiperazin-1-yl)pyridazin-3-yl]phenyl}piperidin-1-ylmethanone; {4-[6-(4-isopropylpiperazin-1-yl)pyridazin-3-yl]phenyl}morpholin-4-ylmethanone; (4-hydroxymethylpiperidin-1-yl)-{4-[6-(4-isopropylpiperazin-1-yl)pyridazin-3-yl]phenyl}-methanone; 4-[6-(4-isopropylpiperazin-1-yl)pyridazin-3-yl]-N,N-dimethylbenzamide; {4-[6-(4-cyclopentylpiperazin-1-yl)pyridazin-3-yl]phenyl}piperidin-1-ylmethanone; {4-[6-(4-isopropylpiperazin-1-yl)pyridazin-3-yl]phenyl}-(4-methylpiperazin-1-yl)methanone; {4-[6-(4-isopropylpiperazin-1-yl)pyridin-3-yl]phenyl}morpholin-4-ylmethanone; 4-[6-(4-isopropylpiperazin-1-yl)pyridin-3-yl]-N,N-dimethylbenzamide; {4-[6-(4-isopropylpiperazin-1-yl)pyridin-3-yl]phenyl}-piperidin-1-ylmethanone; (4-hydroxymethylpiperidin-1-yl)-{4-[6-(4-isopropylpiperazin-1-yl)pyridin-3-yl]phenyl}-methanone; {4-[6-(4-isopropylpiperazin-1-yl)pyridin-3-yl]phenyl}-(4-methylpiperazin-1-yl)methanone; {4-[6-(4-cyclopropylmethylpiperazin-1-yl)pyridin-3-yl]-phenyl}piperidin-1-ylmethanone; {4-[6-(4-cyclopropylpiperazin-1-yl)pyridin-3-yl]phenyl}-piperidin-1-ylmethanone; {4-[6-(4-cyclopentylpiperazin-1-yl)pyridin-3-yl]phenyl}piperidin-1-ylmethanone; {3-[6-(4-isopropylpiperazin-1-yl)pyridin-3-yl]phenyl}morpholin-4-ylmethanone; {3-[6-(4-isopropylpiperazin-1-yl)pyridin-3-yl]phenyl}piperidin-1-ylmethanone; 3-[6-(4-isopropylpiperazin-1-yl)pyridin-3-yl]-N,N-dimethylbenzamide; {4-[6-(4-cyclopentylpiperazin-1-yl)pyridin-3-yl]phenyl}-(4-methylpiperazin-1-yl)methanone; {4-[6-(4-cyclopropylpiperazin-1-yl)pyridin-3-yl]phenyl}-(4-methylpiperazin-1-yl)methanone; {4-[6-(4-isopropylpiperazin-1-yl)pyridin-3-yl]phenyl}-(4-methoxymethylpiperidin-1-yl)-ethanone; 4-[6-(4-'cyclopentylpiperazin-1-yl)pyridin-3-yl]-N,N-dimethylbenzamide; {4-[6-(4-cyclopentylpiperazin-1-yl)pyridin-3-yl]-phenyl}morpholin-4-ylmethanone; 3-[6-(4-isopropylpiperazin-1-yl)-4-methylpyridin-3-yl]-N,N-dimethylbenzamide; 3-[6-(4-isopropylpiperazin-1-yl)-5-methylpyridin-3-yl]-N,N-dimethylbenzamide; 4-[6-(4-isopropylpiperazin-1-yl)-4-methylpyridin-3-yl]-N,N-dimethylbenzamide; 4-[4-isopropyl-6-(4-isopropylpiperazin-1-yl)pyridazin-3-yl]-N,N-dimethylbenzamide; 1-cyclopropylmethyl-4-[5-(4-piperidin-1-ylmethylphenyl)pyridin-2-yl]piperazine; {4-[6-(4-isopropylpiperazin-1-yl)pyridin-3-yl]benzyl}dimethylamine; 3-(4-cyclopentylpiperazin-1-yl)-6-(4-piperidin-1-ylmethylphenyl)pyridazine; 1-{4-[6-(4-isopropylpiperazin-1-yl)pyridin-3-yl]benzyl}-4-methylpiperazine; (1-{4-[6-(4-isopropylpiperazin-1-yl)pyridin-3-yl]benzyl}piperidin-4-yl)methanol; 1-isopropyl-4-[5-(4-piperidin-1-ylmethylphenyl)pyridin-2-yl]piperazine; {4-[6-(4-isopropylpiperazin-1-yl)pyridazin-3-yl]benzyl}dimethylamine; 3-(4-isopropylpiperazin-1-yl)-6-(4-piperidin-1-ylmethylphenyl)pyridazine; 3-(4-isopropylpiperazin-1-yl)-6-[4-(4-methylpiperazin-1-ylmethyl)phenyl]-pyridazine; (1-{4-[6-(4-isopropylpiperazin-1-yl)pyridazin-3-yl]benzyl}piperidin-4-yl)methanol; 4-{4-[6-(4-isopropylpiperazin-1-yl)pyridazin-3-yl]benzyl}morpholine; 1-cyclopentyl-4-[5-(4-piperidin-1-ylmethylphenyl)pyridin-2-yl]piperazine; 1-cyclopropyl-4-[5-(4-piperidin-1-ylmethylphenyl)pyridin-2-yl]piperazine; 3-(4-cyclopropylmethylpiperazin-1-yl)-6-(4-piperidin-1-ylmethylphenyl)pyridazine; 3-(4-cyclopropylpiperazin-1-yl)-6-(4-piperidin-1-ylmethylphenyl)pyridazine; 4-{4-[2-(4-cyclopropylpiperazin-1-yl)pyrimidin-5-yl]benzyl}morpholine; N-{3-[6-(4-isopropylpiperazin-1-yl)pyridazin-3-yl]phenyl}acetamide; N-{3-[6-(4-cyclopropylpiperazin-1-yl)pyridazin-3-yl]phenyl}acetamide; cyclopropanecarboxylic acid {3-[6-(4-cyclopropylpiperazin-1-yl)pyridazin-3-yl]phenyl}amide; N-{4-[6-(4-cyclopropylpiperazin-1-yl)pyridazin-3-yl]phenyl}acetamide; cyclopropanecarboxylic acid {4-[6-(4-cyclopropylpiperazin-1-yl)pyridazin-3-yl]phenyl}amide; cyclopropanecarboxylic acid {4-[6-(4-cyclopropylperhydro-1,4-diazepin-1-yl)pyridazin-3-yl]-phenyl}amide; N-[4-(4-isopropyl-3,4,5,6-tetrahydro-2H-[1,2']-bipyrazinyl-5'-yl)phenyl]-2,2-dimethylpropionamide; tetrahydropyran-4-carboxylic acid [4-(4-isopropyl-3,4,5,6-tetrahydro-2H-[1,2']bipyrazinyl-5'-yl)phenyl]amide; N-[4-(4-isopropyl-3,4,5,6-tetrahydro-2H-[1,2']bipyrazinyl-5'-yl)phenyl]-N-methylacetamide; cyclopropanecarboxylic acid [4-(4-isopropyl-3,4,5,6-tetrahydro-2H-[1,2']bipyrazinyl-5'-yl)phenyl]methylamide; N-[4-(4-isopropyl-3,4,5,6-tetrahydro-2H-[1,2']bipyrazinyl-5'-yl)-2-methoxyphenyl]acetamide; cyclohexanecarboxylic acid [4-(4-isopropyl-3,4,5,6-tetrahydro-2H-[1,2']bipyrazinyl-5'-yl)phenyl]-amide; 2-[4-(4-isopropyl-3,4,5,6-tetrahydro-2H-[1,2']bipyrazinyl-5'-yl)phenoxy]-N,N-dimethylacetamide; 5'-[4-(1,1-dioxoisothiazolidin-2-yl)phenyl]-4-isopropyl-3,4,5,6-tetrahydro-2H-[1,2']-bipyrazinyl; 6-(4-isopropylpiperazin-1-yl)-[3,3']bipyridinyl; 6-(4-isopropylpiperazin-1-yl)-[3,4']-bipyridinyl; 6'-(4-isopropylpiperazin-1-yl)-[2,3']bipyridinyl; 6'-(4-ethylpiperazin-1-yl)-[2,3']bipyridinyl; 6'-(4-isopropylpiperazin-1-yl)-6-methyl-[2,3']bipyridinyl; 6'-(4-ethylpiperazin-1-yl)-6-methyl-[2,3']bipyridinyl; 2-[6-(4-isopropylpiperazin-1-yl)pyridin-3-yl]quinoline; N-{3-[6-(4-isopropylpiperazin-1-yl)-4-methylpyridazin-3-yl]phenyl}acetamide; N-{3-[6-(4-isopropylpiperazin-1-yl)-5-methylpyridazin-3-yl]phenyl}acetamide; 3-[6-(4-isopropylpiperazin-1-yl)-4-methylpyridazin-3-yl]-N,N-dimethylbenzamide; 3-[6-(4-isopropylpiperazin-1-yl)-5-methylpyridazin-3-yl]-N,N-dimethylbenzamide; 4-[6-(4-isopropylpiperazin-1-yl)-4-methylpyridazin-3-yl]-N,N-dimethylbenzamide; 4-[6-(4-isopropylpiperazin-1-yl)-5-methylpyridazin-3-yl]-N,N-dimethylbenzamide; N-{4-[6-(4-isopropylpiperazin-1-yl)-5-methylpyridazin-3-yl]

phenyl}acetamide; 1'-(6-pyridin-4-ylpyridazin-3-yl)-[1,4']bipiperidinyl; 3-(pyridin-3-yl)-6-[(4-pyrrolidin-1-yl)piperidin-1-yl]pyridazine; 1'-(6-pyridin-3-ylpyridazin-3-yl)-[1,4']bipiperidinyl; 3-(pyridin-4-yl)-6-[(4-pyrrolidin-1-yl)piperidin-1-yl]pyridazine; 4-pyrrolidin-1-yl-3,4,5,6-tetrahydro-2H-[1,2';5',3'']-terpyridine; 1-isopropyl-4-(6-phenylpyridin-3-yl)piperazine; (R)-2-[6-(3,4-dimethoxyphenyl)pyridazin-3-yl]octahydropyrido[1,2-a]pyrazine; N-{3-[6-(4-isopropylpiperazin-1-yl)pyridin-3-yl]benzyl}acetamide; N-{4-[6-(4-isopropylpiperazin-1-yl)pyridin-3-yl]benzyl}-3,3-dimethylbutyramide; N-{3-[6-(4-isopropylpiperazin-1-yl)pyridin-3-yl]benzyl}-3,3-dimethylbutyramide; N-{4-[2-(4-isopropylpiperazin-1-yl)pyrimidin-5-yl]benzyl}isobutyramide; N-{4-[6-(4-isopropylpiperazin-1-yl)pyridin-3-yl]benzyl}-2,2-dimethylpropionamide; N-{3-[6-(4-isopropylpiperazin-1-yl)pyridin-3-yl]benzyl}-2,2-dimethylpropionamide; 4-[2-(4-cyclopropylpiperazin-1-yl)pyrimidin-5-yl]benzylamine; N-{4-[2-(4-cyclopropylpiperazin-1-yl)pyrimidin-5-yl]benzyl}acetamide; N-{4-[6-(4-isopropylpiperazin-1-yl)pyridazin-3-yl]acetamide; N-[4-(4-cyclopropyl-3,4,5,6-tetrahydro-2H-[1,2']bipyrazinyl-5'-yl)phenyl]acetamide; 2-{4-[6-(4-isopropylpiperazin-1-yl)pyridazin-3-yl]-phenoxy}-N,N-dimethylacetamide; cyclohexanecarboxylic acid {4-[6-(4-cyclopropylpiperazin-1-yl)pyridazin-3-yl]phenyl}amide and N-{4-[4-isopropyl-6-(4-isopropylpiperazin-1-yl)pyridazin-3-yl]phenyl}acetamide and salts thereof such as hydrochlorides, dihydrochlorides, trihydrochlorides, trifluoroacetates and dimethanesulfonates.

Combining any one of the above embodiments results in further embodiments and the present invention relates to all possible combinations of the above embodiments and all possible combinations with the claims below.

Herein, the definition of compounds of formula I contains some provisos which have been designated provisos a) through g). These provisos are defined in claim 1 below.

In an embodiment of this invention, proviso a) is worded as follows: "a) when $R^1$ is a group of any of the formula II through VII; W is —N=; X, Y and Z is each a moiety of the general formula —C($R^2$)=; wherein $R^2$ is as defined above; then A cannot be optionally substituted imidazolyl."

In another embodiment of this invention, proviso a) is worded as follows: "a) when $R^X$ is a group of any of the formula II through VII; W is —N=; X, Y and Z is each a moiety of the general formula —C($R^2$)=; wherein $R^2$ is as defined above; then A cannot be optionally substituted heteroaryl."

In an embodiment of this invention, proviso b) is worded as follows: "b) when $R^1$ is a group of the formula VI; X is —C($R^2$)=; $R^{11}$ is $C_{1-8}$-alkyl, $C_{2-8}$-alkenyl, $C_{2-8}$-alkynyl, $C_{3-8}$-cycloalkyl, $C_{3-8}$-cycloalkenyl, $C_{3-8}$-cycloalkyl-$C_{1-3}$-alkyl or $C_{3-8}$-cycloalkenyl-$C_{1-3}$-alkyl; and W, Y, Z is each a moiety of the formula —C($R^2$)= or —N=; wherein $R^2$ is as defined above; then A can not be unsubstituted aryl or substituted heteroaryl, and, if A is substituted, then $R^{12}$ can not be halogen, hydroxy, halo-$C_{1-6}$-alkyl, halo-$C_{1-6}$-alkoxy, $C_{1-6}$-alkoxy, $C_{1-6}$-alkyl, $C_{1-6}$-alkylsulfonyl, cyano, aryl, heteroaryl, $C_{3-8}$-cycloalkyl or a group of the formula —V—$(CH_2)_s$—$(C=O)_r$—$NR^{13}R^{14}$, wherein V is a bond, r and s each is 0 (zero), and $R^{13}$ and $R^{14}$ each is hydrogen or $C_{1-6}$-alkyl."

In an embodiment of this invention, proviso c) is worded as follows: "c) when $R^1$ is a group of the formula VII; X is a moiety of the formula —C($R^2$)=; and W, Y, Z is each a moiety of the formula —C($R^2$)= or —N=; wherein $R^2$ is as defined above; then $R^{12}$ can not be halogen, hydroxy, halo-$C_{1-6}$-alkyl, halo-$C_{1-6}$-alkoxy, $C_{1-6}$-alkoxy, $C_{1-6}$-alkyl, $C_{1-6}$-alkylsulfonyl, cyano, aryl, heteroaryl, $C_{3-8}$-cycloalkyl or a group of the formula —V—$(CH_2)_s$—$(C=O)_r$—$NR^{13}R^{14}$, wherein V is a bond, r and s each is 0 (zero), and $R^{13}$ and $R^{14}$ each is hydrogen or $C_{1-6}$-alkyl."

In an embodiment of this invention, proviso d) is worded as follows: "d) when $R^1$ is a group of the formula VI; $R^{11}$ is $C_{1-8}$-alkyl; Y and Z is each —N=; X is a moiety of the formula —C($R^2$)=, and W is a moiety of the formula —C($R^2$)= or —N=; wherein $R^2$ is as defined above; then $R^{12}$ can not be halogen, hydroxy, halo-$C_{1-6}$-alkoxy, halo-$C_{1-6}$-alkoxy, $C_{1-6}$-alkoxy, $C_{1-6}$-alkyl, $C_{1-6}$-alkylsulfonyl, cyano, aryl, heteroaryl, $C_{3-8}$-cycloalkyl or a group of the formula —V—$(CH_2)_s$—$(C=O)_r$—$NR^{13}R^{14}$, wherein V is a bond, r and s each is 0 (zero), and $R^{13}$ and $R^{14}$ each is hydrogen or $C_{1-6}$-alkyl."

In an embodiment of this invention, proviso e) is worded as follows: "e) when $R^1$ is a group of the formula VII; Y and Z is each —N=; X is a moiety of the formula —C($R^2$)=; and W is a moiety of the formula —C($R^2$)= or —N=; wherein $R^2$ is as defined above; then $R^{12}$ can not be halogen, hydroxy, halo-$C_{1-6}$-alkyl, halo-$C_{1-6}$-alkoxy, $C_{1-6}$-alkoxy, $C_{1-6}$-alkyl, $C_{1-6}$-alkylsulfonyl, cyano, aryl, heteroaryl, $C_{3-8}$-cycloalkyl or a group of the formula —V—$(CH_2)_s$—$(C=O)_r$—$NR^{13}R^{14}$, wherein V is a bond, r and s each is 0 (zero), and $R^{13}$ and $R^{14}$ each is hydrogen or $C_{1-6}$-alkyl."

In an embodiment of this invention, proviso f) is worded as follows: "f) when $R^1$ is formula VI, q is 1, X and W is each a moiety of the general formula —C($R^2$)=, wherein $R^2$ is as defined above, Y and Z is each —N=, $R^{11}$ is $C_{1-8}$-alkyl, and A is phenyl, then $R^{12}$ can not be halogen, hydroxy, halo-$C_{1-6}$-alkoxy, $C_{1-6}$-alkoxy, $C_{1-6}$-alkyl, $C_{1-6}$-alkylsulfanyl, $C_{1-6}$-alkylsulfinyl, $C_{1-6}$-alkylsulfonyl, cyano, aryl, heteroaryl, $C_{3-8}$-cycloalkyl or a group of the formula —V—$(CH_2)_s$—$(C=O)_r$—$NR^{13}R^{14}$, wherein V is a bond, r and s each is 0 (zero), and $R^{13}$ and $R^{14}$ each is hydrogen or $C_{1-6}$-alkyl."

In an embodiment of this invention, proviso g) is worded as follows: "g) when X and Z is each —C($R^2$)=; and one or both of W and Y are —N=; then $R^1$ cannot be a group of the formula II."

In an embodiment of this invention, $R^1$ is different from possibility ii), formula VII, when the ring containing W, X, Y and Z is a pyridazine ring.

In an embodiment of this invention, $R^1$ is different from possibility i), when the ring containing W, X, Y and Z is a pyridazine ring.

In an embodiment of this invention, $R^1$ is different from possibility i), when the ring containing W, X, Y and Z is a pyrimidine ring.

In an embodiment of this invention, $R^1$ is different from possibility i), i.e. $R^1$ is possibility ii).

In an embodiment of this invention, $R^{11}$ is different from hydrogen.

In an embodiment of this invention, $R^{11}$ is different from methyl.

In an embodiment of this invention, $R^{11}$ is different from $C_{1-8}$-alkyl.

In an embodiment of this invention, $R^2$ is different from cyano.

In an embodiment of this invention, at least one of W, X, Y and Z is a moiety of the formula —C($R^2$)= wherein $R^2$ is as defined herein.

In an embodiment of this invention, $R^1$ is not a group of formula II when the ring containing W, X, Y and Z is a pyridazine ring.

In one embodiment of this invention, $R^1$ is different from possibility ii), formula II and III, when W and Y are each —N=; and X and Z are each —C($R^2$)=, wherein $R^2$ is as defined herein.

In one embodiment of this invention, $R^1$ is different from possibility ii), formula II wherein m is 2, n is 1 or 2, and Q is —O—, when W and Y are each —N=; and X and Z are each —C($R^2$)=, wherein $R^2$ is as defined herein.

In one embodiment of this invention, $R^1$ is different from possibility ii), formula III wherein p is 1, m is 2, o is 0 (zero), and —$NR^7R^8$ is heterocyclyl, when W and Y are each —N=; and X and Z are each —C($R^2$)=, wherein $R^2$ is as defined herein.

In one embodiment of this invention, $R^1$ is different from possibility ii), formula II and III, when W and Y are each —N=; and X and Z are each —C($R^2$)=, wherein $R^2$ is as defined herein, and when A is aryl or heteroaryl optionally substituted by halogen, hydroxy, cyano, $C_{1-6}$-alkyl, $C_{3-8}$-cycloalkyl, halo-$C_{1-6}$-alkyl, $C_{1-6}$-alkoxy, halo-$C_{1-6}$-alkoxy or —V—$(CH_2)_s$—$(C=O)_r$—$NR^{13}R^{14}$, wherein V, s, $R^{13}$ and $R^{14}$ are as defined herein.

The compounds of the present invention interact with the histamine H3 receptor and are accordingly particularly useful in the treatment of a variety of diseases or conditions in which histamine H3 interactions are beneficial.

In one aspect, the invention provides the use of a compound according to formula I in a pharmaceutical composition. The pharmaceutical composition may in another aspect of the invention comprise, as an active ingredient, at least one compound according to formula I together with one or more pharmaceutically acceptable carriers or excipients. In another aspect, the invention provides such a pharmaceutical composition in unit dosage form, comprising from about 0.05 mg to about 1000 mg, e.g., from about 0.1 mg to about 500 mg, such as from about 0.5 mg to about 200 mg of the compound according to formula I.

In another aspect, the invention provides the use of a compound of formula I as defined above for the preparation of a pharmaceutical composition for the treatment of diseases and disorders in which an inhibition of the H3 histamine receptor has a beneficial effect.

In another aspect, the invention provides the use of a compound of formula I for the preparation of a pharmaceutical composition having histamine H3 antagonistic activity or histamine H3 inverse agonistic activity.

In another aspect the invention provides the use of a compound of formula I for the preparation of a pharmaceutical composition for the reduction of weight.

In another aspect, the invention provides the use of a compound of formula I for the preparation of a pharmaceutical composition for the treatment of overweight or obesity.

In another aspect, the invention provides the use of a compound of formula I for the preparation of a pharmaceutical composition for the suppression of appetite or for satiety induction.

In another aspect, the invention provides the use of a compound of formula I for the preparation of a pharmaceutical composition for the prevention and/or treatment of disorders and diseases related to overweight or obesity, such as dyslipidaemia, coronary heart disease, gallbladder disease, osteoarthritis and various types of cancer such as endometrial, breast, prostate and colon cancers.

In another aspect, the invention provides the use of a compound of formula I for the preparation of a pharmaceutical composition for the prevention and/or treatment of eating disorders, such as bulimia or binge eating.

In another aspect, the invention provides the use of a compound of formula I for the preparation of a pharmaceutical composition for the treatment of IGT (Impaired glucose tolerance).

In another aspect, the invention provides the use of a compound of formula I for the preparation of a pharmaceutical composition for the treatment of type 2 diabetes.

In another aspect, the invention provides the use of a compound of formula I for the preparation of a pharmaceutical composition for the delaying or prevention of the progression from IGT to type 2 diabetes.

In another aspect, the invention provides the use of a compound of formula I for the preparation of a pharmaceutical composition for the delaying or prevention of the progression from non-insulin requiring type 2 diabetes to insulin requiring type 2 diabetes.

In another aspect, the invention provides the use of a compound of formula I for the preparation of a pharmaceutical composition for the treatment of diseases and disorders in which a stimulation of the H3 histamine receptor has a beneficial effect.

In another aspect, the invention provides the use of a compound of formula I for the preparation of a pharmaceutical composition having histamine H3 agonistic activity.

In another aspect, the invention provides the use of a compound of formula I for the preparation of a pharmaceutical composition for the treatment of allergic rhinitis, ulcer or anorexia.

In another aspect, the invention provides the use of a compound of formula I for the preparation of a pharmaceutical composition for the treatment of Alzheimer's disease, narcolepsy, attention deficit disorders or reduced wakefulness, or for the regulation of sleep.

In another aspect, the invention relates to the use of a compound of formula I for the preparation of a pharmaceutical preparation for the treatment of airway disorders, such as asthma, for regulation of gastric acid secretion, or for treatment of diarrhoea.

In another aspect, the invention provides a method for the treatment of disorders or diseases related to the H3 histamine receptor, the method comprising administering to a subject in need thereof an effective amount of a compound of the general formula I as defined above, or of a pharmaceutical composition comprising such a compound.

In another aspect, the invention provides a method as described above, wherein the effective amount of the compound of the general formula I as defined above is in the range of from about 0.05 mg to about 2000 mg, preferably from about 0.1 mg to about 1000 mg, and more preferably from about 0.5 mg to about 500 mg per day.

In one aspect, the invention relates to compounds which exhibit histamine H3 receptor antagonistic activity or inverse agonistic activity and which may accordingly be useful in the treatment of a wide range of conditions and disorders in which histamine H3 receptor blockade is beneficial.

In another aspect, the invention provides a method for reduction of weight, the method comprising administering to a subject in need thereof an effective amount of a compound of formula I as defined above.

In another aspect, the invention provides a method for treatment of overweight or obesity, the method comprising administering to a subject in need thereof an effective amount of a compound of formula I.

In another aspect, the invention provides a method for suppression of appetite or for satiety induction, the method comprising administering to a subject in need thereof an effective amount of a compound of formula I.

In another aspect, the invention provides a method for prevention and/or treatment of disorders or diseases related to overweight or obesity, such as dyslipidaemia, coronary heart disease, gallbladder disease, osteoarthritis and various types of cancer, e.g. endometrial, breast, prostate or colon cancer, the method comprising administering to a subject in need thereof an effective amount of a compound of formula I.

In another aspect, the invention provides a method for prevention and/or treatment of eating disorders, such as bulimia and binge eating, the method comprising administering to a subject in need thereof an effective amount of a compound of formula I.

In another aspect, the invention provides a method for the treatment of IGT (Impaired glucose tolerance), the method comprising administering to a subject in need thereof an effective amount of a compound of formula I.

In another aspect, the invention provides a method for the treatment of type 2 diabetes, the method comprising administering to a subject in need thereof an effective amount of a compound of formula I.

In another aspect, the invention provides a method for the delaying or prevention of the progression from IGT to type 2 diabetes, the method comprising administering to a subject in need thereof an effective amount of a compound of formula I.

In another aspect, the invention provides a method for the delaying or prevention of the progression from non-insulin requiring type 2 diabetes to insulin requiring type 2 diabetes, the method comprising administering to a subject in need thereof an effective amount of a compound of formula I.

In another aspect, the invention relates to compounds which exhibit histamine H3 receptor agonistic activity and which may accordingly be useful in the treatment of a wide range of conditions and disorders in which histamine H3 receptor activation is beneficial.

Compounds of the present invention may also be used for the treatment of airway disorders (such as asthma), as antidiarrhoeals, and for the modulation of gastric acid secretion.

Furthermore, compounds of the present invention may be used for the treatment of diseases associated with the regulation of sleep and wakefulness, and for the treatment of narcolepsy and attention deficit disorders.

Moreover, compounds of the invention may be used as CNS stimulants or as sedatives.

The present compounds may also be used for the treatment of conditions associated with epilepsy. Additionally, compounds of the invention may be used for the treatment of motion sickness and vertigo. Furthermore, they may be useful as regulators of hypothalamo-hypophyseal secretion, as antidepressants, as modulators of cerebral circulation, and in the treatment of irritable bowel syndrome.

Further, compounds of the present invention may be used for the treatment of dementia and Alzheimer's disease.

Compounds of the present invention may also be useful for the treatment of allergic rhinitis, ulcer or anorexia.

Compounds of the present invention may furthermore be useful for the treatment of migraine [see, e.g., McLeod et al., *The Journal of Pharmacology and Experimental Therapeutics* 287 (1998), 43-50] and for the treatment of myocardial infarction [see Mackins et al., *Expert Opinion on Investigational Drugs* 9 (2000), 2537-2542].

In a further aspect of the invention, treatment of a patient with a compound of the present invention is combined with diet and/or exercise.

In a further aspect of the invention, one or more compounds of the present invention is/are administered in combination with one or more further active substances in any suitable ratio(s). Such further active agents may, for example, be selected from antiobesity agents, antidiabetics, antidyslipidemic agents, antihypertensive agents, agents for the treatment of complications resulting from or associated with diabetes, and agents for the treatment of complications and disorders resulting from or associated with obesity.

Thus, in a further aspect of the invention one or more compounds of the present invention may be administered in combination with one or more antiobesity agents or appetite regulating agents. Such agents may, for example, be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, opioid antagonists (such as naltrexone), exendin-4, GLP-1 and ciliary neurotrophic factor.

In one embodiment of the invention, an antiobesity agent administered in combination with one or more compounds of the invention is leptin.

In another embodiment, such an antiobesity agent is dexamphetamine or amphetamine.

In another embodiment, such an antiobesity agent is fenfluramine or dexfenfluramine.

In still another embodiment, such an antiobesity agent is sibutramine.

In a further embodiment, such an antiobesity agent is orlistat.

In another embodiment, such an antiobesity agent is mazindol or phentermine.

In still another embodiment, such an antiobesity agent is phendimetrazine, diethylpropion, fluoxetine, bupropion, topiramate or ecopipam.

In yet a further aspect of the invention, one or more compounds of the present invention may be administered in combination with one or more antidiabetic agents. Relevant antidiabetic agents include insulin, insulin analogues and derivatives such as those disclosed in EP 0 792 290 (Novo Nordisk A/S), e.g. $N^{\epsilon B29}$-tetradecanoyl des (B30) human insulin, EP 0 214 826 and EP 0 705 275 (Novo Nordisk A/S), e.g. $Asp^{B28}$ human insulin, U.S. Pat. No. 5,504,188 (Eli Lilly), e.g. $LyS^{B28}$ $Pro^{B29}$ human insulin, EP 0 368 187 (Aventis), e.g. Lantus®, all of which are incorporated herein by reference, GLP-1 derivatives, such as those disclosed in WO 98/08871 (Novo Nordisk A/S), incorporated herein by reference, as well as orally active hypoglycaemic agents.

The orally active hypoglycaemic agents preferably comprise imidazolines, sulfonylureas, biguanides, meglitinides, oxadiazolidinediones, thiazolidinediones, insulin sensitizers, α-glucosidase inhibitors, agents acting on the ATP-dependent potassium channel of the β-cells, e.g. potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists, such as one of those disclosed in WO 99/01423 and WO 00/39088 (Novo Nordisk A/S and Agouron Pharmaceuticals, Inc.), both of which are incorporated herein by reference, GLP-1 agonists, such as those disclosed in WO 00/42026 (Novo Nordisk A/S and Agouron Pharmaceuticals, Inc.), incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention, one or more compounds of the present invention may be administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention, one or compounds of the present invention may be administered in combination with a sulfonylurea, e.g. tolbutamide, chlorpropamide, tolazamide, glibenclamide, glipizide, glimepiride, glicazide or glyburide.

In another embodiment of the invention, one or more compounds of the present invention may be administered in combination with a biguanide, e.g. metformin.

In yet another embodiment of the invention, one or more compounds of the present invention may be administered in combination with a meglitinide, e.g. repaglinide or nateglinide.

In still another embodiment of the invention, one or more compounds of the present invention may be administered in combination with a thiazolidinedione insulin sensitizer, e.g. troglitazone, ciglitazone, pioglitazone, rosiglitazone, isaglitazone, darglitazone, englitazone, CS-011/CI-1037 or T 174, or a compound disclosed in WO 97/41097, WO 97/41119, WO 97/41120, WO 00/41121 and WO 98/45292 (Dr. Reddy's Research Foundation), all of which are incorporated herein by reference.

In still another embodiment of the invention, one or more compounds of the present invention may be administered in combination with an insulin sensitizer, e.g. such as GI 262570, YM-440, MCC-555, JTT-501, AR-H039242, KRP-297, GW-409544, CRE-16336, AR-H049020, LY510929, MBX-102, CLX-0940, GW-501516, or a compound disclosed in WO 99/19313, WO 00/50414, WO 00/63191, WO 00/63192 or WO 00/63193 (Dr. Reddy's Research Foundation) or in WO 00/23425, WO 00/23415, WO 00/23451, WO 00/23445, WO 00/23417, WO 00/23416, WO 00/63153, WO 00/63196, WO 00/63209, WO 00/63190 or WO 00/63189 (Novo Nordisk A/S), all of which are incorporated herein by reference.

In a further embodiment of the invention, one or more compounds of the present invention may be administered in combination with an α-glucosidase inhibitor, e.g. voglibose, emiglitate, miglitol or acarbose.

In another embodiment of the invention, one or more compounds of the present invention may be administered in combination with an agent acting on the ATP-dependent potassium channel of the β-cells, e.g. tolbutamide, glibenclamide, glipizide, glicazide, BTS-67582 or repaglinide.

In yet another embodiment of the invention, one or more compounds of the present invention may be administered in combination with nateglinide.

In still another embodiment, one or more compounds of the present invention may be administered in combination with an antihyperlipidemic agent or antilipidemic agent, e.g. cholestyramine, colestipol, clofibrate, gemfibrozil, lovastatin, pravastatin, simvastatin, probucol or dextrothyroxine.

In still another embodiment of the invention, one or more compounds of the present invention may be administered in combination with an antilipidemic agent, e.g. cholestyramine, colestipol, clofibrate, gemfibrozil, lovastatin, pravastatin, simvastatin, probucol or dextrothyroxine.

In another aspect of the invention, one or more compounds of the present invention may be administered in combination with more than one of the above-mentioned compounds, e.g. in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, one or more compounds of the present invention may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

It should be understood that any suitable combination of compounds according to the invention with diet and/or exercise, one or more of the above-mentioned compounds and optionally one or more other active substances are considered to be within the scope of the present invention.

The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates which the present compounds are able to form.

The acid addition salts may be obtained as the direct products of compound synthesis. Alternatively, the free base may be dissolved in a suitable solvent containing the appropriate acid, and the salt isolated by evaporating the solvent or otherwise separating the salt and solvent.

Compounds of the present invention may form solvates with standard low molecular weight solvents using methods well known to the person skilled in the art. Such solvates are also to be understood as being within the scope of the present invention.

The invention also encompasses prodrugs of the present compounds which following administration undergo chemical conversion by metabolic processes before becoming active pharmacological substances. In general, such prodrugs will be functional derivatives of the present compounds which are readily convertible in vivo into the required compound of the formula I. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques, such as those disclosed in Remington: The Science and Practice of Pharmacy, 19$^{th}$ Edition, Gennaro, Ed., Mack Publishing Co., Easton, Pa., 1995. The pharmaceutical compositions may be specifically formulated for administration by any suitable route, such as the oral, rectal, nasal, pulmonary, topical (including buccal and sublingual), transdermal, intracisternal, intraperitoneal, vaginal or parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings, such as enteric coatings, or they can be formulated so as to provide controlled release of the active ingredient, such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also to be understood as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferably from about 0.05 to about 10 mg/kg body weight per day, administered in one or more doses, such as from 1 to 3 doses. The exact dosage will depend upon the frequency and mode of administration, the sex, age, weight and general condition of the subject treated, the nature and severity of the condition treated and any concomitant diseases to be treated, and other factors evident to those skilled in the art.

The formulations may conveniently be presented in unit dosage form by methods known to those skilled in the art. A typical unit dosage form for oral administration one or more times per day, such as from 1 to 3 times per day, may contain from 0.05 to about 1000 mg, preferably from about 0.1 to about 500 mg, and more preferably from about 0.5 mg to about 200 mg of a compound (or a salt or other derivative thereof as set forth above), according to the invention.

For parenteral routes, such as intravenous, intrathecal, intramuscular and similar administration, typical doses are of the order of about half the dose employed for oral administration.

The compounds of this invention are generally utilized as the free substance or as a pharmaceutically acceptable salt thereof. One example is an acid addition salt of a compound having a free base functionality. When a compound of the formula I contains a free base functionality, such salts are prepared in a conventional manner by treating a solution or suspension of the free base form of the compound of formula I with a chemical equivalent (acid-base equivalent) of a pharmaceutically acceptable acid. Representative examples of relevant inorganic and organic acids are mentioned above. Physiologically acceptable salts of a compound of the invention having a hydroxy group include the anion of said compound in combination with a suitable cation, such as sodium or ammonium ion.

For parenteral administration, solutions of the novel compounds of the formula I in sterile aqueous solution, aqueous propylene glycol or sesame or peanut oil may be employed. Such aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylenes or water. Similarly, the carrier or diluent may include any sustained release material known in the art, such as glyceryl monostearate or glyceryl distearate, alone or mixed with a wax. The pharmaceutical compositions formed by combining the novel compounds of the formula I and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier may vary widely, but will usually be from about 25 mg to about 1 g. If a liquid carrier is used, the preparation may be in the form of a syrup, emulsion, soft gelatine capsule or sterile injectable liquid, such as an aqueous or non-aqueous liquid suspension or solution.

A typical tablet, which may be prepared by conventional tabletting techniques, may in the core contain 5.0 mg of a compound of the invention, 67.8 mg of lactosum Ph. Eur., 31.4 mg of cellulose, microcrystalline (Avicel), 1.0 mg of Amberlite®IRP88 (i.e., Polacrillin potassium NF, tablet disintegrant, Rohm and Haas) and magnesii stearas Ph. Eur. q.s. with a coating of approximately 9 mg of hydroxypropyl methylcellulose and approximately 0.9 mg of Mywacett 9-40 T (being acylated monoglyceride used as plasticizer for film coating).

If desired, the pharmaceutical composition of this invention may comprise the compound of the formula I in combination with one or more further pharmacologically active substances, e.g., substances chosen among those described in the foregoing.

Briefly, the compounds of this invention can be prepared in a manner known per se or analogous with known processes.

Tests

The ability of the compounds to interact with the histamine H3 receptor can be determined by the following in vitro binding assay.

Binding Assay

The human H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM (GIBCO-BRL) with glutamax, 10% foetal calf serum, 1% penicillin/streptavidin and 1 mg/ml G 418 at 37° C. and 5% $CO_2$. Before harvesting, the confluent cells are rinsed with phosphate buffered saline (hereinafter designated PBS) and incubated with Versene (proteinase, GIBCO-BRL) for approximately 5 minutes. The cells are flushed with PBS and DMEM and the cell suspension collected in a tube and centrifuged for 5-10 minutes at 1500 rpm in a Heraeus Sepatech Megafuge 1.0. The pellet is resuspended in 10-20 volumes Hepes buffer (20 mM Hepes, 5 mM $MgCl_2$, pH 7.1 (KOH)) and homogenized for 10-20 seconds using an Ultra-Turrax homogenizer. The homogenate is centrifuged for 30 minutes at 23,000 g. The pellet is resuspended in 5-10 ml Hepes buffer, homogenized 5-10 seconds with the Ultra-Turrax and centrifuged for 10 minutes at 23,000 g. Following this centrifugation step, the membrane pellet is resuspended in 2-4 ml Hepes buffer, homogenized with a syringe or Teflon homogenizer, and the protein concentration determined. The membranes are diluted to a protein concentration of 1-5 mg/ml in Hepes buffer, aliquoted and kept at −80° C. until use.

Aliquots of the membrane suspension are incubated for 60 minutes at 25° C. with 30 μM [$^{125}$I]-iodoproxifan, a known compound with high affinity for the H3 receptor, and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analysed by nonlinear regression analysis.

When tested, the present compounds of the formula (I) generally show a high binding affinity to the histamine H3 receptor.

Preferably, the compounds according to the invention have an $IC_{50}$ value as determined by one or more of the assays of less than 10 μM, more preferred of less than 1 μM, and even more preferred of less than 500 nM, such as of less than 100 nM.

Functional Assay I

The ability of the compounds to interact with the histamine H3 receptor as agonists, inverse agonists and/or antagonists, is determined by an in vitro functional assay utilizing membranes from HEK 293 cells expressing the human H3 receptors.

The H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM with glutamax, 10% foetal calf serum, 1% penicillin/streptavidin and 1 mg/ml G 418 at 37° C. and 5% $CO_2$.

The H3 receptor expressing cells are washed once with PBS and harvested using versene (GIBCO-BRL). PBS is added and the cells are centrifuged for 5 minutes at 188 g. The cell pellet is resuspended in stimulation buffer to a concentration of $1 \times 10^6$ cells/ml. cAMP accumulation is measured using the Flash Plate" cAMP assay (NEN™ Life Science Products). The assay is generally performed as described by the manufacturer. Briefly, 50 μl cell suspension is added to each well of the Flashplate which also contained 25 μl 40 μM isoprenaline, to stimulate cAMP generation, and 25 μl of test compound (either agonists or inverse agonists alone, or agonist and antagonist in combination). The assay can be run in "agonist-mode" which means that the test compound is added, in increasing concentration, on its own, to the cells, and cAMP is measured. If cAMP goes up, it is an inverse agonist; if cAMP does not change, it is a neutral antagonist, and if cAMP goes down, it is an agonist. The assay can also be run in the "antagonist-mode" which means that a test compound is added, in increasing concentrations, together with increasing concentrations of a known H3 agonist (e.g. RAMHA). If the compound is an antagonist, increasing concentrations of it cause a right-ward shift in the H3-agonist's dose-response curves. The final volume in each well is 100 μl. Test compounds are dissolved in DMSO and diluted in water. The mixture is shaken for 5 minutes, and allowed to stand for 25 minutes at room temperature. The reaction is stopped with 100 μl "Detection Mix" per well. The plates are then sealed with plastic, shaken for 30 minutes, allowed to stand overnight, and finally the radioactivity is counted in the Cobra II auto gamma topcounter. $EC_{50}$ values are calculated by non-linear regression analysis of dose response curves (6 points minimum) using GraphPad Prism. Kb values are calculated by Schild plot analysis.

Preferably, the antagonists and agonists according to the invention have an $IC_{50}/EC_{50}$ value of less than 10 µM, more preferred of less than 1 µM, and even more preferred of less than 500 nM, such as of less than 100 nM.

Functional Assay II

The ability of the compounds to bind and interact with the human H3 receptor as agonists, inverse agonists and/or antagonists, is determined by a functional assay, named [$^{35}$S] GTPγS assay. The assay measures the activation of G proteins by catalyzing the exchange of guanosine 5'-diphosphate (hereinafter designated GDP) by guanosine 5'-triphosphate (hereinafter designated GTP) at the α-subunit. The GTP-bounded G proteins dissociate into two subunits, $G_{GTP}$ and G, which in turn regulate intracellular enzymes and ion channels. GTP is rapidly hydrolysed by the G-subunit (GTPases) and the G protein is deactivated and ready for a new GTP exchange cycle. To study the function of ligand induced G protein coupled receptor (GPCR) activation by an increase in guanine nucleotide exchange at the G proteins, the binding of [$^{35}$S]-guanosine-5'-O-(3-thio) triphosphate (hereinafter designated [$^{35}$S] GTP S), a non-hydrolysed analogue of GTP, is determined. This process can be monitored in vitro by incubating cell membranes containing the G protein coupled receptor H3 with GDP and [$^{35}$S] GTPγS. Cell membranes are obtained from CHO cells stably expressing the human H3 receptor. The cells are washed twice in PBS, harvested with PBS+1 mM EDTA, pH 7.4 and centrifuged at 1000 rpm for 5 minutes. The cell pellet is homogenized in 10 ml ice-cold Hepes buffer (20 mM Hepes, 10 mM EDTA, pH 7.4 (NaOH)) using an Ultra-Turrax homogenizer for 30 seconds and centrifuged for 15 minutes at 20,000 rpm. Following this centrifugation step, the membrane pellet is resuspended in 10 ml ice-cold Hepes buffer (20 mM Hepes, 0.1 mM EDTA, pH 7.4 (NaOH)) and homogenized as describe above. This procedure is repeated twice except for the last homogenization step, the protein concentration is determined and membranes are diluted to a protein concentration at 2 mg/ml, aliquoted and kept at −80° C. until use.

In order to study the presence and the potency of an inverse agonist/antagonist, the H3-receptor agonist ligand R-α-methyl histamine (hereinafter designated RAMHA) is added. The ability of the test compound to counteract the effect of RAMHA is measured. When studying the effect of an agonist, RAMHA is not added to the assay medium. The test compound is diluted in the assay buffer (20 mM HEPES, 120 mM NaCl, 10 mM $MgCl_2$ pH 7.4 (NaOH)) at various concentrations followed by addition of $10^{-8}$ nM RAMHA (only in the case where an inverse agonist/antagonist is examined), 3 µM GDP, 2.5 µg membranes, 0.5 mg SPA beads and 0.1 nM [$^{35}$S] GTPγS and incubated for 2 hours by slightly shaking at room temperature. The plates are centrifuged at 1500 rpm for 10 minutes and the radioactivity is measured using a Topcounter. The results are analyzed by non linear regression and the $IC_{50}$ value is determined.

RAMHA and other H3 agonists stimulate the binding of [$^{35}$S] GTPγS to membranes expressing the H3 receptor. In the antagonist/inverse agonist test, the ability of increasing amounts of test compound to inhibit the increased [$^{35}$S] GTPγS binding by $10^{-8}$ M RAMHA is measured as a decrease in radioactivity signal. The $IC_{50}$ value determined for an antagonist is the ability of this compound to inhibit the effect of $10^{-8}$ M RAMHA by 50%. In the agonist test, the ability of increasing amounts of test compound is measured as an increase in radioactivity signal. The $EC_{50}$ value determined for an agonist, is the ability of this compound to increase the signal by 50% of the maximal signal that is obtained by $10^{-5}$ M RAMHA.

Preferably, the antagonists and agonists according to the invention have an $IC_{50}/EC_{50}$ value of less than 10 µM, more preferred of less than 1 µM, and even more preferred of less than 500 nM, such as of less than 100 nM.

Test of Food Intake Inhibition

In this type of test rats are acclimatized to the experimental environment for 1-2 weeks before the start of experiments. About 7-10 days before recording of food intake access to food is restricted to 5-7 hours per day. Water remains freely available. On the test day, groups (n=10) of animals receive single administrations of histamine H3 receptor antagonists shortly before presentation of food. After this, food consumption is recorded for 3 h. Preferred compounds are those that produce a statistically significant reduction of 3-hour cumulated food intake. More preferred compounds are those that decrease 3-hour cumulated food intake with 10-20% and the most preferred compounds reduce 3-cumulated food intake with more than 20% without sedation of the animals.

Test of Body Weight Reduction

This test is carried out in rats that have become obese due to over-consumption of dietary energy, i.e. a sustained positive energy balance. Animals are being exposed to the test compound for 7 days. Preferred compounds are those that produce a statistically significant decrease of body weigh compared with control rats given vehicle. More preferred compounds are those that produce a weight reduction of at least 4%, compared with the vehicle control group, and the most preferred compounds are those that reduce body weight with more than 8% compared with vehicle control rats.

General Comments

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability and/or enforceability of such patent documents. The mentioning herein of references is no admission that they constitute prior art.

Herein, the word "comprise" is to be interpreted broadly meaning "include", "contain" or "comprehend" (EPO guidelines C 4.13).

This invention includes all modifications and equivalents of the subject matter recited in the claims appended hereto as permitted by applicable law.

General Experimental Procedures

NMR spectra were recorded at 300 and 400 MHz on a Bruker DRX300, Avance 300, DRX400 or AV400 instrument equipped with 5 mm selective-inverse (SEI, $^1$H and $^{13}$C), 5 mm broad-band inverse (BBI, $^1$H, broad-band) and 5 mm quadro nuclear (QNP, $^1$H, $^{13}$C) probeheads, respectively. Shifts (δ) are given in parts per million (ppm) down field from tetramethylsilane as internal reference standard.

HPLC Method A. The RP-analyses was performed on a Merck-Hitachi series 7000 system (Merck-Hitachi pump L-7100 and Merck-Hitachi autosampler L-7200 or Rheodyne sample injector) using a Hibar™ RT250-4, Lichrosorb™ RP-18, 5.0 µm, 4.0×250 mm; gradient elution, 20% to 80% solvent B (0.1% TFA in acetonitrile) in solvent A (0.1% TFA in water) within 30 min, 1.0 ml/min, detection at 210 nm, temperature 30° C.

HPLC Method B. The RP-purification was performed on a Gilson system (3 Gilson 306 pumps, Gilson 170 DAD detector and a Gilson 215 liquid handler) using a Waters XTerra® Prep RP$_{18}$ (10 µm, 30 mm×150 mm) with gradient elution, 5% to 95% solvent B (acetonitrile) in solvent A (0.05% TFA in water) within 15 min, 40 mL/min, detection at 210 nm, temperature rt. The pooled fractions are either evaporated to dryness in vacuo, or evaporated in vacuo until the acetonitrile is removed, and then frozen and freeze dried.

HPLC Method C. The RP-analyses was performed on a Shimadzu LC-20 using a YMC-ODS, 5.0 µm, 4.6×50 mm; gradient elution, 0% to 30% solvent B (0.1% TFA in acetonitrile) in solvent A (0.1% TFA in water) within 6 min, and then kept for 2 min, 2.5 mL/min, detection at 220 nm, temperature 30° C.

HPLC Method D. The RP-analyses was performed on a Shimadzu LC-20 using a YMC-ODS, 5.0 µm, 4.6×50 mm; gradient elution, 0% to 60% solvent B (0.1% TFA in acetonitrile) in solvent A (0.1% TFA in water) within 8 min, and then kept for 2 min, 2.5 mL/min, detection at 220 nm, temperature 30° C.

HPLC Method E. The RP-analyses was performed on a Shimadzu using a YMC-ODS, 5.0 µm, 4.6×50 mm; gradient elution, 10% to 80% solvent B (0.1% TFA in acetonitrile) in solvent A (0.1% TFA in water) within 6 min, and then kept for 2 min, 2.5 mL/min, detection at 220 nm, temperature 30° C.

HPLC Method F. The RP-purification was performed on a Gilson Nebula Series system using a Luna, 5 µm, 21.2 mm×250 mm with gradient elution, 5% to 30% solvent B (0.1% TFA in acetonitrile) in solvent A (0.1% TFA in water) within 15 min, 80 mL/min, detection at 220 nm, temperature 25° C., injection volume 30 mL. The pooled fractions were evaporated in vacuo until acetonitrile was removed, and then frozen and dried.

HPLC-MS Method G. Column: Waters Xterra MS C-18×3 mm id. Buffer: Linear gradient 5%-95% in 4 min, acetonitrile, 0.01% TFA, flow rate 1.0 ml/min. Detection 210 nm (analog output from diode array detector), MS-detection ionisation mode API-ES, scan 100-1000 amu step 0.1 amu.

Microwave Synthesis. When microwave oven synthesis was applied, the reaction was heated by microwave irradiation in sealed microwave vessels in a single mode Emrys Optimizer EXP from PersonalChemistry®.

The examples below and the general procedures described herein refer to intermediate compounds and final products for general formula I identified in the specification and in the synthesis schemes. The preparation of the compounds of general formula I of the present invention is described in detail using the following examples. Occasionally, the reaction may not be applicable as described to each compound included within the disclosed scope of the invention. The compounds for which this occurs will be readily recognised by those skilled in the art. In these cases, the reactions can be successfully performed by conventional modifications known to those skilled in the art which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may be prepared by a person skilled in the art in analogy with the preparation of similar known compounds or by the General Procedures A through N described herein. The following examples are offered by way of illustration, not by limitation.

General Procedure A

Compounds of the formula I, wherein Y and/or W is —N═, and A, X, Z, and R$^1$ each is as defined for formula I, which compounds here are designated formula Ia, can be prepared as outlined below:

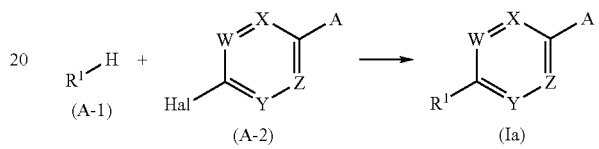

An amine of formula A-1, wherein R$^1$ is as defined herein, may be reacted with a halogen substituted heteroaryl of the formula A-2 wherein A, X, Y, Z, and W each is as defined herein, and Hal represents chlorine or bromine, to give a compound of formula Ia. This reaction may be carried out in a suitable solvent like, for example, dimethylsulfoxide, at a temperature of up to reflux. Compounds of formula A-2 may be prepared according to known procedures described in, for example, WO 03/066604A2, *Tetrahedron* 2000, 56, 9655-9662, and *Tetrahedron Lett.* 2001, 42, 2779-2781.

General Procedure B

Compounds of the formula I, wherein A is aryl or heteroaryl optionally substituted with R—(C═O)NHCH$_2$—, and X, Y, Z, W, and R$^1$ each is as defined for formula I, which compounds here are designated formula Ib, can be prepared as outlined below:

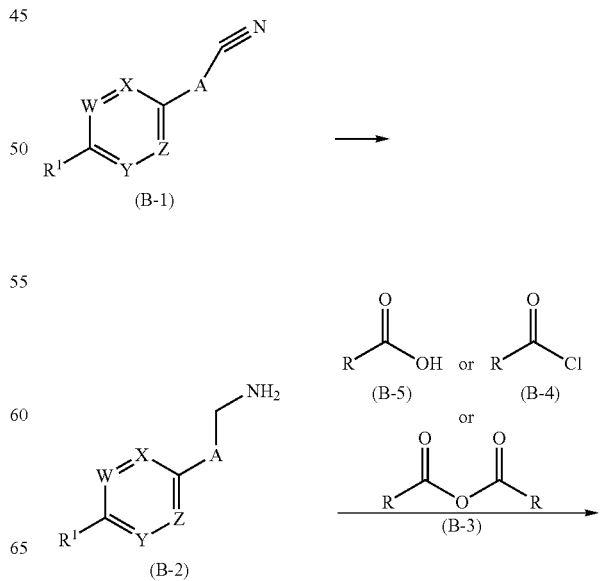

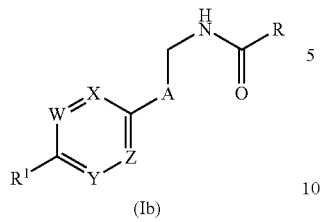

(Ib)

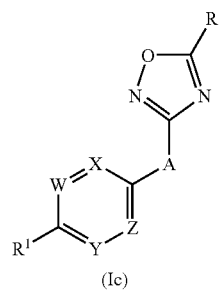

(Ic)

An amine of formula B-2, wherein X, Y, Z, W and $R^1$ each is as defined herein, and A represents an aryl or heteroaryl group, may be acylated with an activated carboxylic acid derivative to give a compound of formula Ib. Such an activated carboxylic acid derivative can be a carboxylic acid chloride or anhydride of formula B-4 or B-3, respectively. This reaction may be carried out in a suitable solvent like, for example, dichloromethane or acetic acid, at a temperature of up to reflux. A carboxylic acid of formula B-5 may also be reacted with an amine of formula B-2 to give an amide of formula Ib. This reaction may be carried out by activation of the carboxylic acid with, for example, HOBt/EDAC in a suitable solvent like, for example, THF and at a temperature of up to reflux. Compounds of formula B-2 may be prepared by hydrogenation of a nitril of formula B-1, wherein X, Y, Z, W and $R^1$ is as defined herein, and A represents an aryl or heteroaryl group. This reaction may be carried out in a suitable solvent like, for example, THF, at a temperature of up to reflux in the presence of a reducing agent like, e.g., $LiAlH_4$. Compounds of formula B-1 may be may be prepared according to other General Procedure(s) described herein.

General Procedure C

Compounds of the formula I, wherein A is aryl or heteroaryl, and X, Y, Z, W, and $R^1$ each is as defined for formula I, which compounds here are designated formula Ic, can be prepared as outlined below:

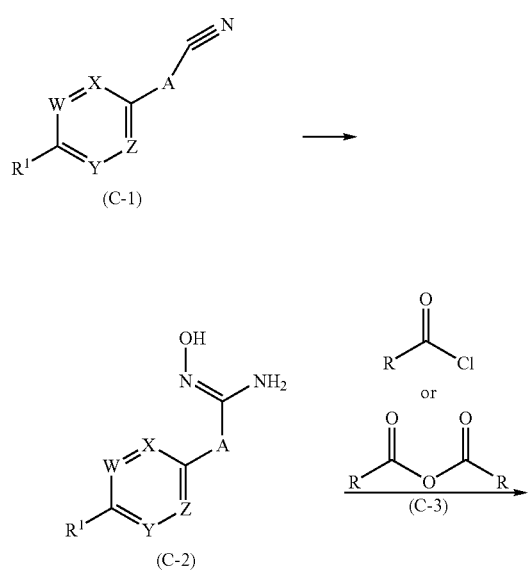

A hydroxyamidine of formula C-2, wherein X, Y, Z, W and $R^1$ each is as defined herein, and A represents an aryl or heteroaryl group, may be reacted with a carboxylic acid chloride or anhydride of formula C-3 to give a compound of formula Ic. This reaction may be carried out in a suitable solvent like, e.g., N,N-dimethylacetamide or acetic acid, at a temperature of up to reflux. Compounds of formula C-2 may be prepared by reaction of a nitril of formula C-1, wherein X, Y, Z, W and $R^1$ is as defined herein, and A represents an aryl or heteroaryl group, with hydroxylamine. This reaction may be carried out in a suitable solvent like, for example, ethanol and water, at a temperature of up to reflux in the presence of a base like, for example, potassium carbonate. Compounds of formula C-1 may be may be prepared according to other General Procedure(s) described herein.

General Procedure D

Compounds of the formula I, wherein X, Y, Z, W, and $R^1$ each is as defined for formula I, which compounds here are designated formula Id, can be prepared as outlined below:

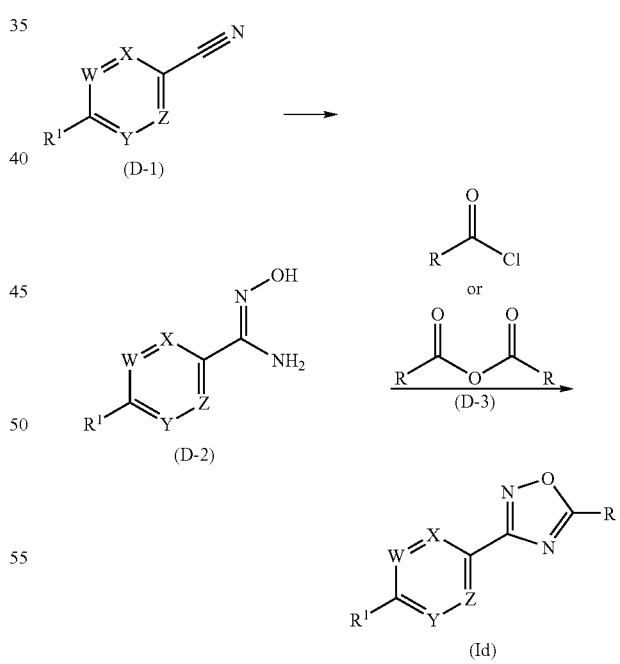

(Id)

A hydroxyamidine of formula D-2, wherein X, Y, Z, W and $R^1$ is as defined herein, may be reacted with a carboxylic acid chloride or anhydride of formula D-3 to give a compound of formula Id. This reaction may be carried out in a suitable solvent like, for example, N,N-dimethylacetamide or acetic acid, at a temperature of up to reflux. Compounds of formula D-2 may be prepared by reaction of a nitril of formula D-1, wherein X, Y, Z, W and R¹ each is as defined herein, with hydroxylamine. This reaction may be carried out in a suitable solvent like, for example, ethanol and water, at a temperature of up to reflux in the presence of a base like, for example, potassium carbonate.

General Procedure E

Compounds of the formula I, wherein X, Y, Z, W, and R¹ are as defined for formula I, which compounds here are designated formula Ie, can be prepared as outlined below:

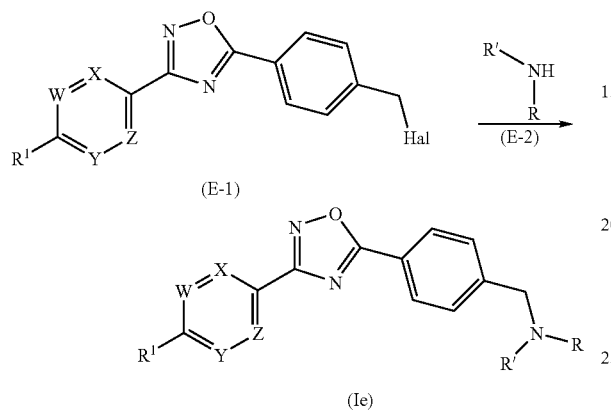

A benzylhalogenide of formula E-1, wherein X, Y, Z, W and R¹ each is as defined herein, and Hal represents chlorine, bromine or iodine, may be reacted with an amine of formula E-2 to give a compound of formula Ie. This reaction may be carried out in a suitable solvent like, for example, ethanol, at a temperature of up to reflux and in the presence of a base like, for example, triethylamine, or excess of the amine of formula E-2. Compounds of formula E-1 may be prepared according to the General Procedure D described above.

General Procedure F

Compounds of the formula I, wherein R¹¹ is represented by R¹¹ᵃ—CH—R¹¹ᵇ, and q, A, X, Y, W and Z each is as defined for formula I, which compounds here are designated formula If, can be prepared as outlined below:

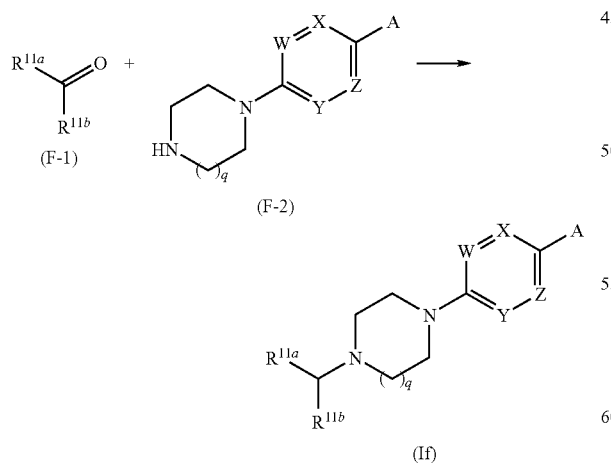

A carbonyl compound of formula F-1, wherein R¹¹ᵃ and R¹¹ᵇ each is as defined herein, may be reacted with an amine of the formula F-2, wherein q, A, X, Y, Z, and W are as defined herein, in the presence of a reducing agent, to give a compound of formula If. This reaction may be carried out in a suitable solvent like, for example, tetrahydrofuran or 1,2-dichloroethane, at a temperature of up to reflux. The reducing agent may be, for example, NaCNBH₃ or NaBH(OAc)₃, eventually in the presence of a acidic catalyst like, for example, acetic acid. Compounds of formula F-2 may be may be prepared according to other General Procedure(s) described herein.

General Procedure G

Compounds of the formula I, wherein A is aryl or heteroaryl optionally substituted with a group of the general formula R—(C=O)—, and R, X, Y, Z, W, and R¹ each is as defined formula I, which compounds here are designated formula Ig, can be prepared as outlined below:

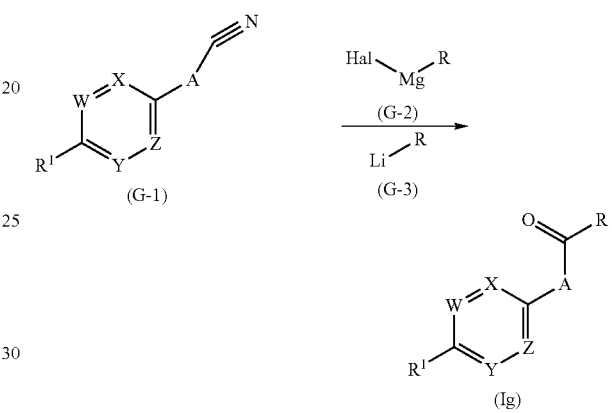

A cyano compound of formula G-1, wherein X, Y, Z, W and R¹ is as defined herein, and A represents an aryl or heteroaryl group, may be reacted with a organometallic compound of formula G-2 or G-3, followed by acidic hydrolysis with, for example, aqueous hydrochloric acid, to give a compound of formula Ig. This reaction may be carried out in a suitable solvent like, for example, tetrahydrofuran or tetrahydrofuran/toluene, at a temperature of up to reflux. Compounds of formula G-1 may be may be prepared according to other General Procedure(s) described herein.

General Procedure H

Compounds of the formula I, wherein R¹¹, q, A, X, Y, W and Z are as defined for formula I, which compounds here are designated formula Ih, can be prepared as outlined below:

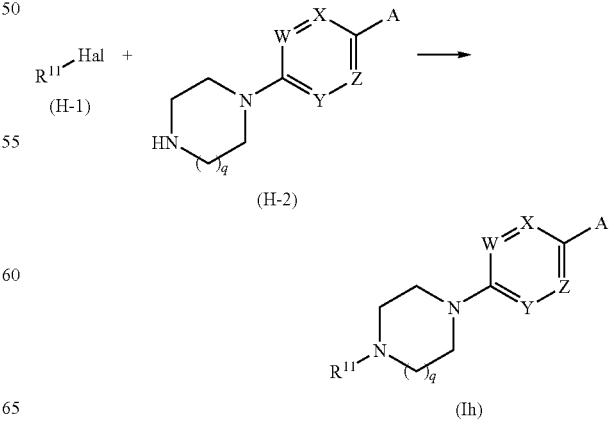

A compound of formula H-1, wherein Hal represents chlorine, bromine or iodine, may be reacted with an amine of the formula H-2, wherein q, A, X, Y, Z, and W are as defined herein, to give a compound of formula Ih. This reaction may be carried out in a suitable solvent like, for example, dimethylformamide, dimethylsulfoxide, acetonitril or 2-butanone, at a temperature of up to reflux. The reaction may be carried out in the presence of a base such as, for example, sodium hydride, potassium carbonate or N,N-diisopropylethylamine, and a catalyst like, for example, potassium iodide. Compounds of formula H-2 may be may be prepared according to other General Procedure(s) described herein.

General Procedure I

Compounds of the formula I, wherein A, X, Y, W, Z and $R^1$ each is as defined for formula I, which compounds here are designated formula Ii, can be prepared as outlined below:

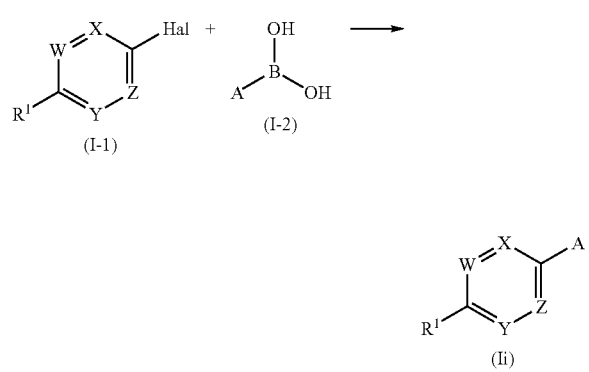

A compound of formula I-1, wherein X, Y, W, Z and $R^1$ each is as defined herein, and Hal represents chlorine, bromine or iodine, may be reacted with a boronic acid derivative of the formula I-2, or a corresponding boronic acid ester derivative, wherein A is as defined herein, to give a compound of formula Ii. This reaction may be carried out in a suitable solvent like, for example, acetonitrile/water, at a temperature of up to 150° C. in the presence of a suitable catalyst like, for example, bistriphenylphosphinpalladium(II)dichloride and sodium carbonate. This reaction may also be performed in the other way round starting from reactants wherein the halogen and boronic acid moieties have been interchanged. This reaction may be carried out under similar conditions as described above.

General Procedure J

Compounds of the formula I, wherein A is aryl or heteroaryl optionally substituted with —C(=O)—NR'R, and X, Y, Z, W, and $R^1$ each is as defined for formula I, which compounds here are designated formula Ij, can be prepared as outlined below:

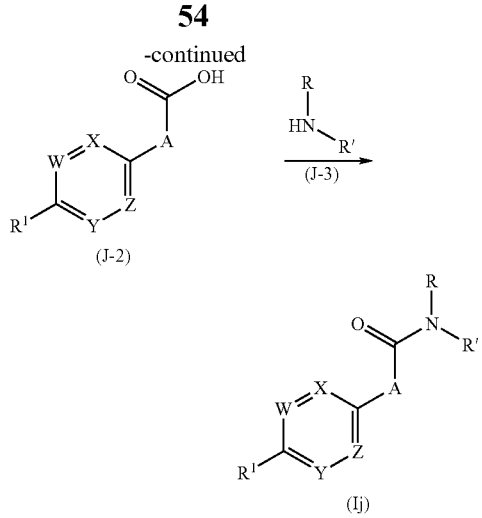

A carboxylic acid of formula J-2, wherein A, X, Y, Z, W, and $R^1$ each is as defined herein, may be reacted with an amine of formula R'RNH to give an amide of formula Ij. This reaction may be carried out by activation of the carboxylic acid with, for example, HOBt/EDAC in a suitable solvent like, for example, THF and at a temperature of up to reflux. A carboxylic acid of formula J-2 may be prepared by hydrolysis of a nitrile of formula J-1, wherein A, X, Y, Z, W, and $R^1$ each is as defined herein. This reaction may be carried out under strong acidic conditions, for example, in 6 N hydrochloric acid at a temperature of up to reflux. Compounds of formula J-1 may be prepared according to other General Procedure(s) described herein.

General Procedure K

Compounds of the formula I, wherein A is aryl or heteroaryl optionally substituted with —CH$_2$—NR'R, and X, Y, Z, W, and $R^1$ each is as defined for formula I, which compounds here are designated formula Ik, can be prepared as outlined below:

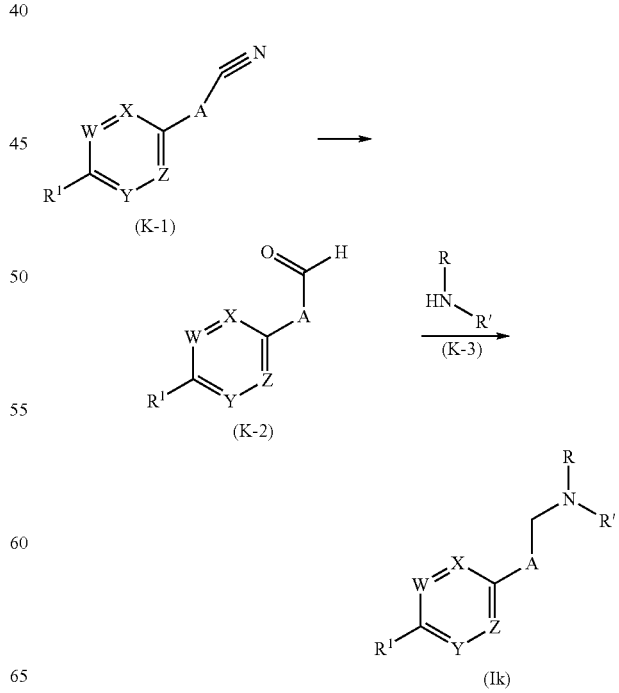

A carboxaldehyde of formula K-2, wherein A, X, Y, Z, W, and $R^1$ each is as defined herein, may be reacted with an amine of formula R'RNH under reducing conditions to give an amine of formula Ik. This reaction may be carried out in a suitable solvent like, for example, tetrahydrofuran or 1,2-dichloroethane, at a temperature of up to reflux. The reducing agent may be, for example, $NaCNBH_3$ or $NaBH(OAc)_3$, eventually in the presence of a acidic catalyst like, for example, acetic acid. A carboxaldehyde of formula K-2 may be prepared from a nitrile of formula K-1, wherein A, X, Y, Z, W, and $R^1$ each is as defined herein. This reaction may be carried out in the presence of a reducing agent, for example, DIBAL-H or $LiAlH_4$ in a suitable solvent, for example, THF at a temperature from $-40°$ C. up to reflux. Compounds of formula K-1 may be prepared according to other General Procedure(s) described herein.

General Procedure L

Compounds of the formula I, wherein A is aryl or heteroaryl optionally substituted with R—C(=O)NH—, and X, Y, Z, W, and $R^1$ each is as defined for formula I, which compounds here are designated formula Il, can be prepared as outlined below:

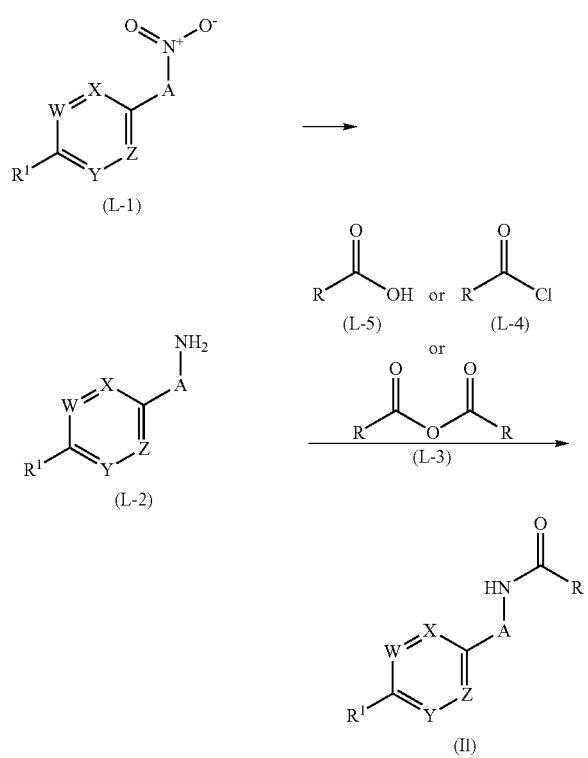

An aromatic amine of formula L-2, wherein X, Y, Z, W and $R^1$ each is as defined herein, and A represents an aryl or heteroaryl group, may be acylated with an activated carboxylic acid derivative to give a compound of formula Il. Such an activated carboxylic acid derivative can be a carboxylic acid chloride or anhydride of formula L-4 or L-3, respectively. This reaction may be carried out in a suitable solvent like, for example, dichloromethane or acetic acid, at a temperature of up to reflux. A carboxylic acid of formula L-5 may also be reacted with an amine of formula L-2 to give an amide of formula Il. This reaction may be carried out by activation of the carboxylic acid with, for example, HOBt/EDAC in a suitable solvent like, for example, THF and at a temperature of up to reflux. Compounds of formula L-2 may be prepared by hydrogenation of a nitro compound of formula L-1, wherein X, Y, Z, W and $R^1$ is as defined herein, and A represents an aryl or heteroaryl group. This reaction may be carried out in a suitable solvent like, for example, ethanol and/or water, at a temperature of up to reflux in the presence of a reducing agent, for example, Fe powder. Other reducing conditions may be hydrogenation with hydrogen gas in the presence a suitable catalyst, for example, Pd/C at a pressure up to 3000 psi. Compounds of formula L-1 may be may be prepared according to other General Procedure(s) described herein.

General Procedure M

Compounds of the formula I, wherein A is aryl or heteroaryl optionally substituted with R—$(CH)_2$—O—, and X, Y, Z, W, and $R^1$ each is as defined for formula I, which compounds here are designated formula Im, can be prepared as outlined below:

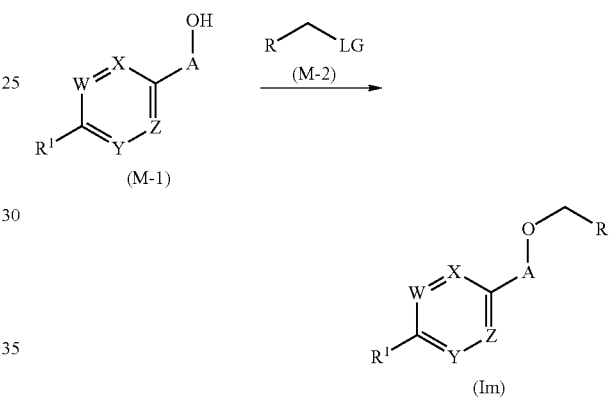

An aromatic alcohol of formula M-1, wherein X, Y, Z, W and $R^1$ each is as defined herein, and A represents an aryl or heteroaryl group, may be alkylated with a compound of formula M-2, wherein LG represents a suitable leaving group such as, for example, halogen or mesylate. This reaction may be carried out in a suitable solvent like, for example, DMF, at a temperature of up to reflux and in the presence of a base like, for example, sodium hydride. Compounds of formula M-1 may be may be prepared according to other General Procedure(s) described herein.

General Procedure N

Compounds of the formula I, wherein A is aryl or heteroaryl optionally substituted with a cyclic sulphonamide and wherein p is 1-4, and X, Y, Z, W, and $R^1$ each is as defined for formula I, which compounds here are designated formula In, can be prepared as outlined below:

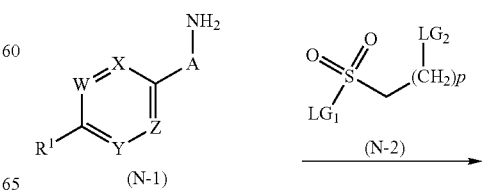

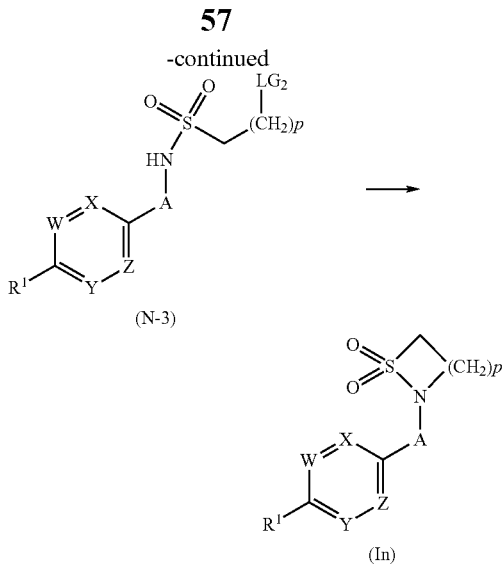

(N-3)

(In)

An aromatic amine of formula N-1, wherein X, Y, Z, W and $R^1$ each is as defined herein, and A represents an aryl or heteroaryl group, may be reacted with an activated sulfonic acid of formula N-2, wherein p is 1-4 and $LG_1$ and $LG_2$ represents suitable leaving groups such as, for example, halogen, to give a compound of formula N-3. This reaction may be carried out in a suitable solvent like, for example, DMF, at a temperature of up to reflux and in the presence of a base like, for example, TEA. A compound of formula N-3 may be ring-closed to give a compound of formula In. This reaction may be carried out in a suitable solvent like, for example, DMF, at a temperature of up to reflux and in the presence of a base like, for example, NaH. Compounds of formula N-1 may be may be prepared according to other General Procedure(s) described herein.

EXAMPLE 1

General Procedure A

1-[5-(4-Chlorophenyl)pyridin-2-yl]-4-isopropylpiperazine, dihydrochloride

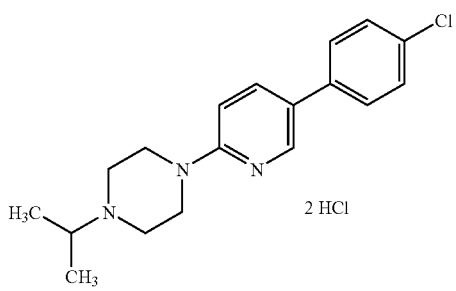 [SMILES: CC(C)N1CCN(c2ccc(-c3ccc(Cl)cc3)cn2)CC1 ; "2 HCl"]

A mixture of 2-chloro-5-(4-chlorophenyl)pyridine (500 mg, 2.23 mmol), DMSO (2.0 mL) and 1-isopropylpiperazine (3 mL, 23.4 mmol) was stirred and heated on a 100° C. oil-bath overnight. The reaction mixture was poured into water (75 mL), and the solid was isolated by filtration, washed with water and dried. The crude product was purified by column chromatography on silica gel (Kiselgel 60, mesh 0.040-0.63) eluting with a mixture of ethyl acetate and methanol (4:1). Collecting the proper fractions afforded 600 mg (85%) of 1-[5-(4-chlorophenyl)pyridin-2-yl]-4-isopropylpiperazine.

$^1$H NMR (300 MHz, CDCl$_3$) δ 1.10 (d, 6H), 2.63-2.68 (m, 4H), 2.75 (hept, 1H), 3.59-3.66 (m, 4H), 6.69 (d, 1H), 7.35-7.45 (m, 4H), 7.67 (dd, 1H), 8.40 (d, 1H).

The free base was dissolved into a mixture of a 0.5 N hydrochloric acid solution and ethanol. When dissolved, the mixture was evaporated and then re-evaporated with ethanol. The solid residue was recrystallized from ethanol (50 mL) to give 740 mg (81%) of 1-[5-(4-chlorophenyl)pyridin-2-yl]-4-isopropylpiperazine, dihydrochloride.

$^1$H NMR (300 MHz, DMSO-d$_6$) δ 1.32 (d, 6H), 3.05-3.22 (m, 2H), 3.45-3.67 (m, 5H), 4.49-4.61 (m, 2H), 4.9 (brs, 6H), 7.23-7.31 (m, 1H), 7.52 (d, 2H), 7.73 (d, 2H), 8.13-8.19 (m, 1H), 8.42-8.46 (m, 1H), 11.4 (brs, 1H).

Microanalysis for $C_{18}H_{22}ClN_3$, 2×HCl, 2.5×H$_2$O:

Calculated: C, 49.84%; H, 6.74%; N, 9.69%.

Found: C, 49.82%; H, 6.66%, N, 9.36%.

EXAMPLE 2

General Procedure A

1-Isopropyl-4-[5-(4-methoxyphenyl)pyridin-2-yl]piperazine, dihydrochloride

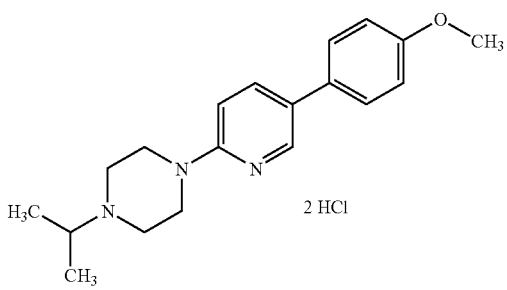 [SMILES: COc1ccc(-c2ccc(N3CCN(C(C)C)CC3)nc2)cc1 ; "2 HCl"]

A mixture of 2-chloro-5-(4-methoxyphenyl)pyridine (200 mg, 0.91 mmol), dry DMSO (2.0 mL) and 1-isopropylpiperazine (500 mg, 3.9 mmol) was stirred and heated on a 130° C. oil-bath overnight, then at 150° C. for 4 h, left 2 days at rt and finally heated at 140° C. overnight. The reaction mixture was allowed to cool and then poured into water (100 mL). The mixture was extracted with ethyl acetate (100 mL), and the organic extract was washed with water and dried (MgSO$_4$). The solvent was evaporated to give a solid residue which was dissolved into 0.5 N hydrochloric acid (20 mL). A small insoluble solid was removed by filtration, and the aqueous solution was evaporated to give a residue which was re-evaporated with absolute ethanol. The resulting solid was re-crystallised from absolute ethanol to give 210 mg (60%) of 1-[5-(4-methoxyphenyl)pyridin-2-yl]-4-isopropylpiperazine, dihydrochloride.

$^1$H NMR (400 MHz, CDCl$_3$) δ 1.51 (d, 6H), 3.23-3.34 (m, 2H), 3.49-3.59 (m, 1H), 3.60-3.67 (m, 2H), 3.86 (s, 3H), 4.30-4.40 (m, 2H), 4.64-4.71 (m, 2H), 7.00 (d, 2H), 7.19 (d, 1H), 7.43 (d, 2H), 8.20 (d, 1H), 8.31 (s, 1H), 12.9 (brs, 1H).

Microanalysis for $C_{19}H_{25}N_3O$, 2×HCl, 3×H$_2$O:

Calculated: C, 52.06%; H, 7.59%; N, 9.58%.

Found: C, 51.99%; H, 7.47%, N, 9.21%.

EXAMPLE 3

General Procedure A

1-Isopropyl-4-[5-(4-trifluoromethoxyphenyl)pyridin-2-yl]piperazine, dihydrochloride

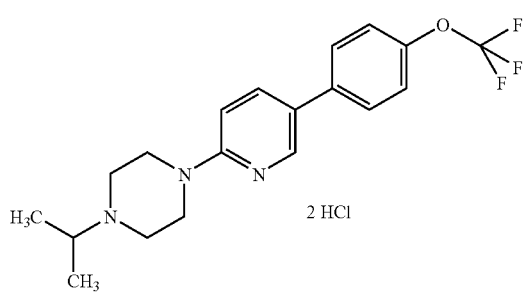 [SMILES: CC(C)N1CCN(c2ccc(-c3ccc(OC(F)(F)F)cc3)cn2)CC1 ; "2 HCl"]

The title compound was prepared by a similar procedure to that described in Example 1, starting from 2-chloro-5-(4-trifluoromethoxyphenyl)pyridine and 1-isopropylpiperazine.

Mp=271-273° C.

$^1$H NMR (300 MHz, DMSO-d$_6$) δ 1.32 (d, 6H), 3.05-3.21 (m, 2H), 3.45-3.67 (m, 5H), 4.50-4.61 (m, 2H), 7.28 (d, 1H), 7.46 (d, 2H), 7.82 (d, 2H), 8.17 (d, 1H), 8.46 (s, 1H), 11.4 (brs, 1H).

Microanalysis for C$_{19}$H$_{22}$F$_3$N$_3$O, 2×HCl:
Calculated: C, 52.06%; H, 5.52%; N, 9.59%.
Found: C, 52.07%; H, 5.53%, N, 9.36%.

EXAMPLE 4

General Procedure A

1-{4-[6-(4-Isopropylpiperazin-1-yl)pyridin-3-yl]phenyl}ethanone, dihydrochloride

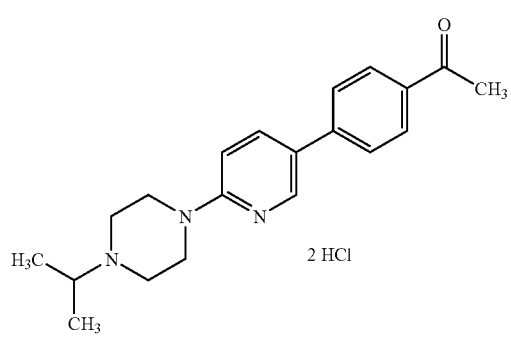

The title compound was prepared by a similar procedure to that described in Example 1, starting from 2-chloro-5-(4-acetylphenyl)pyridine and 1-isopropylpiperazine.

Mp=288-290° C.

$^1$H NMR (300 MHz, DMSO-d$_6$) δ 1.32 (d, 6H), 2.61 (s, 3H), 3.05-3.22 (m, 2H), 3.40-3.67 (m, 5H), 4.51-4.62 (m, 2H), 7.27 (d, 1H), 7.86 (d, 2H), 8.03 (d, 2H), 8.22 (d, 1H), 8.55 (s, 1H), 11.4 (brs, 1H).

Microanalysis for C$_{20}$H$_{25}$N$_3$O, 2×HCl, 1.25×H$_2$O:
Calculated: C, 57.35%; H, 7.10%; N, 10.03%.
Found: C, 57.06%; H, 7.05%, N, 9.78%.

EXAMPLE 5

General Procedure A

1-[5-(2,6-Difluorophenyl)pyridin-2-yl]-4-isopropylpiperazine, dihydrochloride

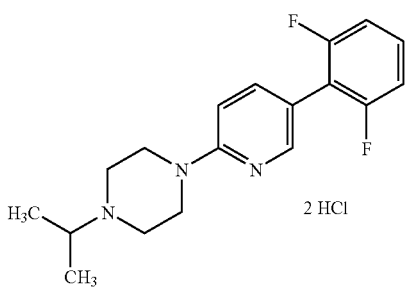 [SMILES: CC(C)N1CCN(c2ccc(-c3c(F)cccc3F)cn2)CC1 ; "2 HCl"]

The title compound was prepared by a similar procedure to that described in Example 1, starting from 2-chloro-5-(2,6-difluorophenyl)pyridine and 1-isopropylpiperazine.

$^1$H NMR (300 MHz, DMSO-d$_6$) δ 1.33 (d, 6H), 3.05-3.20 (m, 2H), 3.44-3.65 (m, 5H), 4.50-4.60 (m, 2H), 7.19-7.31 (m, 3H), 7.43-7.54 (m, 1H), 7.88 (d, 1H), 8.24 (s, 1H), 11.4 (brs, 1H).

Microanalysis for C$_{18}$H$_{21}$F$_2$N$_3$, 2×HCl, 0.5×H$_2$O:
Calculated: C, 54.14%; H, 6.06%; N, 10.52%.
Found: C, 54.02%; H, 6.04%, N, 10.25%.

EXAMPLE 6

General Procedure A

1-[5-(4-Fluorophenyl)pyridin-2-yl]-4-isopropylpiperazine, dihydrochloride

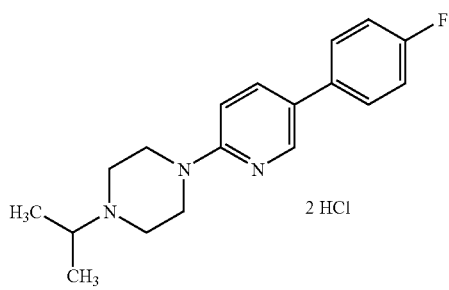 [SMILES: CC(C)N1CCN(c2ccc(-c3ccc(F)cc3)cn2)CC1 ; "2 HCl"]

The title compound was prepared by a similar procedure to that described in Example 1, starting from 2-chloro-5-(4-fluorophenyl)pyridine and 1-isopropylpiperazine.

$^1$H NMR (300 MHz, DMSO-d$_6$) δ 1.32 (d, 6H), 3.06-3.20 (m, 2H), 3.45-3.67 (m, 5H), 4.49-4.59 (m, 2H), 7.25-7.35 (m, 3H), 7.70-7.77 (m, 2H), 8.15 (d, 1H), 8.40 (s, 1H), 11.4 (brs, 1H).

Microanalysis for C$_{18}$H$_{22}$FN$_3$, 2×HCl, 3.5×H$_2$O:
Calculated: C, 49.66%; H, 7.18%; N, 9.65%.
Found: C, 50.01%; H, 7.05%, N, 9.47%.

Example 7

General Procedure A

1-[5-(3-Fluorophenyl)pyridin-2-yl]-4-isopropylpiperazine, hydrochloride

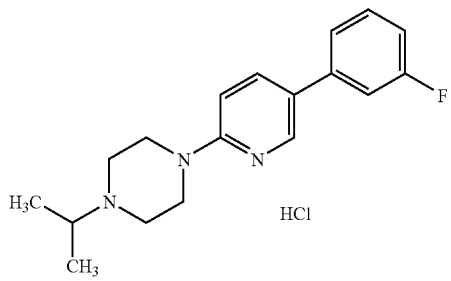 [SMILES: CC(C)N1CCN(c2ccc(-c3cccc(F)c3)cn2)CC1 ; Cl]

The title compound was prepared by a similar procedure to that described in Example 1, starting from 2-chloro-5-(3-fluorophenyl)pyridine and 1-isopropylpiperazine.

$^1$H NMR (300 MHz, DMSO-$d_6$) δ 1.32 (d, 6H), 2.99-3.14 (m, 2H), 3.36-3.67 (m, 5H), 4.45-4.55 (m, 2H), 7.06-7.19 (m, 2H), 7.43-7.57 (m, 3H), 8.02 (d, 1H), 8.55 (s, 1H), 11.0 (brs, 1H).

Microanalysis for $C_{18}H_{22}FN_3$, HCl, 0.5×$H_2O$:
Calculated: C, 62.69%; H, 7.01%; N, 12.18%.
Found: C, 62.93%; H, 6.88%, N, 11.91%.

EXAMPLE 8

General Procedure A

1-[5-(2-Fluorophenyl)pyridin-2-yl]-4-isopropylpiperazine, dihydrochloride

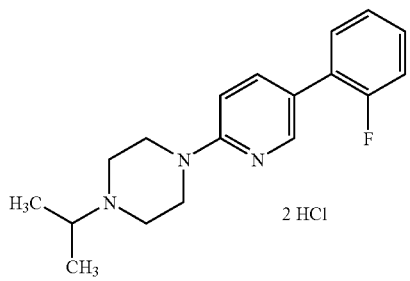 [SMILES: CC(C)N1CCN(c2ccc(-c3ccccc3F)cn2)CC1 ; "2 HCl"]

The title compound was prepared by a similar procedure to that described in Example 1, starting from 2-chloro-5-(2-fluorophenyl)pyridine and 1-isopropylpiperazine.

$^1$H NMR (300 MHz, DMSO-$d_6$) δ 1.33 (d, 6H), 3.06-3.22 (m, 2H), 3.44-3.69 (m, 5H), 4.50-4.61 (m, 2H), 7.25-7.48 (m, 4H), 7.59 (t, 1H), 7.82 (d, 2H), 8.03 (d, 1H), 8.31 (s, 1H), 11.4 (brs, 1H).

Microanalysis for $C_{18}H_{22}FN_3$, 2×HCl:
Calculated: C, 58.07%; H, 6.50%; N, 11.29%.
Found: C, 58.16%; H, 6.61%, N, 10.94%.

EXAMPLE 9

General Procedure A

1-{4-[6-(4-Cyclopentylpiperazin-1-yl)pyridin-3-yl]phenyl}ethanone, dihydrochloride

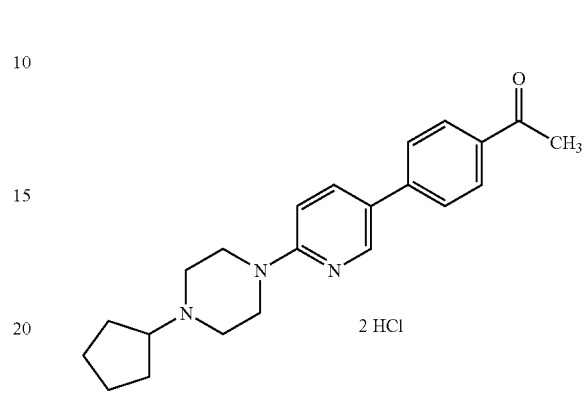

The title compound was prepared by a similar procedure to that described in Example 1, starting from 2-chloro-5-(4-acetylphenyl)pyridine and 1-cyclopentylpiperazine.

$^1$H NMR (300 MHz, DMSO-$d_6$) δ 1.47-1.63 (m, 2H), 1.68-1.95 (m, 4H), 1.96-2.09 (m, 2H), 2.61 (s, 3H), 3.03-3.19 (m, 2H), 3.44-3.65 (m, 5H), 4.47-4.57 (m, 2H), 7.23 (d, 1H), 7.85 (d, 2H), 8.03 (d, 2H), 8.19 (d, 1H), 8.56 (s, 1H), 11.5 (brs, 1H).

Microanalysis for $C_{22}H_{27}N_3O$, 2×HCl, 2×$H_2O$:
Calculated: C, 57.64%; H, 7.26%; N, 9.17%.
Found: C, 58.06%; H, 7.23%, N, 9.10%.

EXAMPLE 10

General Procedure A

4-[6-(4-Isopropylpiperazin-1-yl)pyridin-3-yl]benzonitrile, dihydrochloride

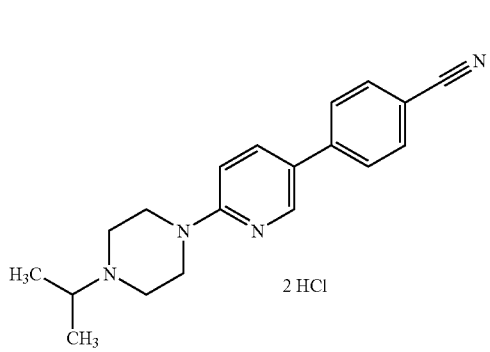 [SMILES: CC(C)N1CCN(c2ccc(-c3ccc(C#N)cc3)cn2)CC1 ; "2 HCl"]

The title compound was prepared by a similar procedure to that described in Example 1, starting from 2-chloro-5-(4-cyanophenyl)pyridine and 1-isopropylpiperazine.

$^1$H NMR (300 MHz, DMSO-$d_6$) δ 1.32 (d, 6H), 3.04-3.19 (m, 2H), 3.46-3.66 (m, 5H), 4.52-4.62 (m, 2H), 5.05 (brs, 6H), 7.24 (d, 1H), 7.91 (s, 4H), 8.19 (dd, 1H), 8.56 (d, 1H), 11.4 (brs, 1H).

Microanalysis for $C_{19}H_{22}N_4$, 2×HCl, 2.5×$H_2O$:
Calculated: C, 53.78%; H, 6.89%; N, 13.20%.
Found: C, 53.51%; H, 6.82%, N, 12.59%.

EXAMPLE 11

General Procedure A (4-(2-Pyrrolidin-1-ylethyl)piperidin-1-yl)-5-(4-trifluoromethylphenyl)pyridine, hydrochloride

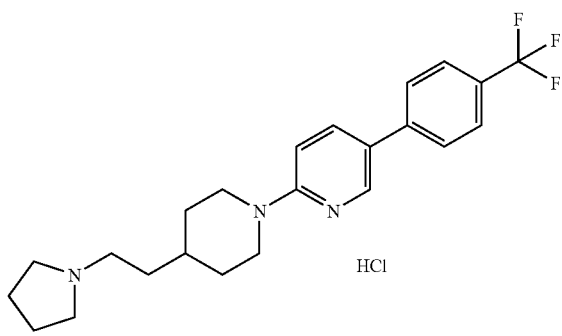 [SMILES: FC(F)(F)c1ccc(-c2ccc(N3CCC(CCN4CCCC4)CC3)nc2)cc1 ; Cl]

The title compound was prepared by a similar procedure to that described in Example 1, starting from 2-chloro-5-(4-trifluoromethylphenyl)pyridine and 4-(2-pyrrolidinoethyl)piperidine. Mp=166-168° C.

$^1$H NMR (300 MHz, $CDCl_3$) δ 1.35-2.31 (m, 11H), 2.76-2.97 (m, 2H), 3.10-3.26 (m, 2H), 3.38 (t, 2H), 3.69-3.87 (m, 2H), 4.48-4.67 (m, 2H), 7.15 (d, 1H), 7.64 (d, 2H), 7.73 (d, 2H), 8.09 (d, 1H), 8.41 (s, 1H), 12.2 (brs, 1H), 15.5 (brs, 1H).

EXAMPLE 12

General Procedure A 1-(3-Piperidin-1-ylpropyl)-4-[5-(4-trifluoromethylphenyl)pyridin-2-yl]piperazine, dihydrochloride

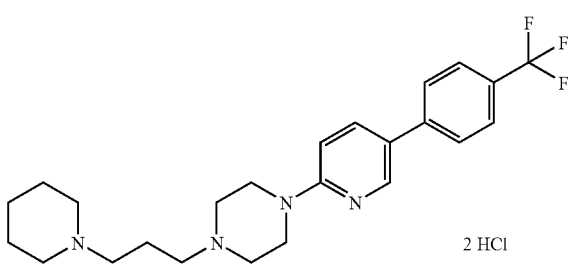 [SMILES: FC(F)(F)c1ccc(-c2ccc(N3CCN(CCCN4CCCCC4)CC3)nc2)cc1 ; "2 HCl"]

The title compound was prepared by a similar procedure to that described in Example 1, starting from 2-chloro-5-(4-trifluoromethylphenyl)pyridine and 1-(3-piperidinopropyl)piperazine.

HPLC (Method A): $t_r$=12.05 min (100%).

EXAMPLE 13

General Procedure A

1'-[6-(4-Methanesulfonylphenyl)pyridazin-3-yl]-[1,4']bipiperidinyl

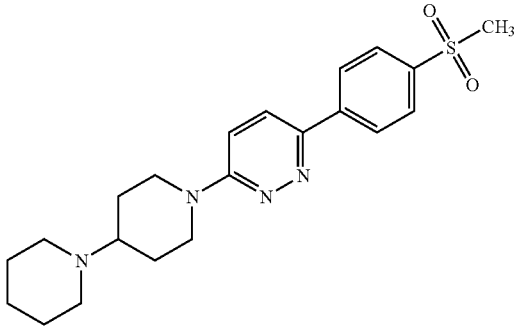 [SMILES: CS(=O)(=O)c1ccc(-c2ccc(N3CCC(N4CCCCC4)CC3)nn2)cc1]

The title compound was prepared by a similar procedure to that described in Example 1, starting from 3-chloro-6-(4-methanesulfonylphenyl)pyridazine and 4-(piperid-1-yl)piperidine.

$^1$H NMR (400 MHz, $CDCl_3$) δ 1.24 (t, J=6.82 Hz, 1H), 1.38-1.51 (m, 2H), 1.52-1.69 (m, 5H), 1.98 (d, J=12.63 Hz, 2H), 2.47-2.63 (m, 4H), 2.95-3.07 (m, 2H), 3.09 (s, 3H), 3.72 (q, J=7.07 Hz, 1H), 4.56 (d, J=13.14 Hz, 2H), 7.01 (d, J=9.60 Hz, 1H), 7.67 (d, J=9.60 Hz, 1H), 8.02 (d, J=8.59 Hz, 2H), 8.20 (d, J=8.59 Hz, 2H).

Microanalysis for $C_{21}H_{28}N_4O_2S$, 0.25×$H_2O$:
Calculated: C, 62.27%; H, 7.09%; N, 13.83%.
Found: C, 61.85%; H, 6.84%; N, 13.49%.

EXAMPLE 14

General Procedure A

Dimethyl-(3-{4-[6-(4-trifluoromethylphenyl)pyridazin-3-yl]piperazin-1-yl}propyl)amine, dihydrochloride

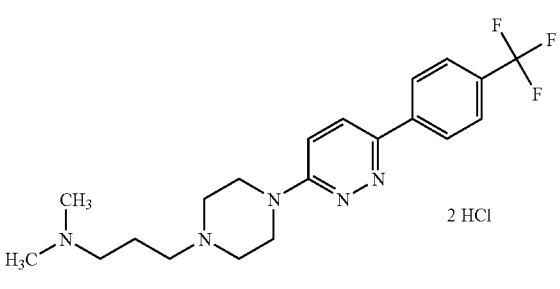 [SMILES: CN(C)CCCN1CCN(c2ccc(-c3ccc(C(F)(F)F)cc3)nn2)CC1 ; "2 HCl"]

The title compound was prepared by a similar procedure to that described in Example 1, starting from 3-chloro-6-(4-trifluoromethylphenyl)pyridazine and (3-dimethylaminoprop-1-yl)piperazine.

$^1$H NMR (400 MHz, $D_2O$) δ 2.06-2.35 (m, 2H), 2.85 (s, 5H), 3.13-3.23 (m, 2H), 3.23-3.32 (m, 2H), 3.49 (s, 3H), 4.70

(s, 7H), 7.68 (d, J=10.11 Hz, 1H), 7.78 (d, J=8.59 Hz, 2H), 7.90 (d, J=8.59 Hz, 2H), 8.08 (d, J=9.60 Hz, 1H).

Microanalysis for $C_{20}H_{26}N_5F_3$, 2×HCl, 2.75×$H_2O$:
Calculated: C, 46.56%; H, 6.54%; N, 13.57%.
Found: C, 46.53%; H, 6.35%; N, 13.32%.

EXAMPLE 15

General Procedure A

3-[4-(1-Methylpiperidin-3-ylmethyl)piperazin-1-yl]-6-(4-trifluoromethylphenyl)pyridazine

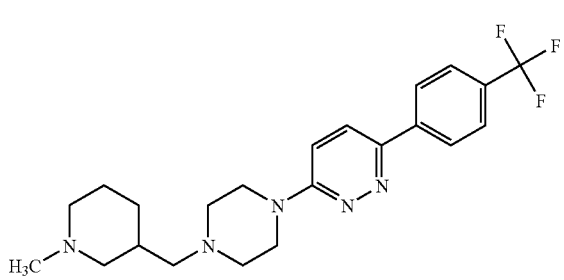 [SMILES: CN1CCCC(CN2CCN(c3ccc(-c4ccc(C(F)(F)F)cc4)nn3)CC2)C1]

The title compound was prepared by a similar procedure to that described in Example 1, starting from 3-chloro-6-(4-trifluoromethylphenyl)pyridazine and (1-methylpiperidin-3-ylmethyl)piperazine.

$^1$H NMR (400 MHz, DMSO-$d_6$) δ 1.12-1.31 (m, 1H), 1.71-2.01 (m, 2H), 2.54-2.97 (m, 4H), 3.04-3.33 (m, 3H), 3.40 (d, J=10.61 Hz, 1H), 3.53-3.86 (m, 9H), 4.62 (brs, 1H), 7.78 (d, J=10.11 Hz, 1H), 7.91 (d, J=8.08 Hz, 2H), 8.23-8.37 (m, 3H).

EXAMPLE 16

General Procedure A

3-[4-(1-Methylpiperidin-4-ylmethyl)piperazin-1-yl]-6-(4-trifluoromethylphenyl)pyridazine, dihydrochloride

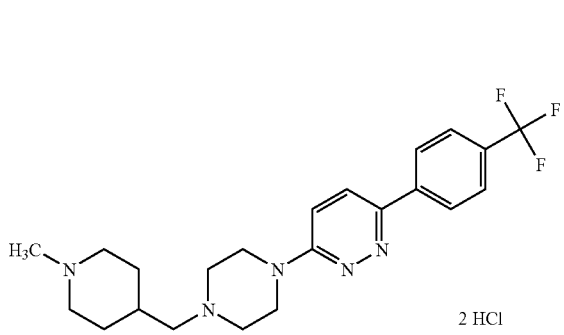 [SMILES: CN1CCC(CN2CCN(c3ccc(-c4ccc(C(F)(F)F)cc4)nn3)CC2)CC1 ; "2 HCl"]

The title compound was prepared by a similar procedure to that described in Example 1, starting from 3-chloro-6-(4-trifluoromethylphenyl)pyridazine and (1-methylpiperidin-4-ylmethyl)piperazine.

$^1$H NMR (400 MHz, DMSO-$d_6$) δ 1.48-1.64 (m, 2H), 2.05-2.20 (m, 3H), 2.68-2.79 (m, 3H), 2.94 (t, J=11.87 Hz, 2H) 3.06-3.25 (m, 4H) 3.69 (d, J=12.13 Hz, 4H) 4.58 (d, J=13.64 Hz, 2H) 7.65 (d, J=9.60 Hz, 1H) 7.89 (d, J=8.59 Hz, 2H) 8.23 (d, J=9.60 Hz, 1H) 8.29 (d, J=8.08 Hz, 2H).

Microanalysis for $C_{22}H_{28}N_5F_3$, 2×HCl, 2.75×$H_2O$:
Calculated: C, 48.85%; H, 6.43%; N, 12.95%.
Found: C, 49.00%; H, 6.23%; N, 12.80%.

EXAMPLE 17

General Procedure A

4-{6-[4-(1-Methylpiperidin-4-ylmethyl)piperazin-1-yl]pyridazin-3-yl}benzonitrile, hydrochloride

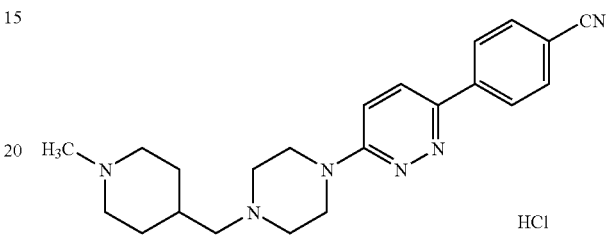

The title compound was prepared by a similar procedure to that described in Example 1, starting from 3-chloro-6-(4-cyanophenyl)pyridazine and (1-methylpiperidin-4-ylmethyl)piperazine.

$^1$H NMR (400 MHz, $D_2O$) δ 1.45-1.62 (m, 2H), 2.06 (d, J=14.15 Hz, 2H), 2.17-2.32 (m, 1H), 2.74-2.84 (m, 3H), 2.98 (t, 1H), 3.19 (d, J=7.07 Hz, 2H), 3.25-3.63 (m, 7H), 3.80-4.30 (broad m, 3H), 7.66 (d, 1H), 7.78 (d, 2H), 7.87 (d, 2H), 8.06 (d, J=10.11 Hz, 1H).

EXAMPLE 18

General Procedure A

4-{6-[4-(1-Methylpiperidin-3-ylmethyl)piperazin-1-yl]pyridazin-3-yl}benzonitrile, trihydrochloride

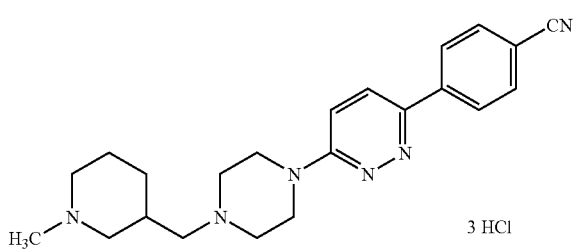 [SMILES: CN1CCCC(CN2CCN(c3ccc(-c4ccc(C#N)cc4)nn3)CC2)C1 ; "3 HCl"]

The title compound was prepared by a similar procedure to that described in Example 1, starting from 3-chloro-6-(4-cyanophenyl)pyridazine and (1-methylpiperidin-3-ylmethyl)piperazine.

$^1$H NMR (400 MHz, $D_2O$) δ 1.30 (m, 1H), 1.74 (m, 1H), 1.99 (m, 2H), 2.41 (dd, J=6.82, 3.28 Hz, 1H), 2.84 (m, 5H), 3.21 (d, J=6.57 Hz, 2H), 3.49 (m, 6H), 4.03 (m, 4H), 7.81 (m, 3H) 7.91 (d, 2H), 8.17 (d, J=9.60 Hz, 1H).

Microanalysis for $C_{22}H_{28}N_6$, 3×HCl, 3.75×$H_2O$:
Calculated: C, 47.75%; H, 7.01%; N, 15.18%.
Found: C, 47.99%; H, 6.96%; N, 15.01%.

EXAMPLE 19

General Procedure A (S)-3-(4-Butylsulfanylphenyl)-6-(2-pyrrolidin-1-ylmethylpyrrolidin-1-yl)pyridazine, hydrochloride

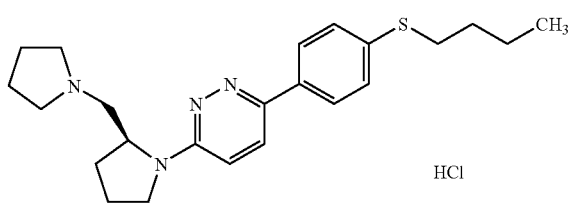 [SMILES: CCCCSc1ccc(-c2ccc(N3CCC[C@H]3CN3CCCC3)nn2)cc1 ; Cl]

The title compound was prepared by a similar procedure to that described in Example 1, starting from 3-chloro-6-(4-butylsulfanylphenyl)pyridazine and (2S)-(pyrrolidin-1-ylmethyl)pyrrolidine.

$^1$H NMR (400 MHz, D$_2$O) δ 0.74 (t, J=7.33 Hz, 3H), 1.00 (t, J=7.07 Hz, 2H), 1.27 (m, 2H), 1.49 (m, 2H), 2.04 (m, 5H) 2.88 (t, J=7.58 Hz, 2H), 3.24 (m, 6H), 3.62 (m, 3H), 4.46 (m, J=6.06 Hz, 1H), 7.28 (d, J=8.59 Hz, 2H), 7.47 (d, J=10.11 Hz, 1H), 7.55 (d, J=8.59 Hz, 2H), 8.00 (d, J=9.60 Hz, 1H).

EXAMPLE 20

General Procedure A (S)-3-(4-Ethanesulfonylphenyl)-6-(2-pyrrolidin-1-ylmethylpyrrolidin-1-yl)pyridazine, hydrochloride

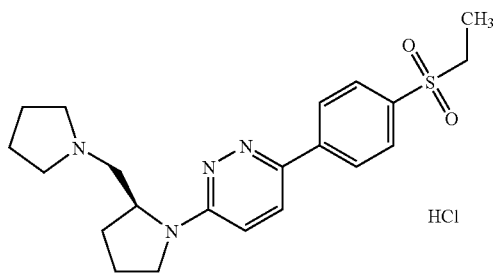 [SMILES: CCS(=O)(=O)c1ccc(-c2ccc(N3CCC[C@H]3CN3CCCC3)nn2)cc1 ; Cl]

The title compound was prepared by a similar procedure to that described in Example 1, starting from 3-chloro-6-(4-ethanesulfonylphenyl)pyridazine and (2S)-(pyrrolidin-1-ylmethyl)pyrrolidine.

$^1$H NMR (400 MHz, D$_2$O) δ 1.12 (t, J=7.33 Hz, 3H), 2.10 (m, 8H), 3.16 (m, 2H), 3.27 (q, J=7.58 Hz, 2H), 3.36 (m, 2H), 3.47 (m, 1H), 3.67 (m, 2H), 3.82 (s, 1H), 4.59 (m, 1H), 7.42 (d, J=9.60 Hz, 1H), 7.87 (m, 2H), 7.94 (m, 2H), 8.02 (d, J=9.60 Hz, 1H).

EXAMPLE 21

General Procedure A (S)-3-(4-Ethanesulfinylphenyl)-6-(2-pyrrolidin-1-ylmethylpyrrolidin-1-yl)pyridazine, hydrochloride

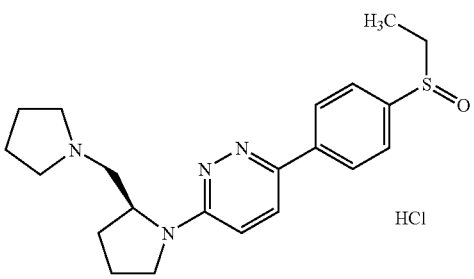 [SMILES: CCS(=O)c1ccc(-c2ccc(N3CCC[C@H]3CN3CCCC3)nn2)cc1 ; Cl]

The title compound was prepared by a similar procedure to that described in Example 1, starting from 3-chloro-6-(4-ethanesulfinylphenyl)pyridazine and (2S)-(pyrrolidin-1-ylmethyl)pyrrolidine.

$^1$H NMR (400 MHz, D$_2$O) δ 1.03 (t, J=7.33 Hz, 3H), 2.04 (m, 8H), 2.89 (m, 1H), 3.02 (m, 3H), 3.31 (m, 3H), 3.57 (m, 2H), 3.79 (m, 1H), 4.50 (q, J=5.73 Hz, 1H), 7.33 (d, J=9.60 Hz, 1H), 7.65 (d, J=7.07 Hz, 2H), 7.89 (d, J=8.08 Hz, 2H), 7.97 (d, J=9.60 Hz, 1H).

EXAMPLE 22

General Procedure A (S)-3-(4-Ethylsulfanylphenyl)-6-(2-pyrrolidin-1-ylmethylpyrrolidin-1-yl)pyridazine, hydrochloride

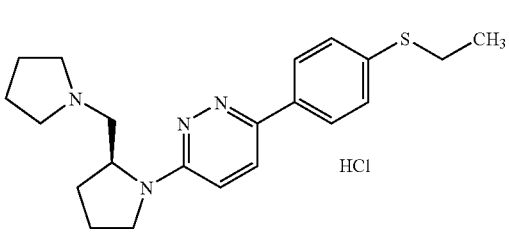 [SMILES: CCSc1ccc(-c2ccc(N3CCC[C@H]3CN3CCCC3)nn2)cc1 ; Cl]

The title compound was prepared by a similar procedure to that described in Example 1, starting from 3-chloro-6-(4-ethylsulfanylphenyl)pyridazine and (2S)-(pyrrolidin-1-ylmethyl)pyrrolidine.

$^1$H NMR (400 MHz, CD$_3$OD) δ 1.37 (t, J=7.33 Hz, 3H), 2.20 (m, 7H), 3.10 (q, J=7.07 Hz, 2H), 3.47 (m, 6H), 3.84 (brs, 2H), 3.97 (brs, 1H), 4.73 (brs, 1H), 7.52 (d, J=7.58 Hz, 2H), 7.91 (m, J=7.58 Hz, 3H), 8.41 (m, 1H).

EXAMPLE 23

General Procedure A 5-(4-Chlorophenyl)-2-(4-isopropylpiperazin-1-yl)pyrimidine, dihydrochloride

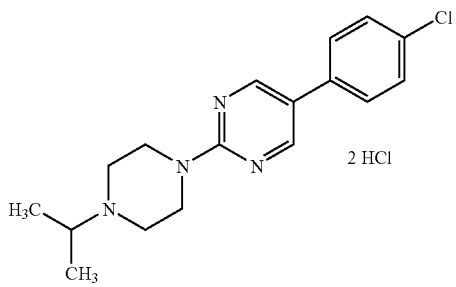 [SMILES: CC(C)N1CCN(c2ncc(-c3ccc(Cl)cc3)cn2)CC1 ; "2 HCl"]

The title compound was prepared by a similar procedure to that described in Example 1, starting from 2-chloro-5-(4-chlorophenyl)pyrimidine and 1-isopropylpiperazine.

$^1$H NMR (300 MHz, DMSO-$d_6$) δ 1.33 (d, J=6.41 Hz, 6H), 3.08 (m, 2H), 3.53 (m, 5H), 4.82 (d, J=13.94 Hz, 2H), 7.54 (d, J=8.67 Hz, 2H), 7.74 (d, J=8.67 Hz, 2H), 8.82 (s, 2H).

Microanalysis for $C_{17}H_{21}N_4Cl$, 2×HCl:
Calculated: C, 52.39%; H, 5.95%; N, 14.37%.
Found: C, 52.90%; H, 6.04%; N, 14.18%.

EXAMPLE 24

General Procedure A 2-(4-Isopropylpiperazin-1-yl)-5-(4-trifluoromethylphenyl)pyrimidine, hydrochloride

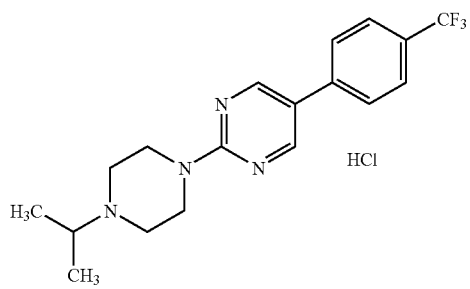 [SMILES: CC(C)N1CCN(c2ncc(-c3ccc(C(F)(F)F)cc3)cn2)CC1 ; Cl]

The title compound was prepared by a similar procedure to that described in Example 1, starting from 2-chloro-5-(4-trifluoromethylphenyl)pyrimidine and 1-isopropylpiperazine.

$^1$H NMR (400 MHz, DMSO-$d_6$) δ 1.31 (d, J=6.57 Hz, 6H), 3.05 (m, 2H), 3.51 (m, 5H), 4.82 (d, J=14.65 Hz, 2H), 7.81 (d, J=8.08 Hz, 2H), 7.93 (d, J=8.08 Hz, 2H), 8.89 (m, 2H), 11.23 (brs, 1H).

Microanalysis for $C_{18}H_{21}F_3N_4$, 1.75×HCl:
Calculated: C, 52.20%; H, 5.54%; N, 13.53%.
Found: C, 52.41%; H, 5.54%; N, 13.26%.

EXAMPLE 25

General Procedure A

4-[2-(4-Isopropylpiperazin-1-yl)pyrimidin-5-yl]benzonitrile, dihydrochloride

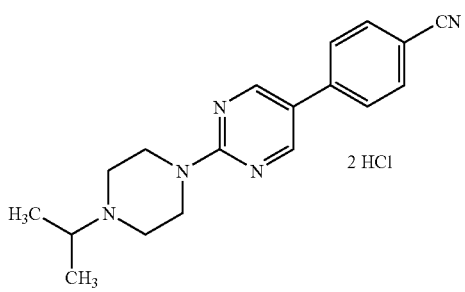 [SMILES: CC(C)N1CCN(c2ncc(-c3ccc(C#N)cc3)cn2)CC1 ; "2 HCl"]

The title compound was prepared by a similar procedure to that described in Example 1, starting from 2-chloro-5-(4-cyanophenyl)pyrimidine and 1-isopropylpiperazine.

$^1$H NMR (400 MHz, DMSO-$d_6$) δ 1.31 (d, J=6.57 Hz, 6H), 3.07 (m, 2H), 3.52 (m, 5H), 4.81 (d, J=14.15 Hz, 2H), 7.93 (s, 4H), 8.91 (s, 2H), 11.34 (brs, 1H).

Microanalysis for $C_{18}H_{21}N_5$, 2×HCl, 0.75×$H_2O$:
Calculated: C, 54.90%; H, 6.27%; N, 17.78%.
Found: C, 55.23%; H, 6.45%; N, 17.54%.

EXAMPLE 26

General Procedure A 5-(4-Fluorophenyl)-2-(4-isopropylpiperazin-1-yl)pyrimidine, dimethanesulfonate

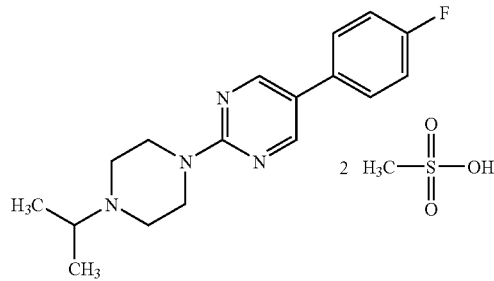

The title compound was prepared by a similar procedure to that described in Example 1, starting from 2-chloro-5-(4-fluorophenyl)pyrimidine and 1-isopropylpiperazine.

$^1$H NMR (400 MHz, DMSO-$d_6$+$D_2O$) δ 1.29 (d, J=7.07 Hz, 6H), 2.39 (s, 6H), 3.10 (m, 2H), 3.32 (t, J=12.38 Hz, 2H), 3.55 (m, 3H), 7.31 (t, J=8.84 Hz, 2H), 7.73 (dd, J=8.84, 5.31 Hz, 2H), 8.79 (s, 2H), 9.52 (brs, 1H).

Microanalysis for $C_{17}H_{21}N_4F$, 2×$CH_3SO_3H$:
Calculated: C, 46.33%; H, 5.93%; N, 11.37%.
Found: C, 46.05%; H, 6.07%; N, 11.06%.

EXAMPLE 27

General Procedure A 2-(4-Isopropylpiperazin-1-yl)-5-(4-trifluoromethoxyphenyl)pyrimidine, dimethanesulfonate

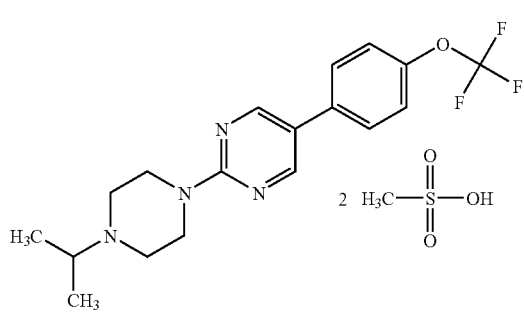

The title compound was prepared by a similar procedure to that described in Example 1, starting from 2-chloro-5-(4-trifluoromethoxyphenyl)pyrimidine and 1-isopropylpiperazine.

$^1$H NMR (400 MHz, DMSO-d$_6$+D$_2$O) δ 1.31 (d, J=6.57 Hz, 6H), 2.41 (s, 6H), 3.12 (m, 2H), 3.34 (t, J=12.13 Hz, 2H), 3.56 (m, 3H), 4.86 (d, J=14.15 Hz, 2H), 7.48 (d, J=8.08 Hz, 2H), 7.83 (d, J=8.59 Hz, 2H), 8.84 (s, 2H).

Microanalysis for C$_{18}$H$_{21}$F$_3$N$_4$O, 2×CH$_3$SO$_3$H, 0.75×H$_2$O:

Calculated: C, 41.99%; H, 5.37%; N, 9.79%.

Found: C, 42.17%; H, 5.34%; N, 9.74%.

EXAMPLE 28

General Procedure A 2-(4-Isopropylpiperazin-1-yl)-5-(4-methoxyphenyl)pyrimidine, dimethanesulfonate

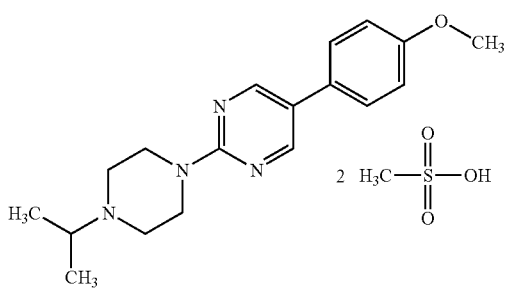

The title compound was prepared by a similar procedure to that described in Example 1, starting from 2-chloro-5-(4-methoxyphenyl)pyrimidine and 1-isopropylpiperazine.

$^1$H NMR (400 MHz, DMSO-d$_6$) δ 1.29 (d, J=6.57 Hz, 6H), 2.40 (s, 6H), 3.07 (m, 2H), 3.31 (t, J=12.13 Hz, 2H), 3.54 (m, J=11.37, 11.37 Hz, 3H), 3.79 (s, 3H), 4.81 (d, J=14.15 Hz, 2H), 7.03 (d, J=8.59 Hz, 2H), 7.61 (d, J=9.10 Hz, 2H), 8.75 (s, 2H), 9.52 (brs, 1H).

EXAMPLE 29

General Procedure A (S)-3-(2-Pyrrolidin-1-ylmethylpyrrolidin-1-yl)-6-(4-trifluoromethylphenyl)pyridazine, dihydrochloride

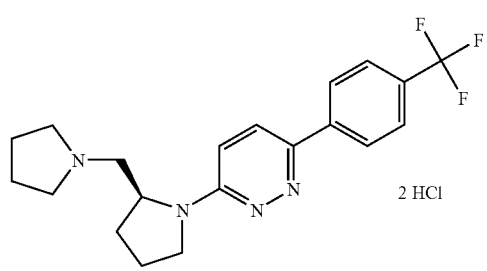 [SMILES: FC(F)(F)c1ccc(-c2ccc(N3CCC[C@H]3CN3CCCC3)nn2)cc1 ; "2 HCl"]

The title compound was prepared by a similar procedure to that described in Example 1, starting from 3-chloro-6-(4-trifluoromethylphenyl)pyridazine and (2S)-(pyrrolidin-1-ylmethyl)pyrrolidine.

$^1$H NMR (400 MHz, CD$_3$OD) δ 2.20 (m, 8H), 3.31 (m, 2H), 3.48 (m, 2H), 3.62 (m, 1H), 3.86 (m, 3H), 4.80 (m, 1H), 7.91 (m, J=8.59 Hz, 3H), 8.20 (d, J=8.08 Hz, 2H), 8.45 (d, J=9.60 Hz, 1H).

Microanalysis for C$_{20}$H$_{23}$F$_3$N$_4$, 2×HCl, 3×H$_2$O:

Calculated: C, 47.72%; H, 6.21%; N, 11.13%.

Found: C, 47.95%; H, 6.35%; N, 10.92%.

EXAMPLE 30

General Procedure A

N-{4-[6-(4-Isopropylpiperazin-1-yl)pyridazin-3-yl]phenyl}acetamide

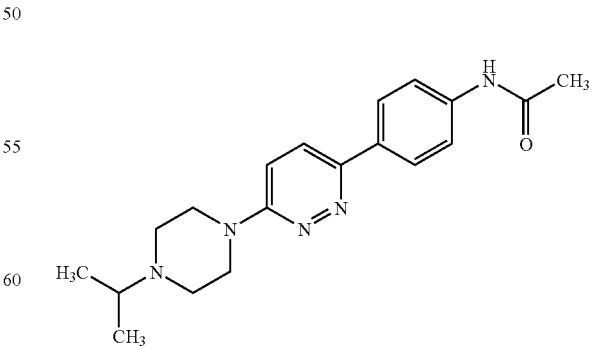

The title compound was prepared by a similar procedure to that described in Example 1, starting from 3-chloro-6-(4-acetylaminophenyl)pyridazine and 1-isopropylpiperazine.

¹H NMR (400 MHz, CDCl₃) δ 1.10 (d, 6H), 2.20 (m, 3H), 2.68 (m, 4H), 2.75 (m, 1H), 3.73 (m, 4H), 6.97 (d, J=9.60 Hz, 1H), 7.38 (s, 1H), 7.61 (dd, J=9.10, 5.05 Hz, 3H), 7.96 (d, J=8.59 Hz, 2H).

EXAMPLE 31

General Procedure A

[1-(1-Ethylpropyl)piperidin-4-yl]-[6-(3-fluoro-4-methoxyphenyl)pyridazin-3-yl]amine

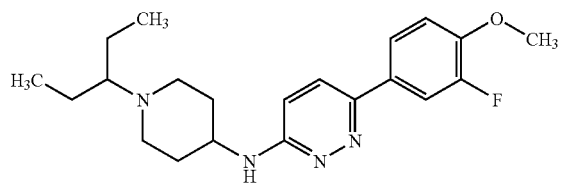 [SMILES: CCC(CC)N1CCC(Nc2ccc(-c3ccc(OC)c(F)c3)nn2)CC1]

The title compound was prepared by a similar procedure to that described in Example 1, starting from 3-chloro-6-(4-methoxy-3-fluorophenyl)pyridazine and 4-amino-1-(1-ethylpropyl)piperidine.

¹H NMR (400 MHz, CD₃OD) δ 0.93 (m, 6H), 1.47 (m, 7H), 2.07 (d, J=11.62 Hz, 2H), 2.20 (m, 1H), 2.45 (m, 2H), 2.83 (d, J=12.13 Hz, 2H), 3.85 (m, 1H), 3.91 (s, 3H), 6.90 (d, J=9.10 Hz, 1H), 7.17 (t, J=8.59 Hz, 1H), 7.68 (m, 3H).

EXAMPLE 32

General Procedure A

[1-(1-Ethylpropyl)piperidin-4-yl]-[6-(4-methanesulfonylphenyl)pyridazin-3-yl]amine

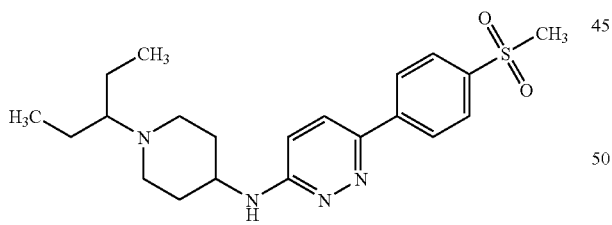

The title compound was prepared by a similar procedure to that described in Example 1, starting from 3-chloro-6-(4-methanesulfonylphenyl)pyridazine and 4-amino-1-(1-ethylpropyl)piperidine.

¹H NMR (400 MHz, CD₃OD) δ 0.93 (m, 6H), 1.49 (m, 7H), 2.08 (d, J=11.62 Hz, 1H), 2.23 (m, 1H), 2.48 (m, 2H), 2.85 (d, J=12.13 Hz, 2H), 3.16 (s, 3H), 3.90 (m, 1H), 6.96 (d, J=9.60 Hz, 1H), 7.83 (d, J=9.60 Hz, 1H), 8.03 (d, J=8.59 Hz, 2H), 8.19 (d, J=8.59 Hz, 2H).

Microanalysis for C₂₁H₃₀N₄O₂S:

Calculated: C, 62.66%; H, 7.51%; N, 13.92%.

Found: C, 62.38%; H, 7.58%; N, 13.31%.

EXAMPLE 33

General Procedure A

1-Isopropyl-4-[5-(4-trifluoromethylphenyl)pyridin-2-yl]piperazine

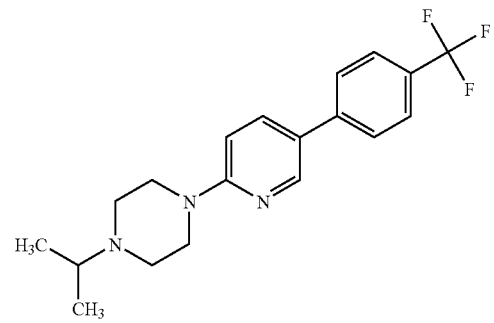 [SMILES: CC(C)N1CCN(c2ccc(-c3ccc(C(F)(F)F)cc3)cn2)CC1]

The title compound was prepared by a similar procedure to that described in Example 1, starting from 2-chloro-5-(4-trifluoromethylphenyl)pyridine and 1-isopropylpiperazine.

¹H NMR (400 MHz, DMSO-d₆) δ 1.00 (d, J=6.57 Hz, 6H), 2.52 (m, 4H), 2.69 (m, 1H), 3.55 (m, 4H), 6.93 (d, J=9.09 Hz, 1H), 7.75 (m, 2H), 7.85 (m, 2H), 7.93 (dd, J=8.84, 2.78 Hz, 1H), 8.53 (d, J=2.53 Hz, 1H).

Microanalysis for C₁₉H₂₂F₃N₃:

Calculated: C, 65.31%; H, 3.35%; N, 12.03%.

Found: C, 65.08%; H, 6.23%; N, 12.05%.

EXAMPLE 34

General Procedure A 3-(2,3-Dihydrobenzo[1,4]dioxin-6-yl)-6-(4-isopropylpiperazin-1-yl)pyridazine, dihydrochloride

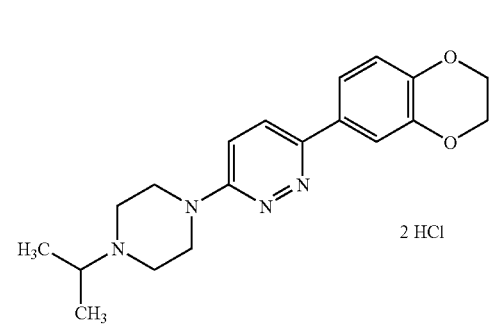 [SMILES: CC(C)N1CCN(c2ccc(-c3ccc4c(c3)OCCO4)nn2)CC1 ; "2 HCl"]

The title compound was prepared by a similar procedure to that described in Example 1, starting from 3-chloro-6-(4-(2,3-dihydrobenzo[1,4]dioxin-6-yl)-phenyl)pyridazine and 1-isopropylpiperazine.

¹H NMR (400 MHz, DMSO-d₆) δ 1.32 (d, J=6.57 Hz, 6H), 3.18 (m, 2H), 3.53 (m, J=12.13 Hz, 3H), 3.75 (t, J=12.38 Hz, 2H), 4.32 (s, 4H), 4.60 (d, J=13.64 Hz, 2H), 7.05 (d, J=8.08 Hz, 1H), 7.59 (m, 2H), 7.95 (d, J=10.11 Hz, 1H), 8.37 (d, J=9.60 Hz, 1H), 11.68 (brs, 1H).

Microanalysis for $C_{19}H_{24}N_4O_2$, 2×HCl:
Calculated: C, 55.21%; H, 6.34%; N, 13.55%.
Found: C, 55.25%; H, 6.40%; N, 13.55%.

EXAMPLE 35

General Procedure A

4-{6-[1-(1-Ethylpropyl)piperidin-4-ylamino]pyridazin-3-yl}benzonitrile

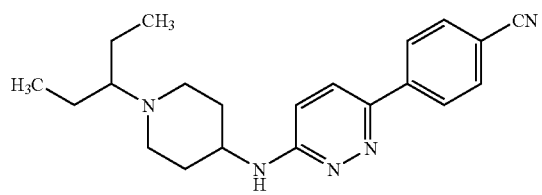 [SMILES: CCC(CC)N1CCC(Nc2ccc(-c3ccc(C#N)cc3)nn2)CC1]

The title compound was prepared by a similar procedure to that described in Example 1, starting from 3-chloro-6-(4-cyanophenyl)pyridazine and 4-amino-1-(1-ethylpropyl)piperidine.

$^1$H NMR (400 MHz, DMSO-$d_6$) δ 0.87 (t, J=7.33 Hz, 6H), 1.35 (m, 7H), 1.98 (m, 2H), 2.17 (m, 1H), 2.36 (t, J=10.36 Hz, 2H), 2.71 (m, J=12.13 Hz, 2H), 6.89 (d, J=9.60 Hz, 1H), 7.09 (d, J=7.58 Hz, 1H), 7.91 (m, 3H), 8.17 (d, J=8.08 Hz, 2H).

EXAMPLE 36

General Procedure A

Dimethyl-(2-{4-[5-(4-trifluoromethylphenyl)pyridin-2-yl]piperazin-1-yl}ethyl)amine

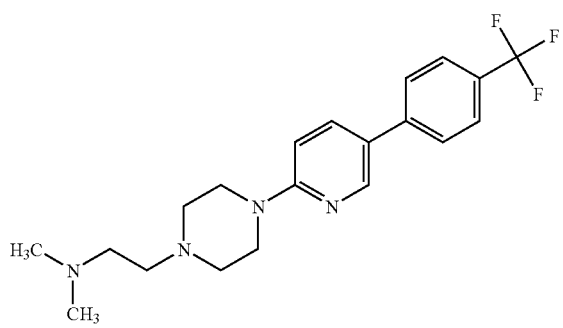 [SMILES: CN(C)CCN1CCN(c2ccc(-c3ccc(C(F)(F)F)cc3)cn2)CC1]

The title compound was prepared by a similar procedure to that described in Example 1, starting from 2-chloro-5-(4-trifluoromethylphenyl)pyridine and (2-dimethylaminoethyl)piperazine.

$^1$H NMR (400 MHz, CDCl$_3$) δ 2.29 (s, 6H), 2.53 (m, 4H), 2.61 (m, 4H), 3.64 (m, 4H), 6.72 (d, J=9.10 Hz, 1H), 7.64 (m, 4H), 7.72 (dd, J=9.10, 2.53 Hz, 1H), 8.45 (d, J=2.53 Hz, 1H).

EXAMPLE 37

General Procedure A 1-(Tetrahydropyran-4-yl)-4-[5-(4-trifluoromethylphenyl)pyridin-2-yl]piperazine

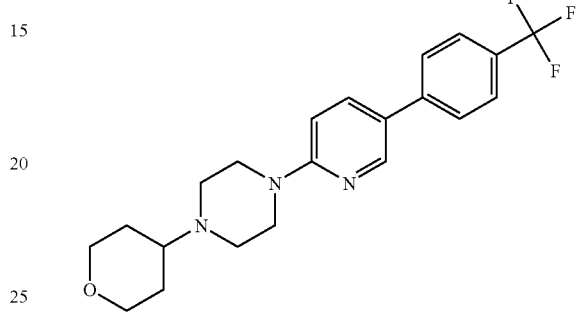

The title compound was prepared by a similar procedure to that described in Example 57, starting from 4-(5-(4-trifluoromethylphenyl)pyridin-2-yl)piperazine and 4-chloro-tetrahydropyran.

$^1$H NMR (400 MHz, CDCl$_3$) δ 1.63 (m, 2H), 1.82 (m, 2H), 2.50 (m, 1H), 2.70 (m, 4H), 3.40 (t, J=10.86 Hz, 2H), 3.64 (m, 4H), 4.05 (dd, J=11.12, 4.04 Hz, 2H), 6.73 (d, J=9.10 Hz, 1H), 7.64 (m, 4H), 7.73 (dd, J=9.10, 2.53 Hz, 1H), 8.46 (d, J=2.53 Hz, 1H).

EXAMPLE 38

General Procedure A

1-[6-(4-Trifluoromethylphenyl)pyridazin-3-yl]piperidin-3-ylamine, hydrochloride

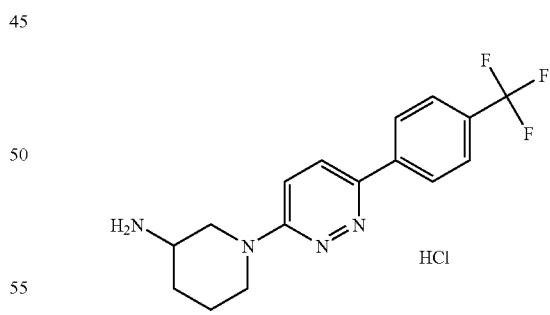

3-Chloro-6-(4-trifluoromethylphenyl)pyridazine (0.2 g, 0.77 mmol), 3-aminopiperidine dihydrochloride (0.27 g, 1.54 mmol) and potassium carbonate (0.53 g, 3.87 mmol) were mixed in acetone (4 mL) in a 20 mL microwave vessel. The reaction mixture was heated in a microwave oven for 2 h at 120° C. The reaction mixture was filtered and the precipitate was washed with MeOH. The combined organic phases were evaporated. The crude oil was purified on a silicagel column (0.04-0.063 mesh) using dichloromethane/MeOH (9:1) as eluent. This afforded 110 mg of a oil that was dissolved in MeOH and acidified with concentrated HCl (5 mL). The mixture was evaporated and the residue was dissolved in MeOH (1 mL) and ether (100 mL) was added with stirring. The mixture was evaporated to give 76 mg (25%) of the title compound as a yellow solid.

Mp=97-135° C.

$^1$H NMR (400 MHz, CD$_3$OD) δ1.74 (m, 2H) 1.93 (m, 1H) 2.16 (m, 1H) 3.35 (m, 3H) 3.44 (m, 1H) 4.14 (d,d, 1H) 4.45 (d,d, 1H) 4.97 (s, 3H) 7.39 (d, 1H) 7.75 (d, 2H) 7.78 (s, 2H) 7.95 (s, 1H) 8.13 (d, 2H).

HPLC-MS (Method G): M+1=323; t$_r$=1.117 min.

EXAMPLE 39

General Procedure A

N-{4-[6-(4-Isopropylpiperazin-1-yl)pyridin-3-yl]benzyl}acetamide, dihydrochloride

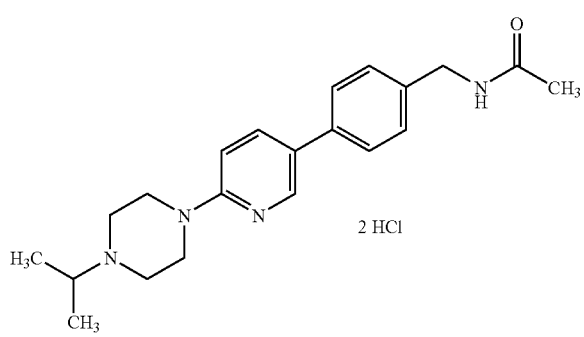 [SMILES: CC(=O)NCc1ccc(-c2ccc(N3CCN(C(C)C)CC3)nc2)cc1 ; "2 HCl"]

Step 1

4-(6-(4-Isopropylpiperazin-1-yl)pyridin-3-yl]benzylamine

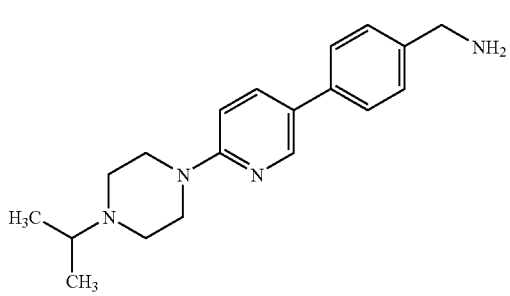 [SMILES: CC(C)N1CCN(c2ccc(-c3ccc(CN)cc3)cn2)CC1]

A mixture of a 1 M solution of LiAlH$_4$ in THF (1.1 mL, 1.1 mmol) and dry THF (10 mL) was placed under an atmosphere of nitrogen. A solution of 4-(6-(4-isopropylpiperazin-1-yl)pyridin-3-yl)benzonitrile (306 mg, 1.0 mmol, prepared as described in Example 10) in dry THF (5 mL) was added dropwise. The reaction mixture was then stirred at rt for 3 h and quenched with 1 N NaOH. The mixture was filtered and the volatiles were removed. The residue was re-evaporated with THF to give 310 mg (100%) of 4-(6-(4-isopropylpiperazin-1-yl)pyridin-3-yl]benzylamine.

$^1$H NMR (300 MHz, CDCl$_3$) δ 1.10 (d, 6H), 2.63-2.68 (m, 4H), 2.75 (hept, 1H), 3.59-3.64 (m, 4H), 3.90 (s, 2H), 6.70 (d, 1H), 7.37 (d, 2H), 7.48 (d, 2H), 7.71 (dd, 1H), 8.44 (d, 1H).

Step 2

A mixture of the above benzylamine (310 mg, 1.0 mmol), glacial acetic acid (15 mL) and acetic anhydride (0.2 mL, 2.1 mmol) was stirred for 2 days at rt. The reaction mixture was evaporated to dryness, and the residue was stirred with a mixture of ethyl acetate (200 mL) and 2 M sodium carbonate (50 mL). The phases were separated and the organic phase was dried (MgSO$_4$). The solvent was evaporated to give a solid residue which was stirred with a small portion of acetonitril. The solid was isolated by filtration and dried to give 250 mg (71%) of N{4-[6-(4-isopropylpiperazin-1-yl)pyridin-3-yl]benzyl}acetamide.

Mp=188-190° C.

$^1$H NMR (300 MHz, CDCl$_3$) δ 1.10 (d, 6H), 2.03 (s, 3H), 2.64-2.68 (m, 4H), 2.75 (hept, 1H), 3.58-3.66 (m, 4H), 4.46 (d, 2H), 5.83 (brs, 1H), 6.72 (d, 1H), 7.33 (d, 2H), 7.47 (d, 2H), 7.68 (dd, 1H), 8.43 (d, 1H).

The free base (250 mg) was dissolved into a 0.5 N hydrochloric acid solution. When dissolved, the mixture was evaporated and then re-evaporated with acetonitril. The solid residue was stirred with ethyl acetate, filtered and dried to give 270 mg (69%) of the title compound.

$^1$H NMR (300 MHz, DMSO-d$_6$) δ 1.32 (d, 6H), 1.89 (s, 3H), 3.05-3.21 (m, 2H), 3.45-3.66 (m, 5H), 4.28 (d, 2H), 4.48-4.59 (m, 2H), 7.27 (d, 1H), 7.34 (d, 2H), 7.64 (d, 2H), 8.16 (d, 1H), 8.40 (s, 1H), 8.45 (t, 1H), 11.3 (brs, 1H).

Microanalysis for C$_{21}$H$_{28}$N$_4$O, 2×HCl, 1.5×H$_2$O:

Calculated: C, 55.75%; H, 7.35%; N, 12.38%.

Found: C, 55.53%; H, 7.38%, N, 12.17%.

EXAMPLE 40

General Procedure A

1-Isopropyl-4-{5-[4-(5-methyl[1,2,4]oxadiazol-3-yl)phenyl]pyridin-2-yl}piperazine, hydrochloride

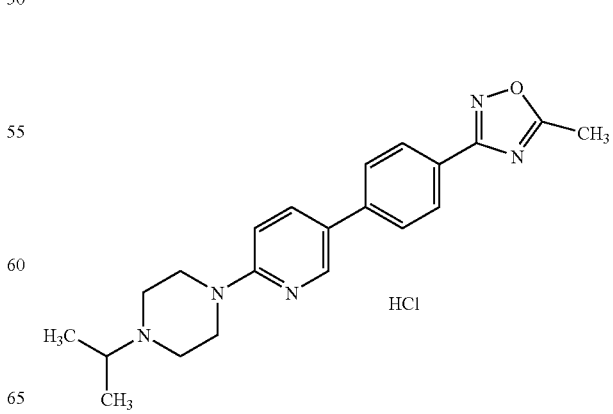

Step 1

N-Hydroxy-4-(6-(4-isopropylpiperazin-1-yl)pyridine-3-yl)benzmidine

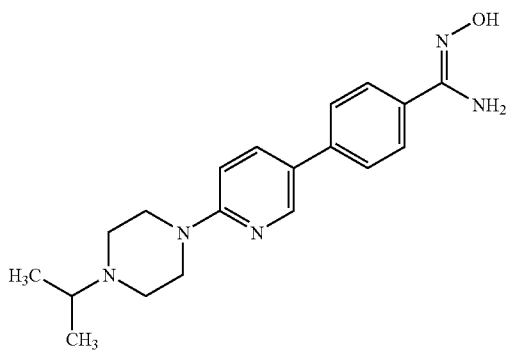 [SMILES: CC(C)N1CCN(c2ccc(-c3ccc(/C(N)=N/O)cc3)cn2)CC1]

A mixture of 4-(6-(4-isopropylpiperazin-1-yl)pyridin-3-yl)benzonitrile (330 mg, 1.1 mmol, prepared as described in Example 10), ethanol (15 mL), hydroxylamine hydrochloride (225 mg, 3.2 mmol), potassium carbonate (240 mg, 1.7 mmol) and water (1.5 mL) was stirred at reflux temperature overnight. The reaction mixture was allowed to cool to rt, and the solid was isolated by filtration and dried. The solid was then stirred with water (10 mL) to remove inorganic residues. The mixture was filtered and the solid was washed with water and a small portion of ethanol. Drying in vacuo afforded 260 mg (71%) of N-hydroxy-4-(6-(4-isopropylpiperazin-1-yl)pyridine-3-yl)benzamidine.

$^1$H NMR (300 MHz, DMSO-d$_6$) δ 1.00 (d, 6H), 2.50-2.55 (m, 4H), 2.67 (hept, 1H), 3.49-3.54 (m, 4H), 5.81 (brs, 2H), 6.88 (d, 1H), 7.62 (d, 2H), 7.73 (d, 2H), 7.86 (dd, 1H), 8.48 (d, 1H), 9.65 (s, 1H).

Step 2

A mixture of the above N-hydroxybenzamidine (260 mg, 0.76 mmol), glacial acetic acid (10 mL) and acetic anhydride (0.56 mL) was stirred for 2 days at rt. The reaction mixture was then heated at reflux temperature for 45 min. The mixture was evaporated to give an oily residue which was stirred with a mixture of ethyl acetate (100 mL) and 2 M sodium carbonate (25 mL). The phases were separated and the organic phase was dried (MgSO$_4$). The solvent was evaporated to give a solid residue which was boiled with acetonitril. The mixture was allowed to cool, and the solid was isolated by filtration and dried to give 110 mg (28%) of 1-isopropyl-4-{5-[4-(5-methyl[1,2,4]oxadiazol-3-yl)phenyl]pyridin-2-yl}piperazine.

$^1$H NMR (300 MHz, CDCl$_3$) δ 1.11 (d, 6H), 2.64-2.69 (m, 4H), 2.67 (s, 3H), 2.75 (hept, 1H), 3.63-3.67 (m, 4H), 6.73 (d, 1H), 7.63 (d, 2H), 7.76 (dd, 1H), 8.10 (d, 2H), 8.50 (d, 1H).

The free base (110 mg) was dissolved into a 0.5 N hydrochloric acid solution. When dissolved, the mixture was evaporated and then re-evaporated with acetonitril. The solid residue was re-crystallised from absolute ethanol to give 120 mg (28%) of the title compound.

$^1$H NMR (300 MHz, DMSO-d$_6$) δ 1.32 (d, 6H), 2.69 (s, 3H), 3.06-3.23 (m, 2H), 3.40-3.66 (m, 5H), 4.51-4.63 (m, 2H), 7.29 (d, 1H), 7.90 (d, 2H), 8.07 (d, 2H), 8.23 (d, 1H), 8.54 (s, 1H), 11.3 (brs, 1H).

EXAMPLE 41

General Procedure A

1-(5-(5-(4-Chloromethylphenyl)[1,2,4]oxadiazol-3-yl)pyridine-2-yl)-4-isopropylpiperazine

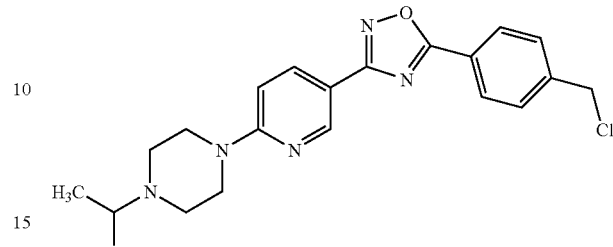

Step 1

6-(4-Isopropylpiperazin-1-yl)nicotinonitrile, hydrochloride

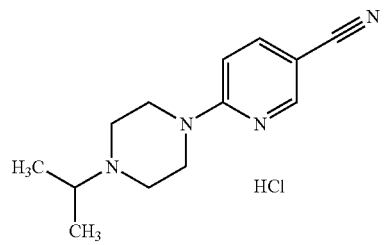 [SMILES: CC(C)N1CCN(c2ccc(C#N)cn2)CC1 ; Cl]

A mixture of 2-chloropyridine-5-carbonitrile (5.0 g, 36.1 mmol), DMSO (10 mL) and 1-isopropylpiperazine (10.7 mL, 75.8 mmol) was stirred under an atmosphere of nitrogen and heated on a 100° C. oil-bath for 3 h. The reaction mixture was allowed to cool, and then poured into cold water (500 mL). The solid was isolated by filtration, washed with water and dried to give 6.8 g (82%) of 6-(4-isopropylpiperazin-1-yl)nicotinonitrile.

$^1$H NMR (400 MHz, CDCl$_3$) δ 1.08 (d, 6H), 2.59-2.64 (m, 4H), 2.75 (hept, 1H), 3.67-3.72 (m, 4H), 6.59 (d, 1H), 7.60 (dd, 1H), 8.40 (d, 1H).

The free base (500 mg) was dissolved into methanol (50 mL) and 1 N hydrochloric acid solution (3 mL) was added. The mixture was evaporated and then re-evaporated with ethanol. The solid residue was stirred with 2-propanol, filtered and dried to give 570 mg (98%) of 6-(4-isopropylpiperazin-1-yl)nicotinonitrile, hydrochloride.

$^1$H NMR (300 MHz, DMSO-d$_6$) δ 1.30 (d, 6H), 2.97-3.12 (m, 2H), 3.41-3.61 (m, 5H), 4.52-4.63 (m, 2H), 7.06 (d, 1H), 7.97 (dd, 1H), 8.56 (d, 1H), 11.5 (brs, 1H).

Step 2

N-Hydroxy-6-(4-isopropylpiperazin-1-yl)nicotinamidine

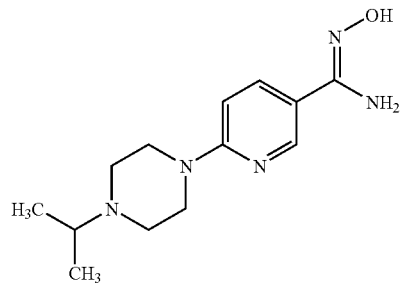 [SMILES: CC(C)N1CCN(c2ccc(/C(N)=N/O)cn2)CC1]

A mixture of 6-(4-isopropylpiperazin-1-yl)nicotinonitrile (2.3 g, 10 mmol), ethanol (25 mL), hydroxylamine hydrochloride (2.1 g, 30 mmol), potassium carbonate (2.2 g, 16 mmol) and water (5 mL) was stirred for 30 min at rt and then at reflux temperature for 3 h. The reaction mixture was left at rt for 2 days and then the solid formed was isolated by filtration. The solid was dried, boiled with ethanol (200 mL) and filtered hot to remove inorganic impurities. The filtrate was evaporated to give 2.0 g (76%) of N-hydroxy-6-(4-isopropylpiperazin-1-yl)nicotinamidine.

$^1$H NMR (400 MHz, DMSO-$d_6$) δ 0.98 (d, 6H), 2.67 (hept, 1H), 3.31-3.51 (m, 8H), 5.74 (brs, 2H), 6.79 (d, 1H), 7.75 (dd, 1H), 8.38 (d, 1H), 9.4 (brs, 1H).

Step 3

The above N-hydroxynicotinamidine (263 mg, 1.0 mmol) was dissolved into N,N-dimethylacetamide (10 mL) and 4-chloromethylbenzoyl chloride (190 mg, 1.0 mmol) was added. The reaction was stirred for 1 h at rt and then heated at 105° C. for 2 h. The mixture was allowed to cool to rt and then filtered. The solid was washed with ethyl acetate and dried. This afforded 280 mg (65%) of 1-(5-(5-(4-chloromethylphenyl)[1,2,4]oxadiazol-3-yl)pyridine-2-yl)-4-isopropylpiperazine, hydrochloride. The hydrochloride (400 mg) was stirred with water (30 mL) and a potassium carbonate solution was added until alkaline reaction. The mixture was extracted with several portions of ethyl acetate (total 100 mL). The combined organic extracts were dried and evaporated to give 300 mg of 1-(5-(5-(4-chloromethylphenyl)[1,2,4]oxadiazol-3-yl)pyridine-2-yl)-4-isopropylpiperazine.

$^1$H NMR (300 MHz, CDCl$_3$) δ 1.09 (d, 6H), 2.59-2.67 (m, 4H), 2.68-2.80 (m, 1H), 3.66-3.72 (m, 4H), 4.66 (s, 2H), 6.71 (d, 1H), 7.57 (d, 2H), 8.16 (dd, 1H), 8.20 (d, 2H), 8.95 (d, 1H).

EXAMPLE 42

General Procedure A

4-{3-[6-(4-Isopropylpiperazin-1-yl)pyridin-3-yl][1,2,4]oxadiazol-5-yl}benzonitrile, hydrochloride

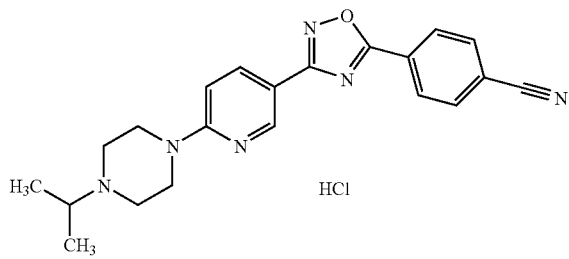 [SMILES: CC(C)N1CCN(c2ccc(-c3noc(-c4ccc(C#N)cc4)n3)cn2)CC1 ; Cl]

The title compound was prepared by a similar procedure to that described in Example 41, starting from N-hydroxy-6-(4-isopropylpiperazin-1-yl)nicotinamidine and 4-cyanobenzoylchloride.

$^1$H NMR (300 MHz, CDCl$_3$) δ 1.50 (d, 6H), 2.86-3.03 (m, 2H), 3.41-3.55 (m, 3H), 3.97-4.10 (m, 2H), 4.49-4.60 (m, 2H), 6.78 (d, 1H), 7.87 (d, 2H), 8.25 (dd, 1H), 8.33 (d, 2H), 8.96 (d, 1H), 12.9 (brs, 1H).

EXAMPLE 43

General Procedure A

1-[5-(5-Cyclopropyl[1,2,4]oxadiazol-3-yl)pyridin-2-yl]-4-isopropylpiperazine, dimethanesulfonate

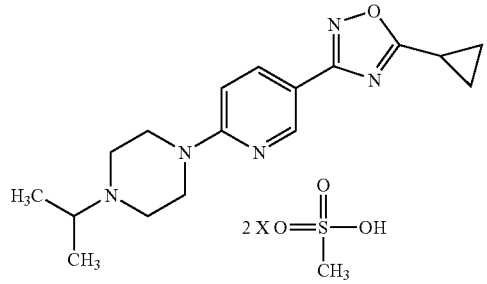

The title compound was prepared by a similar procedure to that described in Example 42, starting from N-hydroxy-6-(4-isopropylpiperazin-1-yl)nicotinamidine and cyclopropylcarbonylchloride.

$^1$H NMR (300 MHz, CDCl$_3$) δ 1.26-1.32 (m, 4H), 1.45 (d, 6H), 2.20-2.28 (m, 1H), 2.80 (s, 6H), 3.29-3.45 (m, 2H), 3.54-3.69 (m, 3H), 4.02-4.16 (m, 2H), 4.59-4.70 (m, 2H), 7.31 (d, 1H), 8.42 (dd, 1H), 8.72 (d, 1H), 10.9 (brs, 1H).

EXAMPLE 44

General Procedure A

1-Isopropyl-4-{5-[5-(4-piperidin-1-ylmethylphenyl)[1,2,4]oxadiazol-3-yl]pyridin-2-yl}piperazine, dihydrochloride

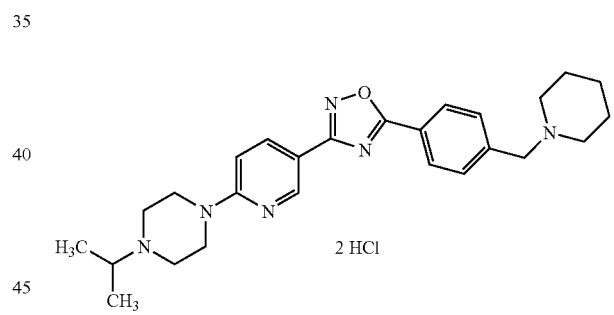

A mixture of 1-(5-(5-(4-chloromethylphenyl)[1,2,4]oxadiazol-3-yl)pyridine-2-yl)-4-isopropylpiperazine, hydrochloride (280 mg, 0.65 mmol, prepared as described in Example 41, 96% ethanol (20 mL) and piperidine (0.2 mL, 2.1 mmol) heated at reflux temperature for 4 h. The mixture was evaporated to give a solid residue which was purified by column chromatography on silica gel (75 g, Kiselgel 60, mesh 0.040-0.63) eluting with a mixture of dichloromethane and methanol (7:3). Collecting the proper fractions afforded 310 mg (100%) of 1-isopropyl-4-{5-[5-(4-piperidin-1-ylmethylphenyl)[1,2,4]oxadiazol-3-yl]pyridin-2-yl}piperazine. The free base (310 mg) was dissolved into ethanol (20 mL) and a 1 N hydrochloric acid solution (1.5 mL) was added. When dissolved, the mixture was evaporated and the solid residue was re-crystallised from ethanol to give 240 mg (67%) of the title compound.

$^1$H NMR (300 MHz, D$_2$O) δ 1.42 (d, 6H), 1.61-1.94 (m, 6H), 3.12-3.50 (m, 8H), 3.55-3.69 (m, 1H), 3.82-4.05 (m, 4H), 4.37 (s, 2H), 7.02 (d, 1H), 7.73 (d, 2H), 8.12 (d, 1H), 8.18 (d, 2H), 8.64 (s, 1H).

EXAMPLE 45

General Procedure A 1-(4-{3-[6-(4-Isopropylpiperazin-1-yl)pyridin-3-yl][1,2,4]oxadiazol-5-yl}benzyl)piperidine-4-carboxylic acid amide, dihydrochloride

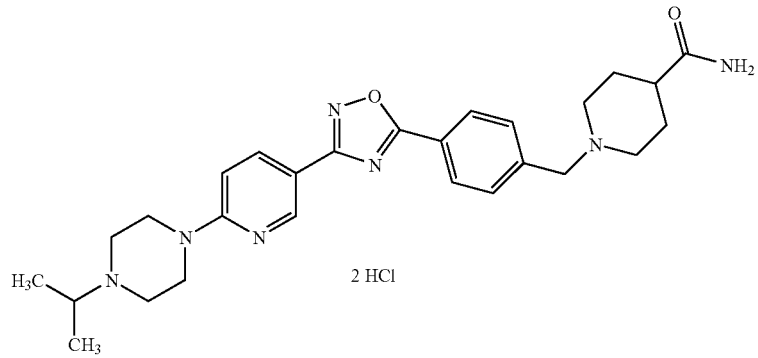 [SMILES: CC(C)N1CCN(c2ccc(-c3noc(-c4ccc(CN5CCC(C(N)=O)CC5)cc4)n3)cn2)CC1 ; "2 HCl"]

2 HCl

The title compound was prepared by a similar procedure to that described in Example 44, starting from 1-(5-(5-(4-chloromethylphenyl)[1,2,4]oxadiazol-3-yl)pyridine-2-yl)-4-isopropylpiperazine and isonipecotamide.

$^1$H NMR (300 MHz, DMSO-d$_6$) δ 1.32 (d, 6H), 1.85-1.97 (m, 3H), 2.26-2.40 (m, 1H), 2.87-3.24 (m, 4H), 3.29-3.62 (m, 6H), 4.36-4.48 (m, 2H), 4.53-4.65 (m, 2H), 6.88-7.04 (2×brs, 1H), 7.17 (d, 1H), 7.38-7.52 (2×brs, 1H), 7.90-8.00 (m, 2H), 8.19-8.28 (m, 3H), 8.84 (s, 1H), 11.0 (brs, 1H), 11.3 (brs, 1H).

EXAMPLE 46

General Procedure A

1-Prop-1-yl-4-[5-(4-trifluoromethylphenyl)pyridin-2-yl]piperazine

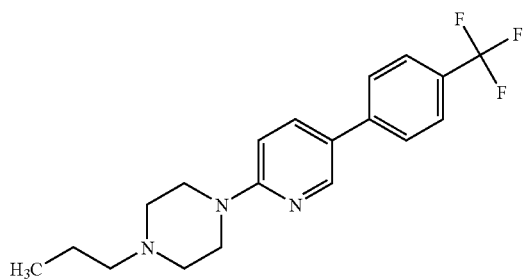 [SMILES: CCCN1CCN(c2ccc(-c3ccc(C(F)(F)F)cc3)cn2)CC1]

The title compound was prepared by a similar procedure to that described in Example 213, starting from 4-(5-(4-trifluoromethylphenyl)pyridin-2-yl)piperazine and propionaldehyde.

$^1$H NMR (400 MHz, CDCl$_3$) δ 0.95 (t, 3H), 1.57 (m, 2H), 2.37 (m, 2H), 2.58 (m, 4H), 3.64 (m, 4H), 6.73 (d, J=9.10 Hz, 1H), 7.64 (m, 4H), 7.72 (dd, J=9.10, 2.53 Hz, 1H), 8.46 (d, J=2.53 Hz, 1H).

EXAMPLE 47

General Procedure A

1-Cyclohexyl-4-[5-(4-trifluoromethylphenyl)pyridin-2-yl]piperazine, hydrochloride

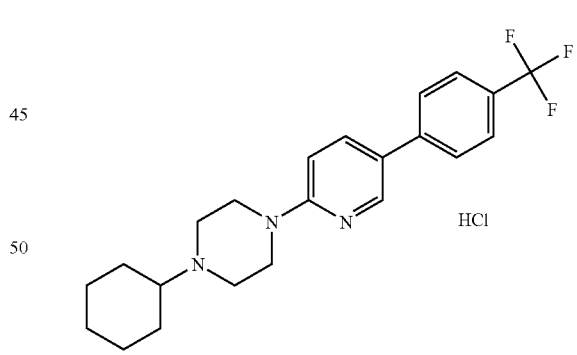

HCl

The title compound was prepared by a similar procedure to that described in Example 213, starting from 4-(5-(4-trifluoromethylphenyl)pyridin-2-yl)piperazine and cyclohexanone.

$^1$H NMR (400 MHz, DMSO-d$_6$) δ 1.18 (m, 3H), 1.46 (m, 2H), 1.62 (m, 1H), 1.82 (m, 2H), 2.18 (m, 2H), 3.17 (m, 3H), 3.59 (m, 4H), 4.53 (d, 2H), 7.25 (d, J=9.09 Hz, 1H), 7.81 (d, J=8.08 Hz, 2H), 7.93 (d, J=8.59 Hz, 2H), 8.18 (m, 1H), 8.54 (d, J=2.53 Hz, 1H), 11.47 (brs, 1H).

EXAMPLE 48

General Procedure A

1-{4-[6-(4-Isopropylpiperazin-1-yl)pyridazin-3-yl]phenyl}ethanone

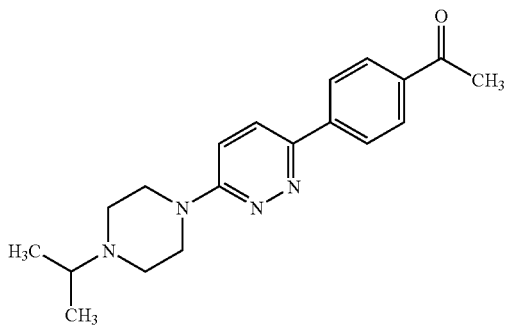 [SMILES: CC(=O)c1ccc(-c2ccc(N3CCN(C(C)C)CC3)nn2)cc1]

To a suspension of 4-[6-(4-isopropylpiperazin-1-yl)pyridazin-3-yl]benzonitrile (0.36 g, 1.17 mmol, prepared by a similar procedure to that described in Example 1) in dry THF (5 mL) was added a 1.4 M methylmagnesium bromide solution in toluene/THF. The reaction mixture was stirred at room temperature for 24 h, 1 M hydrochloric acid (7 mL) was added and the solution stirred for 1 h. The mixture was made alkaline by addition of excess NaHCO$_3$ solution and extracted with dichloromethane. The organic phase was dried over magnesium sulphate, the solvent was removed and the solid was re-crystallized from ethanol to give the title compound, 163 mg (43%).

$^1$H NMR (400 MHz, DMSO-d$_6$) δ 1.01 (d, J=6.57 Hz, 6H), 2.57 (m, 4H), 2.62 (s, 3H), 2.71 (m, 1H), 3.66 (m, 4H), 7.37 (d, J=9.60 Hz, 1H), 8.04 (m, J=9.10, 9.10 Hz, 3H), 8.19 (d, J=8.59 Hz, 2H).

Microanalysis for C$_{19}$H$_{24}$N$_4$O:
Calculated: C, 70.34%; H, 7.46%; N, 17.27%.
Found: C, 70.07%; H, 7.37%; N, 17.18%.

EXAMPLE 49

General Procedure A

1-{4-[5-(4-Trifluoromethylphenyl)pyridin-2-yl]piperazin-1-yl}propan-2-one, hydrochloride

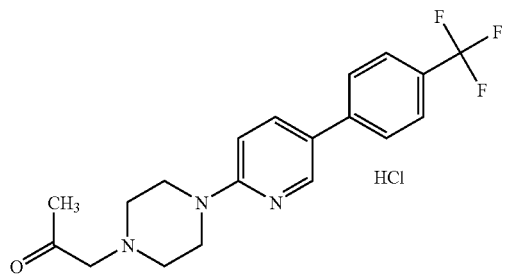 [SMILES: CC(=O)CN1CCN(c2ccc(-c3ccc(C(F)(F)F)cc3)cn2)CC1 ; Cl]

The title compound was prepared by a similar procedure to that described in Example 55, starting from 4-(5-(4-trifluoromethylphenyl)pyridin-2-yl)piperazine and chloroacetone.

$^1$H NMR (400 MHz, CD$_3$OD) δ 2.29 (s, 3H), 3.79 (m, 8H), 4.49 (s, 2H), 7.59 (d, J=9.60 Hz, 1H), 7.82 (m, 2H), 7.89 (m, 2H), 8.42 (m, 1H), 8.50 (dd, J=9.35, 2.27 Hz, 1H).

EXAMPLE 50

General Procedure A

N,N-Dimethyl-2-{4-[5-(4-trifluoromethylphenyl)pyridin-2-yl]-piperazin-1-yl}acetamide, hydrochloride

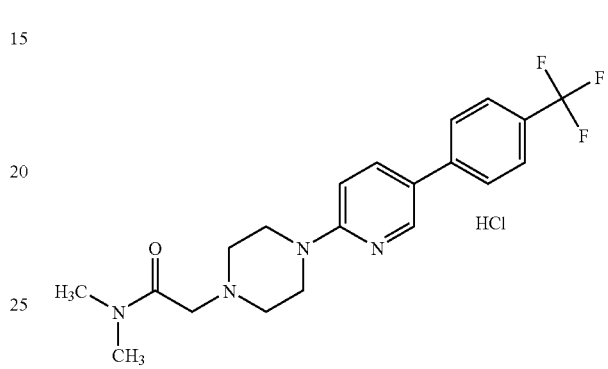

The title compound was prepared by a similar procedure to that described in Example 55, starting from 4-(5-(4-trifluoromethylphenyl)pyridin-2-yl)piperazine and 2-chloro-N,N-dimethylacetamide.

$^1$H NMR (400 MHz, DMSO-d$_6$) δ 2.95 (m, 6H), 3.45 (m, 6H), 4.48 (m, 4H), 7.20 (d, J=9.10 Hz, 1H), 7.80 (d, J=8.08 Hz, 2H), 7.92 (d, J=8.08 Hz, 2H), 8.16 (dd, J=9.09, 2.53 Hz, 1H), 8.57 (d, J=2.02 Hz, 1H), 10.37 (brs, 1H).

EXAMPLE 51

General Procedure A

3-{4-[5-(4-Trifluoromethylphenyl)pyridin-2-yl]piperazin-1-yl}propionitrile

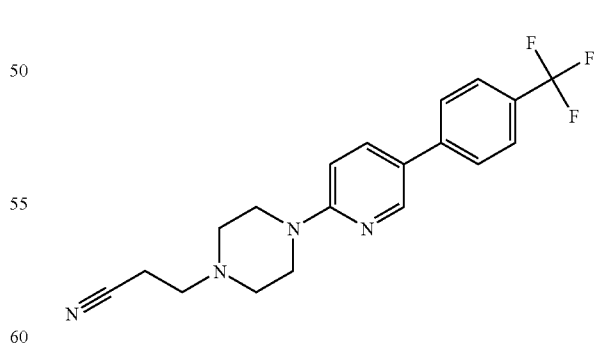

The title compound was prepared by a similar procedure to that described in Example 55, starting from 4-(5-(4-trifluoromethylphenyl)pyridin-2-yl)piperazine and 3-bromopropionitrile.

$^1$H NMR (400 MHz, DMSO-d$_6$) δ 2.54 (m, 4H), 2.62 (t, J=6.57 Hz, 2H), 2.73 (t, J=6.32 Hz, 2H), 3.58 (m, 4H), 6.97

(d, J=8.59 Hz, 1H), 7.76 (m, 2H), 7.86 (m, 2H), 7.94 (dd, J=8.59, 2.53 Hz, 1H), 8.54 (d, J=2.53 Hz, 1H).

EXAMPLE 52

General Procedure A

Diethyl-(2-{4-[5-(4-trifluoromethylphenyl)pyridin-2-yl]piperazin-1-yl}ethyl)amine

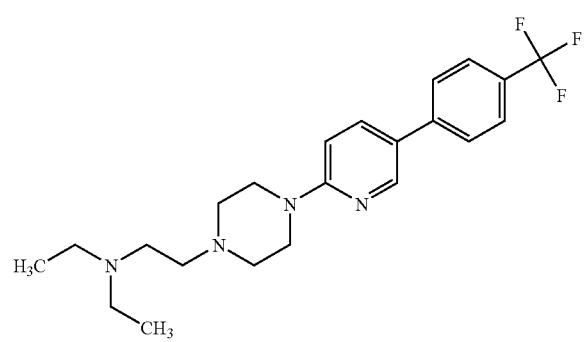 [SMILES: CCN(CC)CCN1CCN(c2ccc(-c3ccc(C(F)(F)F)cc3)cn2)CC1]

The title compound was prepared by a similar procedure to that described in Example 55, starting from 4-(5-(4-trifluoromethylphenyl)pyridin-2-yl)piperazine and 2-diethylaminoethylchloride.

$^1$H NMR (400 MHz, CDCl$_3$) δ 1.05 (t, J=7.07 Hz, 6H), 2.61 (m, 12H), 3.63 (m, 4H), 6.73 (d, J=9.10 Hz, 1H), 7.64 (m, 4H), 7.72 (dd, J=9.10, 2.53 Hz, 1H), 8.46 (d, J=2.53 Hz, 1H).

EXAMPLE 53

General Procedure A 1-(2-Methoxyethyl)-4-[5-(4-trifluoromethylphenyl)pyridin-2-yl]piperazine

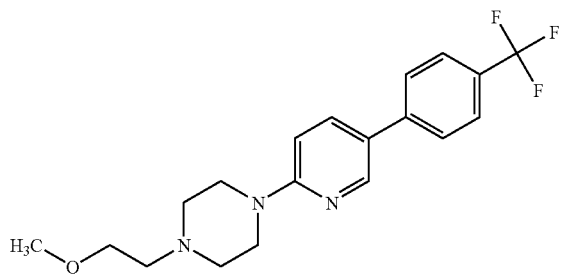 [SMILES: COCCN1CCN(c2ccc(-c3ccc(C(F)(F)F)cc3)cn2)CC1]

The title compound was prepared by a similar procedure to that described in Example 55, starting from 4-(5-(4-trifluoromethylphenyl)pyridin-2-yl)piperazine and 2-methoxyethylbromide.

$^1$H NMR (400 MHz, CDCl$_3$) δ 2.65 (m, 6H), 3.39 (s, 3H), 3.57 (t, J=5.56 Hz, 2H), 3.66 (m, 4H), 6.73 (d, J=8.59 Hz, 1H), 7.64 (m, 4H), 7.72 (dd, J=8.59, 2.53 Hz, 1H), 8.46 (d, J=2.53 Hz, 1H).

EXAMPLE 54

General Procedure A

1-Allyl-4-[5-(4-trifluoromethylphenyl)pyridin-2-yl]piperazine, hydrochloride

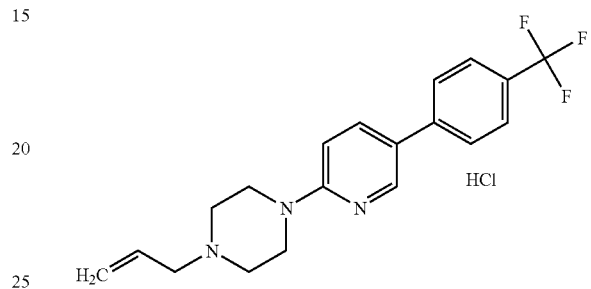

The title compound was prepared by a similar procedure to that described in Example 55, starting from 4-(5-(4-trifluoromethylphenyl)pyridin-2-yl)piperazine and allyliodide.

$^1$H NMR (400 MHz, DMSO-d$_6$) δ 3.08 (d, J=9.10 Hz, 2H), 3.80 (d, J=3.54 Hz, 2H), 4.29 (s, 4H), 4.55 (d, J=14.15 Hz, 2H), 5.54 (m, 2H), 6.06 (m, 1H), 7.24 (d, J=9.09 Hz, 1H), 7.81 (d, J=8.08 Hz, 2H), 7.92 (d, J=8.08 Hz, 2H), 8.19 (dd, J=9.10, 2.53 Hz, 1H), 8.55 (d, J=2.53 Hz, 1H), 11.77 (brs, 1H).

EXAMPLE 55

General Procedure A

1-Isopropyl-4-[6-(4-trifluoromethylphenyl)pyridazin-3-yl]-[1,4]diazepane, dihydrochloride

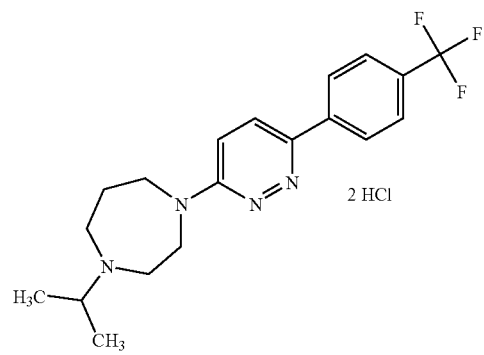 [SMILES: CC(C)N1CCCN(c2ccc(-c3ccc(C(F)(F)F)cc3)nn2)CC1 ; "2 HCl"]

4-[6-(4-Trifluoromethylphenyl)pyridazin-3-yl]-[1,4]diazepane, dihydrochloride (0.028 g, 0.071 mmol) was suspended in THF (4 mL) and triethylamine (0.022 g, 0.21 mmol) was added. Sodium hydride (0.0085 g, 0.35 mmol) was added and the reaction mixture was stirred at rt for 20 min. Dry N,N-dimethylformamide (1 mL) and 2-chloropropane (0.056 g, 0.71 mmol) was added and the reaction mixture was heated 30 min at 160° C. and 30 min at 180° C. in a microwave oven.

The reaction mixture was purified on a silicagel column (0.04-0.063 mesh) using dichloromethane/MeOH (9:1) as eluent. This afforded a crude oil containing several components that was purified further by preparative HPLC using Method B. This afforded 9 mg of an oil which was dissolved into MeOH. Addition of HCl in diethyl ether afforded 6.5 mg (21%) of the title compound as an oily dihydrochloride.

$^1$H NMR (400 MHz, CD$_3$OD) δ 1.38 (d, J=6.57 Hz, 6H), 2.23-2.46 (m, 2H), 3.32-3.52 (m, 2H), 3.53-3.85 (m, 4H), 3.88-4.15 (m, 2H), 4.26-4.55 (m, 1H), 7.60 (d, J=9.60 Hz, 1H), 7.84 (d, J=8.08 Hz, 2H), 8.05-8.28 (m, 3H)

LC-MS (Method G): M+1=365; t$_r$=1.178 min.

EXAMPLE 56

General Procedure A

N-[4-(4-Isopropyl-3,4,5,6-tetrahydro-2H-[1,2']bipyrazinyl-5'-yl)phenyl]acetamide, trifluoroacetate

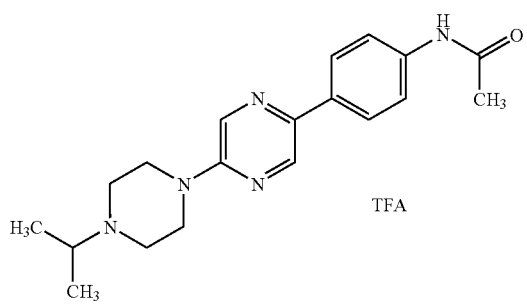 [SMILES: CC(=O)Nc1ccc(-c2cnc(N3CCN(C(C)C)CC3)cn2)cc1]

Step 1

4-Isopropyl-3,4,5,6-tetrahydro-2H-[1,2']bipyrazinyl

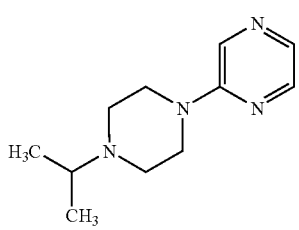

Chloropyrazine (2.3 g, 20 mmol) and triethylamine (3 g, 30 mmol) were mixed in acetone (8 mL) in a 20 mL microwave vessel. 1-Isopropylpiperazine (2.8 g, 22 mmol) was added and the reaction mixture was heated for 3300 seconds at 120° C. in a microwave oven. The reaction mixture was evaporated and the residue was purified on a silicagel column with dichloromethane/MeOH (9:1) as eluent. Yield: 1.64 g solid 4-isopropyl-3,4,5,6-tetrahydro-2H-[1,2']bipyrazinyl.

$^1$H NMR (400 MHz, CDCl$_3$) δ1.08 (d, J=6.57 Hz, 6H) 2.61-2.65 (m, 4H) 2.68-2.77 (m, 1H) 3.58-3.62 (m, J=4.55 Hz, 4H) 7.70-7.91 (m, 1H) 8.03-8.08 (m, 1H) 8.13 (s, 6H).

$^{13}$C NMR (400 MHz, CDCl$_3$) δ 18.82, 45.16, 48.66, 54.94, 77.17, 77.48, 77.80, 131.30, 133.10, 142.00, 155.30.

Step 2

5-Bromo-4-isopropyl-3,4,5,6-tetrahydro-2H-[1,2']bipyrazinyl

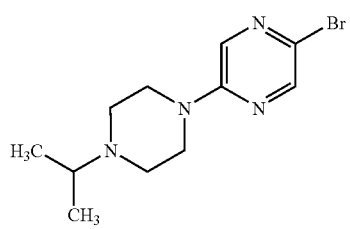

4-Isopropyl-3,4,5,6-tetrahydro-2H-[1,2']bipyrazinyl (1.0 g, 4.8 mmol) was dissolved in dichloromethane (30 mL) and the solution was placed on an ice-bath and brominated according to literature (Tetrahedron 44, 10, 1988, 2977-2984) in very bad yield. N-Bromosuccinimide (3.45 g, 19.4 mmol) was added slowly at 0° C. and then left overnight at rt. No reaction was observed. An additional 3.45 g of N-bromosuccinimide was added during 8 h, and then the reaction mixture was left at rt for 2 days. Aqueous concentrated Na$_2$CO$_3$ was added and the mixture was extracted with dichloromethane (3×75 mL). The combined organic extracts were dried (MgSO$_4$), filtered and evaporated. The oily residue was purified on a silica gel column with dichloromethane/MeOH (9:1) as eluent. Yield: 196 mg (28%) of 5-bromo-4-isopropyl-3,4,5,6-tetrahydro-2H-[1,2']bipyrazinyl as an oil.

$^1$H NMR (400 MHz, CDCl$_3$) δ1.09 (d, J=6.57 Hz, 6H) 2.55-2.67 (m, 4H) 2.72-2.83 (m, 1H) 3.44-3.65 (m, 4H) 7.87 (s, 1H) 8.12 (s, 1H).

$^{13}$C NMR (400 MHz, CDCl$_3$) δ 18.71, 30.05, 45.19, 48.39, 48.68, 54.92, 126.04, 130.51, 144.16, 154.31.

Step 3

5-Bromo-4-isopropyl-3,4,5,6-tetrahydro-2H-[1,2']bipyrazinyl (0.196 g, 0.68 mmol), 4-acetamidophenylboronic acid (0.123 g, 0.69 mmol), bistriphenylphosphinpalladium (II)dichloride (0.015 g, 0.021 mmol) and Na$_2$CO$_3$ (0.168 g, 1.37 mmol, dissolved in 2 mL H$_2$O) were mixed in acetonitril (16 mL) under a nitrogen atmosphere in a 20 mL microwave vessel. The reaction mixture was heated 400 seconds at 150° C. in a microwave oven. Some debromination was observed by LC-MS of the reaction mixture. The reaction mixture was evaporated and the residue was redissolved in a mixture of dichloromethane and H$_2$O. The phases were separated and the aqueous phase was extracted with dichloromethane (3×50 mL). The combined organic extracts were evaporated and the residue was dissolved in MeOH and purified according to preparative HPLC Method B. This afforded 49 mg (15%) of the title compound as the trifluoroacetic acid salt.

$^1$H NMR (400 MHz, DMSO-d$_6$) δ1.30 (d, J=6.57 Hz, 6H) 2.03-2.11 (m, 3H) 3.09-3.20 (m, 2H) 3.23-3.34 (m, 2H) 3.56-3.66 (m, 5H) 4.55 (d, J=11.62 Hz, 2H) 7.69 (d, J=8.59 Hz, 2H) 7.94 (d, J=8.59 Hz, 2H) 8.49 (s, 1H) 8.71 (s, 1H) 10.13 (brs, 2H).

$^{13}$C NMR (400 MHz, DMSO-d$_6$) δ16.78, 24.38, 42.00, 47.27, 57.62, 119.49, 125.98, 131.08, 131.36, 138.06, 139.79, 141.19, 152.67, 168.76.

EXAMPLE 57

General Procedure A

[4-(4-Isopropyl-3,4,5,6-tetrahydro-2H-[1,2']bipyrazinyl-5'-yl)phenyl]acetonitrile, triuoroacetate

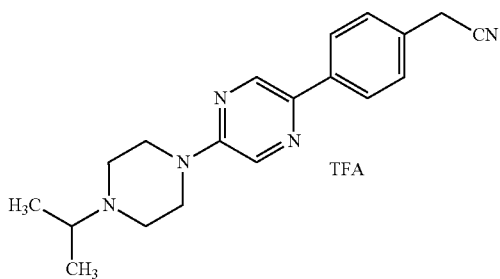 [SMILES: CC(C)N1CCN(c2cnc(-c3ccc(CC#N)cc3)cn2)CC1]

4-Cyanomethylphenylboronic acid (0.137 g, 0.85 mmol), 5-bromo-4-isopropyl-3,4,5,6-tetrahydro-2H-[1,2']bipyrazinyl (0.242 g, 0.85 mmol), bistriphenylphosphinpalladium(II) dichloride (0.035 g, 0.080 mmol) and a 1 N $Na_2CO_3$ solution in $H_2O$ (1.7 mL)) were mixed in acetonitril (2 mL) under an atmosphere of nitrogen in a 5 mL microwave vessel. The reaction mixture was heated 600 seconds at 120° C. in a microwave oven. The reaction mixture was evaporated and the residue was dissolved in a mixture of $H_2O$ and dichloromethane. The phases were separated and the aqueous phase was extracted with dichloromethane (3×25 mL). The organic extracts were combined and trifluoroacetic acid was added. The volatiles were evaporated and the residue was dissolved in MeOH and purified according to preparative HPLC Method B to give 35 mg (10%) of the title compound.

$^1$H NMR (400 MHz, $CDCl_3$) δ1.40 (d, J=6.57 Hz, 6H) 2.92-3.03 (m, 2H) 3.54-3.65 (m, 5H) 3.81 (s, 2H) 4.48 (d, J=13.64 Hz, 2H) 7.42 (d, J=8.08 Hz, 2H) 7.91 (d, J=8.08 Hz, 2H) 8.24 (s, 1H) 8.55 (s, 1H) 12.43-13.00 (m, 1H).

$^{13}$C NMR (400 MHz, $CDCl_3$) δ 16.96, 23.78, 42.43, 47.56, 58.32, 118.13, 126.86, 128.92, 130.44, 130.50, 136.78, 139.24, 142.57, 152.99.

EXAMPLE 58

General Procedure A 5-(4-Ethanesulfonylphenyl)-4-isopropyl-3,4,5,6-tetrahydro-2H-[1,2']bipyrazinyl, trifluoroacetate

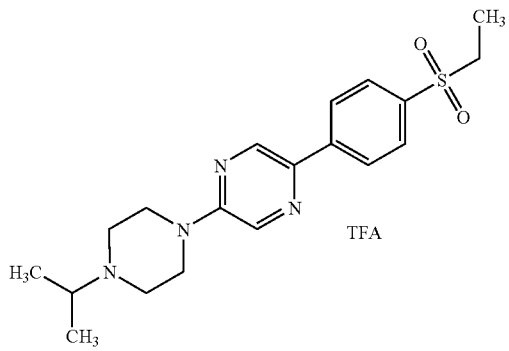 [SMILES: CCS(=O)(=O)c1ccc(-c2cnc(N3CCN(C(C)C)CC3)cn2)cc1]

4-Ethansulfonylphenylboronic acid (0.182 g, 0.85 mmol), 5-bromo-4-isopropyl-3,4,5,6-tetrahydro-2H-[1,2']bipyrazinyl (0.242 g, 0.85 mmol), bistriphenylphosphinpalladium(II) dichloride (0.035 g, 0.080 mmol) and a 1 N $Na_2CO_3$ solution in $H_2O$ (1.7 mL)) were mixed in acetonitril (2 mL) under an atmosphere of nitrogen in a 5 mL microwave vessel. The reaction mixture was heated 400 seconds at 120° C. in a microwave oven. The reaction mixture was evaporated and the residue was dissolved in a mixture of $H_2O$ and dichloromethane. The phases were separated and the aqueous phase was extracted with dichloromethane (3×25 mL). The organic extracts were combined and trifluoroacetic acid was added. The volatiles were evaporated and the residue was dissolved in MeOH and purified according to HPLC Method B to give 60 mg (12%) of the title compound.

$^1$H NMR (400 MHz, $CD_3OD$) δ 1.24 (t, J=7.33 Hz, 3H), 1.42 (d, J=6.57 Hz, 6H), 3.20 (q, J=7.58 Hz, 2H), 3.28-3.39 (m, 4H), 3.56-3.68 (m, 3H), 4.60-4.79 (m, 2H), 4.86 (brs, 6H), 7.96 (d, J=8.59 Hz, 2H), 8.20 (d, 2H), 8.44 (s, 1H), 8.76 (s, 1H).

$^{13}$C NMR (400 MHz, $CD_3OD$) δ 8.04, 17.47, 43.47, 51.67, 60.46, 127.68, 130.30, 132.37, 139.42, 141.14, 141.74, 143.74, 155.02.

EXAMPLE 59

General Procedure A

N-{4-[6-(4-Isopropylpiperazin-1-yl)pyridin-3-yl]phenyl}acetamide, dihydrochloride

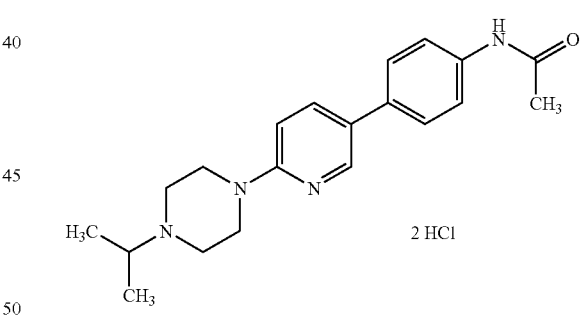

The title compound was prepared by a similar procedure to that described in Example 56, starting from 1-(5-bromo-pyridin-2-yl)-4-isopropyl-piperazine and 4-acetamidophenylboronic acid.

$^1$H NMR (400 MHz, DMSO-$d_6$) δ 11.25 (brs, 1H), 10.18 (s, 1H), 8.38 (s, 1H), 8.16 (d, 1H), 7.70 (d, 2H), 7.62 (d, 2H), 7.28 (d, 1H), 4.53 (d, 2H), 3.65-3.45 (m, 5H), 3.20-3.08 (m, 2H), 2.06 (s, 3H), 1.33 (d, 6H).

Microanalysis for $C_{20}H_{26}N_4O$, 2×HCl, 1.5×$H_2O$:

Calculated: C, 54.80%; H, 7.13%; N, 12.78%.

Found: C, 54.55%; H, 6.84%, N, 12.42%.

EXAMPLE 60

General Procedure A

Cyclopropanecarboxylic acid [4-(4-isopropyl-3,4,5,6-tetrahydro-2H-[1,2']bipyrazinyl-5'-yl)phenyl]amide, dihydrochloride

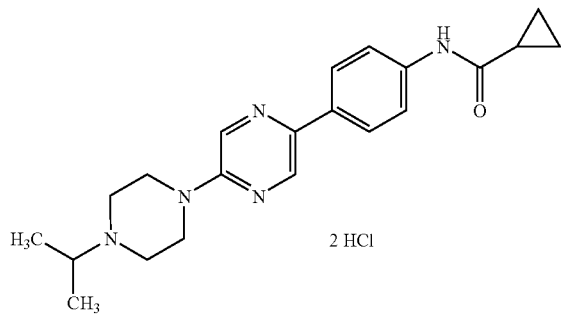 [SMILES: CC(C)N1CCN(c2cnc(-c3ccc(NC(=O)C4CC4)cc3)cn2)CC1 ; "2 HCl"]

The title compound was prepared by a similar procedure to that described in Example 176, starting from 4-(4-isopropyl-3,4,5,6-tetrahydro-2H-[1,2']bipyrazinyl-5'-yl)phenylamine and cyclopropanecarboxylic acid. $^1$H NMR (400 MHz, DMSO-$d_6$) δ 11.24 (brs, 1H), 10.52 (s, 1H), 8.70 (s, 1H), 8.47 (s, 1H), 7.92 (d, 2H), 7.72 (d, 2H), 4.49 (d, 2H), 3.55-3.44 (m, 5H), 3.15-3.04 (m, 2H), 1.91-1.83 (m, 1H), 1.32 (d, 6H), 0.83-0.75 (m, 4H).

Microanalysis for $C_{21}H_{27}N_5O$, 2×HCl, 2.25×$H_2O$:
Calculated: C, 52.67%; H, 7.05%; N, 14.62%.
Found: C, 52.79%; H, 7.00%, N, 14.53%.

EXAMPLE 61

General Procedure A

2-Cyclopropyl-N-[4-(4-isopropyl-3,4,5,6-tetrahydro-2H-[1,2']bipyrazinyl-5'-yl)phenyl]-acetamide, dihydrochloride

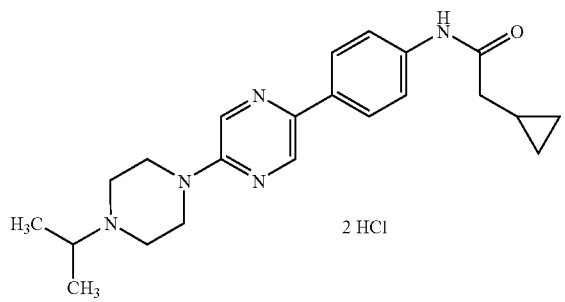 [SMILES: CC(C)N1CCN(c2cnc(-c3ccc(NC(=O)CC4CC4)cc3)cn2)CC1 ; "2 HCl"]

The title compound was prepared by a similar procedure to that described in Example 176, starting from 4-(4-isopropyl-3,4,5,6-tetrahydro-2H-[1,2']bipyrazinyl-5'-yl)phenylamine and cyclopropylacetic acid. $^1$H NMR (400 MHz, DMSO-$d_6$) δ 11.00 (brs, 1H), 10.06 (s, 1H), 8.71 (s, 1H), 8.46 (s, 1H), 7.92 (d, 2H), 7.71 (d, 2H), 4.49 (d, 2H), 3.52-3.42 (m, 5H), 3.15-3.04 (m, 2H), 2.23 (d, 2H), 1.30 (d, 6H), 1.10-1.00 (m, 1H), 0.50-0.44 (m, 2H), 0.22-0.17 (m, 2H).

Microanalysis for $C_{22}H_{29}N_5O$, 2×HCl, 0.75×$H_2O$:
Calculated: C, 56.71%; H, 7.03%; N, 15.05%.
Found: C, 56.51%; H, 6.73%, N, 14.82%.

EXAMPLE 62

General Procedure A

4-Methoxycyclohexanecarboxylic acid [4-(4-isopropyl-3,4,5,6-tetrahydro-2H-[1,2']bipyrazinyl-5'-yl)phenyl]amide, dihydrochloride

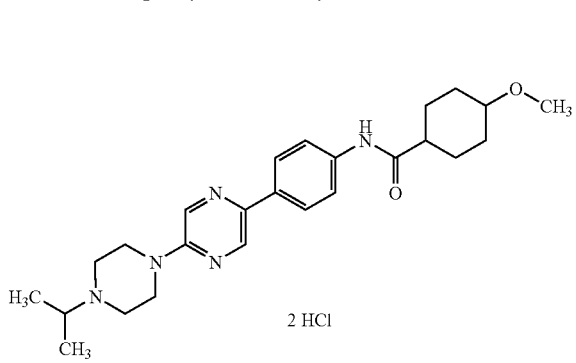

The title compound was prepared by a similar procedure to that described in Example 176, starting from 4-(4-isopropyl-3,4,5,6-tetrahydro-2H-[1,2']bipyrazinyl-5'-yl)phenylamine and 4-methoxycyclohexanecarboxylic acid. $^1$H NMR (400 MHz, DMSO-$d_6$) δ 11.22 (brs, 1H), 10.08 (d, 1H), 8.71 (s, 1H), 8.48 (s, 1H), 7.93 (d, 2H), 7.71 (d, 2H), 4.51 (d, 2H), 3.55-3.38 (m, 5H), 3.25+3.22 (2×s, 3H), 3.16-3.04 (m, 2H), 2.47-2.29 (m, 1H), 2.11-1.06 (m, 14H).

Microanalysis for $C_{25}H_{35}N_5O_2$, 2×HCl, 1.25×$H_2O$:
Calculated: C, 56.33%; H, 7.47%; N, 13.14%.
Found: C, 56.27%; H, 7.38%, N, 12.61%.

EXAMPLE 63

General Procedure A

4-{4-[6-(4-Isopropylpiperazin-1-yl)pyridin-3-yl]benzyl}morpholine, trifluoroacetate

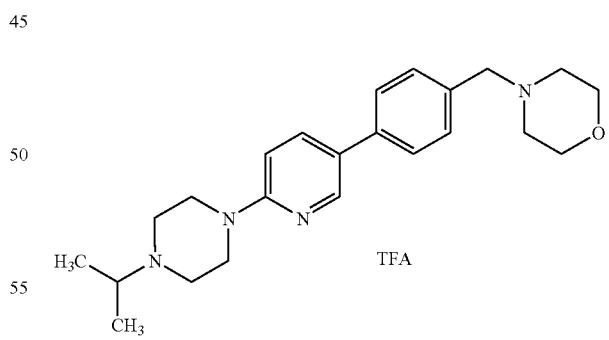

The title compound was prepared by a similar procedure to that described in Example 153, starting from 4-[6-(4-isopropyl-piperazin-1-yl)-pyridin-3-yl]-benzaldehyde and morpholine.

$^1$H NMR (300 MHz, $D_2O$) δ 8.29 (dd, 1H), 8.21 (d, 1H), 7.65 (d, 2H), 7.52 (d, 2H), 7.34 (d, 1H), 4.36-4.32 (m, 4H), 4.02-3.98 (m, 2H), 3.71-3.50 (m, 7H), 3.37-3.12 (m, 6H), 1.28 (d 6H).

HPLC (Method D): $t_r$=2.45 min (97%).

EXAMPLE 64

General Procedure A

4-[2-(4-Isopropylpiperazin-1-yl)pyrimidin-5-yl]benzonitrile

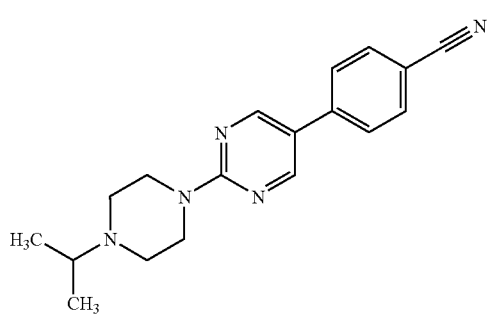 [SMILES: CC(C)N1CCN(c2ncc(-c3ccc(C#N)cc3)cn2)CC1]

The title compound was prepared by a similar procedure to that described in Example 1, starting from 1-isopropylpiperazine and 4-(2-chloro-pyrimidin-5-yl)benzonitrile.

$^1$H NMR (400 MHz, DMSO-d$_6$) δ 11.34 (brs, 1H), 8.91 (s, 2H), 7.92 (s, 4H), 4.81 (d, 2H), 3.63-3.43 (m, 5H), 3.12-3.01 (m, 2H), 1.31 (d, 6H).

Microanalysis for C$_{18}$H$_{21}$N$_5$, 2×HCl, 0.75×H$_2$O:

Calculated: C, 54.90%; H, 6.27%; N, 17.78%.

Found: C, 55.23%; H, 6.45%, N, 17.54%.

EXAMPLE 65

N-{4-[2-(4-Isopropylpiperazin-1-yl)pyrimidin-5-yl]benzyl}acetamide, dihydrochloride

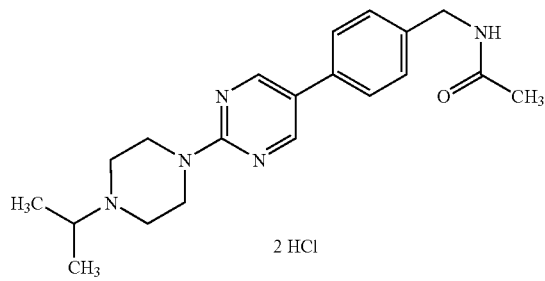 [SMILES: CC(=O)NCc1ccc(-c2cnc(N3CCN(C(C)C)CC3)nc2)cc1 ; "2 HCl"]

The title compound was prepared by a similar procedure to that described in Example 39, starting from 4-[2-(4-Isopropylpiperazin-1-yl)pyrimidin-5-yl]benzonitrile.

$^1$H NMR (300 MHz, CDCl$_3$) δ 8.79 (s, 2H), 7.53 (d, 2H), 7.45 (d, 2H), 5.06 (d, 2H), 4.47 (s, 2H), 4.15-4.01 (m, 2H), 3.65-3.52 (m, 3H), 3.32-3.19 (m, 2H), 2.13 (s, 3H), 1.48 (d, 6H).

HPLC (Method A): t$_r$=6.66 min (100%).

Microanalysis for C$_{20}$H$_{27}$N$_5$O, 2×HCl, 4×H$_2$O:

Calculated: C, 48.19%; H, 7.48%; N, 14.05%.

Found: C, 48.19%; H, 7.03%, N, 13.66%.

EXAMPLE 66

General Procedure A

4-[6-(4-Cyclopropylpiperazin-1-yl)-piperidin-3-yl]-N,N-dimethylbenzamide, dihydrochloride

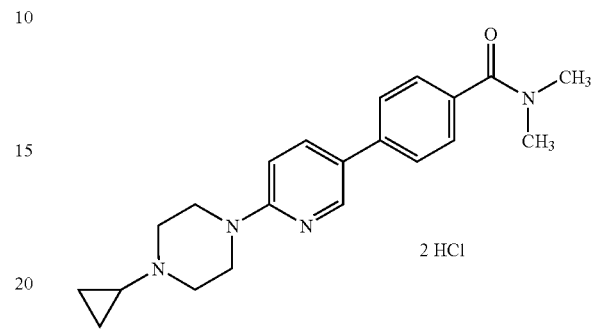

Step 1

1-(5-Bromopyridin-2-yl)-piperazine

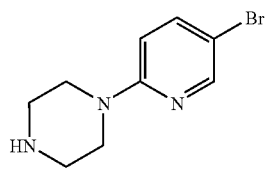

A mixture of piperazine (107 g, 1.24 mol) and 2-chloro-5-bromopyridine (30 g, 156 mmol) in toluene (150 mL) was heated at 130° C. for 2 hours, The reaction mixture was cooled to room temperature and toluene (400 mL) and water (200 mL) were added. The organic phase was isolated and the aqeuous phase was extracted once with toluene (100 mL). The collected organic phases were washed with water (150 mL) and brine (100 mL), dried over magnesium sulphate and evaporated to dryness in vacuo to give 30.1 g (80%) of 1-(5-bromopyridin-2-yl)-piperazine.

$^1$H NMR (400 MHz, CDCl$_3$) δ 8.19 (d, 1H), 7.52 (dd, 1H), 6.54 (d, 1H), 3.47 (m, 4H), 2.97 (m, 4H), 1.77 (broad s, 1H)

Step 2

1-(5-Bromopyridin-2-yl)-4-cyclopropylpiperazine

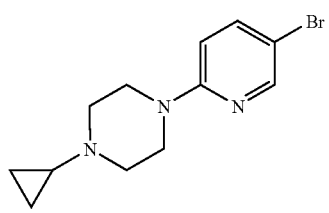 [SMILES: Brc1ccc(N2CCN(C3CC3)CC2)nc1]

[(1-Ethoxy-cyclopropyl)oxy]trimethylsilane (26 mL, 129.3 mmol) was added to a solution of 1-(5-bromopyridin- 2-yl)-piperazine (15 g, 62.0 mmol) in THF (120 mL). Water (24 mL), acetic acid (11 mL), and 1 M NaCNBH$_3$ in THF (90 mL, 90 mmol) were added to the reaction mixture, which was then heated at reflux temperature for 3 hours. The resulting solution was cooled to rt and evaporated to dryness in vacuo. The residue was dissolved in a mixture of dichloromethane (200 mL) and water (50 mL) and 4 N sodium hydroxide (20 mL) was added to pH 8-9. The organic phase was isolated and the aqueous phase was extracted with further dichloromethane (100 mL). The combined organic phases were evaporated to dryness in vacuo and the residue was purified on a silica gel column (gradient: from 5% ethyl acetate in heptane to 100% ethyl acetate over 40 min.). This afforded 13.1 g (75%) of 1-(5-bromopyridin-2-yl)-4-cyclopropylpiperazine.

$^1$H NMR (400 MHz, CDCl$_3$) δ 8.19 (d, 1H), 7.52 (dd, 1H), 6.54 (d, 1H), 3.47 (m, 4H), 2.70 (m, 4H), 1.64 (m, 1H), 0.48 (m, 4H).

Step 3

A mixture of 1-(5-bromopyridin-2-yl)-4-cyclopropylpiperazine, (2.5 g, 8.86 mmol), 4-(N,N-dimethylaminocarbonyl)-phenyl boronic acid (2.5 g, 13.0 mmol), tetrakis(triphenylphosphine)palladium(0) (300 mg, 0.26 mmol), and anhydrous sodium carbonate (2.0 g, 18.9 mmol) was purged with nitrogen. 1,2-Dimethoxyethane (30 mL) and water (7 mL) were added and the reaction mixture was heated at 80° C. for 1.5 hours and filtered upon cooling to 0-5° C. The crystals were washed with water (20 mL), dried and then dissolved in acetone (130 mL). Addition of HCl$_g$ in methanol afforded 1.41 g (37%) of 4-[6-(4-cyclopropylpiperazin-1-yl)piperidin-3-yl]-N,N-dimethylbenzamide, dihydrochloride.

$^1$H NMR (400 MHz, DMSO-d$_6$) δ 11.36 (brs, 1H), 8.50 (d, 1H), 8.18 (dd, 1H) 7.75 (d, 2H), 7.50 (d, 2H), 7.26 (d, 1H), 4.51 (d, 2H), 3.56 (m, 4H), 3.53 (brs, 2H), 3.00 (s, 3H), 2.96 (s, 3H), 2.89 (brs, 1H), 1.20 (m, 2H), 0.82 (m, 2H).

EXAMPLE 67

General Procedure A

N-{4-[6-(4-Cyclopropylpiperazin-1-yl)pyridazin-3-yl]-2-methoxyphenyl}acetamide

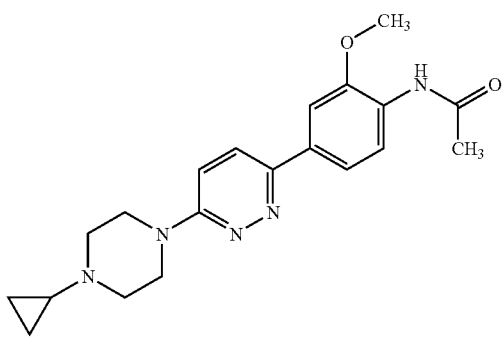 [SMILES: COc1cc(-c2ccc(N3CCN(C4CC4)CC3)nn2)ccc1NC(C)=O]

The title compound was prepared from 3-chloro-6-(4-cyclopropyl-piperazin-1-yl)-pyridazine (4.6 g, 19.3 mmol), 1 M sodium carbonate solution (50 mL, 100.5 mmol), acetonitrile (50 mL), bis(triphenylphosphine)palladium(II) chloride (0.68 g, 0.96 mmol) and N-[2-methoxy-4-(4,4,5,5-tetramethyl-1,3,2-dioxaborolan-2-yl)phenyl]acetamide (6.73 g, 23.1 mmol), yield 3.39 g (40%).

$^1$H NMR (400 MHz, CDCl$_3$) δ 8.44 (d, 1H), 7.94 (d, 1H), 7.86 (s, 1H), 7.66 (d, 1H), 7.34 (dd, 1H), 6.98 (d, 1H), 3.98 (s, 3H), 3.69 (m, 4H), 2.77 (m, 4H), 2.23 (s, 3H), 1.67 (m, 1H), 0.49 (m, 4H).

EXAMPLE 68

General Procedure A

N-{3-[6-(4-Isopropylpiperazin-1-yl)-4-methylpyridin-3-yl]phenyl}acetamide

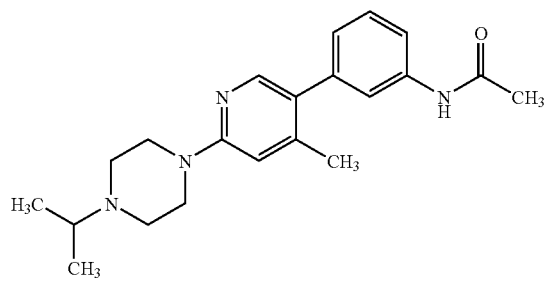 [SMILES: CC(=O)Nc1cccc(-c2cnc(N3CCN(C(C)C)CC3)cc2C)c1]

Step 1

1-(5-Bromo-4-methyl-pyridin-2-yl)-4-isopropyl-piperazine

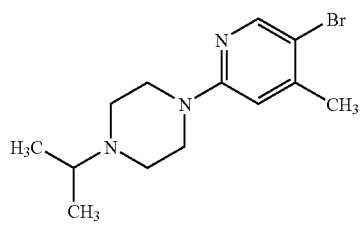 [SMILES: Cc1cc(N2CCN(C(C)C)CC2)ncc1Br]

To a solution of 2,5-dibromo-4-methyl-pyridine (5.0 g, 20 mmol) and isopropyl-piperazine (25.6 g, 200 mmol) were added pyridine (2.06 g, 206 mmol). The reaction mixture was refluxed for 5 h under a nitrogen atmosphere. Brine was added and the mixture was extracted with EtOAc. The organic extract was washed with brine and 0.5 N hydrochloric acid. The acidic layer was made alkaline with Na$_2$CO$_3$ to pH 8 and then extracted with CH$_2$Cl$_2$. The organic extract was dried (Na$_2$SO$_4$) and concentrated to give 5.4 g (90%) of 1-(5-bromo-4-methyl-pyridin-2-yl)-4-isopropyl-piperazine.

$^1$H NMR (300 MHz, CDCl$_3$) δ 8.15 (s, 1H), 6.51 (s, 1H), 3.50 (t, 4H), 2.81-2.65 (m, 1H), 2.61 (t, 4H), 2.29 (s, 3H), 1.08 (d, 6H).

Step 2

To a solution of 1-(5-bromo-4-methyl-pyridin-2-yl)-4-isopropyl-piperazine (0.59 g, 2 mmol) in 1,4-dioxane (12 mL) and water (3 mL) was added 3-acetylamino-phenylboronic acid (430 mg, 2.4 mmol), Pd(PPh$_3$)$_4$ (231 mg, 0.2 mmol) and TEA (404 mg, 4 mmol). The resulting mixture was degassed and heated at 100° C. for 4 h under a nitrogen atmosphere. The mixture was diluted with EtOAc and water. The organic layer was separated and the aqueous phase was extracted with EtOAc. The combined organic layers were washed with brine, dried (Na$_2$SO$_4$), concentrated and purified by chromatography on silica gel eluting with CH₂Cl₂/MeOH (100:1). This afforded 138 mg (15%) of the title compound.

¹H NMR (300 MHz, CDCl₃) δ 8.00 (s, 1H), 7.57-7.50 (m, 2H), 7.50-7.29 (m, 2H), 7.00 (d, 1H), 6.52 (s, 1H), 3.59 (t, 4H), 2.79-2.70 (m, 1H), 2.66 (t, 4H), 2.30 (s, 3H), 2.16 (s, 3H), 1.10 (d, 6H).

HPLC (Method D): t$_r$=3.90 min (96%).

EXAMPLE 69

General Procedure A

N-{3-[6-(4-Isopropylpiperazin-1-yl)-5-methylpyridin-3-yl]phenyl}acetamide

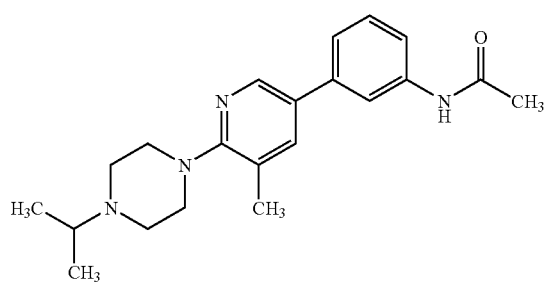 [SMILES: CC(=O)Nc1cccc(-c2cnc(N3CCN(C(C)C)CC3)c(C)c2)c1]

The title compound was prepared by a similar procedure to that described in Example 68, starting from 1-(5-bromo-3-methyl-pyridin-2-yl)-4-isopropyl-piperazine and 3-acetylaminophenylboronic acid. ¹H NMR (300 MHz, CDCl₃) δ 8.35 (d, 1H), 7.77 (s, 1H), 7.58 (d, 1H), 7.46 (d, 2H), 7.35 (t, 1H), 3.32 (t, 4H), 2.92-2.75 (m, 5H), 2.30 (s, 3H), 2.19 (s, 3H), 1.14 (d, 6H).

HPLC (Method D): t$_r$=4.49 min (97%).

EXAMPLE 70

General Procedure A

N-{4-[6-(4-Isopropylpiperazin-1-yl)-4-methylpyridin-3-yl]phenyl}acetamide, trifluoroacetate

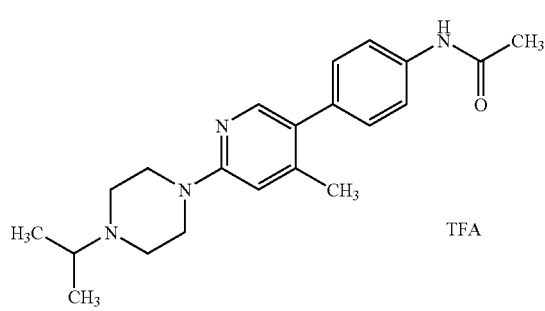 [SMILES: CC(=O)Nc1ccc(-c2cnc(N3CCN(C(C)C)CC3)cc2C)cc1]

The title compound was prepared by a similar procedure to that described in Example 68, starting from 1-(5-bromo-4-methyl-pyridin-2-yl)-4-isopropyl-piperazine and 4-acetylaminophenylboronic acid. ¹H NMR (300 MHz, CD₃OD) δ 7.91 (s, 1H), 7.67 (d, 2H), 7.28 (d, 2H), 7.18 (s, 1H), 4.75-3.35 (m, 9H), 2.35 (s, 3H), 2.14 (s, 3H), 1.41 (d, 6H).

HPLC (Method D): t$_r$=2.93 min (98%).

EXAMPLE 71

General Procedure A

N-{4-[6-(4-Isopropylpiperazin-1-yl)-5-methylpyridin-3-yl]phenyl}acetamide, triuoroacetate

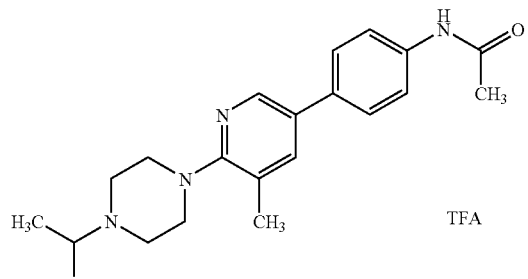

The title compound was prepared by a similar procedure to that described in Example 68, starting from 1-(5-bromo-3-methyl-pyridin-2-yl)-4-isopropyl-piperazine and 4-acetylaminophenylboronic acid.

¹H NMR (300 MHz, CD₃OD) δ 8.37 (d, 1H), 8.06 (s, 1H), 7.68 (d, 2H), 7.58 (d, 2H), 3.99-3.71 (m, 2H), 3.62-3.55 (m, 3H), 3.52-3.31 (m, 4H), 2.44 (s, 3H), 2.13 (s, 3H), 1.42 (d, 6H).

HPLC (Method E): t$_r$=3.53 min (98%).

EXAMPLE 72

General Procedure A

N-{4-[6-(4-Isopropylpiperazin-1-yl)-4-methylpyridazin-3-yl]phenyl}acetamide, trifluoroacetate

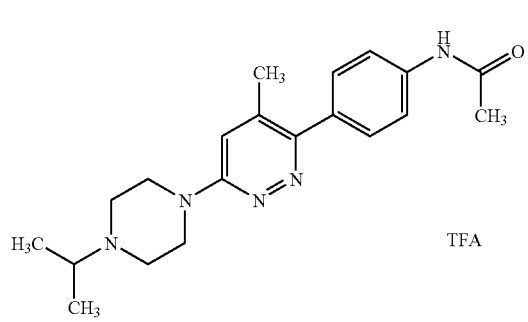 [SMILES: CC(=O)Nc1ccc(-c2nnc(N3CCN(C(C)C)CC3)cc2C)cc1]

Step 1

N-[4-(6-Chloro-5-methyl-pyridazin-3-yl)-phenyl]-acetamide and N-[4-(6-chloro-4-metridazin-3-yl)-phenyl]-acetamide

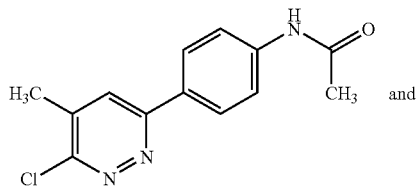

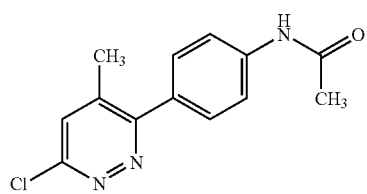

A solution of 4-acetamidophenylboronic acid (2.7 g, 15 mmol), 3,6-dichloro-4-methylpyridazine (1.6 g, 10 mmol) and Pd(PPh$_3$)$_4$ (1.2 g, 1 mmol) in DMF (58 mL, degassed) was stirred at rt for 1 h. Then sodium carbonate (3.9 g in 15 mL water, degassed) was added and the mixture was heated with stirring at 80° C. overnight. The mixture was filtered and the filtrate was concentrated under reduced pressure. The residue was diluted with EtOAc (30 mL), washed with brine, dried (sodium sulfate) and concentrated to give a crude product, which was purified by column chromatography on silica gel (EtOAc/petroleum ether=1:1). This afforded 1 g (39%) of a mixture of N-[4-(6-chloro-5-methyl-pyridazin-3-yl)-phenyl]-acetamide and N-[4-(6-chloro-4-methyl-pyridazin-3-yl)-phenyl]-acetamide, which was used directly in the next step.

Step 2

The mixture of isomers (0.85 g, 3.2 mmol) from the previous step and 1-isopropyl-piperazine (2.1 g, 16 mmol) was heated at 200° C. under a nitrogen atmosphere for 1 h. The mixture was cooled to rt and diluted with dichloromethane (15 mL). The mixture was washed with brine, dried (sodium sulfate) and concentrated to give a crude product, which was purified by preparative HPLC Method F to give 261 mg (8%) of N-{4-[6-(4-isopropyl-piperazin-1-yl)-4-methyl-pyridazin-3-yl]-phenyl}-acetamide and 74 mg (2%) of N-{4-[6-(4-isopropyl-piperazin-1-yl)-5-methyl-pyridazin-3-yl]-phenyl}-acetamide as the TFA salts. N-{4-[6-(4-isopropyl-piperazin-1-yl)-4-methyl-pyridazin-3-yl]-phenyl}-acetamide:

$^1$H NMR (300 MHz, CD$_3$OD) δ 7.89 (s, 1H), 7.82 (d, 2H), 7.56 (d, 2H), 4.70-3.30 (m, 9H), 2.44 (s, 3H), 2.17 (s, 3H), 1.42 (d, 6H).

HPLC (Method D): t$_r$=2.88 min (99%).

EXAMPLE 73

General Procedure A

N-{3-[6-(4-Cyclopropylpiperazin-1-yl)-4-methylpyridin-3-yl]phenyl}acetamide, trifluoroacetate

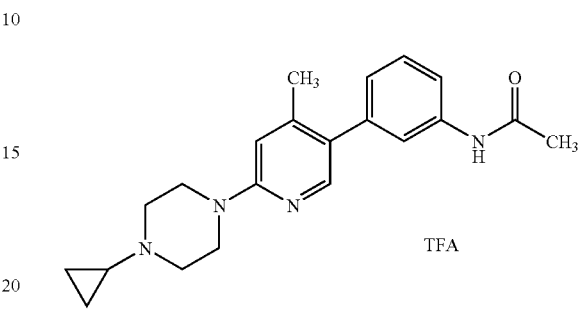

The title compound was prepared by a similar procedure to that described in Example 68, starting from 1-(5-bromo-4-methyl-pyridin-2-yl)-4-cyclopropyl-piperazine and 3-acetylaminophenylboronic acid. $^1$H NMR (300 MHz, CD$_3$OD) δ 7.92 (s, 1H), 7.72 (d, 1H), 7.53-7.40 (m, 2H), 7.34 (s, 1H), 7.10-7.05 (m, 1H), 4.05-3.92 (m, 4H), 3.68-3.58 (m, 4H), 2.95-2.85 (m, 1H), 2.39 (s, 3H), 2.13 (s, 3H), 1.15-0.95 (m, 4H).

HPLC (Method D): t$_r$=2.99 min (94%).

EXAMPLE 74

General Procedure A

3-[6-(4-Cyclopropylpiperazin-1-yl)-4-methylpyridin-3-yl]-N,N-dimethylbenzamide, trifluoroacetate

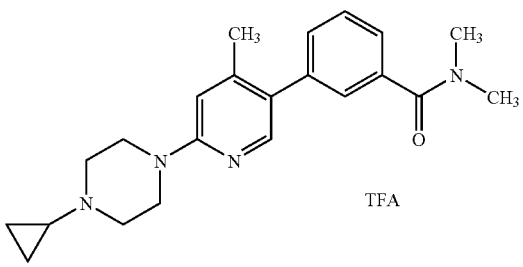 [SMILES: Cc1cc(N2CCN(C3CC3)CC2)ncc1-c1cccc(C(=O)N(C)C)c1]

The title compound was prepared by a similar procedure to that described in Example 68, starting from 1-(5-bromo-4-methyl-pyridin-2-yl)-4-cyclopropyl-piperazine and 3-(N,N-dimethylamino-carbonyl)-phenylboronic acid. $^1$H NMR (300 MHz, CD$_3$OD): δ 7.96 (s, 1H), 7.62-7.52 (m, 1H), 7.52-7.45 (m, 2H), 7.45-7.38 (m, 1H), 4.05-3.88 (m, 4H), 3.68-3.55 (m, 4H), 3.11 (s, 3H), 3.03 (s, 3H), 2.95-2.85 (m, 1H), 2.37 (s, 3H), 1.15-0.95 (m, 4H).

HPLC (Method D): t$_r$=3.04 min (98%).

EXAMPLE 75

General Procedure A

N-{4-[6-(4-Cyclopropylpiperazin-1-yl)-4-methylpyridin-3-yl]phenyl}acetamide, trifluoroacetate

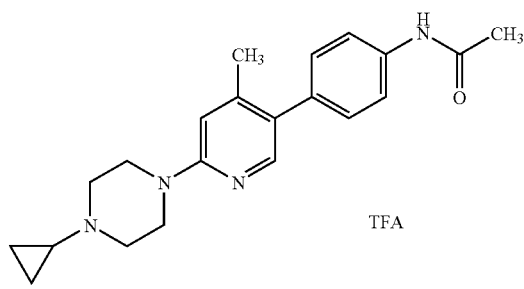 [SMILES: CC(=O)Nc1ccc(-c2cnc(N3CCN(C4CC4)CC3)cc2C)cc1]

The title compound was prepared by a similar procedure to that described in Example 68, starting from 1-(5-bromo-4-methyl-pyridin-2-yl)-4-cyclopropyl-piperazine and 4-acetamidophenylboronic acid. $^1$H NMR (300 MHz, CD$_3$OD): δ 7.90 (s, 1H), 7.67 (d, 2H), 7.35-7.22 (m, 3H), 4.05-3.88 (m, 4H), 3.68-3.55 (m, 4H), 2.95-2.82 (m, 1H), 2.37 (s, 3H), 2.14 (s, 3H), 1.15-0.95 (m, 4H).

HPLC (Method D): $t_r$=2.68 min (99%).

EXAMPLE 76

General Procedure A

4-[6-(4-Cyclopropylpiperazin-1-yl)-4-methylpyridin-3-yl]-N,N-dimethylbenzamide, trifluoroacetate

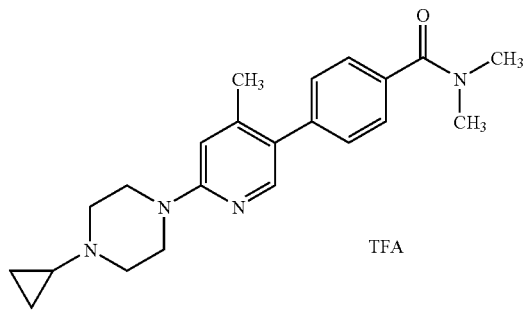 [SMILES: Cc1cc(N2CCN(C3CC3)CC2)ncc1-c1ccc(C(=O)N(C)C)cc1]

The title compound was prepared by a similar procedure to that described in Example 68, starting from 1-(5-bromo-4-methyl-pyridin-2-yl)-4-cyclopropyl-piperazine and 4-(N,N-dimethylamino-carbonyl)-phenylboronic acid. $^1$H NMR (300 MHz, CD$_3$OD): δ 7.95 (s, 1H), 7.55 (d, 2H), 7.46 (d, 2H), 7.34 (s, 1H), 4.05-3.88 (m, 4H), 3.68-3.55 (m, 4H), 3.12 (s, 3H), 3.04 (s, 3H), 2.97-2.85 (m, 1H), 2.39 (s, 3H), 1.18-0.95 (m, 4H).

HPLC (Method D): $t_r$=3.04 min (94%).

EXAMPLE 77

General Procedure A 5-1,3-Benzodioxol-5-yl-2-(4-cyclopropylpiperazin-1-yl)pyrimidine, dihydrochloride

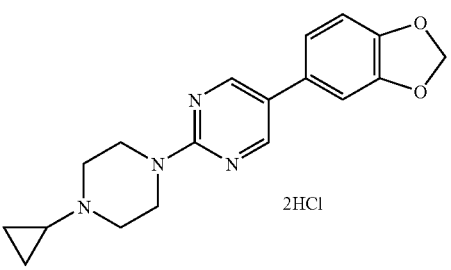 [SMILES: c1cc2c(cc1-c1cnc(N3CCN(C4CC4)CC3)nc1)OCO2 ; "2HCl"]

The title compound was prepared by a similar procedure to that described in Example 68, starting from 5-bromo-2-(4-cyclopropyl-piperazin-1-yl)-pyrimidine and 3,4-(methylenedioxy)phenylboronic acid. Mp=275-279° C.

$^1$H NMR (300 MHz, DMSO-d$_6$) δ 11.0 (brs, 1H), 8.73 (s, 2H), 7.30 (s, 1H), 7.14 (d, 1H), 7.01 (d, 1H), 6.06 (s, 2H), 4.76-4.71 (m, 2H), 3.58-3.18 (m, 6H), 2.91-2.80 (m, 1H), 1.20-1.12 (m, 2H), 0.86-0.78 (m, 2H).

HPLC (Method Rx): $t_r$=11.49 min (100%).

EXAMPLE 78

General Procedure A

N-{4-[6-(4-Isopropylperhydro-1,4-diazepin-1-yl)pyridazin-3-yl]phenyl}acetamide, dihydrochloride

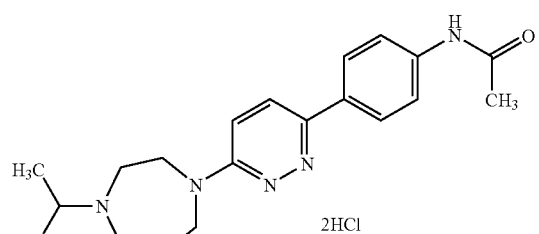

The title compound was prepared by a similar procedure to that described in Example 68, starting from 1-(6-chloro-pyridazin-3-yl)-4-isopropyl-perhydro-1,4-diazepine and 4-acetamidophenylboronic acid. $^1$H NMR (400 MHz, CD$_3$OD) δ 8.43 (d, 1H), 8.03 (d, 1H), 7.94 (m, 2H), 7.84 (m, 2H), 4.36 (m, 1H), 4.17 (m, 1H), 4.03 (m, 1H), 3.73 (m, 4H), 3.42 (m, 2H), 2.50 (m, 1H), 2.39 (m, 1H), 2.17 (s, 3H), 1.41 (d, 6H).

HPLC-MS (Method G): M+1=354; $t_r$=0.73 min.

EXAMPLE 79

General Procedure A

4-[6-(4-Isopropyl-perhydro-1,4-diazepin-1-yl)-pyridazin-3-yl]-phenylamine

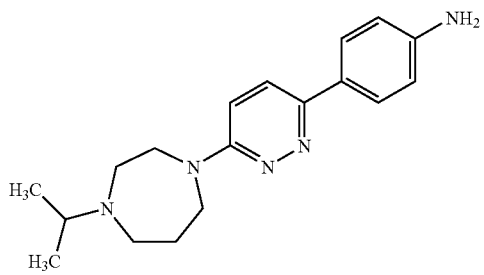 [SMILES: CC(C)N1CCCN(c2ccc(-c3ccc(N)cc3)nn2)CC1]

The title compound was prepared by a similar procedure to that described in Example 68, starting from 1-(6-chloro-pyridazin-3-yl)-4-isopropyl-perhydro-1,4-diazepine and 4-aminophenylboronic acid, pinacol cyclic ester. ¹H NMR (400 MHz, CDCl₃) δ 7.82 (d, 2H), 7.53 (d, 1H), 6.76 (m, 3H), 3.86 (t, 2H), 3.77 (m, 4H), 2.93 (heptet, 1H), 2.81 (m, 2H), 2.58 (m, 2H), 1.95 (m, 2H), 1.00 (d, 6H).

HPLC-MS (Method G): M+1=312; t$_r$=0.61 min.

EXAMPLE 80

General Procedure A

N-{4-[6-(4-Cyclopropyl-[1,4]diazepan-1-yl)pyridazin-3-yl]phenyl}acetamide, dihydrochloride

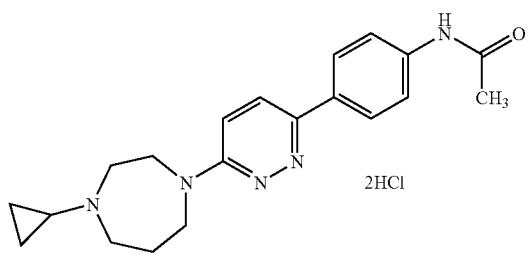 [SMILES: CC(=O)Nc1ccc(-c2ccc(N3CCCN(C4CC4)CC3)nn2)cc1 ; "2HCl"]

The title compound was prepared by a similar procedure to that described in Example 68, starting from 1-(6-chloro-pyridazin-3-yl)-4-cyclopropyl-perhydro-1,4-diazepine and 4-acetamidophenylboronic acid. ¹H NMR (400 MHz, CD₃OD) δ 8.47 (d, 1H), 8.08 (d, 1H), 7.94 (d, 2H), 7.85 (d, 2H), 4.33 (broad m, 1H), 4.12 (broad m, 1H), 3.91 (broad m, 4H), 3.62 (broad m, 2H), 2.97 (hept, 1H), 2.55 ((broad m, 1H), 2.43 (broad m, 1H), 2.17 (s, 3H), 1.24 (broad m, 2H), 1.01 (d, 2H).

HPLC-MS (Method G): M+1=352; t$_r$=0.82 min.

EXAMPLE 81

General Procedure A

7-[6-(4-Cyclopropyl-piperazin-1-yl)-pyridazin-3-yl]-4-methyl-3,4-dihydro-2H-1,4-benzoxazine, dihydrochloride

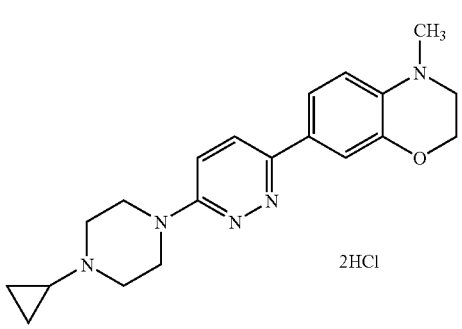 [SMILES: CN1CCOc2cc(-c3ccc(N4CCN(C5CC5)CC4)nn3)ccc21 ; "2HCl"]

The title compound was prepared by a similar procedure to that described in Example 68, starting from 3-chloro-6-(4-cyclopropyl-piperazin-1-yl)-pyridazine and 4-methyl-7-(4,4,5,5-tetramethyl-1,3,2-dioxaborolan-2-yl)-3,4-dihydro-2H-1,4-benzoxazine. ¹H NMR (400 MHz, DMSO-d₆) δ 8.47 (d, 1H), 8.04 (d, 1H), 7.61 (m, 1H), 7.49 (m, 1H), 6.85 (d, 1H), 4.50 (broad m, 2H), 4.26 (m, 2H), 3.61 (broad m, 4H), 3.40 (m, 4H), 2.97 (s, 3H), 2.88 (broad m, 1H), 1.23 (m, 2H), 0.82 (m, 2H).

HPLC-MS (Method G): M+1=352; t$_r$=0.83 min.

EXAMPLE 82

General Procedure A 3-(4-Cyclopropylpiperazin-1-yl)-6-(2,3-dihydro-1,4-benzodioxin-6-yl)pyridazine, dihydrochloride

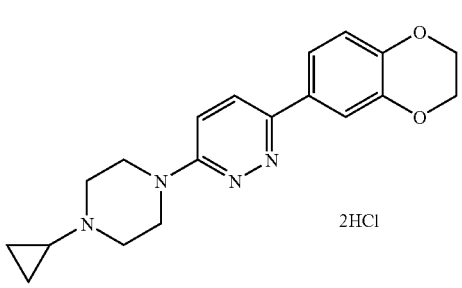 [SMILES: c1cc2c(cc1-c1ccc(N3CCN(C4CC4)CC3)nn1)OCCO2 ; "2HCl"]

The title compound was prepared by a similar procedure to that described in Example 68, starting from 3-chloro-6-(4-cyclopropyl-piperazin-1-yl)-pyridazine and 1,4-benzodioxane-6-boronic acid. ¹H NMR (400 MHz, DMSO-d₆) δ 8.38 (d, 1H), 7.95 (d, 1H), 7.63 (m, 1H), 7.58 (m, 1H), 7.05 (d, 1H), 4.57 (broad m, 2H), 4.32 (m, 4H), 3.63 (broad m, 4H), 3.39 (broad m, 2H), 2.88 (broad m, 1H), 1.23 (m, 2H), 0.82 (m, 2H).

HPLC-MS (Method G): M+1=339; t$_r$=0.84 min.

EXAMPLE 83

General Procedure A

5-[6-(4-Cyclopropylpiperazin-1-yl)pyridazin-3-yl]-1H-indole, dihydrochlorde

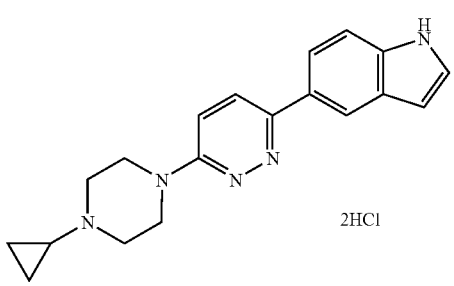 [SMILES: c1cc2cc(-c3ccc(N4CCN(C5CC5)CC4)nn3)ccc2[nH]1 ; "2HCl"]

The title compound was prepared by a similar procedure to that described in Example 68, starting from 3-chloro-6-(4-cyclopropyl-piperazin-1-yl)-pyridazine and 5-indoleboronic acid.

$^1$H NMR (400 MHz, DMSO-d$_6$) δ 11.49 (s, 1H), 8.43 (d, 1H), 8.28 (s, 1H), 7.93 (d, 1H), 7.82 (dd, 1H), 7.57 (d, 1H), 7.48 (t, 1H), 6.58 (s, 1H), 4.54 (d, 2H), 3.70-3.45 (m, 4H), 3.45-3.30 (m, 2H), 2.88 (m, 1H), 1.21 (m, 2H), 0.83 (m, 2H).

HPLC-MS (Method G): M+1=320; t$_r$=0.75 min.

EXAMPLE 84

General Procedure A

{4-[2-(4-Isopropylpiperazin-1-yl)pyrimidin-5-yl]phenyl}acetonitrile, dihydrochloride

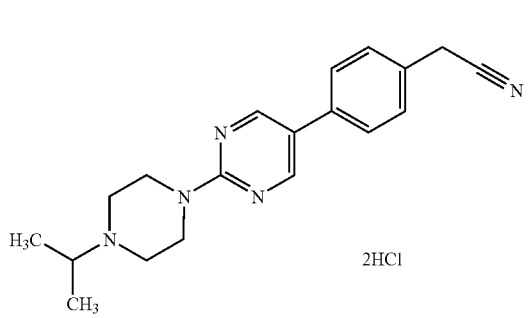 [SMILES: CC(C)N1CCN(c2ncc(-c3ccc(CC#N)cc3)cn2)CC1 ; "2HCl"]

The title compound was prepared by a similar procedure to that described in Example 57, starting from 5-bromo-2-(4-isopropylpiperazin-1-yl)-pyrimidine and 4-cyanomethylphenylboronic acid.

EXAMPLE 85

General Procedure A

N-{4-[2-(4-Isopropylpiperazin-1-yl)pyrimidin-5-yl]phenyl}acetamide, dihydrochloride

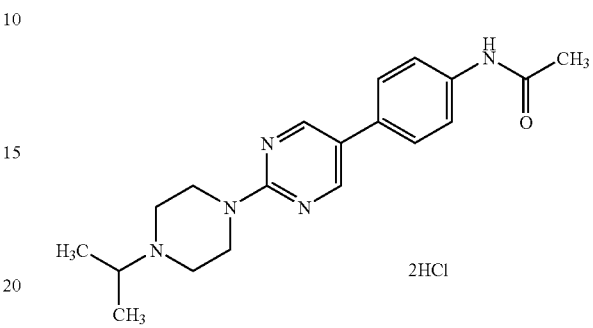

The title compound was prepared by a similar procedure to that described in Example 57, starting from 5-bromo-2-(4-isopropylpiperazin-1-yl)-pyrimidine and 4-acetamidophenylboronic acid.

Mp>275° C.

$^1$H-NMR (400 MHz, CD$_3$OD) δ 8.65 (s, 2H), 7.65 (d, 2H), 7.50 (d, 2H), 5.0 (m, 2H), 3.65-3.55 (m, 3H), 3.35-3.25 (m, 2H), 3.20-3.10 (m, 2H), 2.15 (s, 3H), 1.40 (d, 6H).

HPLC-MS (Method G): M+1=340; t$_r$=0.919 min.

EXAMPLE 86

General Procedure A

1-{4-[2-(4-Isopropylpiperazin-1-yl)pyrimidin-5-yl]phenyl}ethanone, dihydrochloride

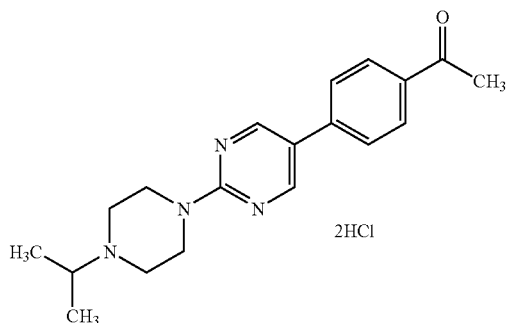 [SMILES: CC(=O)c1ccc(-c2cnc(N3CCN(C(C)C)CC3)nc2)cc1 ; "2HCl"]

The title compound was prepared by a similar procedure to that described in Example 57, starting from 5-bromo-2-(4-isopropylpiperazin-1-yl)-pyrimidine and 4-acetylphenylboronic acid.

$^1$H-NMR (400 MHz, CD$_3$OD) δ 8.75 (s, 2H), 8.10 (d, 2H), 7.70 (d, 2H), 5.10-5.00 (m, 2H), 3.65-3.55 (m, 3H), 3.40-3.30 (m, 2H), 3.25-3.15 (m, 2H), 2.65 (s, 3H), 1.40 (d, 6H).

HPLC-MS (Method G): M+1=322; t$_r$=1.07 min.

EXAMPLE 87

General Procedure A 2-(4-Isopropylpiperazin-1-yl)-5-pyridin-3-ylpyrimidine, trihydrochloride

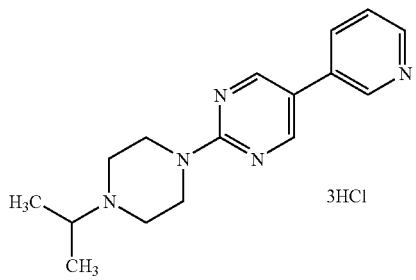 [SMILES: CC(C)N1CCN(c2ncc(-c3cccnc3)cn2)CC1 ; "3HCl"]

The title compound was prepared by a similar procedure to that described in Example 57, starting from 5-bromo-2-(4-isopropylpiperazin-1-yl)-pyrimidine and 3-pyridylboronic acid.

$^1$H-NMR (400 MHz, CD$_3$OD) δ 9.15 (s, 1H), 8.85 (s, 2H), 8.80 (m, 2H), 8.05 (m, 1H), 5.15-5.05 (m, 2H), 3.65-3.55 (m, 3H), 3.45-3.35 (m, 2H), 3.25-3.10 (m, 2H), 1.40 (d, 6H).

HPLC-MS (Method G): M+1=284; t$_r$=0.38 min.

EXAMPLE 88

General Procedure A 2-(4-Isopropylpiperazin-1-yl)-5-pyridin-4-ylpyrimidine, trihydrochloride

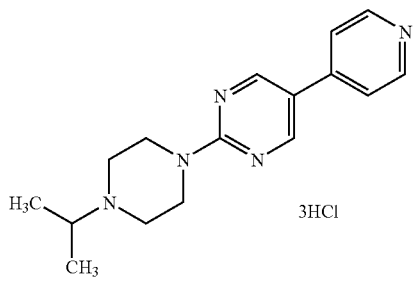 [SMILES: CC(C)N1CCN(c2ncc(-c3ccncc3)cn2)CC1 ; "3HCl"]

The title compound was prepared by a similar procedure to that described in Example 57, starting from 5-bromo-2-(4-isopropylpiperazin-1-yl)-pyrimidine and 4-pyridylboronic acid.

$^1$H-NMR (400 MHz, CD$_3$OD) δ 9.10 (s, 2H), 8.80 (d, 2H), 8.30 (d, 2H), 5.25-5.05 (m, 2H), 3.70-3.55 (m, 3H), 3.55-3.35 (m, 2H), 3.35-3.15 (m, 2H), 1.40 (d, 6H).

HPLC-MS (Method G): M+1=284; t$_r$=0.337 min.

EXAMPLE 89

General Procedure A

{4-[2-(4-Isopropylpiperazin-1-yl)pyrimidin-5-yl]phenyl}dimethylamine, trihydrochloride

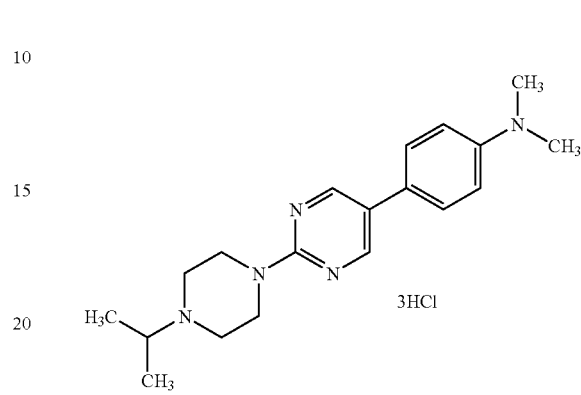

The title compound was prepared by a similar procedure to that described in Example 57, starting from 5-bromo-2-(4-isopropylpiperazin-1-yl)-pyrimidine and N,N-dimethylaminophenylboronic acid.

$^1$H-NMR (400 MHz, CD$_3$OD) δ 8.70 (s, 2H), 7.75 (d, 2H), 7.55 (d, 2H), 5.10-5.00 (m, 2H), 3.65-3.55 (m, 3H), 3.40-3.30 (m, 2H), 3.25 (s, 6H), 3.22-3.10 (m, 2H), 1.40 (d, 6H).

HPLC-MS (Method G): M+1=326; t$_r$=0.729 min.

EXAMPLE 90

General Procedure A

3-[2-(4-Isopropylpiperazin-1-yl)pyrimidin-5-yl]-N,N-dimethylbenzamide, dihydrochloride

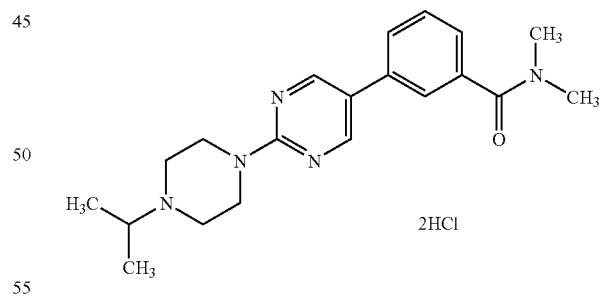

The title compound was prepared by a similar procedure to that described in Example 57, starting from 5-bromo-2-(4-isopropylpiperazin-1-yl)-pyrimidine and 3-(dimethylaminocarbonyl)phenylboronic acid.

Mp=217-220° C.

$^1$H-NMR (400 MHz, CD$_3$OD) δ 8.70 (s, 2H), 7.70 (d, 1H), 7.65 (s, 1H), 7.55 (d, d, 1H), 7.40 (d, 1H), 5.05-4.95 (m, 2H), 3.65-3.55 (m, 3H), 3.35-3.25 (m, 2H), 3.20-3.10 (m, 2H), 3.12 (s, 3H), 3.05 (s, 3H), 1.40 (d, 6H).

HPLC-MS (Method G): M+1=354; t$_r$=0.938 min.

EXAMPLE 91

General Procedure A

N,N-Diisopropyl-4-(4-isopropyl-3,4,5,6-tetrahydro-2H-[1,2']bipyrazinyl-5'-yl)benzamide, hydrochloride

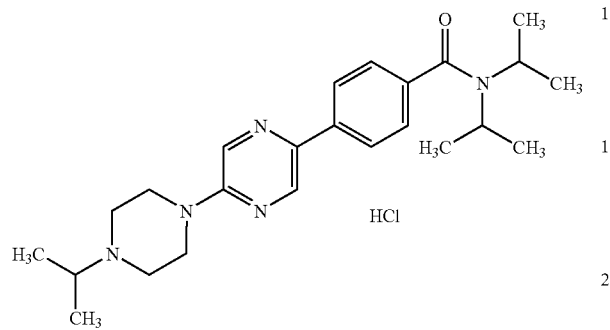

The title compound was prepared by a similar procedure to that described in Example 57, starting from 5-bromo-4-isopropyl-3,4,5,6-tetrahydro-2H-[1,2']bipyrazinyl and 4-diisopropylaminocarbonylphenylboronic acid.

$^1$H NMR (400 MHz, DMSO-$d_6$) δ 8.63 (s, 1H), 8.32 (s, 1H), 8.00 (d, 1H), 7.91 (s, 1H), 7.55 (dd, 1H); 7.33 (d, 1H), 4.60-4.50 (m, 2H), 3.95-3.85 (m, 1H), 3.70-3.60 (m, 1H), 3.65-3.55 (m, 3H), 3.25-3.10 (m, 4H), 1.60-1.50 (brs, 6H), 1.25-1.10 (brs, 6H).

HPLC-MS (Method G): M+1=410; $t_r$=1.32 min.

EXAMPLE 92

General Procedure A

[4-(4-Isopropyl-3,4,5,6-tetrahydro-2H-[1,2']bipyrazinyl-5'-yl)phenyl]-(4-methylpiperidin-1-yl)methanone, hydrochloride

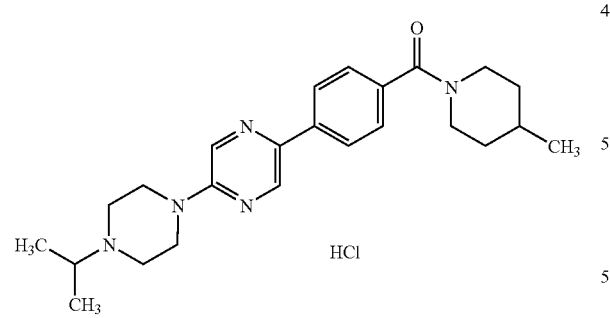

The title compound was prepared by a similar procedure to that described in Example 57, starting from 5-bromo-4-isopropyl-3,4,5,6-tetrahydro-2H-[1,2']bipyrazinyl and (4-methylpiperidin-1-yl)carbonylphenylboronic acid.

$^1$H-NMR (400 MHz, CD$_3$OD) δ 8.65 (s, 1H), 8.35 (s, 1H), 8.02 (d, 2H), 7.50 (d, 2H), 4.65-4.55 (m, 3H), 3.80-3.70 (m, 1H), 3.65-3.55 (m, 3H), 1.85-1.75 (m, 1H), 1.75-1.60 (m, 2H), 1.40 (d, 6H), 1.25-1.05 (m, 2H), 0.95 (d, 3H).

HPLC-MS (Method G): M+1=408; $t_r$=1.31 min.

EXAMPLE 93

General Procedure A 4-(4-Isopropyl-3,4,5,6-tetrahydro-2H-[1,2']bipyrazinyl-5'-yl)-N,N-dimethylbenzamide, hydrochloride

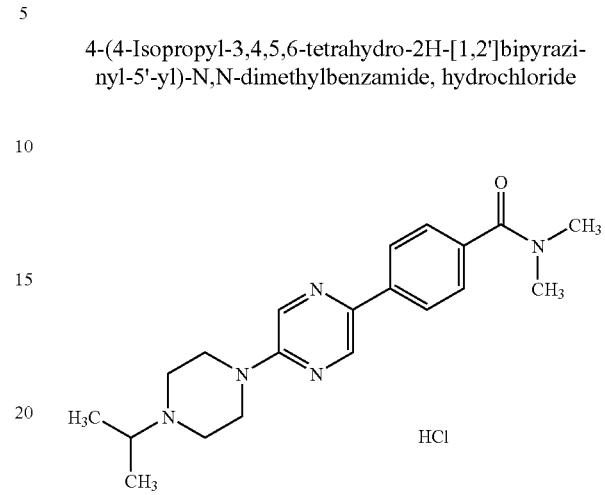

The title compound was prepared by a similar procedure to that described in Example 57, starting from 5-bromo-4-isopropyl-3,4,5,6-tetrahydro-2H-[1,2']bipyrazinyl and 4-dimethylaminocarbonylphenylboronic acid.

$^1$H-NMR (400 MHz, CD$_3$OD) δ 8.65 (s, 1H), 8.35 (s, 1H), 8.02 (d, 2H), 7.53 (d, 2H), 4.65-4.55 (m, 2H), 3.65-3.55 (m, 3H), 3.35-3.15 (m, 4H), 3.13 (s, 3H), 3.04 (s, 3H), 1.40 (d, 6H).

HPLC-MS (Method G): M+1=354; $t_r$=0.93 min.

EXAMPLE 94

General Procedure A

[3-(4-Isopropyl-3,4,5,6-tetrahydro-2H-[1,2']bipyrazinyl-5'-yl)phenyl]morpholin-4-ylmethanone, hydrochloride

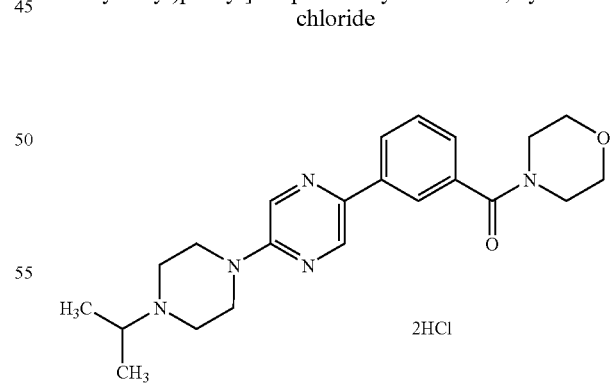

The title compound was prepared by a similar procedure to that described in Example 57, starting from 5-bromo-4-isopropyl-3,4,5,6-tetrahydro-2H-[1,2']bipyrazinyl and N-(morpholin-4-yl) 3-boronobenzamide.

¹H-NMR (400 MHz, CD₃OD) δ 8.70 (s, 1H), 8.45 (s, 1H), 8.07 (d, 1H), 8.01 (s, 1H), 7.58 (dd, 1H), 7.45 (d, 1H), 4.75-4.65 (m, 2H), 3.85-3.43 (m, 11H), 3.40-3.20 (m, 4H), 1.40 (d, 6H).

EXAMPLE 95

General Procedure A

N-{4-[5-(Octahydropyrido[1,2-a]pyrazin-2-yl)pyrazin-2-yl]phenyl}acetamide, hydrochloride

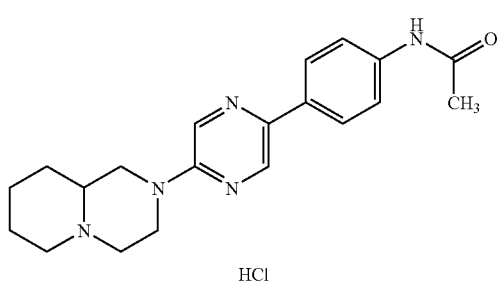 [SMILES: CC(=O)Nc1ccc(-c2cnc(N3CCN4CCCCC4C3)cn2)cc1 ; Cl]

HCl

The title compound was prepared by a similar procedure to that described in Example 57, starting from 2-(5-bromopyrazin-2-yl)octahydropyrido[1,2-a]pyrazine and 4-acetamidophenylboronic acid.

¹H-NMR (400 MHz, CD₃OD) δ 8.95 (s, 1H), 8.47 (s, 1H), 7.85 (d, 2H), 7.80 (d, 2H), 4.80-4.60 (m, 2H), 3.60-3.50 (m, 3H), 3.45-3.29 (m, 3H), 3.15-3.00 (m, 1H), 2.15 (s, 3H), 2.10-2.05 (m, 1H), 2.02-1.90 (m, 3H), 1.79-1.62 (m, 2H).

HPLC-MS (Method G): M+1=352; $t_r$=0.92 min.

EXAMPLE 96

General Procedure A 4-(4-Isopropyl-3,4,5,6-tetrahydro-2H-[1,2']bipyrazinyl-5'-yl)phenol, dihydrochloride

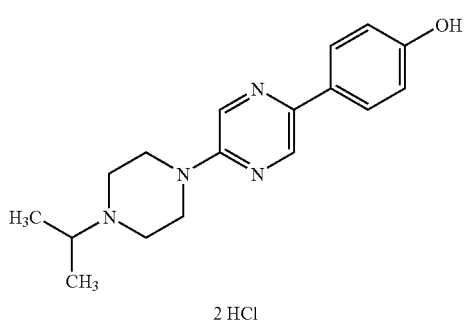 [SMILES: CC(C)N1CCN(c2cnc(-c3ccc(O)cc3)cn2)CC1 ; "2 HCl"]

2 HCl

The title compound was prepared by a similar procedure to that described in Example 57, starting from 5-bromo-4-isopropyl-3,4,5,6-tetrahydro-2H-[1,2']bipyrazinyl and 4-hydroxyphenylboronic acid.

¹H-NMR (400 MHz, CD₃OD) δ 9.08 (s, 1H), 8.45 (s, 1H), 7.75 (d, 2H), 7.0 (d, 2H), 4.72 (d, 2H), 3.7-3.5 (m, 4H), 3.3 (m, 3H), 1.45 (d, 6H).

HPLC-MS (Method G): M+1=299; $t_r$=1.045 min.

EXAMPLE 97

General Procedure A

N-[4-(4-Isopropyl-3,4,5,6-tetrahydro-2H-[1,2']bipyrazinyl-5'-yl)phenyl]-N-methylamine, tritrifluoroacetate

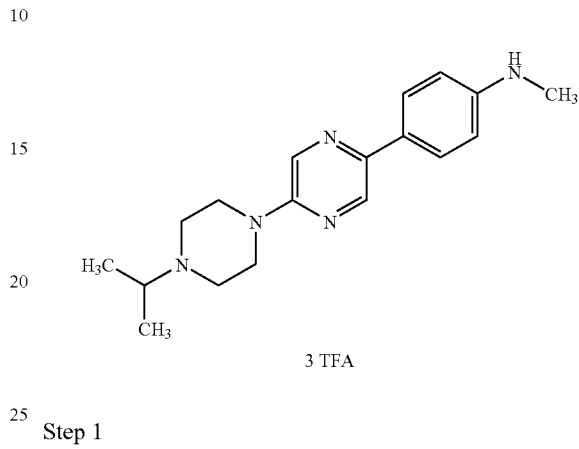

3 TFA

Step 1

[4-(4-Isopropyl-3,4,5,6-tetrahydro-2H-[1,2']bipyrazinyl-5'-yl)phenyl]methylcarbamic acid tert-butyl ester, trifluoroacetate

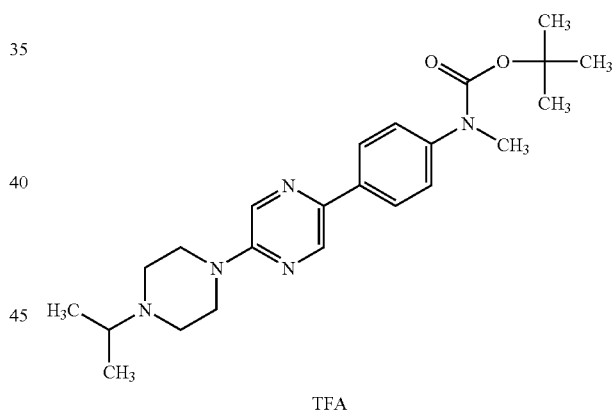

TFA

[4-(4-Isopropyl-3,4,5,6-tetrahydro-2H-[1,2']bipyrazinyl-5'-yl)phenyl]methylcarbamic acid tert-butyl ester, trifluoroacetic acid was prepared by a similar procedure to that described in Example 59, starting from 5-bromo-4-isopropyl-3,4,5,6-tetrahydro-2H-[1,2']bipyrazinyl and tertbutyl-N-methyl-N-[4-(4,4,5,5-tetramethyl-1,3,2-dioxaborolan-2-yl)phenyl]-carbamate.

¹H-NMR (400 MHz, CDCl₃) δ 8.5 (s, 1H), 8.15 (s, 1H), 7.85 (d, 2H), 7.25 (d, 2H), 3.65 (m, 4H), 3.45 (s, 3H), 2.7 (hept, 1H), 2.6 (m, 4H), 1.45 (s, 9H), 1.1 (d, 6H).

HPLC-MS (Method G): M+1=412; $t_r$=1.60 min.

Step 2

[4-(4-Isopropyl-3,4,5,6-tetrahydro-2H-[1,2']bipyrazinyl-5'-yl)phenyl]methylcarbamic acid tert-butyl ester (0.38 g, 0.92 mmol) was dissolved in DCM (10 mL) and TFA (10 mL) was added. The reaction mixture was stirred at rt for 2 h and then evaporated in vacuo. The solid residue (20 mg) was purified by preparative HPLC Method B.

$^1$H-NMR (400 MHz, CDCl$_3$) δ 8.5 (s, 1H), 8.2 (s, 1H), 8.0 (brs, 1H), 7.8 (d, 2H), 7.35 (d, 2H), 4.45 (d, 2H), 3.7 (m, 2H), 3.65 (hept, 1H), 3.45 (m, 4H), 3.1 (s, 3H), 3.0 (m, 2H), 1.4 (d, 6H).

HPLC-MS (Method G): M+1=312; t$_r$=0.909 min.

EXAMPLE 98

General Procedure A

4-Isopropyl-5'-(4-morpholin-4-ylphenyl)-3,4,5,6-tetrahydro-2H-[1,2']bipyrazinyl, trihydrochloride

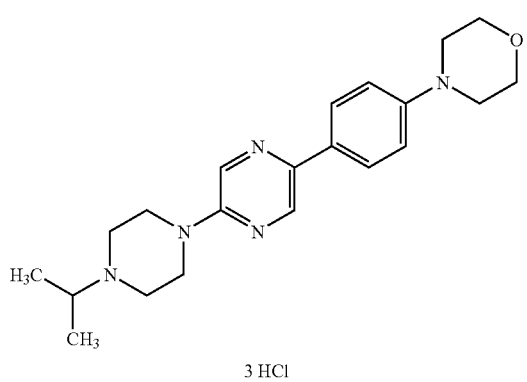 [SMILES: CC(C)N1CCN(c2cnc(-c3ccc(N4CCOCC4)cc3)cn2)CC1 ; "3 HCl"]

3 HCl

The title compound was prepared by a similar procedure to that described in Example 57, starting from 5-bromo-4-isopropyl-3,4,5,6-tetrahydro-2H-[1,2']bipyrazinyl and 4-morpholinophenylboronic acid.

$^1$H-NMR (400 MHz, CD$_3$OD) δ 8.90 (s, 1H), 8.68 (s, 1H), 8.18 (d, 2H), 8.01 (d, 2H), 4.81-4.75 (m, 2H), 4.20 (m, 4H), 3.80 (m, 4H), 3.76-3.65 (m, 5H), 3.44-3.32 (m, 2H), 1.45 (d, 6H).

HPLC-MS (Method G): M+1=368; t$_r$=1.021 min.

EXAMPLE 99

General Procedure A

5'-1,3-Benzodioxol-5-yl-4-isopropyl-3,4,5,6-tetrahydro-2H-1,2'-bipyrazinyl, dihydrochloride

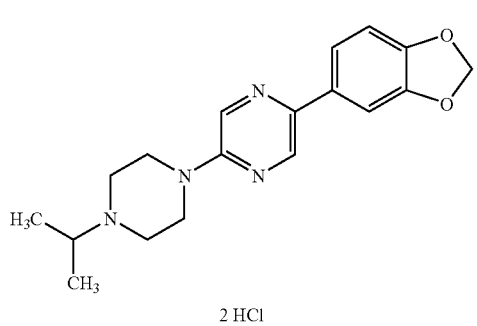 [SMILES: CC(C)N1CCN(c2cnc(-c3ccc4c(c3)OCO4)cn2)CC1 ; "2 HCl"]

2 HCl

The title compound was prepared by a similar procedure to that described in Example 57, starting from 5-bromo-4-isopropyl-3,4,5,6-tetrahydro-2H-[1,2']bipyrazinyl and 3,4-methylenedioxyphenylboronic acid.

$^1$H-NMR (400 MHz, CD$_3$OD) δ 8.70 (s, 1H), 8.47 (s, 1H), 7.40 (m, 2H), 6.95 (d, 1H), 6.03 (s, 2H), 4.70-4.62 (m, 2H), 3.67-3.57 (m, 3H), 3.42-3.32 (m, 2H), 3.31-3.21 (m, 2H), 1.45 (d, 6H).

HPLC-MS (Method G): M+1=327; t$_r$=1.115 min.

EXAMPLE 100

General Procedure A 4-(4-Isopropyl-3,4,5,6-tetrahydro-2H-[1,2']bipyrazinyl-5'-yl)-2-methoxyphenylamine, trihydrochloride

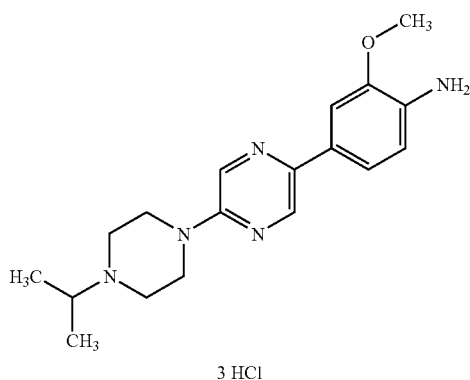 [SMILES: COc1cc(-c2cnc(N3CCN(C(C)C)CC3)cn2)ccc1N ; "3 HCl"]

3 HCl

The title compound was prepared by a similar procedure to that described in Example 57, starting from 5-Bromo-4-isopropyl-3,4,5,6-tetrahydro-2H-[1,2']bipyrazinyl and 4-amino-3-methoxyphenylboronic acid pinacol ester.

$^1$H-NMR (400 MHz, CD$_3$OD) δ 8.80 (s, 1H), 8.50 (s, 1H), 7.80 (s, 1H), 7.65 (d, 1H), 7.50 (s, 1H), 4.75-4.65 (m, 2H), 4.10 (s, 3H), 3.70-3.60 (m, 3H), 3.55-3.45 (m, 2H), 3.35-3.25 (m, 2H), 1.45 (d, 6H).

HPLC-MS (Method G): M+1=328; t$_r$=0.676 min.

EXAMPLE 101

General Procedure A

2-Chloro-4-(4-isopropyl-3,4,5,6-tetrahydro-2H-[1,2']bipyrazinyl-5'-yl)-6-methoxyphenol, dihydrochloride

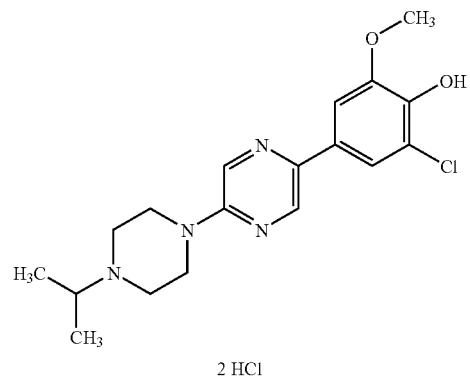 [SMILES: COc1cc(-c2cnc(N3CCN(C(C)C)CC3)cn2)cc(Cl)c1O ; "2 HCl"]

2 HCl

The title compound was prepared by a similar procedure to that described in Example 57, starting from 5-bromo-4-isopropyl-3,4,5,6-tetrahydro-2H-[1,2']bipyrazinyl and 3-chloro-4-hydroxy-5-methoxyphenylboronic acid.

$^1$H-NMR (400 MHz, CD$_3$OD) δ 8.85 (s, 1H), 8.38 (s, 1H), 7.48 (s, 1H), 7.43 (s, 1H), 4.73-4.65 (m, 2H), 4.00 (s, 3H), 3.70-3.60 (m, 3H), 3.58-3.46 (m, 2H), 3.35-3.25 (m, 2H), 1.45 (d, 6H).

HPLC-MS (Method G): M+1=363, rt=1.066 min.

EXAMPLE 102

General Procedure A

5'-(3,4-Dimethoxyphenyl)-4-isopropyl-3,4,5,6-tetrahydro-2H-[1,2']bipyrazinyl, dihydrochloride

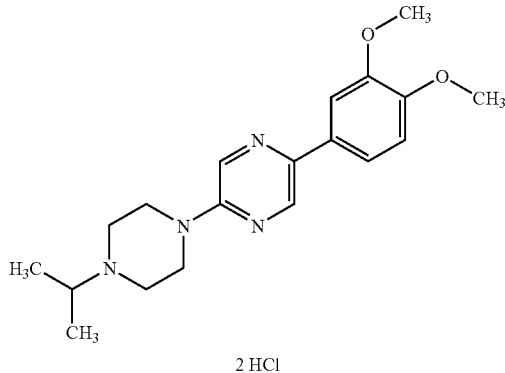 [SMILES: COc1ccc(-c2cnc(N3CCN(C(C)C)CC3)cn2)cc1OC ; "2 HCl"]

2 HCl

The title compound was prepared by a similar procedure to that described in Example 57, starting from 5-bromo-4-isopropyl-3,4,5,6-tetrahydro-2H-[1,2']bipyrazinyl and 3,4-dimethoxyphenylboronic acid.

$^1$H-NMR (400 MHz, CD$_3$OD) δ 8.65 (s, 1H), 8.3 (s, 1H), 7.55 (brs, 1H), 7.45 (dd, 1H), 7.05 (dd, 1H), 4.6 (d, 2H), 3.9 (s, 3H), 3.85 (s, 3H), 3.6 (m, 3H), 3.35 (m, 2H), 3.2 (m, 2H), 1.45 (d, 6H).

$^{13}$C-NMR (400 MHz, CD$_3$OD) δ 154.38, 151.64, 151.25, 143.61, 140.62, 130.88, 130.66, 120.21, 113.47, 111.03, 60.43, 56.92, 48.79, 43.77, 17.53.

HPLC-MS (Method G): M+1=343; t$_r$=1.051 min.

EXAMPLE 103

General Procedure A

4-Isopropyl-5'-(3,4,5-trimethoxyphenyl)-3,4,5,6-tetrahydro-2H-[1,2']bipyrazinyl, dihydrochloride

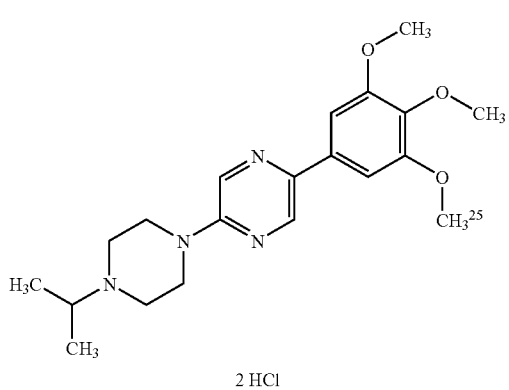

2 HCl

The title compound was prepared by a similar procedure to that described in Example 57, starting from 5-bromo-4-isopropyl-3,4,5,6-tetrahydro-2H-[1,2']bipyrazinyl and 3,4,5-trimethoxyphenylboronic acid.

$^1$H-NMR (400 MHz, CD$_3$OD) δ 8.93 (s, 1H), 8.40 (s, 1H), 7.20 (s, 2H), 4.73-4.68 (m, 2H), δ 3.95 (s, 6H), 3.81 (s, 3H), 3.70-3.60 (m, 3H), 3.57-3.47 (m, 2H), 3.35-3.25 (m, 2H), 1.45 (d, 6H).

HPLC-MS (Method G): M+1=373; t$_r$=1.106 min.

EXAMPLE 104

General Procedure A

N-[4-(4-Isopropyl-3,4,5,6-tetrahydro-2H-[1,2']bipyrazinyl-5'-yl)benzyl]acetamide, dihydrochloride

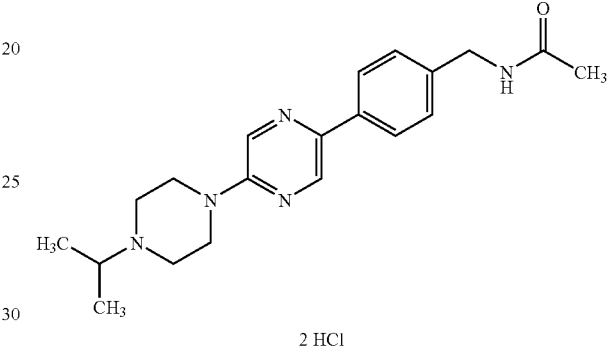

2 HCl

The title compound was prepared by a similar procedure to that described in Example 57, starting from 5-bromo-4-isopropyl-3,4,5,6-tetrahydro-2H-[1,2']bipyrazinyl and 4-(N-acetylaminomethyl)phenylboronic acid.

$^1$H-NMR (400 MHz, CD$_3$OD) δ 8.65 (s, 1H), 8.45 (s, 1H), 7.85 (d, 2H), 7.35 (d, 2H), 4.6 (d, 2H), 4.4 (s, 2H), 3.6 (m, 3H), 3.1-3.4 (m, 4H), 2.05 (s, 3H), 1.45 (d, 6H).

HPLC-MS (Method G): M+1=354; t$_r$=0.867 min.

EXAMPLE 105

General Procedure A 4,4'''-Diisopropyl-3,4,5,6,3''',4''',5''',6'''-octahydro-2H,2'''H-[1,2';5',2'';5'',1''']quaterpyrazine, ditrifluoroacetate

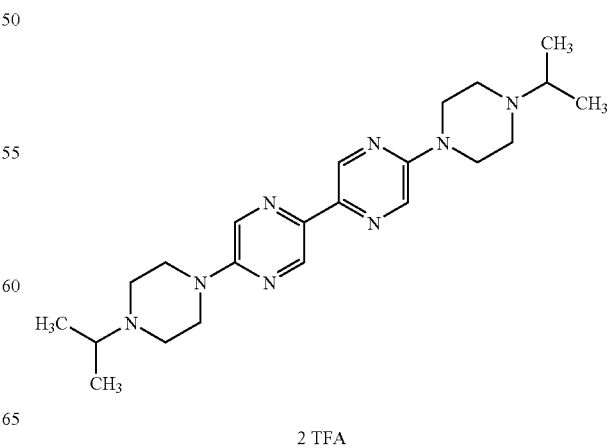

2 TFA

The title compound was isolated as a by-product in Example 104.

$^1$H-NMR (400 MHz, CD$_3$OD) δ 8.9 (s, 1H), 8.35 (s, 1H), 4.65 (d, 2H), 3.65 (m, 3H), 3.15-3.4 (m, 5H), 1.4 (d, 6H).

$^{13}$C-NMR (400 MHz, CD$_3$OD) δ 155.04, 141.60, 140.50, 131.63, 60.40, 48.62, 43.62, 17.45.

EXAMPLE 106

General Procedure A

4-Isopropyl-5'-(6-methoxypyridin-3-yl)-3,4,5,6-tetrahydro-2H-[1,2']bipyrazinyl, trifluoroacetate

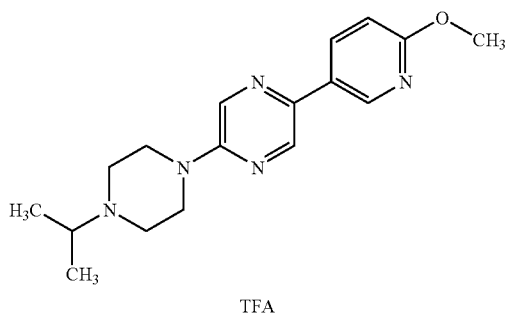 [SMILES: "TFA" ; COc1ccc(-c2cnc(N3CCN(C(C)C)CC3)cn2)cn1]

TFA

The title compound was prepared by a similar procedure to that described in Example 57, starting from 5-bromo-4-isopropyl-3,4,5,6-tetrahydro-2H-[1,2']bipyrazinyl and 2-methoxy-5-pyridineboronic acid.

$^1$H NMR (400 MHz, CDCl$_3$) δ 8.75 (dd, 1H), 8.46 (dd, 1H), 8.22 (s, 1H), 8.2 (dd, 1H), 7.42 (brs, 3H), 6.93 (d, 1H), 4.49 (d, 2H), 4.08 (s, 3H), 3.72-3.41 (m, 5H), 3.20-2.79 (m, 2H), 1.39 (d, 6H).

$^{13}$C-NMR (400 MHz, CDCl$_3$) δ 161.82, 150.81, 141.04, 137.90, 136.58, 136.12, 128.39, 124.52, 109.14, 56.50, 52.87, 48.49, 45.57, 40.21, 14.72.

HPLC-MS (Method G): M+1=314; t$_r$=0.965 min.

EXAMPLE 107

General Procedure A

N,N-Diisopropyl-4-[6-(4-isopropylpiperazin-1-yl)pyridin-3-yl]benzamide, dihydrochloride

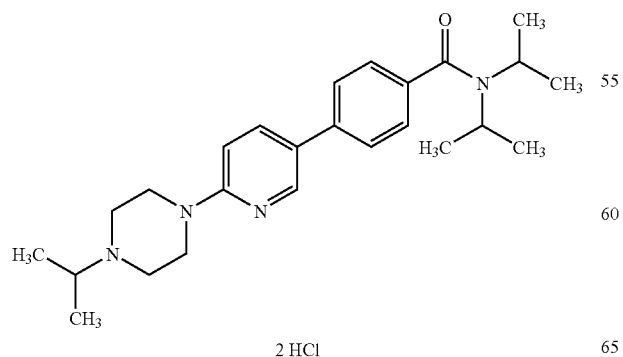

2 HCl

The title compound was prepared by a similar procedure to that described in Example 57, starting from 1-(5-bromo-pyridin-2-yl)-4-isopropyl-piperazine and 4-((N,N-diisopropylamino)carbonyl)phenylboronic acid.

$^1$H-NMR (400 MHz, CD$_3$OD) δ 8.5 (dd, 1H), 8.45 (d, 1H), 7.75 (d, 2H), 7.15 (d, 1H), 7.45 (d, 2H), 4.55 (d, 2H), 3.6-3.9 (m, 7H), 3.4 (t, 2H), 1.55 (m, 6H), 1.45 (d, 6H), 1.15 (m, 6H).

HPLC-MS (Method G): M+1=409; t$_r$=1.229 min.

EXAMPLE 108

General Procedure A

{4-[6-(4-Isopropylpiperazin-1-yl)pyridin-3-yl]phenyl}-(4-methylpiperidin-1-yl)methanone, dihydrochloride

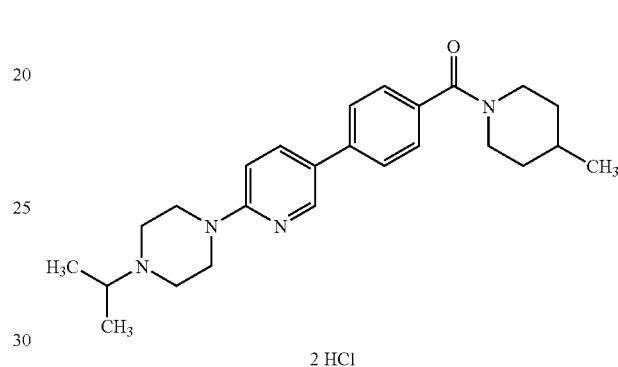

2 HCl

The title compound was prepared by a similar procedure to that described in Example 57, starting from 1-(5-bromo-pyridin-2-yl)-4-isopropyl-piperazine and 4-((4-methylpiperidin-1-yl)carbonyl)phenylboronic acid.

$^1$H NMR (400 MHz, CDCl$_3$) δ (d, 1H), 7.75 (dd, 2H), 7.55 (d, 2H), 7.45 (d, 2H), 6.7 (d, 1H), 4.65 (brs, 1H), 3.75 (brs, 1H), 3.6 (t, 4H), 3.0 (brs, 1H), 2.75 (hept, 1H), 2.7 (t, 4H), 1.85-1.6 (m, 3H), 1.4-1.15 (m, 2H), 1.1 (d, 6H), 0.95 (d, 3H).

$^{13}$C-NMR (400 MHz, CDCl$_3$) δ 170.10, 158.82, 147.90, 146.18, 139.50, 135.96, 134.57, 132.00, 128.42, 127.61, 125.91, 125.06, 106.74, 54.64, 54.55, 48.47, 48.37, 48.16, 45.38, 44.88, 42.56, 34.71, 33.87, 31.15, 21.75, 18.50, 18.43.

HPLC-MS (Method G): M+1=407; t$_r$=1.20 min.

EXAMPLE 109

General Procedure A

6'-(4-Isopropylpiperazin-1-yl)-6-methoxy-[3,3']bipyridinyl, trifluoroacetate

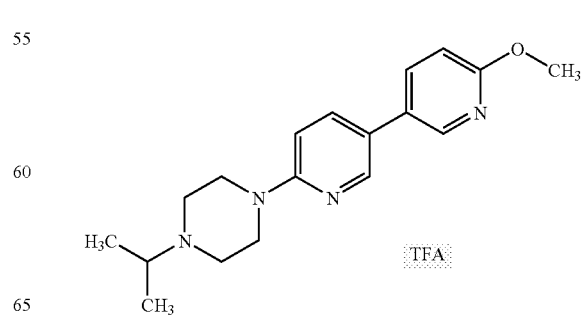

TFA

121

The title compound was prepared by a similar procedure to that described in Example 57, starting from 5-bromo-4-isopropyl-3,4,5,6-tetrahydro-2H-[1,2']bipyrazinyl and 2-methoxy-5-pyridineboronic acid.

$^1$H-NMR (400 MHz, CD$_3$OD) δ 8.5 (d, 1H), 8.37 (m, 2H), 8.15 (d, 1H), 7.55 (d, 1H), 7.05 (d, 1H), 4.5 (m, 2H), 4.05 (s, 3H), 3.4-3.9 (m, 6H), 1.45 (d, 6H).

$^{13}$C-NMR (400 MHz, CD$_3$OD) δ 165.51, 154.05, 144.56, 143.82, 140.69, 137.18, 126.29, 125.93, 114.58, 112.86, 60.68, 55.97, 48.93, 45.24, 17.74.

EXAMPLE 110

General Procedure A 4-(4-Isopropyl-3,4,5,6-tetrahydro-2H-[1,2']bipyrazinyl-5'-yl)benzonitrile, ditrifluoroacetate

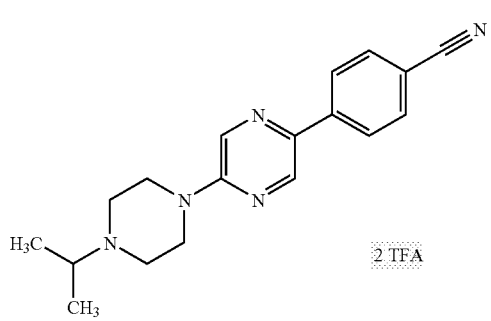

The title compound was prepared by a similar procedure to that described in Example 57, starting from 5-bromo-4-isopropyl-3,4,5,6-tetrahydro-2H-[1,2']bipyrazinyl and 4-cyanophenylboronic acid.

$^1$H-NMR (400 MHz, CD$_3$OD) δ 8.75 (s, 1H), 8.45 (s, 1H), 8.1 (d, 2H), 7.75 (d, 2H), 4.7 (m, 2H), 3.6 (m, 3H), 3.2-3.5 (m, 4H), 1.4 (d, 6H).

EXAMPLE 111

General Procedure A

4-Isopropyl-5'-(4-trifluoromethylphenyl)-3,4,5,6-tetrahydro-2H-[1,2']bipyrazinyl, trifluoroacetate

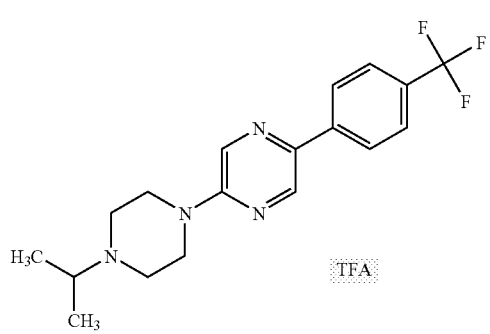

The title compound was prepared by a similar procedure to that described in Example 57, starting from 5-bromo-4-isopropyl-3,4,5,6-tetrahydro-2H-[1,2']bipyrazinyl and 4-(trifluoromethyl)phenylboronic acid.

$^1$H-NMR (400 MHz, CD$_3$OD) δ 8.75 (s, 1H), 8.45 (s, 1H), 8.15 (d, 2H), 7.75 (d, 2H), 4.7 (m, 2H), 3.7-3.55 (m, 3H), 3.4-3.15 (m, 4H), 1.4 (d, 6H).

$^{13}$C-NMR (400 MHz, CD$_3$OD) δ 169.07, 154.98, 142.12, 140.85, 132.28, 127.54, 127.19, 60.417, 43.55, 17.45.

HPLC-MS (Method G): M+1=351; t$_r$=1.523 min.

EXAMPLE 112

General Procedure A

6'-(4-Isopropylpiperazin-1-yl)-5-trifluoromethyl-[2,3']bipyridinyl, dihydrochloride

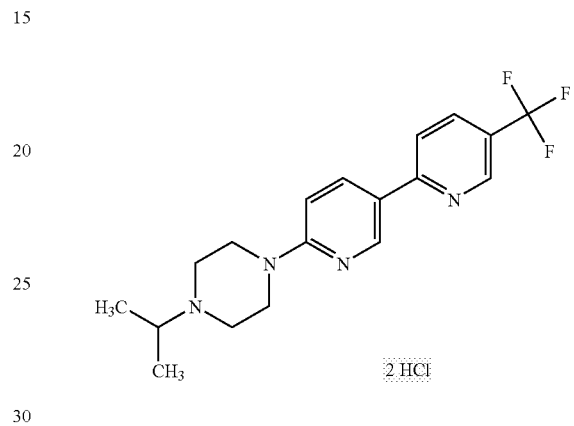

The title compound was prepared by a similar procedure to that described in Example 57, starting from 1-[5-(5,5-dimethyl-1,3,2-dioxaborinan-2-yl)-pyridin-2-yl]-4-isopropyl-piperazine and 2-bromo-5-trifluoromethylpyridine.

$^1$H-NMR (400 MHz, CDCl$_3$) δ 8.85 (d, 1H), 8.8 (d, 1H), 8.2 (dd, 1H), 7.9 (dd, 1H), 7.7 (d, 1H), 6.65 (d, 1H), 3.65 (m, 4H), 2.75 (hept, 1H), 2.6 (m, 4H), 1.1 (d, 6H).

HPLC-MS (Method G): M+1=351; t$_r$=1.203 min.

EXAMPLE 113

General Procedure A

4-Isopropyl-5'-[4-(piperidine-1-sulfonyl)phenyl]-3,4,5,6-tetrahydro-2H-[1,2']bipyrazinyl, hydrochloride

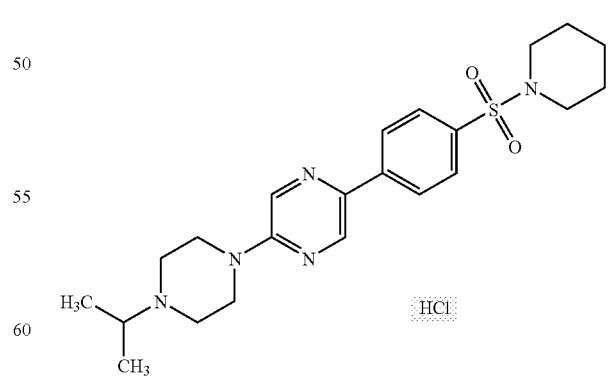

The title compound was prepared by a similar procedure to that described in Example 57, starting from 5-bromo-4-isopropyl-3,4,5,6-tetrahydro-2H-[1,2']bipyrazinyl and 4-(piperidine-1-sulfonyl)phenylboronic acid.

¹H-NMR (400 MHz, CD₃OD) δ 8.75 (s, 1H), 8.45 (s, 1H), 8.18 (d, 2H), 7.82 (d, 2H), 4.75-4.68 (m, 2H), 3.80-3.55 (m, 4H), 3.45-3.22 (m, 4H), 3.00 (m, 4H), 1.68-1.60 (m, 4H), 1.45 (m, 7H).

EXAMPLE 114

General Procedure A

4-Isopropyl-5'-(4-(piperidin-1-yl)phenyl)-3,4,5,6-tetrahydro-2H-[1,2']bipyrazinyl, trihydrochloride

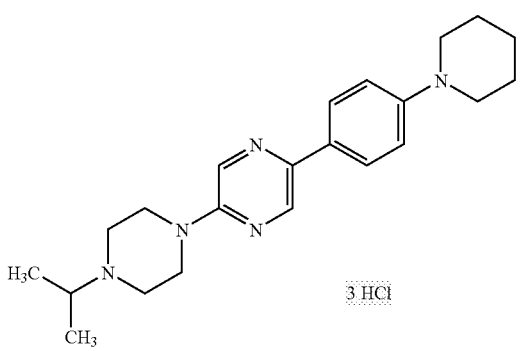

The title compound was prepared by a similar procedure to that described in Example 57, starting from 5-bromo-3,4,5,6-tetrahydro-2H-[1,2']bipyrazinyl and 4-(piperindin-1-yl)phenylboronic acid.

¹H-NMR (400 MHz, CD₃OD) δ 8.80 (s, 1H), 8.52 (s, 1H), 8.18 (d, 2H), 7.89 (d, 2H), 4.77-4.68 (m, 2H), 3.74-3.60 (m, 7H), 3.58-3.46 (m, 2H), 3.35-3.25 (m, 2H), 2.17-2.08 (m, 4H), 1.90-1.80 (m, 2H), 1.45 (d, 6H).

HPLC-MS (Method G): M+1=366; $t_r$=0.798 min.

EXAMPLE 115

General Procedure A

[4-(4-Isopropyl-3,4,5,6-tetrahydro-2H-[1,2']bipyrazinyl-5'-yl)-2-methylphenyl]dimethylamine, trihydrochloride

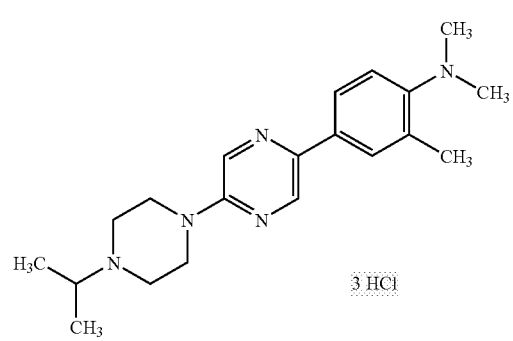

The title compound was prepared by a similar procedure to that described in Example 57, starting from 5-bromo-3,4,5,6-tetrahydro-2H-[1,2']bipyrazinyl and 4-(dimethylamino)-3-methylphenylboronic acid.

¹H-NMR (400 MHz, CD₃OD) δ 8.80 (s, 1H), 8.50 (s, 1H), 8.05 (m, 2H), 7.87 (d, 1H), 4.75-4.68 (m, 2H), 3.70-3.58 (m, 3H), 3.54-3.43 (m, 2H), 3.37 (s, 6H), 3.33-3.22 (m, 2H), 2.65 (s, 3H), 1.45 (d, 6H).

HPLC-MS (Method G): M+1=340; $t_r$=0.718 min.

EXAMPLE 116

General Procedure A

5'-(6-Ethoxypyridin-3-yl)-4-isopropyl-3,4,5,6-tetrahydro-2H-[1,2']bipyrazinyl, trihydrochloride

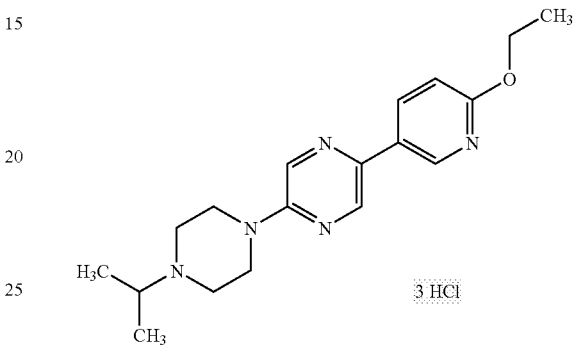

The title compound was prepared by a similar procedure to that described in Example 57, starting from 5-bromo-3,4,5,6-tetrahydro-2H-[1,2']bipyrazinyl and 2-ethoxy-5-pyridineboronic acid.

¹H-NMR (400 MHz, CDCl₃) δ 8.62 (s, 1H), 8.45 (s, 1H), 8.19 (s, 1H), 8.10 (d, 1H), 6.80 (d, 1H), 4.40 (q, 4H), 3.65 (m, 4H), 2.75 (m, 1H), 2.65 (m, 4H), 1.42 (t, 3H), 1.10 (d, 6H).

HPLC-MS (Method G): M+1=328; $t_r$=1.122 min.

EXAMPLE 117

General Procedure A

5'-Benzofuran-2-yl-4-isopropyl-3,4,5,6-tetrahydro-2H-[1,2']bipyrazinyl, dihydrochloride

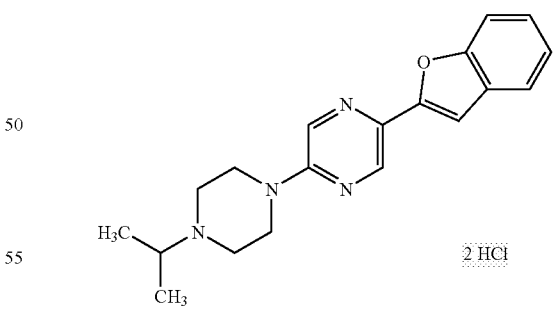

The title compound was prepared by a similar procedure to that described in Example 57, starting from 5-bromo-3,4,5,6-tetrahydro-2H-[1,2']bipyrazinyl and 2-benzofuranboronic acid.

¹H-NMR (400 MHz, DMSO-d₆) δ 8.70 (s, 1H), 8.55 (s, 1H), 7.70-7.60 (m, 2H), 7.47 (s, 1H), 7.46-7.25 (m, 2H), 4.63-4.55 (m, 2H), 3.60-3.45 (m, 5H), 3.18-3.06 (m, 2H), 1.32 (d, 6H)

HPLC-MS (Method G): M+1=323; $t_r$=1.354 min. .

EXAMPLE 118

General Procedure A 5-(4-Isopropyl-3,4,5,6-tetrahydro-2H-[1,2']bipyrazi-nyl-5'-yl)thiophene-2-carbonitrile, ditrifluoroacetate

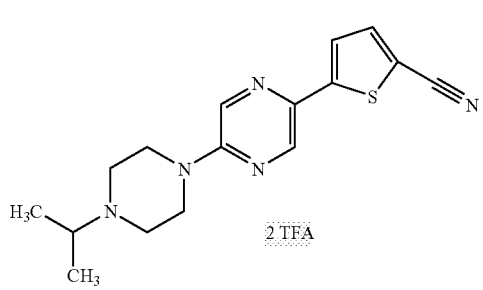

The title compound was prepared by a similar procedure to that described in Example 57, starting from 5-bromo-3,4,5,6-tetrahydro-2H-[1,2']bipyrazinyl and 5-cyano-2-thiopheneboronic acid.

$^1$H-NMR (400 MHz, CD$_3$OD) δ 8.70 (s, 1H), 8.33 (s, 1H), 7.72 (d, 1H), 7.61 (d, 1H), 4.75-4.65 (m, 2H), 3.70-3.55 (m, 3H), 3.40-3.20 (m, 4H), 1.42 (d, 6H).

HPLC-MS (Method G): M+1=314; t$_r$=1.147 min.

EXAMPLE 119

General Procedure A

4-Isopropyl-5'-(2-methylpyridin-4-yl)-3,4,5,6-tetrahydro-2H-[1,2']bipyrazinyl, trihydrochloride

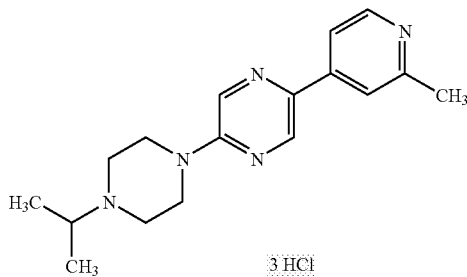

The title compound was prepared by a similar procedure to that described in Example 57, starting from 5-bromo-3,4,5,6-tetrahydro-2H-[1,2']bipyrazinyl and 2-methyl-4-pyridineboronic acid.

$^1$H-NMR (400 MHz, CD$_3$OD) δ 9.05 (s, 1H), 8.65 (d, 1H), 8.60 (s, 1H), 8.50 (s, 1H), 8.45 (d, 1H), 4.90-4.82 (m, 2H), 3.70-3.50 (m, 5H), 3.35-3.24 (m, 2H), 2.83 (s, 3H), 1.45 (d, 6H).

HPLC-MS (Method G): M+1=298; t$_r$=0.413 min.

EXAMPLE 120

General Procedure A (R)-2-(6-1,3-Benzodioxol-5-ylpyridazin-3-yl)oc-tahydropyrido[1,2-a]pyrazine, dihydrochloride

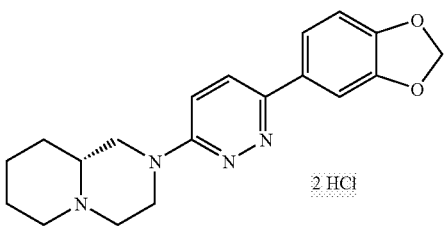

The title compound was prepared by a similar procedure to that described in Example 57, starting from (R)-2-(6-chloro-pyridazin-3-yl)octahydropyrido[1,2-a]pyrazine and 3,4-methylenedioxyphenylboronic acid.

$^1$H-NMR (400 MHz, CD$_3$OD) δ 8.45 (brs, 1H), 8.20 (brs, 1H), 7.50 (d, 1H), 7.47 (s, 1H), 7.10 (d, 1H), 6.15 (s, 2H), 4.75-4.55 (m, 2H), 3.80-3.30 (m, 6H), 3.20-3.05 (m, 1H), 2.15-1.92 (m, 4H), 1.85-1.65 (m, 2H).

HPLC-MS (Method G): M+1=339; t$_r$=0.827 min.

EXAMPLE 121

General Procedure A

4-Isopropyl-5'-(5-trifluoromethyl-pyridin-2-yl)-3,4,5,6-tetrahydro-2H-[1,2']bipyrazinyl, trifluoroacetate

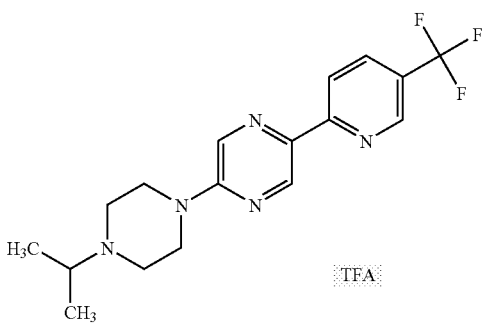

5-Bromo-3,4,5,6-tetrahydro-2H-[1,2']bipyrazinyl (0.50 g, 1.75 mmol) was dissolved in dry THF and cooled to −78° C. under an atmosphere of nitrogen. A 1.6 N solution of n-butyl lithium in hexanes (0.124 g, 1.93 mmol) was added keeping the temperature below −60° C. Tributyltin chloride (0.628 g, 1.93 mmol) was added and the reaction mixture was allowed to reach rt. The reaction mixture was transferred to a 5 mL microwave vial and 2-bromo-5-trifluoromethylpyridine (0.33 g, 1.93 mmol), triphenylphosphinpalladium(II)dichloride (0.088 g, 0.0615 mmol), caesium fluoride (0.581 g, 3.85 mmol) and TEA (0.389 g, 0.385 mmol) were added. This reaction mixture was heated 1.6 h at 100° C. in a microwave oven. The reaction mixture was evaporated in vacuo and the oily residue was purified on a silica gel column with DCM/

MeOH (9:1) as eluent. The product isolated was treated with HCl in diethyl ether followed by evaporation. This afforded 49 mg (9%) of the title compound.

HPLC-MS (Method G): M+1=352; $t_r$=1.29 min.

EXAMPLE 122

General Procedure A

N-{4-[6-(4-Cyclobutylpiperazin-1-yl)pyridin-3-yl]phenyl}acetamide, trifluoroacetate

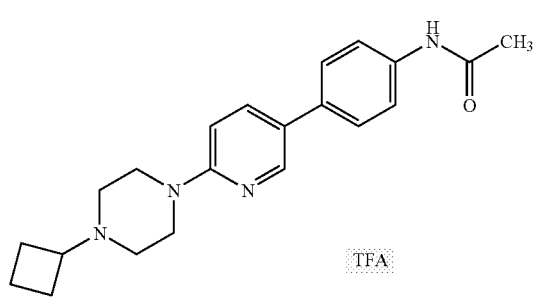

The title compound was prepared by a similar procedure to that described in Example 59, starting from 1-(5-bromo-pyridin-2-yl)-4-cyclobutyl-piperazine and 4-acetamidophenylboronic acid.

$^1$H-NMR (400 MHz, DMSO-d$_6$) δ 8.48 (d, 1H), 7.92 (dd, 1H), 7.65 (d, 2H), 7.55 (d, 2H), 7.05 (d, 1H), 4.5 (d, 2H), 3.75 (pent, 1H), 3.45 (d, 2H), 3.15 (m, 2H), 2.9 (m, 2H), 2.2 (m, 4H), 2.05 (s, 3H), 1.75 (m, 2H).

HPLC-MS (Method G): M+1=351; $t_r$=0.74 min.

EXAMPLE 123

General Procedure A

4-[6-(4-Cyclobutyl-piperazin-1-yl)-pyridin-3-yl]-N,N-dimethyl-benzamide, trifluoroacetate

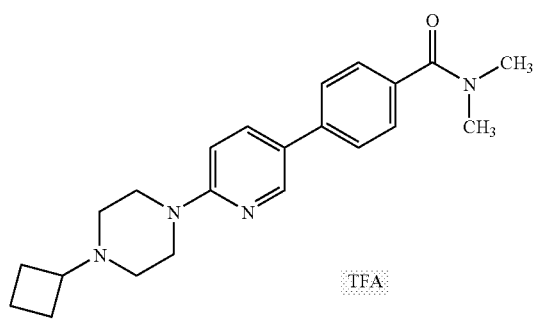

The title compound was prepared by a similar procedure to that described in Example 57, starting from 1-(5-bromo-pyridin-2-yl)-4-cyclobutyl-piperazine and 4-(dimethylaminocarbonyl)phenylboronic acid.

$^1$H-NMR (400 MHz, CD$_3$OD) δ 8.45 (d, 1H), 8.1 (dd, 1H), 7.65 (d, 2H), 7.5 (dd, 2H), 7.18 (d, 1H), 3.2-4.5 (m, 8H), 3.1 (s, 3H), 3.0 (s, 3H), 2.3 (m, 4H), 1.8-1.95 (m, 2H).

HPLC-MS (Method G): M+1=365; $t_r$=0.931 min.

EXAMPLE 124

General Procedure A

N-{4-[6-(4-Cyclobutylpiperazin-1-yl)pyridazin-3-yl]-2-methoxyphenyl}acetamide, dihydrochloride

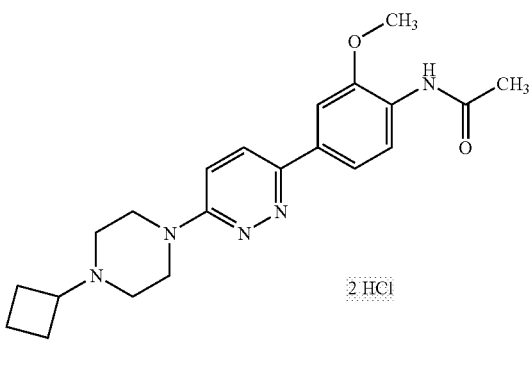

The title compound was prepared by a similar procedure to that described in Example 57, starting from 3-chloro-6-(4-cyclobutyl-piperazin-1-yl)-pyridazine and N-[2-methoxy-4-(4,4,5,5-tetramethyl-1,3,2-dioxaborolan-2-yl)phenyl]acetamide.

$^1$H-NMR (400 MHz, CD$_3$OD) δ 8.57 (d, 1H), 8.42 (d, 1H), 8.20 (d, 1H), 7.62 (s, 1H), 7.54 (d, 1H), 4.70-4.60 (m, 2H), 4.05 (s, 3H), 3.86-3.75 (m, 1H), 3.74-3.60 (m, 4H), 3.20-3.10 (m, 2H), 2.50-2.32 (m, 4H), 2.23 (s, 3H), 2.00-1.81 (m, 2H).

HPLC-MS (Method G): M+1=382; $t_r$=0.787 min.

EXAMPLE 125

General Procedure A

{4-[6-(4-Isopropylpiperazin-1-yl)pyridazin-3-yl]phenyl}piperidin-1-ylmethanone, trifluoroacetate

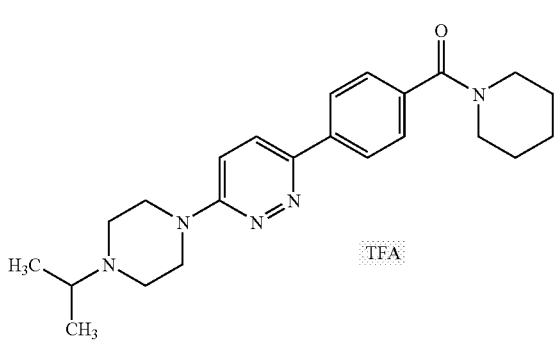

Step 1

4-[6-(4-Isopropyl-piperazin-1-yl)-pyridazin-3-yl]-benzonitrile

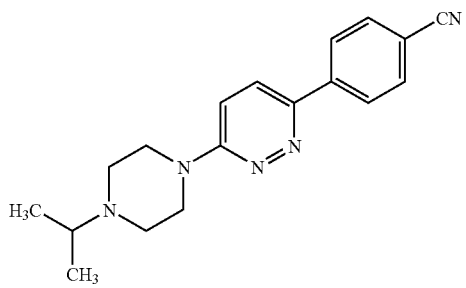 [SMILES: CC(C)N1CCN(c2ccc(-c3ccc(C#N)cc3)nn2)CC1]

To a solution of 4-(6-chloro-pyridazin-3-yl)-benzonitrile (20 g, 92.8 mmol) in 1-butanol (150 mL) was added 1-isopropyl-piperazine hydrochloride (29.8 g, 148.5 mmol) and $NH_4Cl$ (4.96 g, 92.8 mmol). The reaction mixture was heated at reflux for 48 h and then concentrated under reduced pressure. The residue was dissolved into a 10% solution of citric acid in water and filtered. Solid $K_2CO_3$ was added to the filtrate until pH 9. The precipitate was isolated and washed with water to give 4-[6-(4-isopropyl-piperazin-1-yl)-pyridazin-3-yl]-benzonitrile (20 g, 70%).

Step 2

4-[6-(4-Isopropyl-piperazin-1-yl)-pyridazin-3-yl]-benzoic acid, hydrochloride

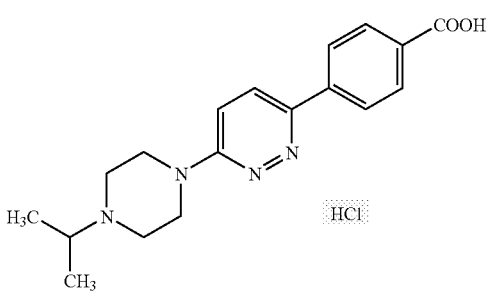

4-[6-(4-Isopropyl-piperazin-1-yl)-pyridazin-3-yl]-benzonitrile (10 g, 32.6 mmol) was dissolved in 6 N hydrochloric acid (100 mL). The reaction mixture was heated at reflux for 6 h and concentrated under reduced pressure to give 10.3 g (79%) 4-[6-(4-isopropyl-piperazin-1-yl)pyridazin-3-yl]-benzoic acid, hydrochloride.

Step 3

To a solution of 4-[6-(4-isopropyl-piperazin-1-yl)-pyridazin-3-yl]-benzoic acid, hydrochloride (2 g, 5 mmol) in $CH_2Cl_2$ was added EDAC (1.91 g, 10 mmol) and HOBt (0.81 g, 6 mmol) followed by piperidine (2.56 g, 30 mmol). The reaction mixture was stirred for 60 h at rt and then concentrated under reduced pressure. The residue was purified by column chromatography eluting with $CH_2Cl_2$ on silica gel to give a crude product, which was further purified by HPLC (Method F) to give 850 mg (43%) of the title compound as a TFA salt.

$^1$H NMR (300 MHz, $D_2O$) δ 8.25 (d, 1H), 7.90 (d, 1H), 7.84 (d, 2H), 7.50 (d, 2H), 4.51-4.48 (m, 2H), 3.59-3.42 (m, 7H), 3.40-3.16 (m, 4H), 1.57-1.49 (m, 4H), 1.45-1.34 (m, 2H), 1.34 (d, 6H).

HPLC (Method D): $t_r$=2.94 min (98%).

EXAMPLE 126

General Procedure A

{4-[6-(4-Cyclopropylmethylpiperazin-1-yl)pyridazin-3-yl]phenyl}piperidin-1-ylmethanone, trifluoroacetate

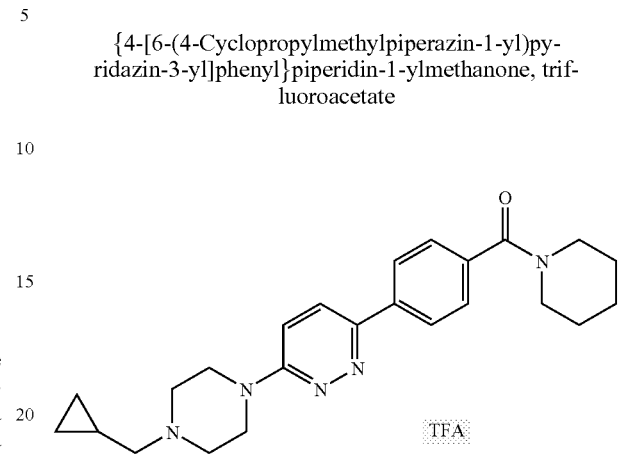

The title compound was prepared by a similar procedure to that described in Example 125 starting from 4-[6-(4-cyclopropylmethyl-piperazin-1-yl)-pyridazin-3-yl]-benzoic acid, hydrochloride and piperidine.

$^1$H NMR (300 MHz, CDCl3) δ 8.24 (d, 1H), 7.91-7.81 (m, 3H), 7.48 (d, 2H), 4.48-4.43 (m, 2H), 3.76-3.69 (m, 2H), 3.53-3.43 (m, 4H), 3.30-3.09 (m, 4H), 3.02 (d, 2H), 1.53-1.39 (m, 6H), 1.07-0.92 (m, 1H), 0.63 (d, 2H), 0.27 (d, 2H).

HPLC (Method D): $t_r$=3.04 min (98%).

EXAMPLE 127

General Procedure A

{4-[6-(4-Isopropylpiperazin-1-yl)pyridazin-3-yl]phenyl}morpholin-4-ylmethanone, trifluoroacetate

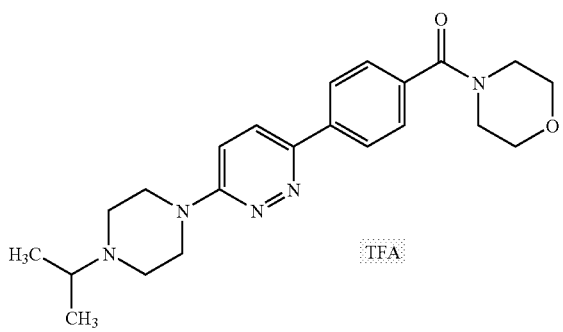

To a solution of 4-[6-(4-isopropyl-piperazin-1-yl)-pyridazin-3-yl]-benzoic acid, hydrochloride (2 g, 5 mmol) in $CH_2Cl_2$ was added EDAC (1.91 g, 10 mmol) and HOBt (0.81 g, 6 mmol). Then morpholine (2.61 g, 30 mmol) was added. The reaction mixture was stirred for 60 h at rt and concentrated under reduced pressure. The residue was purified by column chromatography on silica gel to give the product, which was further purified by HPLC Method F. This afforded 600 mg (30%) of the title compound as a TFA salt.

¹H NMR (300 MHz, D₂O) δ 8.26 (d, 1H), 7.91 (d, 1H), 7.84 (d, 2H), 7.53 (d, 2H), 4.56-4.46 (m, 2H), 3.76-3.63 (m, 4H), 3.57-3.41 (m, 7H), 3.36-3.35 (m, 2H), 3.22-3.14 (m, 2H), 1.20 (d, 6H).

HPLC (Method E): t$_r$=2.28 min (95%).

EXAMPLE 128

General Procedure A (4-Hydroxymethylpiperidin-1-yl)-{4-[6-(4-isopropylpiperazin-1-yl)pyridazin-3-yl]phenyl}-methanone, trifluoroacetate

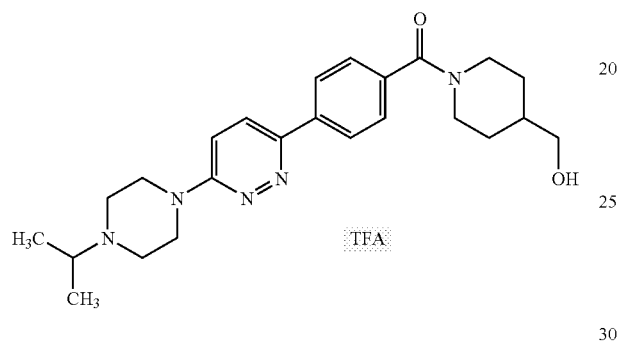

To a solution of 4-[6-(4-isopropylpiperazin-1-yl)-pyridazin-3-yl]-benzoic acid, hydrochloride (2.0 g, 5.0 mmol) in CH₂Cl₂ was added EDAC (1.91 g, 10 mmol) and HOBt (0.81 g, 6 mmol). Then a solution of 4-hydroxymethyl-piperidine (2.56 g, 30 mmol) in CH₂Cl₂ (10 ml) was added. The mixture was stirred for 60 h at rt and concentrated under reduced pressure. The residue was purified by column chromatography on silica gel eluting with CH₂Cl₂ to give a crude product, which was further purified by HPLC Method F. This afforded 580 mg (28%) of the title compound as a TFA salt.

HPLC (Method D): t$_r$=2.32 min (95%).

EXAMPLE 129

General Procedure A

4-[6-(4-Isopropylpiperazin-1-yl)pyridazin-3-yl]-N,N-dimethylbenzamide, trifluoroacetate

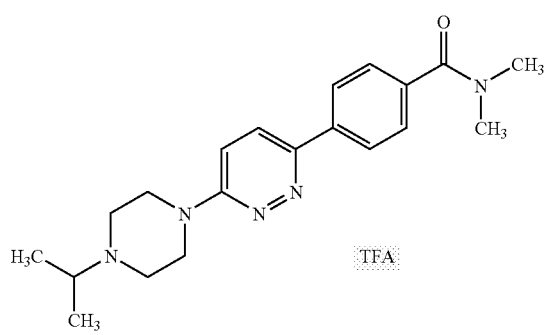

To a solution of 4-[6-(4-isopropylpiperazin-1-yl)-pyridazin-3-yl]-benzoic acid, hydrochloride (2 g, 5 mmol) in CH₂Cl₂ was added EDAC (1.91 g, 10 mmol), HOBt (0.81 g, 6 mmol) and TEA (4.04 g, 40 mmol). Then dimethylamine, hydrochloride (1.63 g, 20 mmol) was added. The reaction mixture was stirred for 60 h at rt and concentrated under reduced pressure. The residue was purified by column chromatography on silica gel eluting with CH₂Cl₂ to give a crude product, which was further purified by HPLC Method F. This afforded 800 mg (45%) of the title compound as a TFA salt.

¹H NMR (300 MHz, D₂O) δ 8.26 (d, 1H), 7.90 (d, 1H), 7.82 (d, 2H), 7.50 (d, 2H), 4.56-4.47 (m, 2H), 3.57-3.40 (m, 5H), 3.22-3.09 (m, 2H), 2.96 (m, 3H), 2.85 (m, 3H), 1.23 (d, 6H).

HPLC (Method E): t$_r$=2.25 min (97%).

EXAMPLE 130

General Procedure A

{4-[6-(4-Cyclopentylpiperazin-1-yl)pyridazin-3-yl]phenyl}piperidin-1-ylmethanone, trifluoroacetate

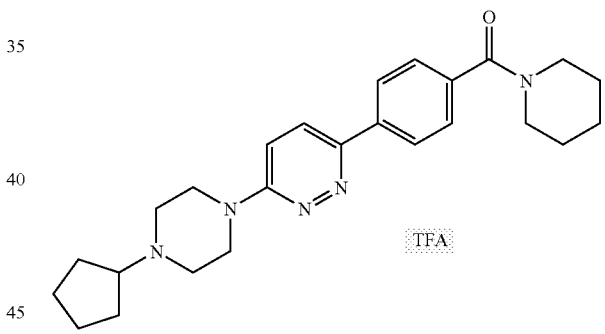

To a solution of 4-[6-(4-cyclopentyl-piperazin-1-yl)-pyridazin-3-yl]-benzoic acid, hydrochloride (2 g, 5 mmol) in CH₂Cl₂ was added EDAC (1.91 g, 10 mmol), HOBt (0.81 g, 6 mmol). Then piperidine (2.52 g, 30 mmol) was added. The reaction mixture was stirred for 60 h at rt and concentrated under reduced pressure. The residue was purified by column chromatography on silica gel eluting with CH₂Cl₂ to give crude product, which was further purified by HPLC Method F to give 600 mg (29%) of the title compound as a TFA salt.

¹H NMR (300 MHz, D₂O) δ 8.18 (d, 1H), 7.80-7.83 (m, 3H), 7.47 (d, 2H), 4.44 (m, 2H), 3.1-3.7 (m, 11H), 2.03 (m, 2H), 1.39-1.64 (m, 12H).

HPLC (Method D): t$_r$=3.27 min (95%).

EXAMPLE 131

General Procedure A

{4-[6-(4-Isopropylpiperazin-1-yl)pyridazin-3-yl]phenyl}-(4-methylpiperazin-1-yl)methanone, trifluoroacetate

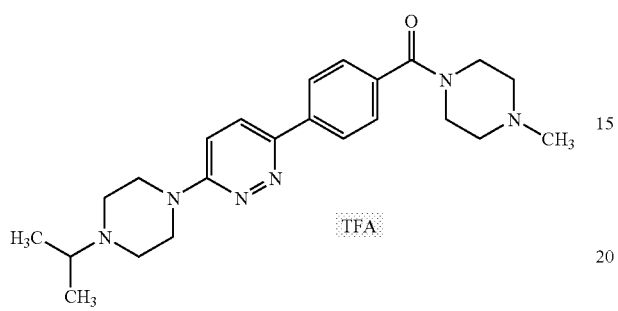

To a solution of 4-[6-(4-isopropylpiperazin-1-yl)pyridazin-3-yl]benzoic acid, hydrochloride (2 g, 5 mmol) in CH$_2$Cl$_2$ was added EDAC (1.91 g, 10 mmol) and HOBt (0.81 g, 6 mmol). Then 1-methyl-piperazine (2.0 g, 20 mmol) was added. The reaction mixture was stirred for 60 h at rt and concentrated under reduced pressure. The residue was purified by column chromatography eluting with CH$_2$Cl$_2$ on silica gel to give crude product, which was further purified by HPLC Method F. This afforded 300 mg (15%) of the title compound as a TFA salt.

$^1$H NMR (300 MHz, D$_2$O) δ 8.01 (d, 1H), 7.85 (d, 2H), 7.59-7.49 (m, 3H), 4.47-4.43 (m, 2H), 3.90-3.84 (m, 1H), 3.50-3.05 (m, 14H), 2.81 (m, 3H), 1.23 (d, 6H).

HPLC (Method D): t$_r$=3.04 min (96%).

EXAMPLE 132

General Procedure A

{4-[6-(4-Isopropylpiperazin-1-yl)pyridin-3-yl]phenyl}morpholin-4-ylmethanone, trifluoroacetate

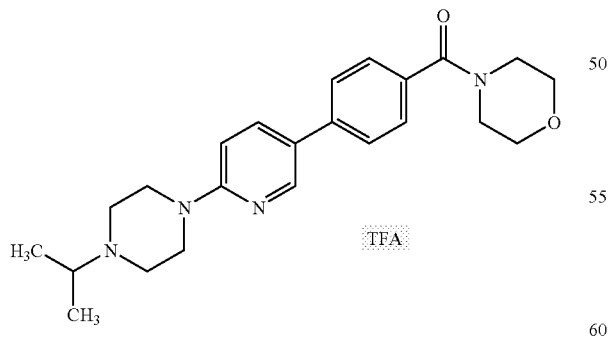

The title compound was prepared by a similar procedure to that described in Example 125, starting from 4-[6-(4-isopropyl-piperazin-1-yl)-pyridin-3-yl]-benzoic acid, hydrochloride and morpholine.

$^1$H NMR (300 MHz, D$_2$O) δ 8.27 (dd, J=2.4 Hz, J=9.6 Hz, 1H) 8.20 (d, J=2.4 Hz, 1H), 7.62 (d, J=8.4 Hz, 2H), 7.44 (d, J=8.1 Hz, 2H), 7.32 (d, J=9.6 Hz, 1H), 4.34-4.30 (m, 2H), 3.73-3.50 (m, 11H), 3.46-3.41 (m, 2H), 3.25 (m, 2H), 1.29 (d, J=6.6 Hz, 6H).

HPLC (Method D): t$_r$=3.75 min (93%).

EXAMPLE 133

General Procedure A

4-[6-(4-Isopropylpiperazin-1-yl)pyridin-3-yl]-N,N-dimethylbenzamide, trifluoroacetate

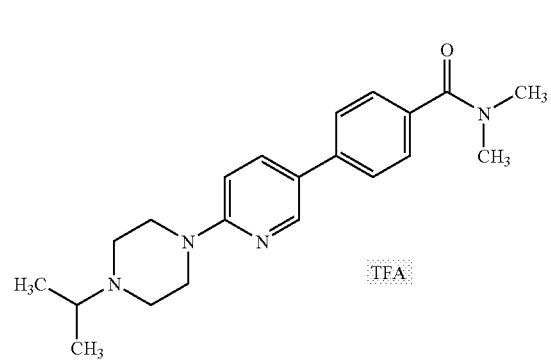

The title compound was prepared by a similar procedure to that described in Example 125, starting from 4-[6-(4-isopropyl-piperazin-1-yl)-pyridin-3-yl]-benzoic acid, hydrochloride and dimethylamine, hydrochloride.

$^1$H NMR (300 MHz, D$_2$O) δ 8.28 (dd, J=2.1 Hz, J=9.3 Hz, 1H), 8.20 (d, J=2.1 Hz, 1H), 7.6 (d, J=8.4 Hz, 2H), 7.44 (d, J=8.1 Hz, 2H), 7.33 (d, J=9.3 Hz, 1H), 4.35-4.30 (m, 2H), 3.64-3.51 (m, 5H), 3.29-3.26 (m, 2H), 3.02 (s, 3H), 2.91 (s, 3H), 1.23 (d, J=7.2 Hz, 6H).

HPLC (Method D): t$_r$=3.73 min (96%).

EXAMPLE 134

General Procedure A

{4-[6-(4-Isopropylpiperazin-1-yl)pyridin-3-yl]phenyl}piperidin-1-ylmethanone, trifluoroacetate

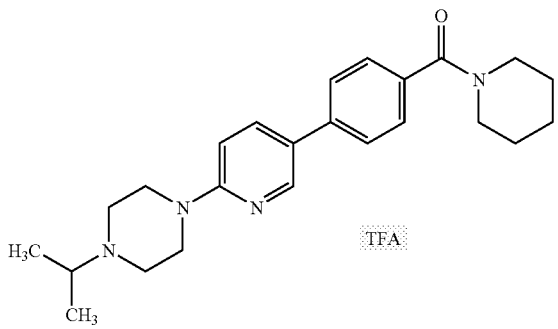

The title compound was prepared by a similar procedure to that described in Example 125, starting from 4-[6-(4-isopropyl-piperazin-1-yl)-pyridin-3-yl]-benzoic acid, hydrochloride and piperidine.

$^1$H NMR (300 MHz, D$_2$O) δ 8.29 (dd, J=2.4 Hz, J=9.6 Hz, 1H), 8.15 (d, J=1.8 Hz, 1H), 7.58 (d, J=8.7 Hz, 2H), 7.38 (d,

J=8.7 Hz, 2H), 7.34 (d, J=9.6 Hz, 1H), 4.32-4.27 (m, 2H), 3.62-3.48 (m, 7H), 3.28-3.19 (m, 4H), 1.53 (m, 4H), 1.38 (m, 2H), 1.26 (d, J=6.6 Hz, 6H).

HPLC (Method D): $t_r$=4.43 min (95%).

EXAMPLE 135

General Procedure A (4-Hydroxymethylpiperidin-1-yl)-{4-[6-(4-isopropylpiperazin-1-yl)pyridin-3-yl]phenyl}-methanone, trifluoroacetate

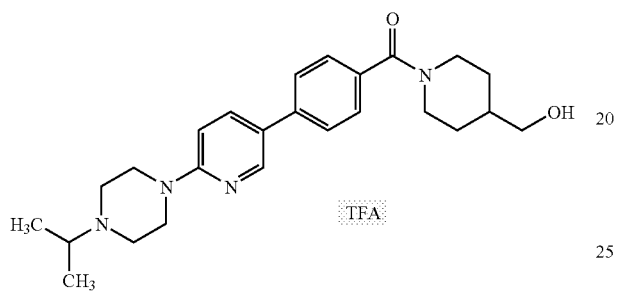

The title compound was prepared by a similar procedure to that described in Example 125, starting from 4-[6-(4-isopropyl-piperazin-1-yl)-pyridin-3-yl]-benzoic acid, hydrochloride and 4-hydroxymethyl-piperidine.

$^1$H NMR (300 MHz, D$_2$O) δ 8.29 (dd, J=2.4 Hz, J=9.6 Hz, 1H), 8.22 (d, J=2.1 Hz, 1H), 7.64 (d, J=8.4 Hz, 2H), 7.43 (d, J=8.4 Hz, 2H), 7.34 (d, J=9.6 Hz, 1H), 4.45-4.32 (m, 3H), 3.65-3.51 (m, 6H), 3.4-3.38 (m, 2H), 3.30-3.27 (m, 2H), 3.11-3.07 (m, 1H), 2.90-2.85 (m, 1H), 1.80-1.76 (m, 1H), 1.29 (d, J=6.6 Hz, 6H), 1.19-1.09 (m, 2H).

HPLC (Method D): $t_r$=3.79 min (97%).

EXAMPLE 136

General Procedure A

{4-[6-(4-Isopropylpiperazin-1-yl)pyridin-3-yl]phenyl}-(4-methylpiperazin-1-yl)methanone, trifluoroacetate

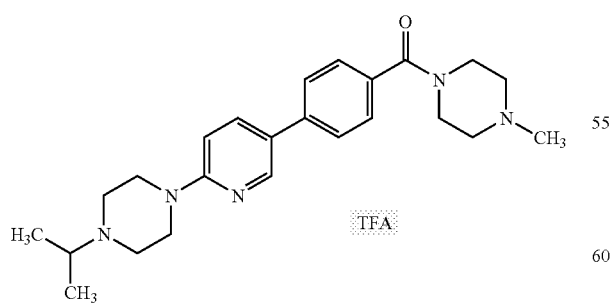

The title compound was prepared by a similar procedure to that described in Example 125, starting from 4-[6-(4-isopropyl-piperazin-1-yl)-pyridin-3-yl]-benzoic acid, hydrochloride and 1-methylpiperazine.

$^1$H NMR (300 MHz, D$_2$O) δ 8.29 (dd, J=2.4, J=9.6 Hz, 1H), 8.16 (d, J=2.4 Hz, 1H), 7.61 (d, J=8.4 Hz, 2H), 7.45 (d, J=8.4 Hz, 2H), 7.34 (d, J=9.3 Hz, 1H), 4.32-4.27 (m, 2H), 3.92-3.84 (m, 1H), 3.61-3.44 (m, 8H), 3.32-3.01 (m, 6H), 2.80 (s, 3H), 1.24 (d, J=6.6 Hz, 6H).

EXAMPLE 137

General Procedure A

{4-[6-(4-Cyclopropylmethylpiperazin-1-yl)pyridin-3-yl]phenyl}piperidin-1-ylmethanone, trifluoroacetate

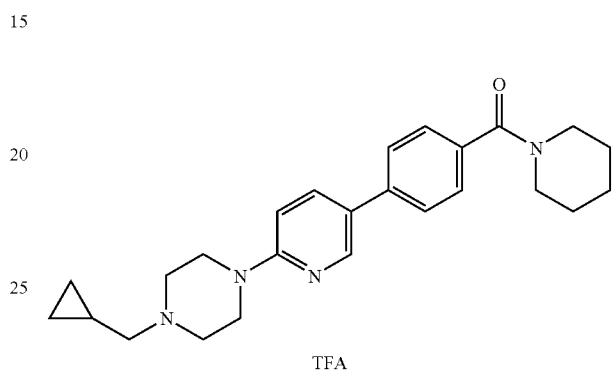

The title compound was prepared by a similar procedure to that described in Example 125, starting from 4-[6-(4-(cyclopropylmethyl)-piperazin-1-yl)-pyridin-3-yl]-benzoic acid, hydrochloride and piperidine.

$^1$H NMR (300 MHz, D$_2$O) δ 8.45 (d, 1H), 8.08 (d, 1H), 7.68 (d, 2H), 7.47 (d, 2H), 7.16 (d, 1H), 4.72-3.34 (m, 12H), 3.12 (d, 2H), 1.77-1.49 (m, 6H), 1.22-1.11 (m, 1H), 0.80 (q, 2H), 0.47 (q, 2H).

HPLC (Method E): $t_r$=3.39 min (96%).

EXAMPLE 138

General Procedure A

{4-[6-(4-Cyclopropylpiperazin-1-yl)pyridin-3-yl]phenyl}piperidin-1-ylmethanone, trifluoroacetate

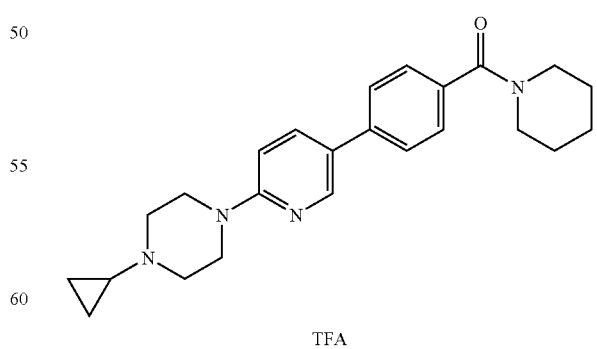

The title compound was prepared by a similar procedure to that described in Example 125, starting from 4-[6-(4-cyclopropyl-piperazin-1-yl)-pyridin-3-yl]-benzoic acid, hydrochloride and piperidine.

¹H NMR (300 MHz, CD₃OD) δ 8.38-8.28 (m, 2H), 7.73 (d, 2H), 7.51 (d, 2H), 7.46-7.41 (m, 1H), 4.03-3.95 (m, 2H), 3.78-3.55 (m, 6H), 3.51-3.35 (m, 4H), 2.93-2.96 (m, 1H), 1.79-1.48 (m, 7H), 1.06-1.04 (m, 3H).
HPLC (Method D): $t_r$=4.43 min (96%).

EXAMPLE 139

General Procedure A

{4-[6-(4-Cyclopentylpiperazin-1-yl)pyridin-3-yl]phenyl}piperidin-1-ylmethanone, trifluoroacetate

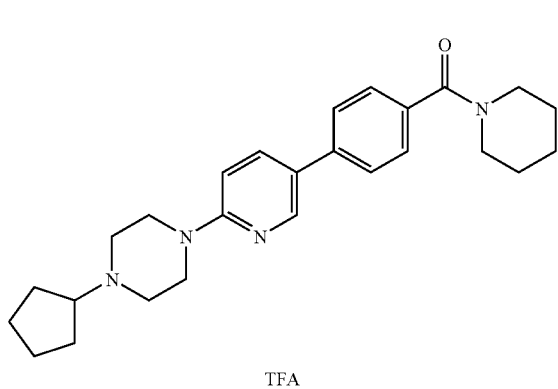 [SMILES: O=C(c1ccc(-c2ccc(N3CCN(C4CCCC4)CC3)nc2)cc1)N1CCCCC1]

TFA

The title compound was prepared by a similar procedure to that described in Example 125, starting from 4-[6-(4-cyclopentyl-piperazin-1-yl)-pyridin-3-yl]-benzoic acid, hydrochloride and piperidine.
¹H NMR (300 MHz, CD₃OD) δ 8.46 (d, 1H), 8.06 (dd, 1H), 7.68 (d, 2H), 7.47 (d, 2H), 7.13 (dd, 1H), 4.70-4.09 (m, 2H), 4.09-3.35 (m, 10H), 3.35-3.28 (m, 1H), 2.35-2.23 (m, 2H), 1.95-1.55 (m, 12H).
HPLC (Method E): $t_r$=3.46 min (98%).

EXAMPLE 140

General Procedure A

{3-[6-(4-Isopropylpiperazin-1-yl)pyridin-3-yl]phenyl}morpholin-4-ylmethanone, trifluoroacetate

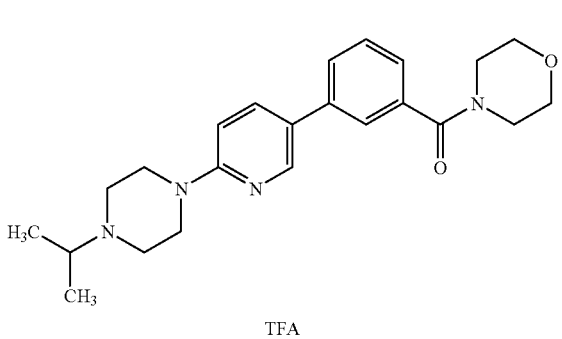 [SMILES: CC(C)N1CCN(c2ccc(-c3cccc(C(=O)N4CCOCC4)c3)cn2)CC1]

TFA

The title compound was prepared by a similar procedure to that described in Example 125, starting from 3-[6-(4-isopropyl-piperazin-1-yl)-pyridin-3-yl]-benzoic acid and morpholine.

¹H NMR (300 MHz, D₂O) δ 8.23 (s, 1H), 8.15 (d, 1H), 7.55-7.52 (t, 2H), 7.37 (d, 1H), 7.66-7.21 (d, 1H), 4.36-4.26 (m, 2H), 3.78-3.40 (m, 13H), 3.30-3.17 (s, 2H), 1.29 (d, 6H).
HPLC (Method C): $t_r$=3.95 min (96%).

EXAMPLE 141

General Procedure A

{3-[6-(4-Isopropylpiperazin-1-yl)pyridin-3-yl]phenyl}piperidin-1-ylmethanone, trifluoroacetate

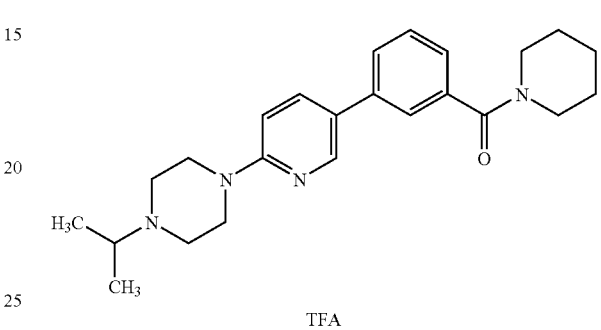

TFA

The title compound was prepared by a similar procedure to that described in Example 125, starting from 3-[6-(4-isopropyl-piperazin-1-yl)-pyridin-3-yl]-benzoic acid and piperidine.
¹H NMR (300 MHz, D₂O) δ 8.31 (d, 1H), 8.17 (s, 1H), 7.64 (d, 2H), 7.52 (t, 2H), 7.37 (d, 2H), 3.65-3.55 (m, 7H), 3.34 (d, 2H), 3.29 (t, 4H), 1.60-1.42 (d, 6H), 1.29 (d, 6H).
HPLC (Method D): $t_r$=4.03 min (97%).

EXAMPLE 142

General Procedure A

3-[6-(4-Isopropylpiperazin-1-yl)pyridin-3-yl]-N,N-dimethylbenzamide, trifluoroacetate

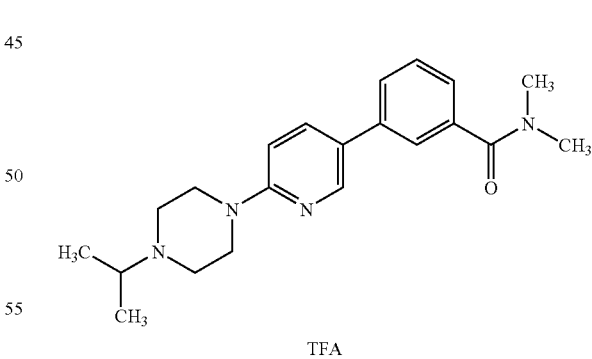

TFA

The title compound was prepared by a similar procedure to that described in Example 125, starting from 3-[6-(4-isopropyl-piperazin-1-yl)-pyridin-3-yl]-benzoic acid and dimethylamine, hydrochloride.
¹H NMR (300 MHz, D₂O) δ 8.26 (d, 2H), 8.20 (s, 1H), 7.56-7.51 (dd, 2H), 7.65 (d, 1H), 7.41-7.33 (dd, 2H), 4.33 (d, 2H), 3.64-3.54 (m, 5H), 3.29 (t, 2H), 3.02 (s, 3H), 2.92 (s, 3H), 1.29 (d, 6H).
HPLC (Method D): $t_r$=2.52 min (97%).

EXAMPLE 143

General Procedure A

{4-[6-(4-Cyclopentylpiperazin-1-yl)pyridin-3-yl]phenyl}-(4-methylpiperazin-1-yl)methanone, trifluoroacetate

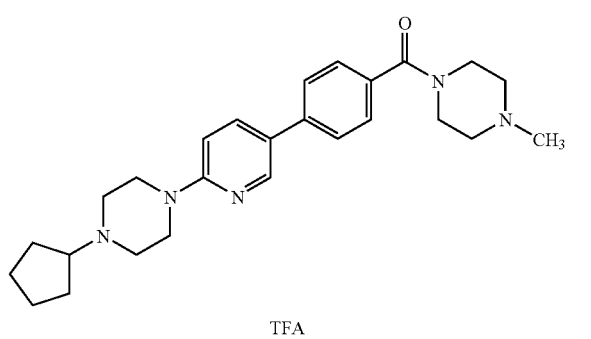 [SMILES: CN1CCN(C(=O)c2ccc(-c3ccc(N4CCN(C5CCCC5)CC4)nc3)cc2)CC1]

TFA

The title compound was prepared by a similar procedure to that described in Example 125, starting from 3-[6-(4-cyclopentyl-piperazin-1-yl)-pyridin-3-yl]-benzoic acid, hydrochloride and 1-methylpiperazine.

$^1$H NMR (300 MHz, CD$_3$OD) δ 8.41-8.32 (m, 2H), 7.77 (d, 2H), 7.62 (d, 2H), 7.47 (d, 1H), 4.62-4.21 (m, 2H), 4.01-3.35 (m, 11H), 3.25-3.05 (m, 2H), 3.05-2.78 (m, 3H), 2.52-2.12 (m, 2H), 2.12-1.98 (m, 4H), 1.98-1.51 (m, 6H).

HPLC (Method C): t$_r$=4.29 min (96%).

EXAMPLE 144

General Procedure A

{4-[6-(4-Cyclopropylpiperazin-1-yl)pyridin-3-yl]phenyl}-(4-methylpiperazin-1-yl)methanone, trifluoroacetate

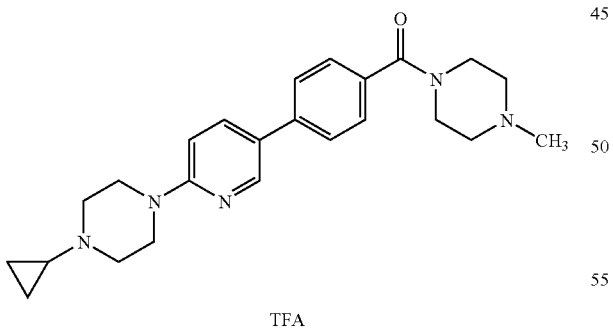

TFA

The title compound was prepared by a similar procedure to that described in Example 125, starting from 3-[6-(4-cyclopropyl-piperazin-1-yl)-pyridin-3-yl]-benzoic acid, hydrochloride and 1-methylpiperazine.

$^1$H NMR (300 MHz, CD$_3$OD) δ 8.41 (s, 1H), 8.12-8.15 (m, 1H), 7.73 (d, 2H), 7.58 (d, 2H), 7.21-7.24 (m, 1H), 4.03-3.95 (m, 5H), 3.78-3.31 (m, 9H), 3.09-3.30 (m, 2H), 2.84-2.96 (m, 4H), 0.92-1.14 (m, 4H).

HPLC (Method D): t$_r$=4.43 min (96%).

EXAMPLE 145

General Procedure A

{4-[6-(4-Isopropylpiperazin-1-yl)pyridin-3-yl]phenyl}-(4-methoxymethylpiperidin-1-yl)methanone, trifluoroacetate

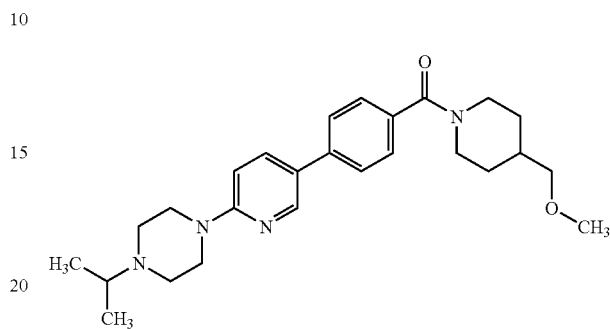

TFA

The title compound was prepared by a similar procedure to that described in Example 125, starting from 3-[6-(4-isopropyl-piperazin-1-yl)-pyridin-3-yl]-benzoic acid, hydrochloride and 4-methoxymethyl-piperidine, hydrochloride.

$^1$H NMR (300 MHz, CD$_3$OD) δ 8.45 (d, 1H), 8.10 (dd, 1H), 7.70 (d, 2H), 7.48 (d, 2H), 7.16 (d, 1H), 4.72-4.45 (m, 2H), 4.22-3.35 (m, 8H), 3.32 (s, 3H), 3.29-3.27 (m, 2H), 3.21-2.95 (m, 2H), 2.95-2.75 (m, 1H), 1.95-1.82 (m, 2H), 1.75-1.62 (m, 1H), 1.42 (d, 6H), 1.41-1.15 (m, 2H).

HPLC (Method D): t$_r$=4.34 min (97%).

EXAMPLE 146

General Procedure A

4-[6-(4-Cyclopentylpiperazin-1-yl)pyridin-3-yl]-N,N-dimethylbenzamide, trifluoroacetate

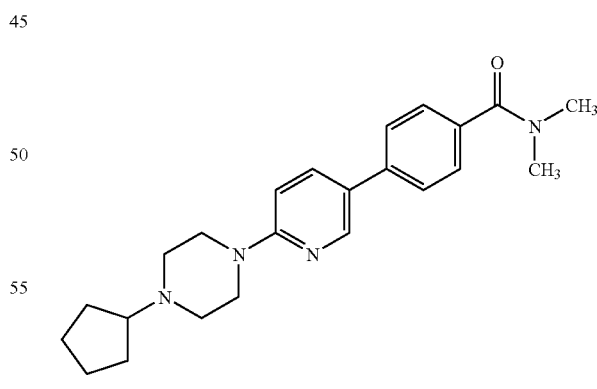

TFA

The title compound was prepared by a similar procedure to that described in Example 125, starting from 3-[6-(4-cyclopentyl-piperazin-1-yl)-pyridin-3-yl]-benzoic acid and dimethylamine.

$^1$H NMR (300 MHz, CD$_3$OD) δ 8.50 (s, 1H), 8.00 (dd, 1H) 7.68 (d, 2H), 7.50 (d, 2H), 7.05 (d, 1H), 4.75-4.50 (m, 2H), 3.85-3.45 (m, 4H), 3.25-3.17 (m, 3H), 3.15-3.02 (m, 6H), 2.33-2.15 (m, 2H), 1.90-1.65 (m, 6H). HPLC (Method D): $t_r$=4.83 min (97%).

EXAMPLE 147

General Procedure A

{4-[6-(4-Cyclopentylpiperazin-1-yl)pyridin-3-yl]phenyl}morpholin-4-ylmethanone, trifluoroacetate

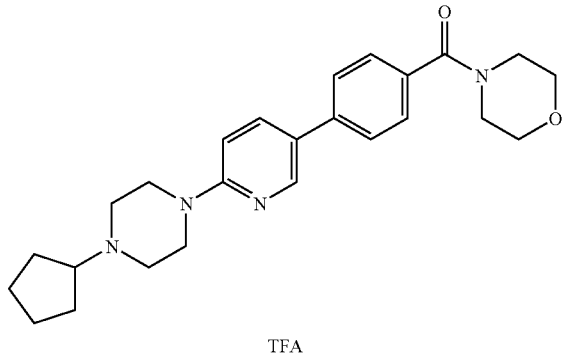 [SMILES: O=C(c1ccc(-c2ccc(N3CCN(C4CCCC4)CC3)nc2)cc1)N1CCOCC1]

TFA

The title compound was prepared by a similar procedure to that described in Example 125, starting from 3-[6-(4-cyclopentyl-piperazin-1-yl)-pyridin-3-yl]-benzoic acid and morpholine. $^1$H NMR (300 MHz, CD$_3$OD) δ 8.50 (s, 1H), 8.05 (d, 1H) 7.68 (d, 2H), 7.50 (d, 2H), 7.10 (d, 1H), 4.80-3.30 (m, 17H), 2.30-2.15 (m, 2H), 1.90-1.55 (m, 6H).

HPLC (Method D): $t_r$=4.77 min (96%).

EXAMPLE 148

General Procedure A

3-[6-(4-Isopropylpiperazin-1-yl)-4-methylpyridin-3-yl]-N,N-dimethylbenzamide, trifluoroacetate

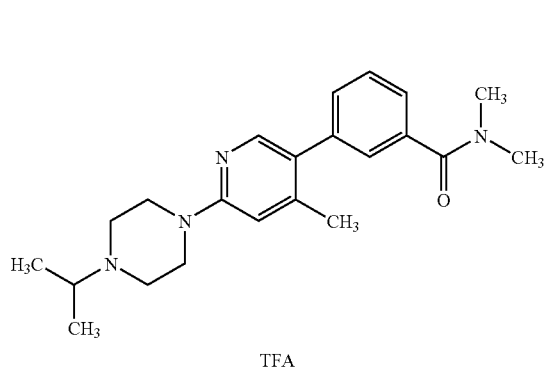 [SMILES: Cc1cc(N2CCN(C(C)C)CC2)ncc1-c1cccc(C(=O)N(C)C)c1]

TFA

The title compound was prepared by a similar procedure to that described in Example 125, starting from 3-[6-(4-isopropyl-piperazin-1-yl)-4-methyl-pyridin-3-yl]-benzoic acid and dimethylamine, hydrochloride. $^1$H NMR (300 MHz, CD$_3$OD) δ 7.98 (s, 1H), 7.58 (t, 1H), 7.48 (t, 2H), 7.41 (s, 1H), 7.20 (s, 1H), 4.81-3.35 (m, 9H), 3.12 (s, 3H), 3.04 (s, 3H), 2.36 (s, 3H), 1.42 (d, 6H).

HPLC (Method D): $t_r$=3.95 min (97%).

EXAMPLE 149

General Procedure A

3-[6-(4-Isopropylpiperazin-1-yl)-5-methylpyridin-3-yl]-N,N-dimethylbenzamide, trifluoroacetate

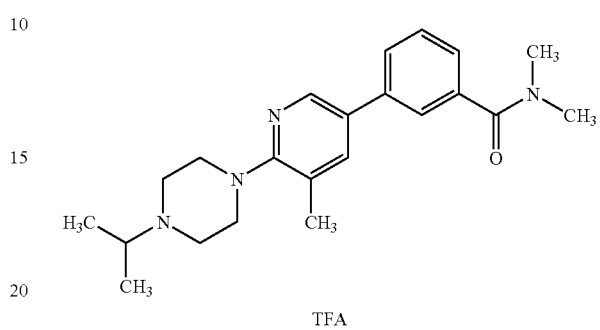

TFA

The title compound was prepared by a similar procedure to that described in Example 125, starting from 3-[6-(4-isopropyl-piperazin-1-yl)-5-methyl-pyridin-3-yl]-benzoic acid and dimethylamine, hydrochloride. $^1$H NMR (300 MHz, CD$_3$OD) δ 8.42 (s, 1H), 7.97 (s, 1H), 7.73 (d, 1H), 7.67 (s, 1H), 7.56 (t, 1H), 7.43 (d, 1H), 3.88-3.70 (m, 2H), 3.70-3.51 (m, 3H), 3.47-3.32 (m, 3H), 3.28-3.15 (m, 4H), 3.03 (s, 3H), 2.42 (s, 3H), 1.43 (d, 6H).

HPLC (Method D): $t_r$=4.14 min (98%).

EXAMPLE 150

General Procedure A

4-[6-(4-Isopropylpiperazin-1-yl)-5-methylpyridin-3-yl]-N,N-dimethylbenzamide, trifluoroacetate

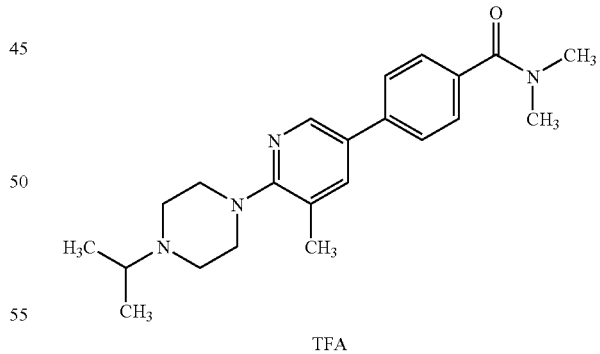

TFA

The title compound was prepared by a similar procedure to that described in Example 125, starting from 4-[6-(4-isopropyl-piperazin-1-yl)-5-methyl-pyridin-3-yl]-benzoic acid and dimethylamine, hydrochloride. $^1$H NMR (300 MHz, CD$_3$OD) δ 8.43 (d, 1H), 8.01 (d, 1H), 7.72 (d, 2H), 7.53 (d, 2H), 3.91-3.72 (m, 2H), 3.70-3.51 (m, 3H), 3.47-3.32 (m, 3H), 3.21-3.09 (m, 4H), 3.04 (s, 3H), 2.38 (s, 3H), 1.43 (d, 6H).

HPLC (Method D): $t_r$=4.11 min (95%).

EXAMPLE 151

General Procedure A

4-[6-(4-Isopropylpiperazin-1-yl)-4-methylpyridin-3-yl]-N,N-dimethylbenzamide, trifluoroacetate

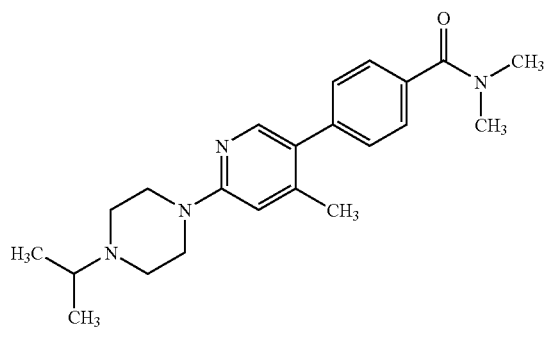

TFA

The title compound was prepared by a similar procedure to that described in Example 125, starting from 4-[6-(4-isopropyl-piperazin-1-yl)-4-methyl-pyridin-3-yl]-benzoic acid and dimethylamine, hydrochloride. $^1$H NMR (300 MHz, CD$_3$OD) δ 7.95 (s, 1H), 7.55 (d, 2H), 7.47 (d, 2H), 7.35 (s, 1H), 4.73-3.35 (m, 9H), 3.13 (s, 3H), 3.04 (s, 3H), 2.39 (s, 3H), 1.42 (d, 6H).

HPLC (Method D): t$_r$=3.93 min (98%).

EXAMPLE 152

General Procedure A

4-[4-Isopropyl-6-(4-isopropylpiperazin-1-yl)pyridazin-3-yl]-N,N-dimethylbenzamide, trifluoroacetate

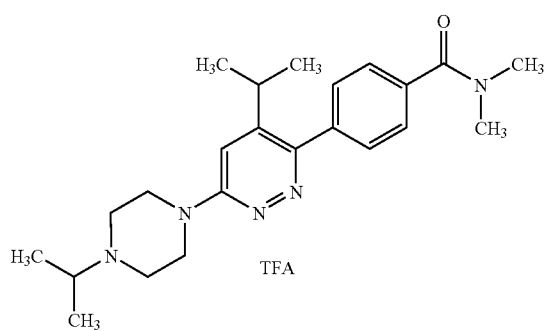 [SMILES: CC(C)c1cc(N2CCN(C(C)C)CC2)nnc1-c1ccc(C(=O)N(C)C)cc1]

TFA

The title compound was prepared by a similar procedure to that described in Example 125, starting from 4-[4-isopropyl-6-(4-isopropylpiperazin-1-yl)-pyridazin-3-yl]-benzoic acid and dimethylamine, hydrochloride.

$^1$H NMR (400 MHz, CD$_3$OD) δ 7.87 (s, 1H), 7.67 (t, 4H), 4.90-3.31 (m, 9H), 3.15 (s, 3H), 3.08-3.05 (m, 4H), 1.44 (d, 6H), 1.27 (d, 6H)

HPLC (Method D): t$_r$=3.46 min (99%).

EXAMPLE 153

General Procedure A

1-Cyclopropylmethyl-4-[5-(4-piperidin-1-ylmethylphenyl)pyridin-2-yl]piperazine, trifluoroacetate

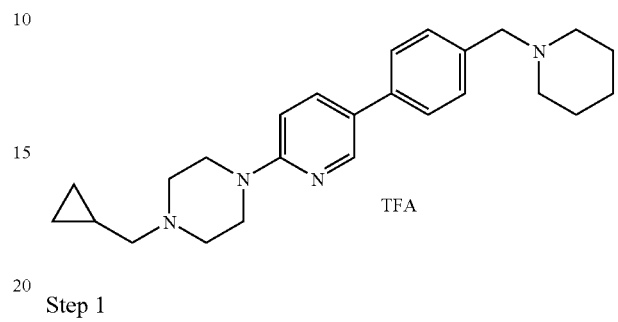

TFA

Step 1

4-[6-(4-Cyclopropylmethyl-piperazin-1-yl)-pyridin-3-yl]-benzonitrile

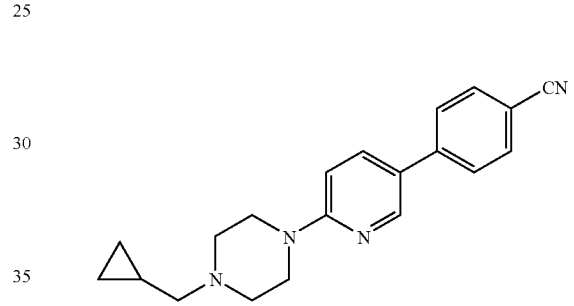

1-Cyclopropylmethyl-piperazine (13 g, 94 mmol) was mixed with 4-(6-chloro-pyridin-3-yl)benzonitrile (5 g, 23 mmol). The mixture was heated at 140° C. for 1.5 hours. The mixture was cooled to rt and purified by column chromatography (EtOAc:petrolether=1:1) on silica gel to give 2.7 g (43%) of 4-[6-(4-cyclopropylmethyl-piperazin-1-yl)-pyridin-3-yl]-benzonitrile.

Step 2

4-[6-(4-Cyclopropylmethyl-piperazin-1-yl)-pyridin-3-yl]-benzaldehyde

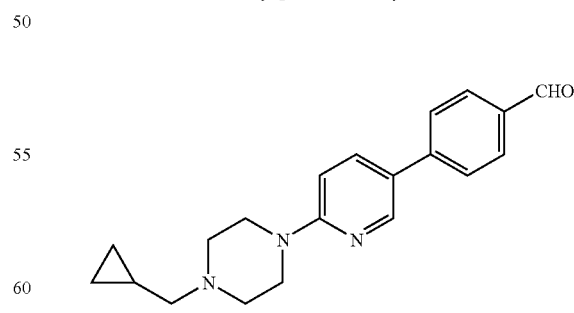

To a solution of 4-[6-(4-cyclopropylmethyl-piperazin-1-yl)-pyridin-3-yl]-benzonitrile (2.0 g 6.3 mmol) dissolved in THF (40 mL) was added DIBAL-H (25 mL, 1 N) at −40° C. The mixture was stirred 2 h at −40° C. and then CH$_3$OH (15 mL), water (100 mL) and 1 N NaOH (15 mL) was added at −40° C. The mixture was extracted with EtOAc (3×300 mL). The combined organic extracts were washed with water (3×50 mL), dried (Na$_2$SO$_4$) and concentrated under reduced pressure to give 1.7 g (51%) of 4-[6-(4-cyclopropylmethyl-piperazin-1-yl)-pyridin-3-yl]-benzaldehyde.

Step 3

To a solution of 4-[6-(4-cyclopropylmethyl-piperazin-1-yl)-pyridin-3-yl]-benzaldehyde (1.7 g, 3.18 mmol) dissolved in THF (15 mL) was added water (0.05 mL), piperidine (0.33 g, 3.8 mmol), acetic acid (0.01 mL) and NaCNBH$_3$ (400 mg, 6.4 mmol). The mixture was stirred overnight at 60° C. and concentrated to give a crude product, which was further purified by HPLC Method F to give 540 mg (26%) of the title compound as a TFA salt.

$^1$H NMR (300 MHz, D$_2$O) δ 8.28 (d, 1H), 8.20 (d, 1H), 7.56 (d, 2H), 7.45 (d, 2H), 7.31 (d, 1H), 4.27-4.21 (m, 2H), 4.13 (m, 2H), 3.77-3.72 (, 2H), 3.59-3.51 (m, 2H), 3.20-3.13 (m, 4H), 3.00 (d, 2H), 2.82-2.75 (m, 2H), 1.77-1.42 (m, 5H), 1.29-1.25 (m, 1H), 1.00-0.95 (m, 1H), 0.62-0.58 (m, 2H), 0.26-0.24 (m, 2H).

HPLC (Method D): t$_r$=3.76 min (96%).

EXAMPLE 154

General Procedure A

{4-[6-(4-Isopropylpiperazin-1-yl)pyridin-3-yl]benzyl}dimethylamine, trifluoroacetate

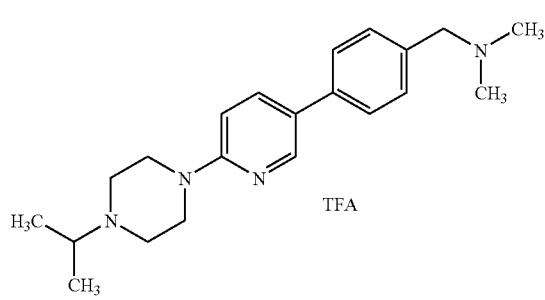 [SMILES: CC(C)N1CCN(c2ccc(-c3ccc(CN(C)C)cc3)cn2)CC1]

The title compound was prepared by a similar procedure to that described in Example 153, starting from 4-[6-(4-isopropyl-piperazin-1-yl)-pyridin-3-yl]-benzaldehyde and dimethylamine, hydrochloride.

$^1$H NMR (300 MHz, D$_2$O) δ 8.30 (d, 1H), 8.26 (d, 1H), 7.62 (d, 2H), 7.48 (d, 2H), 7.33 (d, 1H), 4.33-4.29 (m, 2H), 4.23 (m, 2H), 3.62-3.48 (m, 5H), 3.28-3.15 (m, 2H), 2.73 (s, 6H), 1.26 (d, 6H).

HPLC (Method D): t$_r$=2.69 min (98%).

EXAMPLE 155

General Procedure A 3-(4-Cyclopentylpiperazin-1-yl)-6-(4-piperidin-1-ylmethylphenyl)pyridazine, trifluoroacetate

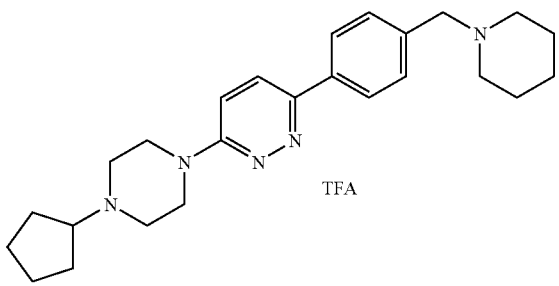 [SMILES: c1cc(-c2ccc(N3CCN(C4CCCC4)CC3)nn2)ccc1CN1CCCCC1]

The title compound was prepared by a similar procedure to that described in Example 153, starting from 4-[6-(4-cyclopentyl-piperazin-1-yl)-pyridazin-3-yl]-benzaldehyde and piperidine.

$^1$H NMR (300 MHz, D$_2$O) δ 8.06 (d, J=9.9 Hz, 1H), 7.80 (d, J=8.1 Hz, 2H), 7.67 (d, J=9.6 Hz, 1H), 7.50 (d, J=8.4 Hz, 2H), 4.44-4.38 (m, 2H), 4.18 (m, 2H), 3.65-3.61 (m, 2H), 3.51-3.30 (m, 5H), 3.16-3.07 (m, 2H), 2.85-2.78 (m, 2H), 2.03-1.96 (m, 2H), 1.77-1.73 (m, 2H), 1.61-1.52 (m, 9H), 1.34-4.22 (m, 1H).

HPLC (Method D): t$_r$=3.69 min (86%).

EXAMPLE 156

General Procedure A

1-{4-[6-(4-Isopropylpiperazin-1-yl)pyridin-3-yl]benzyl}-4-methylpiperazine, trifluoroacetate

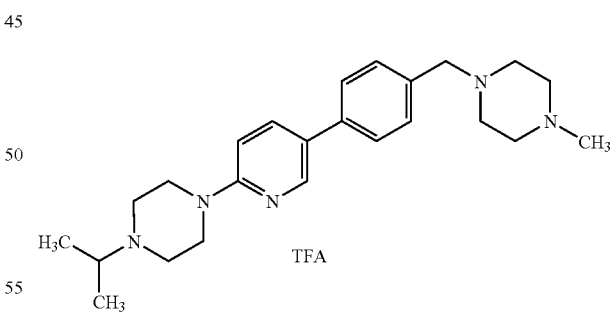

The title compound was prepared by a similar procedure to that described in Example 153, starting from 4-[6-(4-isopropyl-piperazin-1-yl)-pyridin-3-yl]-benzaldehyde and 1-methylpiperazine.

$^1$H NMR (300 MHz, D$_2$O) δ 8.33 (d, 1H), 8.30 (d, 1H), 7.66 (d, 2H), 7.53 (d, 2H), 7.35 (d, 1H), 4.57-4.31 (m, 4H), 3.65-3.53 (m, 13H), 3.31-3.23 (m, 2H), 2.90 (s, 3H), 1.28 (d, 6H).

HPLC (Method C): t$_r$=2.59 min (93%).

EXAMPLE 157

General Procedure A (1-{4-[6-(4-Isopropylpiperazin-1-yl)pyridin-3-yl]benzyl}piperidin-4-yl)methanol, trifluoroacetate

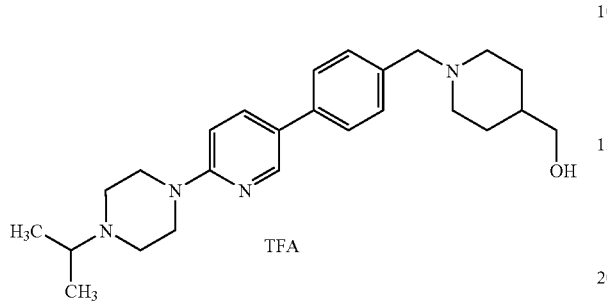

The title compound was prepared by a similar procedure to that described in Example 153, starting from 4-[6-(4-isopropyl-piperazin-1-yl)-pyridin-3-yl]-benzaldehyde and 4-hydroxymethylpiperidine.

$^1$H NMR (300 MHz, D$_2$O) δ 8.32 (d, 1H), 8.18 (d, 1H), 7.61 (d, 2H), 7.48 (d, 2H), 7.35 (d, 1H), 4.34-4.29 (m, 2H), 4.21 (m, 2H), 3.62-3.22 (m, 11H), 2.94-2.86 (m, 2H), 1.87-1.67 (m, 3H), 1.29-1.25 (m, 8H).

HPLC (Method C): t$_r$=2.82 min (97%).

EXAMPLE 158

General Procedure A

1-Isopropyl-4-[5-(4-piperidin-1-ylmethylphenyl)pyridin-2-yl]piperazine, trifluoroacetate

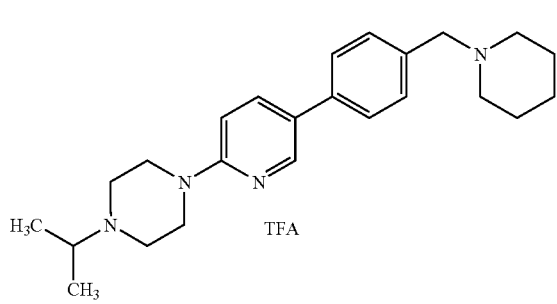 [SMILES: CC(C)N1CCN(c2ccc(-c3ccc(CN4CCCCC4)cc3)cn2)CC1]

The title compound was prepared by a similar procedure to that described in Example 153, starting from 4-[6-(4-isopropyl-piperazin-1-yl)-pyridin-3-yl]-benzaldehyde and piperidine.

$^1$H NMR (300 MHz, D$_2$O) δ 8.27 (d, 1H), 8.16 (d, 1H), 7.59 (d, 2H), 7.45 (d, 2H), 7.31 (d, 1H), 4.31-4.26 (m, 2H), 4.17 (m, 2H), 3.56-3.45 (m, 4H), 3.31-3.17 (m, 4H), 2.84-2.76 (m, 2H), 1.82-1.44 (m, 6H), 1.24 (d, 6H).

HPLC (Method D): t$_r$=4.45 min (87%).

EXAMPLE 159

General Procedure A

{4-[6-(4-Isopropylpiperazin-1-yl)pyridazin-3-yl]benzyl}dimethylamine, trifluoroacetate

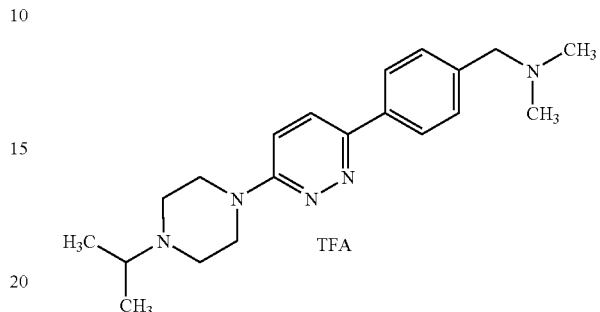

The title compound was prepared by a similar procedure to that described in Example 153, starting from 4-[6-(4-isopropyl-piperazin-1-yl)-pyridazin-3-yl]-benzaldehyde and dimethylamine, hydrochloride.

$^1$H NMR (300 MHz, CD$_3$OD) δ 8.13-8.06 (m, 3H), 7.67-7.61 (m, 3H), 4.38 (s, 2H), 3.89-3.32 (m, 6H), 2.88 (s, 6H), 1.41 (d, 6H).

HPLC (Method C): t$_r$=3.79 min (96%).

EXAMPLE 160

General Procedure A 3-(4-Isopropylpiperazin-1-yl)-6-(4-piperidin-1-ylmethylphenyl)pyridazine, trifluoracetate

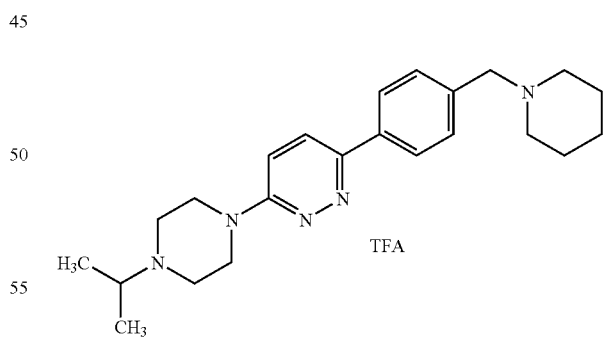

The title compound was prepared by a similar procedure to that described in Example 153, starting from 4-[6-(4-isopropyl-piperazin-1-yl)-pyridazin-3-yl]-benzaldehyde and piperidine.

$^1$H NMR (300 MHz, CD$_3$OD) δ 8.12-8.05 (m, 3H), 7.67-7.60 (m, 3H), 4.35 (s, 2H), 3.89-3.35 (m, 8H), 2.98 (t, 2H), 1.95-1.64 (m, 5H), 1.62-1.48 (m, 1H), 1.41 (d, 6H).

EXAMPLE 161

General Procedure A 3-(4-Isopropylpiperazin-1-yl)-6-[4-(4-methylpiperazin-1-ylmethyl)phenyl]pyridazine, trifluoroacetate

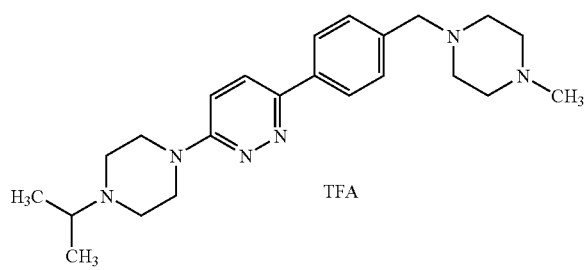 [SMILES: CC(C)N1CCN(c2ccc(-c3ccc(CN4CCN(C)CC4)cc3)nn2)CC1]

The title compound was prepared by a similar procedure to that described in Example 153, starting from 4-[6-(4-isopropyl-piperazin-1-yl)-pyridazin-3-yl]-benzaldehyde and 1-methylpiperazine.

$^1$H NMR (300 MHz, CD$_3$OD) δ 8.19 (d, 1H), 7.98 (d, 1H), 7.76 (d, 1H), 7.62 (d, 1H), 4.01 (s, 2H), 3.78-3.32 (m, 10H), 3.19-3.02 (m, 4H), 2.90 (s, 3H), 1.95-1.64 (m, 5H), 1.62-1.48 (m, 1H), 1.41 (d, 6H).

HPLC (Method C): t$_r$=3.74 min (97%).

EXAMPLE 162

General Procedure A (1-{4-[6-(4-Isopropylpiperazin-1-yl)pyridazin-3-yl]benzyl}piperidin-4-yl)methanol, trifluoroacetate

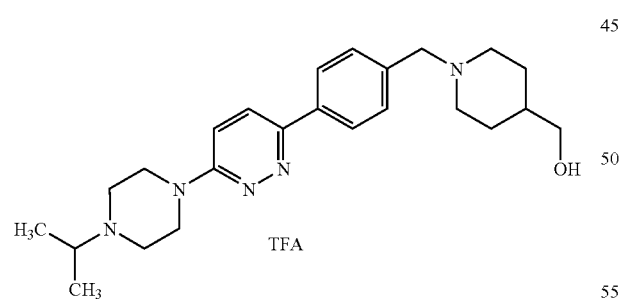

The title compound was prepared by a similar procedure to that described in Example 153, starting from 4-[6-(4-isopropyl-piperazin-1-yl)-pyridazin-3-yl]-benzaldehyde and 4-hydroxymethylpiperidine.

$^1$H NMR (300 MHz, CD$_3$OD) δ 8.05-8.11 (m, 3H), 7.58-7.67 (m, 3H), 4.36 (s, 2H), 3.78-3.38 (m, 10H), 2.99-3.12 (m, 4H), 1.46-2.05 (m, 5H), 1.41 (d, 6H).

HPLC (Method C): t$_r$=3.94 min (96%).

EXAMPLE 163

General Procedure A

4-{4-[6-(4-Isopropylpiperazin-1-yl)pyridazin-3-yl]benzyl}morpholine, trifluoroacetate

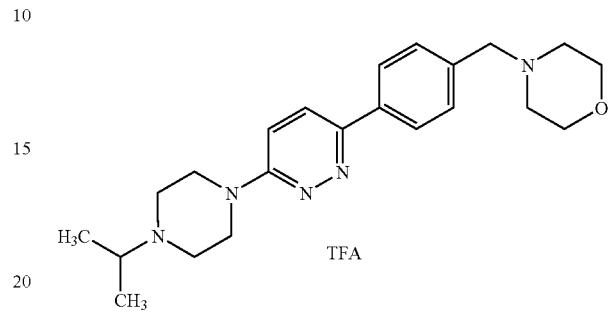

The title compound was prepared by a similar procedure to that described in Example 153, starting from 4-[6-(4-isopropyl-piperazin-1-yl)-pyridazin-3-yl]-benzaldehyde and morpholine.

$^1$H NMR (300 MHz, CD$_3$OD) δ 8.12-8.06 (m, 3H), 7.70-7.59 (m, 3H), 4.43 (s, 2H), 4.33-3.23 (m, 14H), 1.41 (d, 6H).

EXAMPLE 164

General Procedure A

1-Cyclopentyl-4-[5-(4-piperidin-1-ylmethylphenyl)pyridin-2-yl]piperazine, trifluoroacetate

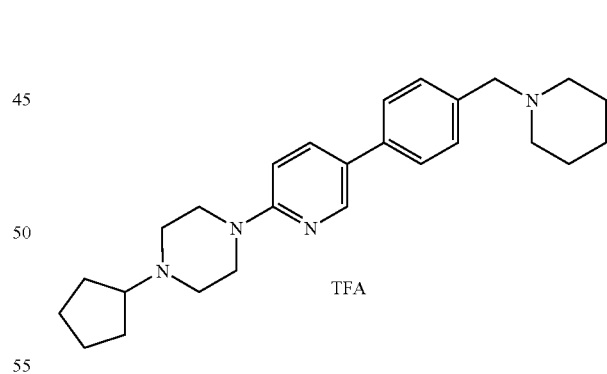

The title compound was prepared by a similar procedure to that described in Example 153, starting from 4-[6-(4-cyclopentyl-piperazin-1-yl)-pyridin-3-yl]-benzaldehyde and piperidine.

$^1$H NMR (300 MHz, D$_2$O) δ 8.26-8.22 (m, 2H), 7.62 (d, 2H), 7.47 (d, 2H), 7.27 (d, 1H), 4.27 (d, 2H), 4.20 (s, 2H), 3.71 (d, 2H), 3.55-3.42 (m, 3H), 3.36 (d, 2H), 3.20 (t, 2H), 2.86 (t, 2H), 2.08 (d, 2H), 1.85-1.51 (m, 11H), 1.41-1.30 (m, 1H).

HPLC (Method D): t$_r$=2.43 min (98%).

EXAMPLE 165

General Procedure A

1-Cyclopropyl-4-[5-(4-piperidin-1-ylmethylphenyl)pyridin-2-yl]piperazine, trifluoroacetate

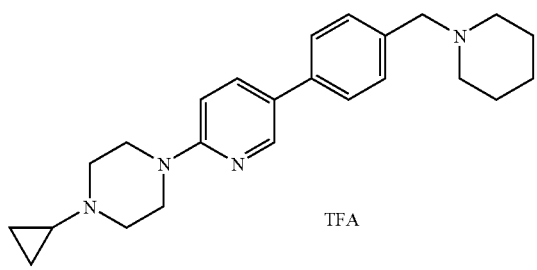 [SMILES: c1cc(-c2ccc(N3CCN(C4CC4)CC3)nc2)ccc1CN1CCCCC1]

The title compound was prepared by a similar procedure to that described in Example 153, starting from 4-[6-(4-cyclopropyl-piperazin-1-yl)-pyridin-3-yl]-benzaldehyde and piperidine.

$^1$H NMR (300 MHz, CD$_3$OD) δ 8.46 (s, 1H), 8.05 (d, 1H), 7.71 (d, 2H), 7.57 (d, 2H), 7.18-7.13 (m, 1H), 4.87 (s, 2H), 4.18-3.72 (m, 4H), 3.65-3.35 (m, 6H), 3.08-2.82 (m, 3H), 1.99-1.62 (m, 5H), 1.39-1.61 (m, 1H), 1.05-1.15 (m, 2H), 1.05-0.89 (m, 2H).

HPLC (Method C): t$_r$=4.43 min (99%).

EXAMPLE 166

General Procedure A 3-(4-Cyclopropylmethylpiperazin-1-yl)-6-(4-piperidin-1-ylmethylphenyl)pyridazine, trifluoroacetate

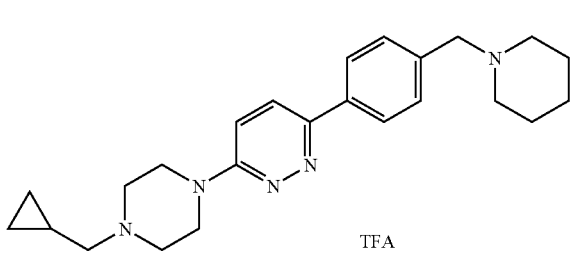 [SMILES: c1cc(-c2ccc(N3CCN(CC4CC4)CC3)nn2)ccc1CN1CCCCC1]

The title compound was prepared by a similar procedure to that described in Example 153, starting from 4-[6-(4-cyclopropyl methyl-piperazin-1-yl)-pyridazin-3-yl]-benzaldehyde and piperidine.

$^1$H NMR (300 MHz, CD$_3$OD) δ 8.24 (d, 1H), 8.08 (d, 2H) 7.80 (d, 1H), 7.70 (d, 2H), 4.89-2.85 (m, 12H), 3.22-2.92 (m, 4H), 2.05-1.89 (m, 2H), 1.89-1.75 (m, 3H), 1.65-1.45 (m, 1H), 1.25-1.06 (m, 1H), 0.83-0.78 (m, 2H), 0.52-0.40 (m, 2H).

HPLC (Method D): t$_r$=3.04 min (98%).

EXAMPLE 167

General Procedure A 3-(4-Cyclopropylpiperazin-1-yl)-6-(4-piperidin-1-ylmethylphenyl)pyridazine, trifluoroacetate

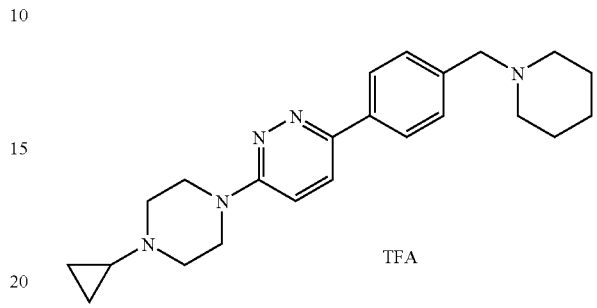

The title compound was prepared by a similar procedure to that described in Example 153, starting from 4-[6-(4-cyclopropyl-piperazin-1-yl)-pyridazin-3-yl]-benzaldehyde and piperidine.

$^1$H NMR (300 MHz, CDCl$_3$): δ 12.00 (s, 1H), 8.08 (d, 2H), 7.81 (d, 1H) 7.62 (d, 2H), 7.15 (d, 1H), 4.25-4.00 (m, 4H), 3.65-3.40 (m, 5H), 2.85-2.40 (m, 6H), 2.15-1.95 (m, 3H), 1.95-1.85 (m, 3H), 1.52-1.31 (m, 2H), 0.91 (d, 2H).

HPLC (Method D): t$_r$=4.01 min (96%).

EXAMPLE 168

General Procedure A

4-{4-[2-(4-Cyclopropylpiperazin-1-yl)pyrimidin-5-yl]benzyl}morpholine, dihydrochloride

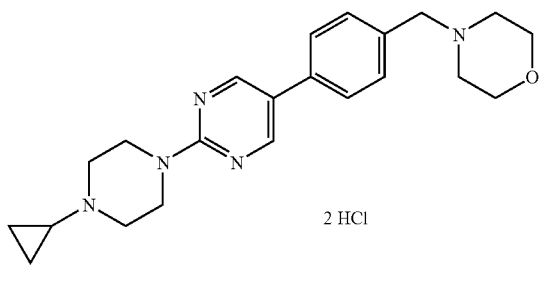 [SMILES: c1cc(-c2cnc(N3CCN(C4CC4)CC3)nc2)ccc1CN1CCOCC1 ; "2 HCl"]

The title compound was prepared by a similar procedure to that described in Example 153, starting from 4-[2-(4-cyclopropyl-piperazin-1-yl)-pyrimidin-5-yl]-benzaldehyde and morpholine.

$^1$H NMR (300 MHz, DMSO-d$_6$) δ 11.6 (brs, 1H), 11.3 (brs, 1H), 8.85 (s, 2H), 7.81-7.71 (m, 4H), 4.82-4.69 (m, 2H), 4.40-4.30 (m, 2H), 4.00-3.77 (m, 4H), 3.61-3.42 (m, 4H), 3.34-3.00 (m, 6H), 2.92-2.79 (m, 1H), 1.25-1.15 (m, 2H), 0.86-0.77 (m, 2H).

HPLC (Method Rx): t$_r$=3.88 min (98%).

EXAMPLE 169

General Procedure A

N-{3-[6-(4-Isopropylpiperazin-1-yl)pyridazin-3-yl]phenyl}acetamide, trifluoroacetate

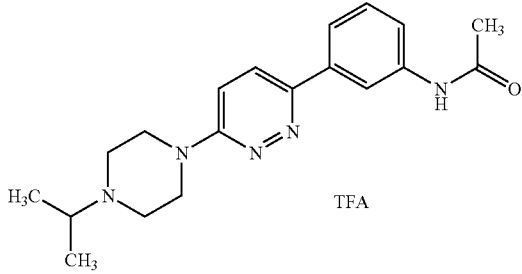 [SMILES: CC(=O)Nc1cccc(-c2ccc(N3CCN(C(C)C)CC3)nn2)c1]

TFA

The title compound was prepared by a similar procedure to that described in Example 170, starting from 3-[6-(4-isopropyl-piperazin-1-yl)-pyridazin-3-yl]-phenylamine and acetyl-chloride.

$^1$H NMR (300 MHz, DMSO-d$_6$) δ 10.08 (s, 1H), 9.78 (s, 1H), 8.33 (s, 1H), 7.97 (d, 1H), 7.62 (t, 2H), 7.53 (d, 1H), 7.40 (t, 1H), 4.60 (d, 2H), 3.61-3.50 (m, 3H), 3.34-3.25 (m, 2H), 3.16-3.13 (m, 2H), 2.05 (s, 3H), 1.28 (d, 6H).

HPLC (Method D): t$_r$=2.28 min (96%).

EXAMPLE 170

General Procedure A

N-{3-[6-(4-Cyclopropylpiperazin-1-yl)pyridazin-3-yl]phenyl}acetamide

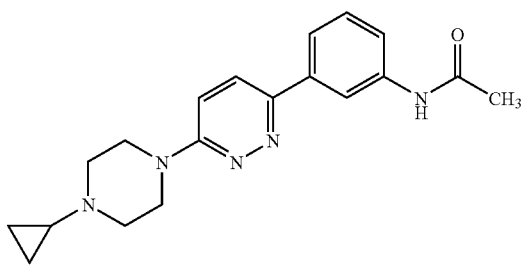 [SMILES: CC(=O)Nc1cccc(-c2ccc(N3CCN(C4CC4)CC3)nn2)c1]

Step 1

3-(4-Cyclopropyl-piperazin-1-yl)-6-(3-nitro-phenyl)-pyridazine

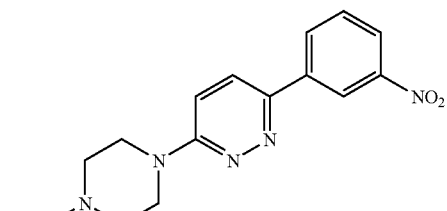

To a solution of 3-chloro-6-(3-nitro-phenyl)-pyridazine (10.0 g, 424 mmol) in n-BuOH (150 mL) was added 1-cyclopropyl-piperazine (8.55 g, 678 mmol) and NH$_4$Cl (2.27 g, 424 mmol) and the mixture was stirred for 48 h at 80° C. The solvent was removed under reduced pressure, and the residue was diluted with water. After alkalization with ammonia, the mixture was extracted with ethyl acetate. The extract was dried (Na$_2$SO$_4$) and concentrated to give 7.2 g of crude 3-(4-cyclopropyl-piperazin-1-yl)-6-(3-nitro-phenyl)-pyridazine.

$^1$H NMR (300 MHz, DMSO-d$_6$) δ 8.85 (s, 1H), 8.45 (d, 1H), 8.22 (d, 1H), 8.11 (d, 1H), 7.89-7.66 (m, 1H), 7.39 (d, 1H), 3.69-3.65 (m, 4H), 2.80-2.76 (m, 4H), 1.78-1.65 (m, 1H), 0.54-0.38 (m, 4H).

Step 2

3-[6-(4-Cyclopropyl-piperazin-1-yl)-pyridazin-3-yl]-phenylamine

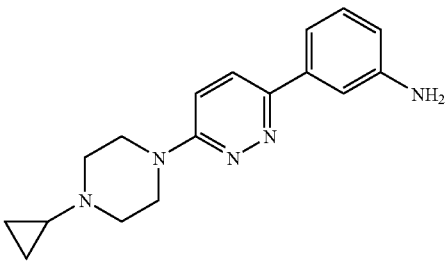 [SMILES: O=[N+]([O-])c1cccc(-c2ccc(N3CCN(C4CC4)CC3)nn2)c1]

A solution of 3-(4-cyclopropyl-piperazin-1-yl)-6-(3-nitro-phenyl)-pyridazine (3.60 g, 11 mmol) in ethanol (18 mL) was added to water (30 mL) and powdered Fe (1.86 g, 33 mmol). The mixture was stirred for 3 h at 80° C. The resulting mixture was filtered and the filtrate was extracted with CH$_2$Cl$_2$. The organic phase was washed with brine, dried (Na$_2$SO$_4$) and concentrated to give 2.32 g (71%) of 3-[6-(4-cyclopropyl-piperazin-1-yl)-pyridazin-3-yl]-phenylamine.

Step 3

To a solution of 3-[6-(4-cyclopropyl-piperazin-1-yl)-pyridazin-3-yl]-phenylamine (400 mg, 1.36 mmol) in CH$_2$Cl$_2$ (25 mL) was added triethylamine (275 mg, 2.72 mmol). Then acetyl chloride (171 mg, 2.18 mmol) was added dropwise and the resulting mixture was stirred overnight at rt. The reaction was quenched with water (15 mL) and the phases were separated. The organic phase was washed with brine, dried (Na₂SO₄) and concentrated to give a crude product, which was recrystallized from MeOH. This afforded 201 mg (48%) of the title compound.

¹H NMR (300 MHz, CD₃OD) δ 8.09 (s, 1H), 7.82 (d, 1H), 7.66-7.62 (m, 2H), 7.44-7.39 (m, 1H), 7.33 (d, 1H), 3.69-3.65 (m, 4H), 2.80-2.76 (m, 4H), 2.15 (s, 3H), 1.74-1.71 (m, 1H), 0.54-0.49 (m, 4H).

HPLC (Method D): t$_r$=2.82 min (95%).

EXAMPLE 171

General Procedure A

Cyclopropanecarboxylic acid {3-[6-(4-cyclopropylpiperazin-1-yl)pyridazin-3-yl]phenyl}amide

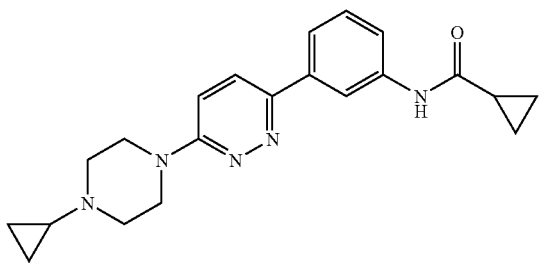 [SMILES: O=C(Nc1cccc(-c2ccc(N3CCN(C4CC4)CC3)nn2)c1)C1CC1]

The title compound was prepared by a similar procedure to that described in Example 170, starting from 3-[6-(4-cyclopropyl-piperazin-1-yl)-pyridazin-3-yl]-phenylamine and cyclopropanecarbonyl chloride. ¹H NMR (300 MHz, CD₃OD) δ 8.08 (d, 1H), 7.82 (d, 1H), 7.66-7.62 (m, 2H), 7.44-7.39 (m, 1H), 7.33 (d, 1H), 3.69-3.65 (m, 4H), 2.80-2.77 (m, 4H), 1.79-1.71 (m, 2H), 0.97-0.94 (m, 2H), 0.89-0.85 (m, 2H), 0.55-0.49 (m, 4H).

HPLC (Method D): t$_r$=3.18 min (97%).

EXAMPLE 172

General Procedure A

N-{4-[6-(4-Cyclopropylpiperazin-1-yl)pyridazin-3-yl]phenyl}acetamide, trifluoroacetate

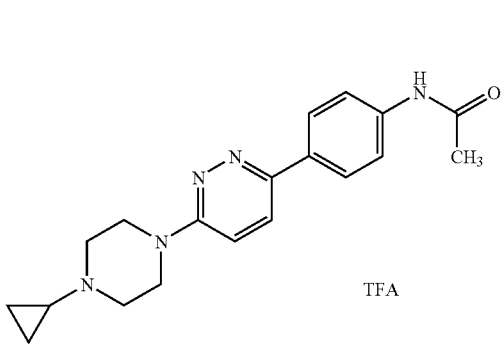 [SMILES: CC(=O)Nc1ccc(-c2ccc(N3CCN(C4CC4)CC3)nn2)cc1]

The title compound was prepared by a similar procedure to that described in Example 170, starting from 4-[6-(4-cyclopropyl-piperazin-1-yl)-pyridazin-3-yl]-phenylamine and acetyl chloride. ¹H NMR (300 MHz, CD₃OD) δ 8.31 (d, 1H), 7.96-7.88 (m, 3H), 7.81 (d, 2H), 4.20-3.95 (m, 4H), 3.70-3.58 (m, 4H), 2.94-2.86 (m, 1H), 2.16 (s, 3H), 1.14-0.96 (m, 4H).

HPLC (Method D): t$_r$=2.74 min (98%).

EXAMPLE 173

General Procedure A

Cyclopropanecarboxylic acid {4-[6-(4-cyclopropylpiperazin-1-yl)pyridazin-3-yl]phenyl}amide

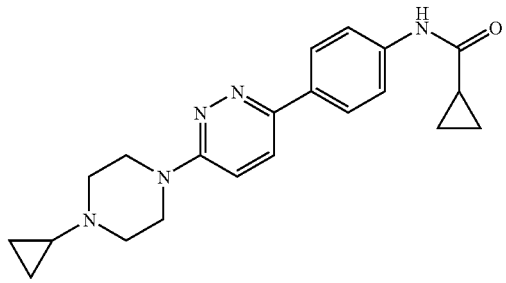 [SMILES: O=C(Nc1ccc(-c2ccc(N3CCN(C4CC4)CC3)nn2)cc1)C1CC1]

The title compound was prepared by a similar procedure to that described in Example 170, starting from 4-[6-(4-cyclopropyl-piperazin-1-yl)-pyridazin-3-yl]-phenylamine and cyclopropanecarbonyl chloride. ¹H NMR (300 MHz, DMSO-d₆) δ 10.30 (s, 1H), 7.93 (d, 2H), 7.86 (d, 1H), 7.67 (d, 2H), 7.30 (d, 1H), 3.57-3.54 (m, 4H), 2.64-2.62 (m, 4H), 1.79-1.74 (m, 1H), 1.65-1.62 (m, 1H), 0.78 (d, 4H), 0.43-0.41 (m, 2H), 0.35-0.30 (m, 2H).

HPLC (Method D): t$_r$=2.52 min (93%).

EXAMPLE 174

General Procedure A

Cyclopropanecarboxylic acid {4-[6-(4-cyclopropylperhydro-1,4-diazepin-1-yl)pyridazin-3-yl]phenyl}amide, dihydrochloride

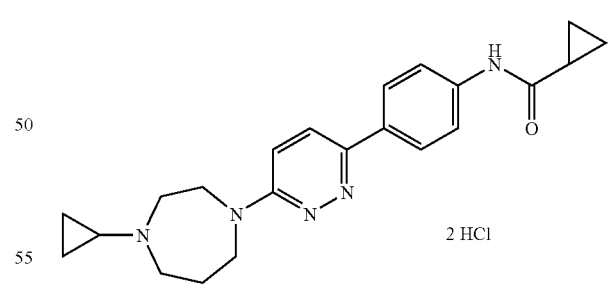

The title compound was prepared by a similar procedure to that described in Example 176, starting from 4-[6-(4-Isopropyl-perhydro-1,4-diazepin-1-yl)-pyridazin-3-yl]-phenylamine and cyclopropanecarboxylic acid.

¹H NMR (400 MHz, CD₃OD) δ 8.44 (d, 1H), 8.03 (d, 1H), 7.94 (m, 2H), 7.85 (m, 2H), 4.22 (broad m, 2H), 3.89 (t, 2H), 3.71 (broad m, 4H), 3.30 (m, 1H), 2.48 (broad m, 2H), 1.82 (m, 1H), 1.22 (m, 2H), 1.00 (m, 4H), 0.91 (m, 2H).

HPLC-MS (Method G): M+1=378; t$_r$=0.96 min.

EXAMPLE 175

General Procedure A

N-[4-(4-Isopropyl-3,4,5,6-tetrahydro-2H-[1,2']bipyrazinyl-5'-yl)phenyl]-2,2-dimethylpropionamide, hydrochloride

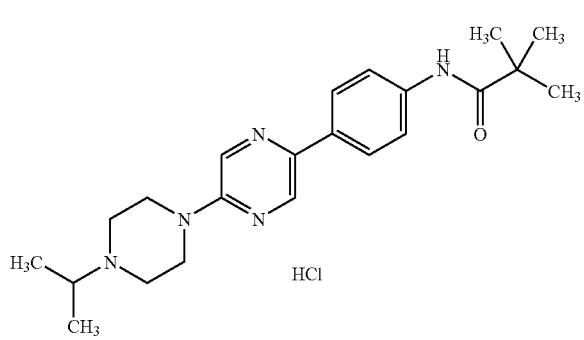 [SMILES: CC(C)N1CCN(c2cnc(-c3ccc(NC(=O)C(C)(C)C)cc3)cn2)CC1 ; Cl]

The title compound was prepared by a similar procedure to that described in Example 176, starting from 4-(4-isopropyl-3,4,5,6-tetrahydro-2H-[1,2']bipyrazinyl-5'-yl)phenylamine and tert-butylcarboxylic acid.

HPLC-MS (Method G): M+1=382; $t_r$=1.23 min.

EXAMPLE 176

General Procedure A

Tetrahydropyran-4-carboxylic acid [4-(4-isopropyl-3,4,5,6-tetrahydro-2H-[1,2']bipyrazinyl-5'-yl)phenyl] amide, dihydrochloride

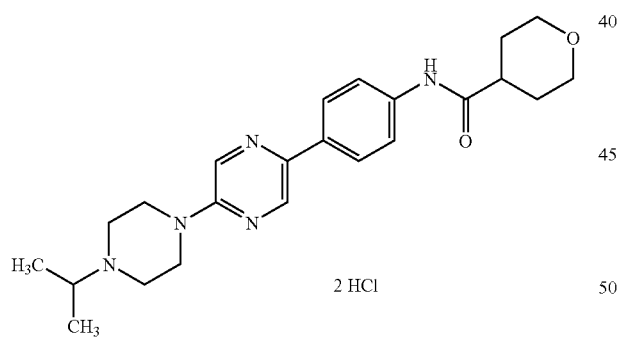

A mixture of tetrahydro-2H-pyran-4-carboxylic acid (0.313 g, 2.19 mmol), HOBt (0.368 g, 2.40 mmol), EDAC (0.46 g, 2.40 mmol) and TEA (0.243 g, 2.40 mmol) in DMF (5 mL) was stirred at rt for 5 min. A solution of 4-(4-isopropyl-3,4,5,6-tetrahydro-2H-[1,2']bipyrazinyl-5'-yl)phenylamine (0.65 g, 2.19 mmol) in DMF (5 mL) was added. The reaction mixture was stirred for an additional 48 h. The reaction mixture was purified by preparative HPLC Method B to give 240 mg of a TFA salt. The TFA salt was dissolved in MeOH and HCl in diethyl ether was added. Evaporation of the volatiles in vacuo afforded 186 mg (18%) of the title compound.

$^1$H-NMR (400 MHz, CD$_3$OD) δ 8.90 (s, 1H), 8.49 (s, 1H), 7.95 (d, 2H), 7.70 (d, 2H), 4.55-4.45 (m, 2H), 3.95-3.87 (m, 2H), 3.55-3.45 (m, 5H), 3.40-3.30 (m, 2H), 3.15-3.05 (m, 2H), 2.70-2.60 (m, 1H), 1.75-1.60 (m, 4H), 1.30 (d, 6H).

HPLC-MS (Method G): M+1=410; $t_r$=1.037 min.

EXAMPLE 177

General Procedure A

N-[4-(4-Isopropyl-3,4,5,6-tetrahydro-2H-[1,2']bipyrazinyl-5'-yl)phenyl]-N-methylacetamide, dihydrochloride

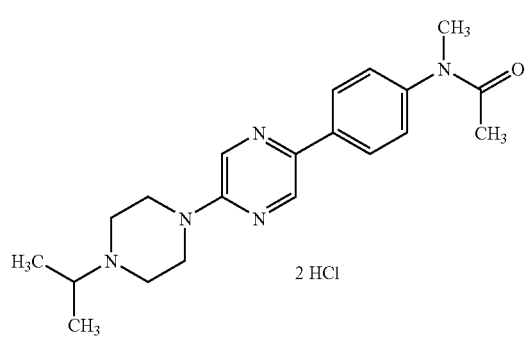 [SMILES: CC(=O)N(C)c1ccc(-c2cnc(N3CCN(C(C)C)CC3)cn2)cc1 ; "2 HCl"]

The title compound was prepared by a similar procedure to that described in Example 170, starting from N-[4-(4-isopropyl-3,4,5,6-tetrahydro-2H-[1,2']bipyrazinyl-5'-yl)phenyl]-N-methylamine and acetic acid anhydride.

$^1$H-NMR (400 MHz, CD$_3$OD) δ 8.95 (s, 1H), 8.60 (s, 1H), 8.04 (d, 2H), 7.35 (d, 2H), 4.80-4.72 (m, 2H), 3.73-3.62 (m, 5H), 3.40-3.28 (m, 5H), 1.95 (brs, 3H), 1.45 (d, 6H).

HPLC-MS (Method G): M+1=354; $t_r$=1.27 min.

EXAMPLE 178

General Procedure A

Cyclopropanecarboxylic acid [4-(4-isopropyl-3,4,5,6-tetrahydro-2H-[1,2']bipyrazinyl-5'-yl)phenyl]methylamide, dihydrochloride

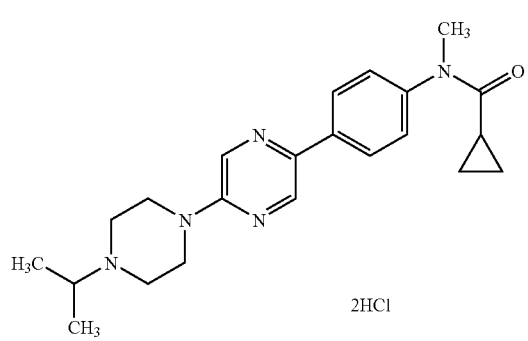 [SMILES: CC(C)N1CCN(c2cnc(-c3ccc(N(C)C(=O)C4CC4)cc3)cn2)CC1 ; "2HCl"]

The title compound was prepared by a similar procedure to that described in Example 176, starting from N-[4-(4-isopropyl-3,4,5,6-tetrahydro-2H-[1,2']bipyrazinyl-5'-yl)phenyl]-N-methylamine and cyclopropanecarboxylic acid.

¹H-NMR (400 MHz, CD₃OD) δ 8.90 (s, 1H), 8.55 (s, 1H), 8.05 (d, 2H), 7.55 (d, 2H), 4.80-4.70 (m, 2H), 3.72-3.55 (m, 5H), 3.40-3.25 (m, 5H), 1.57-1.50 (m, 1H), 1.45 (d, 6H), 0.95 (m, 2H), 0.72 (m, 2H).

HPLC-MS (Method G): M+1=380; $t_r$=1.10 min.

EXAMPLE 179

General Procedure A

N-[4-(4-Isopropyl-3,4,5,6-tetrahydro-2H-[1,2']bipyrazinyl-5'-yl)-2-methoxyphenyl]acetamide, dihydrochloride

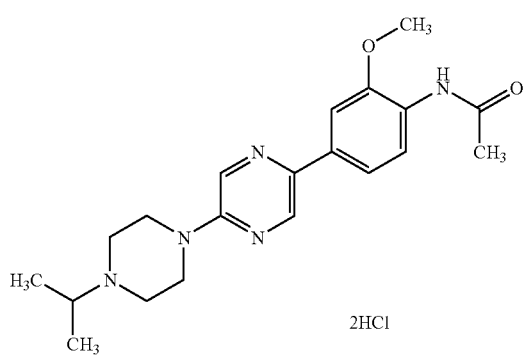 [SMILES: COc1cc(-c2cnc(N3CCN(C(C)C)CC3)cn2)ccc1NC(C)=O ; "2HCl"]

The title compound was prepared by a similar procedure to that described in Example 170, starting from 4-(4-isopropyl-3,4,5,6-tetrahydro-2H-[1,2']bipyrazinyl-5'-yl)-2-methoxyphenylamine and acetic acid anhydride.

¹H-NMR (400 MHz, CD₃OD) δ 8.75 (s, 1H), 8.40 (s, 1H), 8.15 (d, 1H), 7.60 (s, 1H), 7.45 (d, 1H), 4.72-4.65 (m, 2H), 4.00 (s, 3H), 3.68-3.58 (m, 3H), 3.40-3.22 (m, 4H), 2.20 (s, 3H), 1.45 (d, 6H).

HPLC-MS (Method G): M+1=370; $t_r$=1.004 min.

EXAMPLE 180

General Procedure A

Cyclohexanecarboxylic acid [4-(4-isopropyl-3,4,5,6-tetrahydro-2H-[1,2']bipyrazinyl-5'-yl)phenyl]amide, hydrochloride

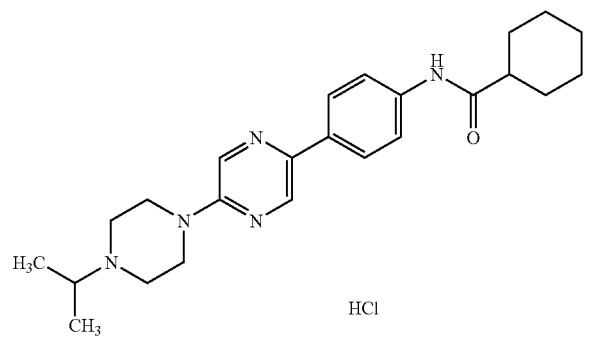 [SMILES: CC(C)N1CCN(c2cnc(-c3ccc(NC(=O)C4CCCCC4)cc3)cn2)CC1 ; Cl]

The title compound was prepared by a similar procedure to that described in Example 176, starting from cyclohexylcarboxylic acid and 4-(4-isopropyl-3,4,5,6-tetrahydro-2H-[1,2']-bipyrazinyl-5'-yl)phenylamine.

HPLC-MS (Method G): M+1=408; $t_r$=1.34 min.

EXAMPLE 181

General Procedure A

2-[4-(4-Isopropyl-3,4,5,6-tetrahydro-2H-[1,2']bipyrazinyl-5'-yl)phenoxy]-N,N-dimethylacetamide, dihydrochloride

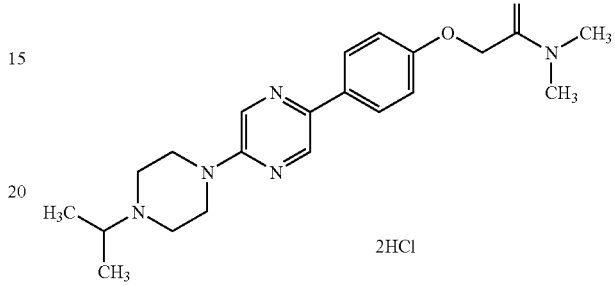

4-(4-Isopropyl-3,4,5,6-tetrahydro-2H-[1,2']bipyrazinyl-5'-yl)phenol (0.15 g, 0.404 mmol) was dissolved in DMF (4 mL) in a 5 mL microwave vial. NaH (0.039 g, 1.62 mmol) was added slowly and the mixture was stirred at rt for 30 min. Chloro-N,N-dimethylacetamide (0.147 g, 1.21 mmol) was added and the reaction mixture was heated for 2.5 h at 130° C. in a microwave oven. The reaction mixture was evaporated in vacuo and the residue was redissolved in a mixture of DCM and water. The phases were separated and the aqueous phase was extracted with DCM (2×25 mL). The combined organic extracts were evaporated, redissolved in MeOH and purified by preparative HPLC Method B. This afforded an oil which was treated with HCl in diethyl ether to give a solid material. Recrystallization from acetone and MeOH afforded 75 mg (41%) of the title compound.

¹H-NMR (400 MHz, CD₃OD) δ 8.75 (s, 1H), 8.35 (s, 1H), 7.85 (d, 2H), 7.1 (d, 2H), 4.65 (d, 2H), 3.65 (m, 3H), 3.2-3.5 (m, 6H), 3.1 (s, 3H), 2.95 (s, 3H), 1.45 (d, 6H).

HPLC-MS (Method G): M+1=384; $t_r$=0.995 min.

EXAMPLE 182

General Procedure A

5'-[4-(1,1-Dioxoisothiazolidin-2-yl)phenyl]-4-isopropyl-3,4,5,6-tetrahydro-2H-[1,2']bipyrazinyl, dihydrochloride

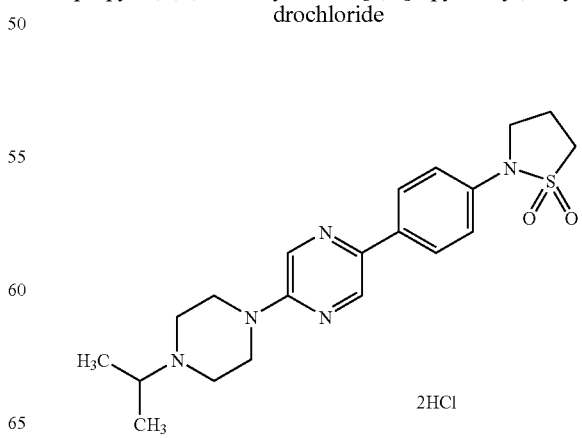

A mixture of 4-(4-isopropyl-3,4,5,6-tetrahydro-2H-[1,2']bipyrazinyl-5'-yl)phenylamine (0.34 g, 1.14 mmol), 3-chloro-1-propanesulfonyl chloride (0.20 g, 1.14 mmol) and TEA (0.12 g, 1.14 mmol) in DMF was stirred at rt for 1 h. NaH (0.055 g, 2.29 mmol) was added and stirring was continued for 5 h. The reaction mixture was transferred to a microwave vial (20 mL) and heated for 1000 s at 80° C. in a microwave oven. The reaction mixture was evaporated in vacuo and redissolved in a mixture of DCM and water. The phases were separated and the aqueous phase was extracted with DCM (2×25 mL). The combined organic extracts were evaporated in vacuo, redissolved in MeOH and purified by preparative HPLC Method B. This afforded 220 mg of a solid which was redissolved in MeOH and treated with HCl in diethyl ether. The volatiles were evaporated to give 126 mg (22%) of the title compound.

$^1$H-NMR (400 MHz, CD$_3$OD) δ 9.05 (s, 1H), 8.5 (s, 1H), 7.86 (d, 2H), 7.4 (d, 2H), 4.75 (d, 2H), 3.85 (t, 2H), 3.65 (m, 7H), 3.5 (t, 2H), 2.55 (m, 2H), 1.45 (d, 6H).

HPLC-MS (Method G): M+1=402; t$_r$=1.114 min.

EXAMPLE 183

General Procedure A 6-(4-Isopropylpiperazin-1-yl)-[3,3']bipyridinyl, trifluoroacetate

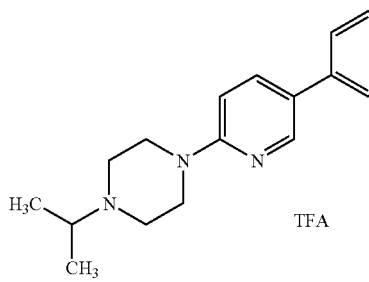

The title compound was prepared by a similar procedure to that described in Example 1, starting from 1-isopropylpiperazine and 6-chloro-[3,3']bipyridinyl.

$^1$H NMR (300 MHz, CD$_3$OD) δ 1.25 (d, 6H), 2.19 (t, 2H), 3.40-3.59 (m, 5H), 4.37 (d, 2H), 7.26 (d, 1H), 8.01 (t, 1H), 8.19 (d, 1H), 8.34 (s, 1H), 8.71-8.64 (m, 1H), 8.93 (s, 1H).

HPLC (Method D): t$_r$=2.51 min (98%).

EXAMPLE 184

General Procedure A 6-(4-Isopropylpiperazin-1-yl)-[3,4']bipyridinyl, trifluoroacetate

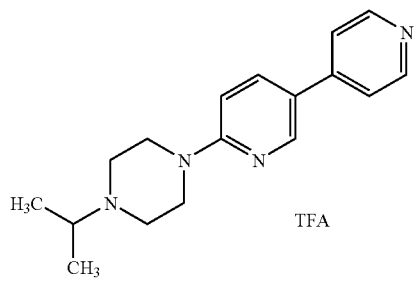 [SMILES: "TFA" ; CC(C)N1CCN(c2ccc(-c3ccncc3)cn2)CC1]

The title compound was prepared by a similar procedure to that described in Example 1, starting from 1-isopropylpiperazine and 6-chloro-[3,4']bipyridinyl.

$^1$H NMR (300 MHz, D$_2$O) δ 1.09 (d, 6H), 3.15 (t, 2H), 3.36 (t, 2H), 3.56-3.46 (m, 3H), 4.57 (d, 2H), 7.10 (d, 1H), 8.16 (dd, 3H), 8.58 (d, 3H).

HPLC (Method D): t$_r$=2.53 min (99%).

EXAMPLE 185

General Procedure A

6'-(4-Isopropylpiperazin-1-yl)-[2,3']bipyridinyl, trifluoroacetate

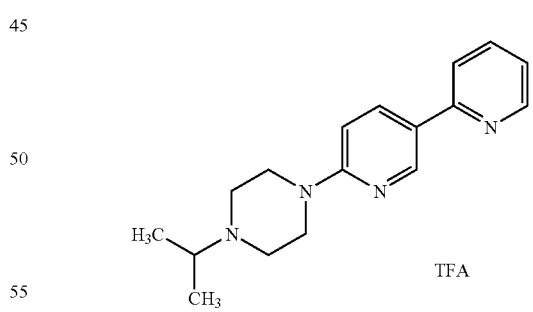

The title compound was prepared by a similar procedure to that described in Example 1, starting from 1-isopropylpiperazine and 6'-chloro-[2,3']bipyridinyl.

$^1$H NMR (300 MHz, D$_2$O) δ 8.75-8.63 (m, 2H), 8.58-8.47 (m, 1H), 8.28-15 (m, 2H), 7.87 (t, J=6.3, 7.2 Hz, 1H), 7.17 (d, J=9.3 Hz, 1H), 4.61 (d, J=14.1 Hz, 2H), 3.75-3.52 (m, 3H), 3.44-3.53 (m, 2H), 3.20-3.43 (m, 2H), 1.39 (d, J=6.9 Hz, 6H).

HPLC (Method C): t$_r$=2.45 min (97%).

EXAMPLE 186

General Procedure A

6'-(4-Ethylpiperazin-1-yl)-[2,3']bipyridinyl

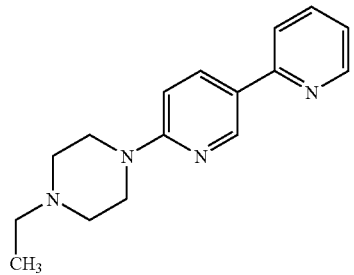 [SMILES: CCN1CCN(c2ccc(-c3ccccn3)cn2)CC1]

The title compound was prepared by a similar procedure to that described in Example 1, starting from 1-ethylpiperazine and 6'-chloro-[2,3']bipyridinyl.

$^1$H NMR (300 MHz, D$_2$O) δ 8.70 (d, J=2.1 Hz, 1H), 8.54 (d, J=4.2 Hz, 1H), 8.13 (dd, J=9.0, 2.7 Hz, 1H), 7.90-7.70 (m, 2H), 7.35-7.24 (m, 1H), 6.92 (d, J=9 Hz, 1H), 3.66 (t, J=5.1 Hz, 4H), 2.63 (t, J=5.1 Hz, 4H), 2.52 (q, J=7.2 Hz, 2H), 1.16 (t, J=7.2 Hz, 3H).

HPLC (Method C): t$_r$=2.23 min (97%).

EXAMPLE 187

General Procedure A

6'-(4-Isopropylpiperazin-1-yl)-6-methyl-[2,3']bipyridinyl, trifluoroacetate

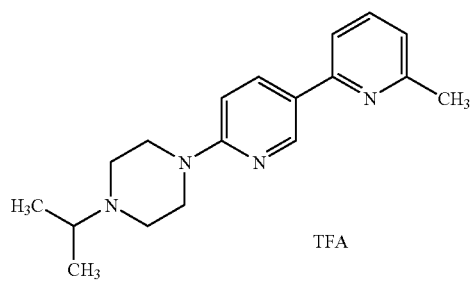 [SMILES: "TFA" ; Cc1cccc(-c2ccc(N3CCN(C(C)C)CC3)nc2)n1]

The title compound was prepared by a similar procedure to that described in Example 1, starting from 1-isopropyl-piperazine and 6'-chloro-6-methyl-[2,3']bipyridinyl.

$^1$H NMR (300 MHz, D$_2$O) δ 8.44 (d, 1H), 8.26 (t, 1H), 8.01 (dd, 1H), 7.83 (d, 1H), 7.60 (d, 1H), 7.05 (d, 1H), 4.45 (d, 2H), 3.60-3.40 (m, 3H), 3.31 (t, 2H), 3.13 (t, 2H), 2.67 (s, 3H), 1.25 (d, 6H).

HPLC (Method C): t$_r$=2.70 min (100%).

EXAMPLE 188

General Procedure A

6'-(4-Ethylpiperazin-1-yl)-6-methyl-[2,3']bipyridinyl

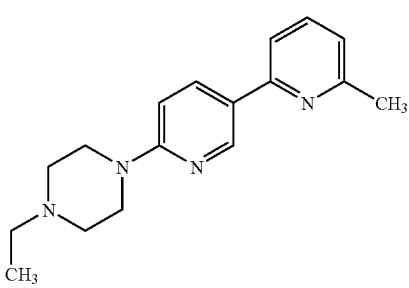 [SMILES: CCN1CCN(c2ccc(-c3cccc(C)n3)cn2)CC1]

The title compound was prepared by a similar procedure to that described in Example 1, starting from 1-ethyl-piperazine and 6'-chloro-6-methyl-[2,3']bipyridinyl.

$^1$H NMR (300 MHz, CD$_3$OD) δ 8.66 (d, 1H), 8.11 (dd, 1H), 7.70 (t, 1H), 7.51 (d, 1H), 7.14 (d, 1H), 6.90 (d, 1H), 3.63 (d, 4H), 2.65-2.40 (m, 9H), 1.15 (t, 3H).

HPLC (Method C): t$_r$=2.42 min (98%).

EXAMPLE 189

General Procedure A

2-[6-(4-Isopropylpiperazin-1-yl)pyridin-3-yl]quinoline, trifluoroacetate

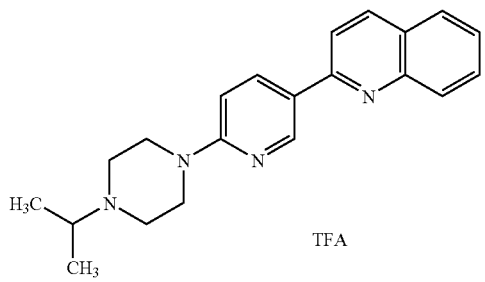 [SMILES: "TFA" ; CC(C)N1CCN(c2ccc(-c3ccc4ccccc4n3)cn2)CC1]

The title compound was prepared by a similar procedure to that described in Example 1, starting from 2-(6-chloro-pyridin-3-yl)-quinoline and 1-isopropyl-piperazine.

$^1$H NMR (300 MHz, CD$_3$OD) δ 8.87 (s, 1H), 8.40-8.25 (m, 2H), 8.04 (d, 1H), 7.95-7.85 (m, 2H), 7.80-7.60 (m, 1H), 7.58-7.48 (m, 1H), 6.96 (d, 1H), 3.67 (t, 4H), 2.80-2.65 (m, 5H), 1.13 (d, 6H).

HPLC (Method D): t$_r$=3.40 min (97%).

EXAMPLE 190

General Procedure A

N-{3-[6-(4-Isopropylpiperazin-1-yl)-4-methylpyridazin-3-yl]phenyl}acetamide, trifluoroacetate

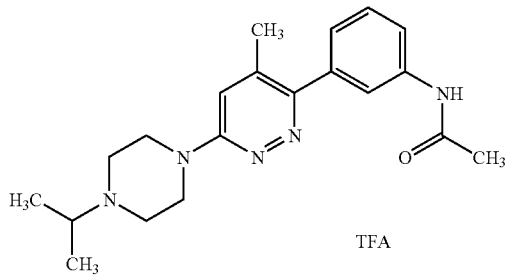 [SMILES: "TFA" ; CC(=O)Nc1cccc(-c2nnc(N3CCN(C(C)C)CC3)cc2C)c1]

Step 1

N-[3-(6-Chloro-5-methyl-pyridazin-3-yl)-phenyl]-acetamide and N-[3-(6-chloro-4-methylpyridazin-3-yl)phenyl]acetamide

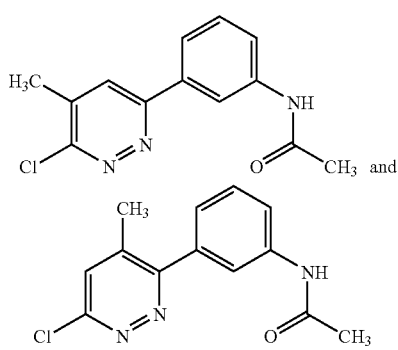

A solution of 3-acetamidophenylboronic acid (6.6 g, 37 mmol), 3,6-dichloro-4-methylpyridazine (5 g, 31 mmol) and Pd(PPh$_3$)$_4$ (3.5 g, 3 mmol) in DMF (180 mL, degassed) was stirred at rt for 1 h. Then sodium carbonate (12.3 g in 45 mL water, degassed) was added. The mixture was heated with stirring at 80° C. overnight. The mixture was filtered and the filtrate was concentrated under reduced pressure. The residue was diluted with EtOAc (100 mL), washed with brine, dried over sodium sulfate and concentrated. The residue was purified by column chromatography on silica gel (EtOAc/petroleum ether=1:1) to give 3 g (38%) of a mixture of N-[3-(6-chloro-5-methyl-pyridazin-3-yl)-phenyl]-acetamide and N-[3-(6-chloro-4-methyl-pyridazin-3-yl)-phenyl]-acetamide, which was used directly in the next step.

Step 2

The mixture of isomers (1.5 g, 5.9 mmol) from the previous step and 1-isopropyl-piperazine (3.7 g, 28.5 mmol) was heated at 200° C. under a nitrogen atmosphere for 1 h. The mixture was cooled to rt and diluted with dichloromethane (30 mL). The mixture was washed with brine, dried (sodium sulfate) and concentrated to give a crude product, which was purified by preparative HPLC Method F to give 358 mg (11%) of N-{3-[6-(4-isopropyl-piperazin-1-yl)-4-methyl-pyridazin-3-yl]-phenyl}-acetamide and 195 mg (6%) of N-{3-[6-(4-isopropyl-piperazin-1-yl)-5-methyl-pyridazin-3-yl]-phenyl}-acetamide as the TFA salts. N-{3-[6-(4-isopropyl-piperazin-1-yl)-4-methyl-pyridazin-3-yl]-phenyl}-acetamide, trifluoroacetate:

$^1$H NMR (300 MHz, D$_2$O) δ 7.90 (s, 1H), 7.76 (d, 1H), 7.63-7.55 (m, 2H), 7.43-7.35 (m, 1H), 4.61 (dd, 2H), 3.72-3.56 (m, 3H), 3.56-3.45 (m, 2H), 3.35-3.20 (m, 2H), 2.42 (s, 3H), 2.17 (s, 3H), 1.37 (d, 6H).

HPLC (Method D): t$_r$=2.85 min (96%).

EXAMPLE 191

General Procedure A

N-{3-[6-(4-Isopropylpiperazin-1-yl)-5-methylpyridazin-3-yl]phenyl}acetamide, trifluoroacetate

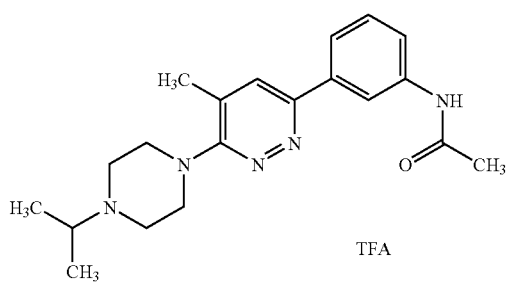 [SMILES: "TFA" ; CC(=O)Nc1cccc(-c2cc(C)c(N3CCN(C(C)C)CC3)nn2)c1]

The title compound was prepared as described in Example 195.

$^1$H NMR (300 MHz, D$_2$O) δ 8.23 (s, 1H), 7.98 (t, 1H), 7.68-7.55 (m, 3H), 4.12-3.98 (m, 2H), 3.70-3.54 (m, 3H), 3.50-3.30 (m, 4H), 2.58 (s, 3H), 2.18 (s, 3H), 1.39 (d, 6H).

HPLC (Method D): t$_r$=3.30 min (97%).

EXAMPLE 192

General Procedure A

3-[6-(4-Isopropylpiperazin-1-yl)-4-methylpyridazin-3-yl]-N,N-dimethylbenzamide, trifluoroacetate

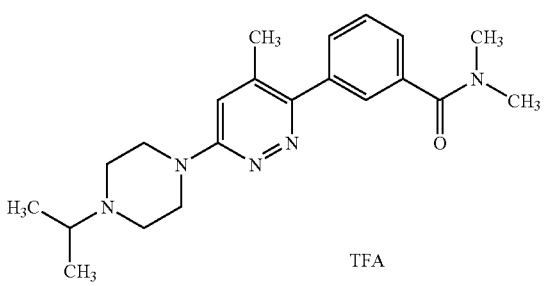 [SMILES: Cc1cc(N2CCN(C(C)C)CC2)nnc1-c1cccc(C(=O)N(C)C)c1]

Step 1

3-(6-Chloro-5-methyl-pyridazin-3-yl)-N,N-dimethyl-benzamide and 3-(6-chloro-4-methylpyridazin-3-yl)-N,N-dimethyl-benzamide

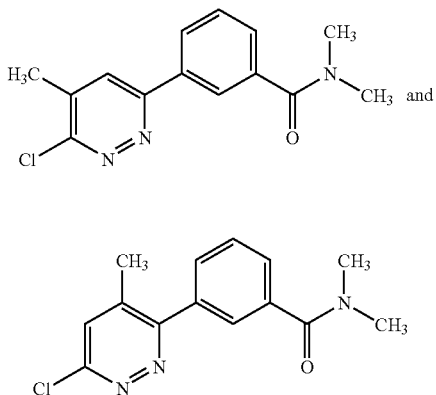

A solution of N,N-dimethylbenzamide-3-boronic acid (7 g, 36.5 mmol), 3,6-dichloro-4-methylpyridazine (5 g, 30.5 mmol) and Pd(PPh$_3$)$_4$ (1.7 g, 1.5 mmol) in DMF (180 mL, degassed) was stirred at rt for 1 h. Then sodium carbonate (12.1 g in 45 mL water, degassed) was added and the mixture was heated with stirring at 80° C. overnight. The mixture was filtered and the filtrate was concentrated under reduced pressure. The residue was diluted with EtOAc (100 mL), washed with brine, dried (sodium sulfate) and concentrated to give a crude product, which was purified by column chromatography on silica gel (EtOAc/petroleum ether=1:1). This afforded 2.8 g (32%) of a mixture of 3-(6-chloro-5-methyl-pyridazin-3-yl)-N,N-dimethyl-benzamide and 3-(6-chloro-4-methyl-pyridazin-3-yl)-N,N-dimethyl-benzamide, which was used directly in the next step.

Step 2

The mixture of isomers (1.5 g, 5.9 mmol) from the previous step and 1-isopropyl-piperazine (3.7 g, 28.5 mmol) was heated at 200° C. under a nitrogen atmosphere for 1 h. The mixture was cooled to rt and diluted with dichloromethane (30 mL). The mixture was washed with brine, dried (sodium sulfate) and concentrated to give a crude product, which was purified by preparative HPLC Method F to give 185 mg (6%) 3-[6-(4-isopropyl-piperazin-1-yl)-4-methylpyridazin-3-yl]-N,N-dimethyl-benzamide and 373 mg (12%) of 3-[6-(4-iso-propyl-piperazin-1-yl)-5-methyl-pyridazin-3-yl]-N,N-dimethyl-benzamide as the TFA salts.

3-[6-(4-Isopropyl-piperazin-1-yl)-4-methyl-pyridazin-3-yl]-N,N-dimethyl-benzamide, trifluoroacetate $^1$H NMR (400 MHz, D$_2$O) δ 7.83 (s, 1H), 7.69-7.56 (m, 3H), 7.56 (s, 1H), 4.53 (d, 2H), 3.63-3.50 (m, 3H), 3.50-3.39 (m, 2H), 3.30-3.15 (m, 2H), 3.01 (s, 3H), 2.92 (s, 3H), 2.33 (s, 3H), 1.29 (d, 6H).

HPLC (Method D): t$_r$=3.02 min (99%).

EXAMPLE 193

General Procedure A

3-[6-(4-Isopropylpiperazin-1-yl)-5-methylpyridazin-3-yl]-N,N-dimethylbenzamide, trifluoroacetate

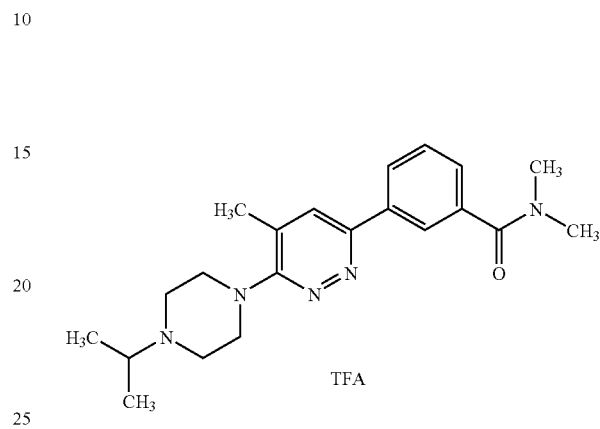

The title compound was prepared as described in Example 197.

$^1$H NMR (400 MHz, D$_2$O) δ 8.24 (s, 1H), 7.90 (d, 1H), 7.81 (s, 1H), 7.70-7.58 (m, 2H), 4.02 (d, 2H), 3.63-3.48 (m, 3H), 3.48-3.27 (m, 4H), 3.03 (s, 3H), 2.92 (s, 3H), 2.53 (s, 3H), 1.31 (d, 6H).

HPLC (Method D): t$_r$=3.49 min (98%).

EXAMPLE 194

General Procedure A

4-[6-(4-Isopropylpiperazin-1-yl)-4-methylpyridazin-3-yl]-N,N-dimethylbenzamide, trifluoroacetate

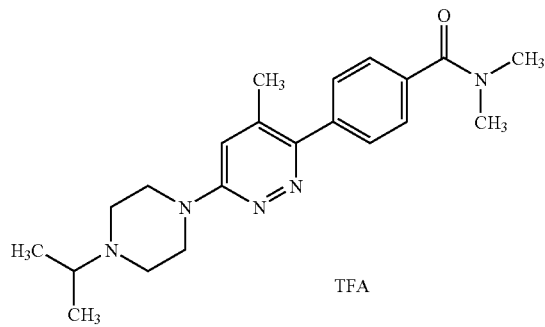 [SMILES: Cc1cc(N2CCN(C(C)C)CC2)nnc1-c1ccc(C(=O)N(C)C)cc1]

Step 1

4-(6-Chloro-5-methyl-pyridazin-3-yl)-N,N-dimethyl-benzamide and 4-(6-chloro-4-methylpyridazin-3-yl)-N,N-dimethyl-benzamide

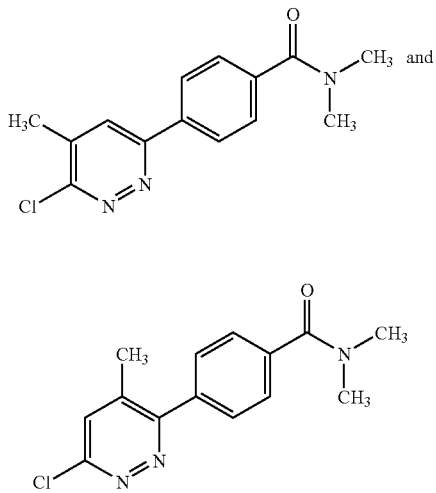

A solution of N,N-dimethylbenzamide-4-boronic acid (7 g, 36.5 mmol), 3,6-dichloro-4-methylpyridazine (5 g, 31 mmol) and Pd(PPh$_3$)$_4$ (1.7 g, 1.5 mmol) in DMF (180 mL, degassed) was stirred at rt for 1 h. Then sodium carbonate (12.3 g in 45 mL water, degassed) was added and the mixture was heated with stirring at 80° C. overnight. The mixture was filtered and the filtrate was concentrated under reduced pressure. The residual was diluted with EtOAc (100 mL), washed with brine, dried (sodium sulfate) and concentrated to give a crude product, which was purified by column chromatography on silica gel (EtOAc/petroleum ether=1:1). This afforded 2.5 g (28%) of a mixture of 4-(6-chloro-5-methyl-pyridazin-3-yl)-N,N-dimethylbenzamide and 4-(6-chloro-4-methyl-pyridazin-3-yl)-N,N-dimethyl-benzamide, which was used directly in the next step.

Step 2

The mixture of isomers (1.5 g, 5.9 mmol) from the previous step and 1-isopropyl-piperazine (3.7 g, 28.5 mmol) was heated at 200° C. under a nitrogen atmosphere for 1 h. The mixture was cooled to rt and diluted with dichloromethane (30 mL). The mixture was washed with brine, dried (sodium sulfate) and concentrated to give a crude product that was purified by preparative HPLC Method F to give 256 mg (8%) of 4-[6-(4-isopropyl-piperazin-1-yl)-4-methyl-pyridazin-3-yl]-N,N-dimethyl-benzamide and 278 mg (9%) of 4-[6-(4-isopropylpiperazin-1-yl)-5-methyl-pyridazin-3-yl]-N,N-dimethyl-benzamide as the TFA salts.

4-[6-(4-isopropyl-piperazin-1-yl)-4-methyl-pyridazin-3-yl]-N,N-dimethyl-benzamide $^1$H NMR (300 MHz, CD$_3$OD) δ 7.76 (s, 1H), 7.70-7.60 (m, 4H), 4.70-3.35 (m, 9H), 3.13 (s, 3H), 3.03 (s, 3H), 2.40 (s, 3H), 1.42 (d, 6H).

HPLC (Method D): t$_r$=2.89 min (92%).

EXAMPLE 195

General Procedure A

4-[6-(4-Isopropylpiperazin-1-yl)-5-methylpyridazin-3-yl]-N,N-dimethylbenzamide, trifluoroacetate

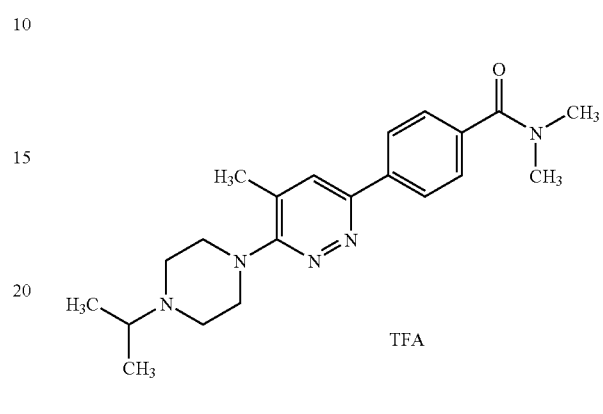

The title compound was prepared as described in Example 194.

$^1$H NMR (300 MHz, CD$_3$OD) δ 8.14 (s, 1H), 8.07 (d, 2H), 7.61 (d, 2H), 4.10-3.90 (m, 2H), 3.70-3.55 (m, 3H), 3.55-3.32 (m, 4H), 3.13 (s, 3H), 3.03 (s, 3H), 2.53 (s, 3H), 1.43 (d, 6H).

HPLC (Method D): t$_r$=3.38 min (91%).

EXAMPLE 196

General Procedure A

N-{4-[6-(4-Isopropylpiperazin-1-yl)-5-methylpyridazin-3-yl]phenyl}acetamide, trifluoroacetate

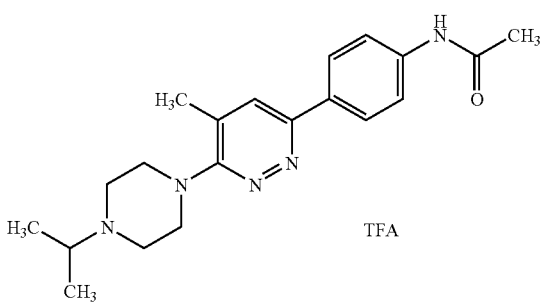 [SMILES: CC(=O)Nc1ccc(-c2cc(C)c(N3CCN(C(C)C)CC3)nn2)cc1]

The title compound was prepared as described in Example 72.

$^1$H NMR (300 MHz, D$_2$O) δ 8.10 (s, 1H), 7.95 (dd, 2H), 7.78 (d, 2H), 4.02-3.85 (m, 2H), 3.70-3.50 (m, 3H), 3.50-3.32 (m, 4H), 2.52 (s, 3H), 2.16 (s, 3H), 1.44 (d, 6H).

HPLC (Method D): t$_r$=3.26 min (94%).

EXAMPLE 197

General Procedure A

1'-(6-Pyridin-4-yl-pyridazin-3-yl)-[1,4']bipiperidinyl

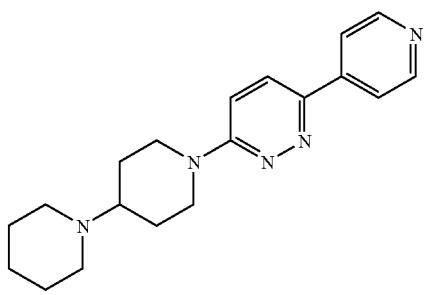 [SMILES: c1cc(-c2ccc(N3CCC(N4CCCCC4)CC3)nn2)ccn1]

The title compound was prepared by a similar procedure to that described in Example 1, starting from 3-chloro-6-pyridin-4-yl-pyridazine and 4-piperidinopiperidine. $^1$H NMR (400 MHz, DMSO-d$_6$) δ 8.67 (dd, 2H), 8.04 (m, 3H), 7.40 (d, 1H), 4.53 (d, 2H), 2.95 (t, 2H), 2.56 (m, 1H), 2.45 (m, 4H), 1.82 (d, 2H), 1.48 (m, 6H) 1.38 (m, 2H).

HPLC-MS (Method G): M+1=324; t$_r$=0.54 min.

EXAMPLE 198

General Procedure A 3-(Pyridin-3-yl)-6-[(4-pyrrolidin-1-yl)piperidin-1-yl]pyridazine

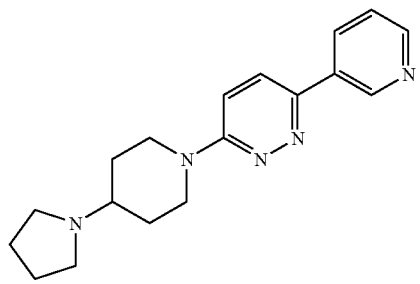 [SMILES: c1cncc(-c2ccc(N3CCC(N4CCCC4)CC3)nn2)c1]

The title compound was prepared by a similar procedure to that described in Example 1, starting from 3-chloro-6-(pyridin-3-yl)-pyridazine and 4-(1-pyrrolidinyl)piperidine. $^1$H NMR (400 MHz, DMSO-d$_6$) δ 9.22 (d, 1H), 8.61 (dd, 1H), 8.39 (dt, 1H), 8.01 (d, 1H), 7.51 (m, 1H), 7.40 (d, 1H), 4.34 (dt, 2H), 3.09 (m, 2H), 2.56 (s, 4H), 2.33 (m, 1H), 1.95 (m, 2H), 1.69 (m, 4H), 1.44 (m, 2H).

HPLC-MS (Method G): M+1=310; t$_r$=0.38 min.

EXAMPLE 199

General Procedure A

1'-(6-Pyridin-3-yl-pyridazin-3-yl)-[1,4']bipiperidinyl

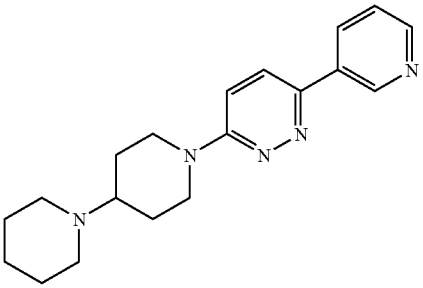 [SMILES: c1cncc(-c2ccc(N3CCC(N4CCCCC4)CC3)nn2)c1]

The title compound was prepared by a similar procedure to that described in Example 1, starting from 3-chloro-6-(pyridin-3-yl)-pyridazine and 4-piperidinopiperidine. $^1$H NMR (400 MHz, CD$_3$OD) δ 9.47 (d, 1H), 9.11 (dt, 1H), 8.93 (d, 1H), 8.40 (d, 1H), 8.15 (q, 1H), 7.94 (d, 1H), 4.66 (d, 2H), 3.66 (m, 1H), 3.58 (d, 2H), 3.36 (t, 2H), 3.08 (t, 2H), 2.38 (d, 2H), 1.80-2.00 (m, 7H), 1.54 (m, 1H).

HPLC-MS (Method G): M+1=324; t$_r$=0.55 min.

EXAMPLE 200

General Procedure A 3-(Pyridin-4-yl)-6-[(4-pyrrolidin-1-yl)piperidin-1-yl]pyridazine

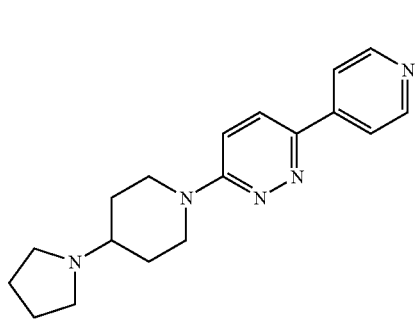 [SMILES: c1cc(-c2ccc(N3CCC(N4CCCC4)CC3)nn2)ccn1]

The title compound was prepared by a similar procedure to that described in Example 1, starting from 3-chloro-6-(pyridin-4-yl)-pyridazine and 4-(1-pyrrolidinyl)piperidine. $^1$H NMR (400 MHz, CDCl$_3$) δ 8.69 (d, 2H), 7.90 (d, 2H), 7.67 (d, 1H), 7.01 (d, 1H), 4.47 (d, 2H), 3.12 (m, 2H), 2.67 (s, 4H), 2.40 (m, 1H), 2.07 (d, 2H), 1.83 (s, 4H), 1.67 (m, 2H).

HPLC-MS (Method G): M+1=310; t$_r$=0.46 min.

EXAMPLE 201

General Procedure A

4-Pyrrolidin-1-yl-3,4,5,6-tetrahydro-2H-[1,2';5',3"]terpyridine

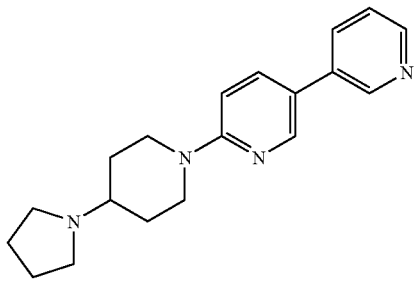 [SMILES: c1cncc(-c2ccc(N3CCC(N4CCCC4)CC3)nc2)c1]

The title compound was prepared by a similar procedure to that described in Example 1, starting from 6-chloro-[3,3']bipyridinyl and 4-(1-pyrrolidinyl)piperidine. $^1$H NMR (400 MHz, CD$_3$OD) δ 8.74 (d, 1H), 8.46 (dd, 1H), 8.39 (d, 1H), 8.03 (dt, 1H), 7.86 (dd, 1H), 7.49 (q, 1H), 6.95 (d, 1H), 4.40 (d, 2H), 2.92 (m, 2H), 2.67 (t, 4H), 2.35 (m, 1H), 2.05 (d, 2H), 1.82 (m, 4H), 1.51 (m, 2H).

HPLC-MS (Method G): M+1=309; t$_r$=0.28 min.

EXAMPLE 202

General Procedure A

1-Isopropyl-4-(6-phenylpyridin-3-yl)piperazine, dihydrochloride

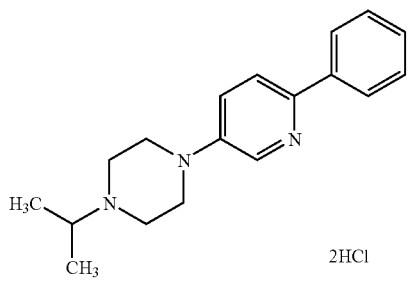 [SMILES: CC(C)N1CCN(c2ccc(-c3ccccc3)nc2)CC1 ; "2HCl"]

The title compound was prepared by a similar procedure to that described in Example 1, starting from 5-bromo-2-phenylpyridine and 1-isopropylpiperazine. $^1$H NMR (400 MHz, CD$_3$OD) δ 8.41 (m, 1H), 8.13 (m, 2H), 7.90-7.85 (m, 2H), 7.63-7.55 (m, 3H), 4.3-4.1 (m, 2H), 3.75-3.55 (m, 3H), 3.50-3.30 (m, 4H), 1.45 (d, J=6.8 Hz, 6H).

HPLC-MS (Method G): M+1=282; t$_r$=0.76 min.

EXAMPLE 203

General Procedure A (R)-2-[6-(3,4-Dimethoxyphenyl)pyridazin-3-yl]octahydropyrido[1,2-a]pyrazine, dihydrochloride

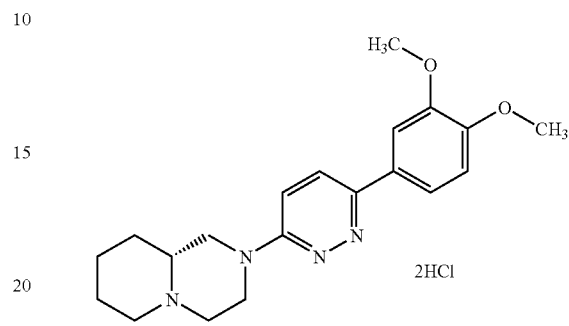

The title compound was prepared by a similar procedure to that described in Example 1, starting from 3-chloro-6-(3,4-dimethoxy-phenyl)-pyridazine and (R)-octahydro-pyridol[1,2-a]-pyrazine, dihydrochloride.

$^1$H-NMR (400 MHz, CD$_3$OD) δ 8.55 (d, 1H), 8.22 (d, 1H), 7.60-7.54 (m, 2H), 7.21 (d, 1H), 4.73-4.58 (m, 2H), 3.98 (s, 3H), 3.95 (s, 3H), 3.72-3.52 (m, 3H), 3.50-3.35 (m, 3H), 3.15-3.05 (m, 1H), 2.12-2.05 (m, 1H), 2.02-1.93 (m, 3H), 1.81-1.63 (m, 2H).

HPLC-MS (Method G): M+1=355; t$_r$=0.955 min.

EXAMPLE 204

General Procedure A

N-{3-[6-(4-Isopropylpiperazin-1-yl)pyridin-3-yl]benzyl}acetamide, trifluoroacetate

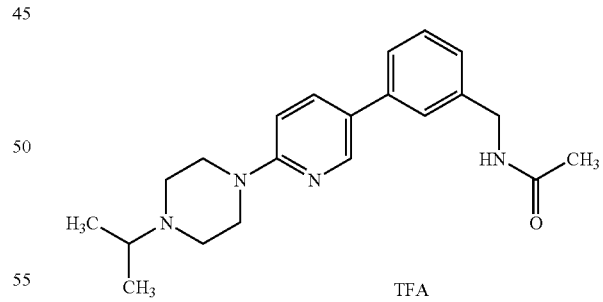

The title compound was prepared by a similar procedure to that described in Example 39, starting from 3-(6-(4-isopropylpiperazin-1-yl)pyridin-3-yl]benzylamine and acetyl chloride.

$^1$H NMR (300 MHz, D$_2$O) δ 8.27 (d, 1H), 8.10 (s, 1H), 7.40-7.24 (m, 5H), 4.32-4.28 (d, 4H), 3.64-3.53 (m, 5H), 3.25 (t, 2H), 1.92 (s, 2H), 1.27 (d, 6H).

HPLC (Method D): t$_r$=2.40 min (97%).

EXAMPLE 205

General Procedure A

N-{4-[6-(4-Isopropylpiperazin-1-yl)pyridin-3-yl]benzyl}-3,3-dimethylbutyramide, trifluoroacetate

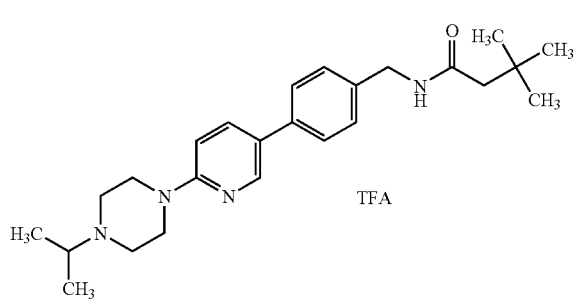 [SMILES: CC(C)N1CCN(c2ccc(-c3ccc(CNC(=O)CC(C)(C)C)cc3)cn2)CC1]

The title compound was prepared by a similar procedure to that described in Example 39, starting from 4-(6-(4-isopropylpiperazin-1-yl)pyridin-3-yl]benzylamine and 3,3-dimethyl-butyryl chloride.

$^{1}$H NMR (400 MHz, D$_2$O) δ 8.29 (dd, 1H), 8.14 (d, 1H), 7.51 (d, 2H), 7.40-7.30 (m, 3H), 4.40-4.25 (m, 4H), 3.70-3.48 (m, 5H), 3.34-3.15 (m, 2H), 2.06 (s, 1H), 1.28 (dd, 6H), 0.86 (s, 9H).

HPLC (Method D): t$_r$=3.38 min (97%).

EXAMPLE 206

General Procedure A

N-{3-[6-(4-Isopropylpiperazin-1-yl)pyridin-3-yl]benzyl}-3,3-dimethylbutyramide, trifluoroacetate

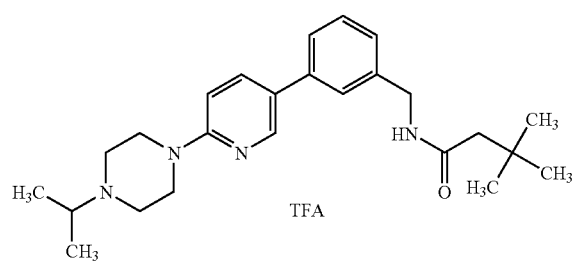 [SMILES: CC(C)N1CCN(c2ccc(-c3cccc(CNC(=O)CC(C)(C)C)c3)cn2)CC1]

The title compound was prepared by a similar procedure to that described in Example 39, starting from 3-(6-(4-isopropylpiperazin-1-yl)pyridin-3-yl]benzylamine and 3,3-dimethyl-butyryl chloride.

$^{1}$H NMR (300 MHz, D$_2$O) δ 8.27 (d, 1H), 8.12 (s, 1H), 7.46-7.28 (m, 5H), 4.32-4.28 (d, 4H), 3.64-3.53 (m, 5H), 3.25 (t, 2H), 2.06 (s, 2H), 1.27 (d, 6H), 0.85 (s, 9H).

HPLC (Method D): t$_r$=3.39 min (90%).

EXAMPLE 207

General Procedure A

N-{4-[2-(4-Isopropylpiperazin-1-yl)pyrimidin-5-yl]benzyl}isobutyramide, dihydrochloride

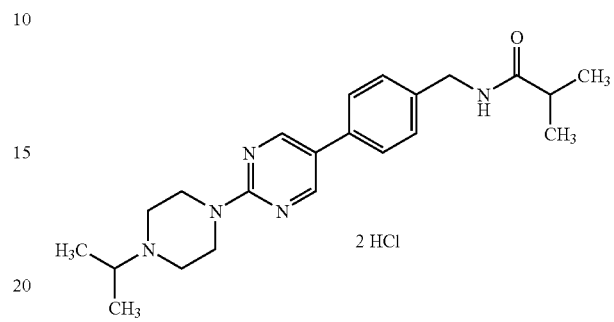

The title compound was prepared by a similar procedure to that described in Example 39, starting from 4-(6-(4-isopropylpiperazin-1-yl)pyrimidin-5-yl]benzonitrile. Mp=287-289° C.

$^{1}$H NMR (300 MHz, CDCl$_3$) δ 13.06 (brs, 1H), 8.68 (s, 2H), 7.47-7.38 (m, 4H), 6.07 (brs, 1H), 5.12 (d, 2H), 4.52-4.47 (m, 2H), 4.25-4.12 (m, 2H), 3.60-3.44 (m, 3H), 3.11-2.76 (m, 2H), 2.52-2.38 (m, 1H), 1.49 (d, 6H), 1.21 (d, 6H).

EXAMPLE 208

General Procedure A

N-{4-[6-(4-Isopropylpiperazin-1-yl)pyridin-3-yl]benzyl}-2,2-dimethylpropionamide, trifluoroacetate

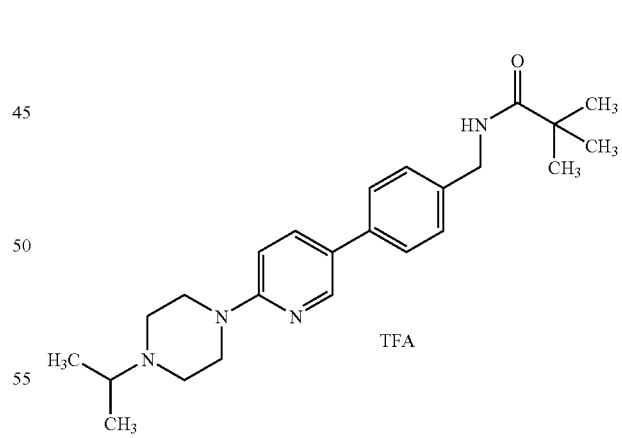

The title compound was prepared by a similar procedure to that described in Example 39, starting from 4-(6-(4-isopropylpiperazin-1-yl)pyridin-3-yl]benzylamine and 2,2-dimethylpropionyl chloride.

$^{1}$H NMR (300 MHz, D$_2$O) δ 8.29 (dd, 1H), 8.13 (d, 1H), 7.50 (d, 2H), 7.35-7.25 (m, 3H), 4.45-4.25 (m, 4H), 3.65-3.45 (m, 5H), 3.34-3.15 (m, 2H), 1.28 (d, 6H), 1.07 (s, 9H).

HPLC (Method D): t$_r$=2.84 min (98%).

EXAMPLE 209

General Procedure A

N-{3-[6-(4-Isopropylpiperazin-1-yl)pyridin-3-yl]benzyl}-2,2-dimethylpropionamide, trifluoroacetate

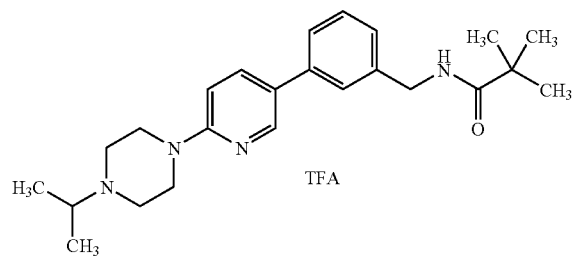 [SMILES: CC(C)N1CCN(c2ccc(-c3cccc(CNC(=O)C(C)(C)C)c3)cn2)CC1]

The title compound was prepared by a similar procedure to that described in Example 39, starting from 3-(6-(4-isopropylpiperazin-1-yl)pyridin-3-yl]benzylamine and 2,2-dimethylpropionyl chloride.

$^1$H NMR (300 MHz, CDCl$_3$) δ 8.41 (d, 1H), 7.02 (t, 1H), 7.43-7.27 (m, 3H), 7.21-7.18 (m, 1H), 6.72 (t, 1H), 6.95-6.93 (m, 1H), 4.49-4.46 (m, 2H), 3.78-3.62 (m, 4H), 2.90-2.65 (m, 5H), 1.17-1.10 (m, 15H). HPLC (Method D): t$_r$=3.10 min (98%).

EXAMPLE 210

General Procedure A

4-[2-(4-Cyclopropylpiperazin-1-yl)pyrimidin-5-yl]benzylamine

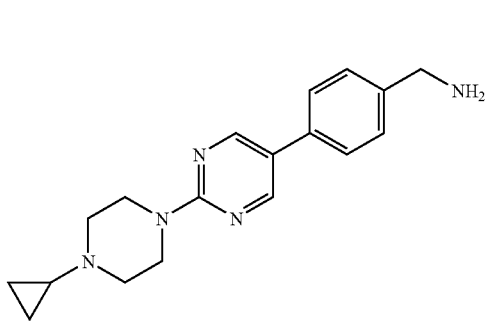 [SMILES: NCc1ccc(-c2cnc(N3CCN(C4CC4)CC3)nc2)cc1]

The title compound was prepared by a similar procedure to that described in Example 39, starting from 4-[2-(4-cyclopropyl-piperazin-1-yl)-pyrimidin-5-yl]-benzonitrile.

Mp=150-152° C.

$^1$H NMR (300 MHz, CDCl$_3$) δ 8.55 (s, 2H), 7.45 (d, 2H), 7.39 (d, 2H), 3.91 (s, 2H), 3.86-3.83 (m, 4H), 2.72-2.68 (m, 4H), 1.69-1.61 (m, 1H), 1.5 (brs, 2H), 0.52-0.46 (m, 4H).

HPLC (Method Rx): t$_r$=3.29 min (99%).

EXAMPLE 211

General Procedure A

N-{4-[2-(4-Cyclopropylpiperazin-1-yl)pyrimidin-5-yl]benzyl}acetamide, dihydrochloride

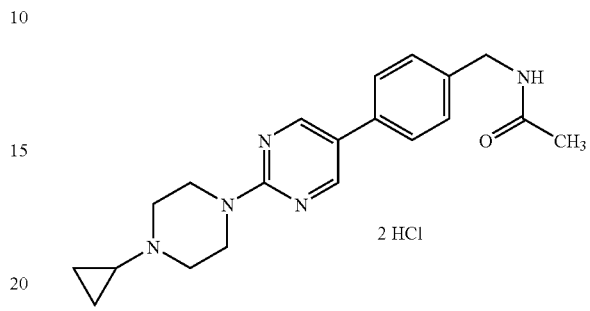

The title compound was prepared by a similar procedure to that described in Example 39, starting from 4-[2-(4-cyclopropyl-piperazin-1-yl)-pyrimidin-5-yl]-benzylamine and acetic anhydride.

Mp=235-236° C.

HPLC (Method Rx): t$_r$=7.11 min (100%).

EXAMPLE 212

General Procedure A

N N-{4-[6-(4-Isopropylpiperazin-1-yl)pyridazin-3-yl]acetamide, ditrifluoroacetate

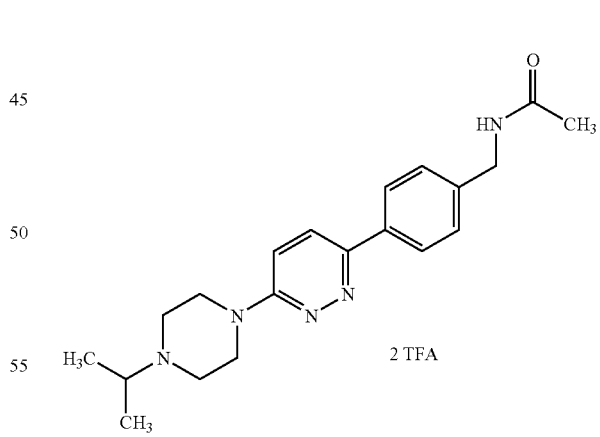

The title compound was prepared by a similar procedure to that described in Example 39, starting from 4-[6-(4-isopropyl-piperazin-1-yl)-pyridazin-3-yl]-benzonitrile.

$^1$H NMR (400 MHz, CD$_3$OD) δ 8.24 (d, 1H), 7.91 (d, 2H), 7.84 (d, 1H), 7.50 (d, 2H), 4.44 (s, 2H), 3.63 (heptet, 1H), 3.70-3.30 (broad m, 8H), 2.02 (s, 3H), 1.42 (d, 6H).

HPLC-MS (Method G): M+1=354; t$_r$=0.66 min.

EXAMPLE 213

General Procedure A

N-[4-(4-Cyclopropyl-3,4,5,6-tetrahydro-2H-[1,2']bipyrazinyl-5'-yl)phenyl]acetamide, hydrochloride

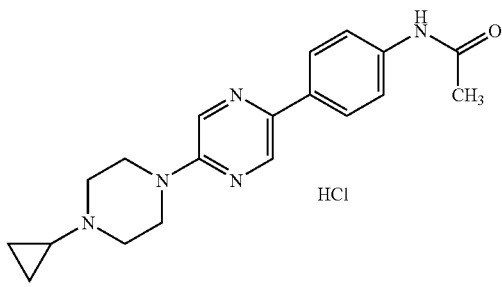 [SMILES: CC(=O)Nc1ccc(-c2cnc(N3CCN(C4CC4)CC3)cn2)cc1 ; Cl]

N-[4-(3,4,5,6-Tetrahydro-2H-[1,2']bipyrazinyl-5'-yl)-phenyl]-acetamide (125 mg, 0.42 mmol) was dissolved in methanol (2 mL) and ethoxycyclopropoxy)trimethylsilane (0.11 g, 0.63 mmol) was added together with acetic acid (0.076 g, 1.26 mmol). The mixture was stirred for 5 min and sodium cyanoborohydride (0.04 g, 0.63 mmol) and water (1 mL) were added. The reaction mixture was heated at 65° C. for 1 h and then another equivalent of sodium cyanoborohydride was added and stirring was continued at 65° C. for 1 h. The reaction mixture was evaporated in vacuo and the crystalline mixture was washed with methanol. Evaporation of the volatiles afforded a residue which after treatment with HCl in diethyl ether afforded 72 mg (46%) of the title compound.

$^1$H-NMR (400 MHz, CD$_3$OD) δ 8.85 (s, 1H), 8.45 (s, 1H), 7.85 (d, 2H), 7.75 (d, 2H), 4.6 (d, 2H), 3.7 (m, 2H), 3.5 (m, 4H), 2.95 (m, 1H), 2.15 (s, 3H), 1.2 (brs, 2H), 1.05 (dd, 2H).

HPLC-MS (Method G): M+1=338; t$_r$=1.51 min.

EXAMPLE 214

General Procedure A

2-{4-[6-(4-Isopropylpiperazin-1-yl)pyridazin-3-yl]phenoxy}-N,N-dimethylacetamide, dihydrochloride

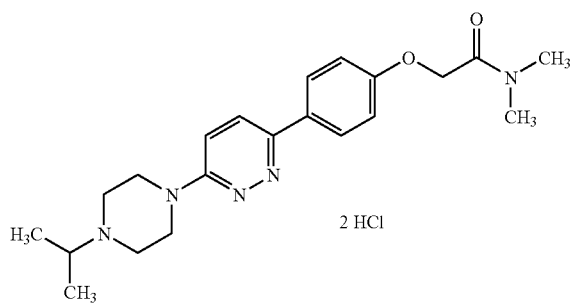 [SMILES: CC(C)N1CCN(c2ccc(-c3ccc(OCC(=O)N(C)C)cc3)nn2)CC1 ; "2 HCl"]

Step 1

4-[6-(4-Isopropyl-piperazin-1-yl)-pyridazin-3-yl]-phenol

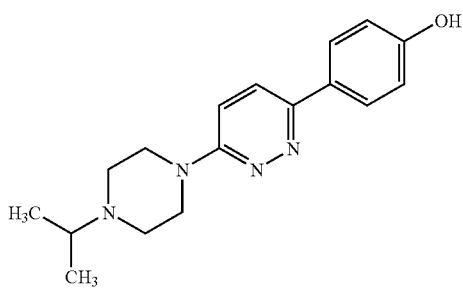 [SMILES: CC(C)N1CCN(c2ccc(-c3ccc(O)cc3)nn2)CC1]

4-[6-(4-Isopropyl-piperazin-1-yl)-pyridazin-3-yl]-phenol was prepared by the general procedure I similar to that described in Example 71, starting from 3-chloro-6-(4-isopropyl-piperazin-1-yl)-pyridazine and (4-hydroxyphenyl)boronic acid.

Step 2

A mixture of 4-[6-(4-isopropyl-piperazin-1-yl)-pyridazin-3-yl]-phenol (110 mg, 0.37 mmol) and 60% sodium hydride (58 mg, 1.45 mmol) in dry DMF (5 mL) was heated at 60° C. for 30 min. 2-Chloro-N,N-dimethylacetamide (54 mg, 0.44 mmol) was added and heating at 60° C. was continued for another 20 h. The reaction mixture was evaporated to dryness and partitioned between water (10 mL) and DCM (10 mL). The organic phase was isolated, washed with brine (5 mL), dried over anhydrous magnesium sulphate, and evaporated to dryness in vacuo. The residue was dissolved in hot ethyl acetate and HCl$_g$ in Et$_2$O was added to give the title compound.

$^1$H NMR (400 MHz, DMSO-d$_6$) δ 11.29 (broad s, 1H), 8.30 (d, 1H), 8.00 (d, 2H), 7.86 (d, 1H), 7.08 (d, 1H), 4.93 (s, 2H), 4.58 (d, 2H), 3.65 (t, 2H), 3.51 (m, 3H), 3.16 (m, 2H), 3.02 (s, 3H), 2.85 (s, 3H), 1.32 (d, 6H).

HPLC-MS (Method G): M+1=384; t$_r$=0.72 min.

EXAMPLE 215

General Procedure A

Cyclohexanecarboxylic acid {4-[6-(4-cyclopropylpiperazin-1-yl)pyridazin-3-yl]phenyl}amide, trifluoroacetate

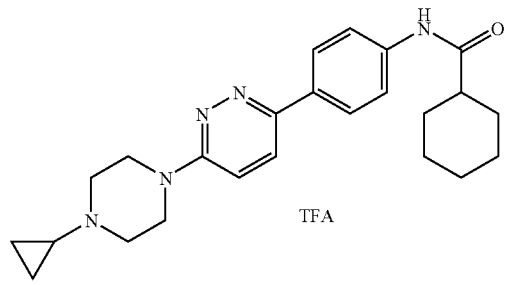 [SMILES: O=C(Nc1ccc(-c2ccc(N3CCN(C4CC4)CC3)nn2)cc1)C1CCCCC1]

The title compound was prepared by a similar procedure to that described in Example 170, starting from 4-[6-(4-cyclopropyl-piperazin-1-yl)-pyridazin-3-yl]-phenylamine and cyclohexylcarbonyl chloride.

$^1$H NMR (300 MHz, CD$_3$OD) δ 8.34 (d, 1H), 7.98-7.82 (m, 5H), 4.05-3.95 (m, 4H), 3.69-3.55 (m, 4H), 2.96-2.85 (m, 1H), 2.44-2.37 (m, 1H), 1.91-1.82 (m, 4H), 1.73 (d, 1H), 1.59-1.19 (m, 5H), 1.09-0.99 (m, 4H).

HPLC (Method D): t$_r$=3.90 min (98%).

EXAMPLE 216

N-{4-[4-Isopropyl-6-(4-isopropylpiperazin-1-yl)pyridazin-3-yl]phenyl}acetamide, trifluoroacetate

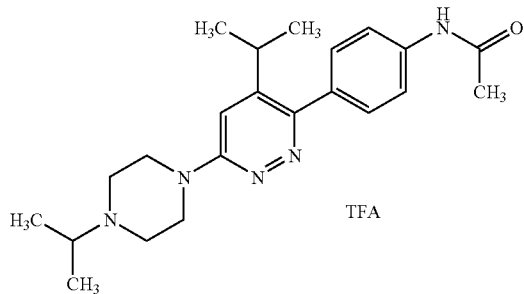 [SMILES: CC(=O)Nc1ccc(-c2nnc(N3CCN(C(C)C)CC3)cc2C(C)C)cc1]

A mixture of 3-(4-bromophenyl)-4-isopropyl-6-(4-isopropyl-piperazin-1-yl)-pyridazine (500 mg, 1.24 mmol), acetamide (87.8 mg, 1.49 mmol), Pd(OAc)$_2$ (13.9 mg, 0.062 mmol), Cs$_2$CO$_3$ (606 mg, 1.86 mmol) and Xantphos (53.8 mg, 0.093 mmol) in 1,4-dioxane (10 mL) was heated at reflux for 12 h. Then water (5 mL) was added. After filtration, the mixture was extracted with EtOAc (3×5 mL). The combined organic extracts were washed with brine, dried (Na$_2$SO$_4$) and concentrated. The residue was purified by HPLC Method F to give 196 mg (38%) of the title compound.

$^1$H NMR (300 MHz, CD$_3$OD) δ 7.96 (s, 1H), 7.89 (d, 2H), 7.57 (d, 2H), 4.90-3.314 (m, 9H), 3.19-3.15 (m, 1H), 2.20 (s, 3H), 1.46 (d, 6H), 1.31 (d, 6H).

HPLC (Method D): t$_r$=3.35 min (100%).

What is claimed is:

1. A compound of the formula I-9:

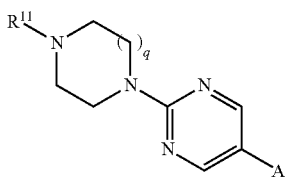

wherein
q is 1; and
R$^{11}$ is either
(i) C$_{3-8}$-alkyl, C$_{3-8}$-cycloalkyl, or C$_{3-8}$-cycloalkyl-C$_{1-3}$-alkyl, or
(ii) C$_{1-6}$-alkyl or C$_{3-8}$-cycloalkyl, which both are substituted with at least one substituent selected from the group consisting of hydroxy, C$_{1-6}$-alkoxy, C$_{1-6}$-alkylcarbonyl, cyano, —NR$^5$R$^6$, —C(=O)NR$^5$R$^6$, arylcarbonyl, heteroarylcarbonyl, C$_{1-6}$-alkylsulfonyl, arylsulfonyl, heterocyclylcarbonyl, C$_{1-6}$-alkoxycarbonyl, aryl-C$_{1-6}$-alkoxycarbonyl, heteroaryl and heterocyclyl, which heterocyclyl may optionally be substituted with C$_{1-6}$-alkyl, and R$^5$ and R$^6$ independently are hydrogen or C$_{1-6}$-alkyl;

A is phenyl substituted with one or more substituents selected independently from R$^{12}$; and
R$^{12}$ is —(CH$_2$)—NR$^{13}$R$^{14}$;
R$^{13}$ is C$_{1-6}$-alkylcarbonyl; and
R$^{14}$ is hydrogen;
or a pharmaceutically acceptable salt thereof.

2. The compound of claim 1 wherein R$^{11}$ is C$_{3-8}$-alkyl, C$_{3-8}$-cycloalkyl or C$_{3-8}$-cycloalkyl-C$_{1-3}$-alkyl.

3. The compound of claim 1, wherein R$^{11}$ is C$_{1-6}$-alkyl or C$_{3-8}$-cycloalkyl, which both are substituted with at least one substituent selected from the group consisting of hydroxy, C$_{1-6}$-alkoxy, C$_{1-6}$-alkylcarbonyl, cyano, —NR$^5$R$^6$, —C(=O)NR$^5$R$^6$, arylcarbonyl, heteroarylcarbonyl, C$_{1-6}$-alkylsulfonyl, arylsulfonyl, heterocyclylcarbonyl, C$_{1-6}$-alkoxycarbonyl, aryl-C$_{1-6}$-alkoxycarbonyl, heteroaryl and heterocyclyl, which heterocyclyl may optionally be substituted with C$_{1-6}$-alkyl.

4. The compound of claim 1, wherein R$^{13}$ is acetyl.

5. A compound selected from the group consisting of:
N-{4-[2-(4-Isopropylpiperazin-1-yl)pyrimidin-5-yl]benzyl}acetamide;
N-{4-[2-(4-Isopropylpiperazin-1-yl)pyrimidin-5-yl]benzyl}isobutyramide; and
N-{4-[2-(4-Cyclopropylpiperazin-1-yl)pyrimidin-5-yl]benzyl}acetamide;
or a pharmaceutically acceptable salt thereof.

6. N-{4-[2-(4-Isopropylpiperazin-1-yl)pyrimidin-5-yl]benzyl}-acetamide, or a pharmaceutically acceptable salt thereof.

7. N-{4-[2-(4-Cyclopropylpiperazin-1-yl)pyrimidin-5-yl]benzyl}-acetamide, or a pharmaceutically acceptable salt thereof.

8. N-{4-[2-(4-Isopropylpiperazin-1-yl)pyrimidin-5-yl]benzyl}isobutyramide, or a pharmaceutically acceptable salt thereof.

9. A pharmaceutical composition comprising a compound of claim 1 and a pharmaceutically acceptable carrier or excipient.

10. A pharmaceutical composition comprising a compound of claim 5 and a pharmaceutically acceptable carrier or excipient.

11. A pharmaceutical composition comprising a compound of claim 6 and a pharmaceutically acceptable carrier or excipient.

12. A pharmaceutical composition comprising a compound of claim 7 and a pharmaceutically acceptable carrier or excipient.

13. A pharmaceutical composition comprising a compound of claim 8 and a pharmaceutically acceptable carrier or excipient.

* * * * *

UNITED STATES PATENT AND TRADEMARK OFFICE
CERTIFICATE OF CORRECTION

PATENT NO.       : 8,501,739 B2  
APPLICATION NO.  : 11/917823  
DATED            : August 6, 2013  
INVENTOR(S)      : Hohlweg et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1350 days.

Signed and Sealed this
Tenth Day of February, 2015

Michelle K. Lee
*Deputy Director of the United States Patent and Trademark Office*